(12) United States Patent
Patel et al.

(10) Patent No.: US 11,273,171 B2
(45) Date of Patent: Mar. 15, 2022

(54) METHODS FOR TREATING OR PREVENTING OPHTHALMOLOGICAL CONDITIONS

(71) Applicant: IVERIC bio, Inc., New York, NY (US)

(72) Inventors: Samir Patel, Princeton, NJ (US);
Richard Everett, Randolph, NJ (US);
Douglas Brooks, Durham, NC (US);
Shane Xinxin Tian, Oakland, NJ (US)

(73) Assignee: IVERIC bio, Inc., New York, NY (US)

( * ) Notice: Subject to any disclaimer, the term of this patent is extended or adjusted under 35 U.S.C. 154(b) by 0 days.

(21) Appl. No.: 17/346,556

(22) Filed: Jun. 14, 2021

(65) Prior Publication Data
US 2021/0369757 A1    Dec. 2, 2021

Related U.S. Application Data

(63) Continuation of application No. 16/434,018, filed on Jun. 6, 2019, now abandoned, which is a continuation of application No. 15/144,429, filed on May 2, 2016, now abandoned, which is a continuation of application No. 14/329,702, filed on Jul. 11, 2014, now abandoned.

(60) Provisional application No. 61/931,135, filed on Jan. 24, 2014, provisional application No. 61/931,116, filed on Jan. 24, 2014, provisional application No. 61/931,125, filed on Jan. 24, 2014, provisional application No. 61/926,812, filed on Jan. 13, 2014, provisional application No. 61/926,848, filed on Jan. 13, 2014, provisional application No. 61/926,825, filed on Jan. 13, 2014, provisional application No. 61/911,854, filed on Dec. 4, 2013, provisional application No. 61/911,894, filed on Dec. 4, 2013, provisional application No. 61/911,860, filed on Dec. 4, 2013, provisional application No. 61/866,502, filed on Aug. 15, 2013, provisional application No. 61/866,507, filed on Aug. 15, 2013, provisional application No. 61/866,503, filed on Aug. 15, 2013, provisional application No. 61/845,936, filed on Jul. 12, 2013, provisional application No. 61/845,938, filed on Jul. 12, 2013, provisional application No. 61/845,935, filed on Jul. 12, 2013.

(51) Int. Cl.
| | |
|---|---|
| *A61K 31/7088* | (2006.01) |
| *A61K 31/713* | (2006.01) |
| *A61K 39/395* | (2006.01) |
| *C12N 15/115* | (2010.01) |
| *A61K 45/06* | (2006.01) |
| *A61K 9/00* | (2006.01) |
| *C07K 16/22* | (2006.01) |
| *A61K 9/14* | (2006.01) |

(52) U.S. Cl.
CPC ........ *A61K 31/7088* (2013.01); *A61K 9/0048* (2013.01); *A61K 9/143* (2013.01); *A61K 31/713* (2013.01); *A61K 39/3955* (2013.01); *A61K 45/06* (2013.01); *C07K 16/22* (2013.01); *C12N 15/115* (2013.01); *C07K 2317/24* (2013.01); *C07K 2317/55* (2013.01); *C07K 2317/76* (2013.01); *C12N 2310/16* (2013.01); *C12N 2310/314* (2013.01); *C12N 2310/317* (2013.01); *C12N 2310/321* (2013.01); *C12N 2310/322* (2013.01); *C12N 2310/351* (2013.01); *C12N 2320/30* (2013.01); *C12N 2320/31* (2013.01)

(58) Field of Classification Search
None
See application file for complete search history.

(56) References Cited

U.S. PATENT DOCUMENTS

| | | |
|---|---|---|
| 4,601,704 A | 7/1986 | Larkin |
| 4,914,210 A | 4/1990 | Levenson et al. |
| 5,194,596 A | 3/1993 | Tischer et al. |
| 5,270,163 A | 12/1993 | Gold et al. |
| 5,322,691 A | 6/1994 | Darougar et al. |
| 5,459,015 A | 10/1995 | Janjic et al. |
| 5,475,096 A | 12/1995 | Gold et al. |
| 5,496,938 A | 3/1996 | Gold et al. |
| 5,668,264 A | 9/1997 | Janjic et al. |
| 5,670,637 A | 9/1997 | Gold et al. |

(Continued)

FOREIGN PATENT DOCUMENTS

| | | |
|---|---|---|
| CA | 2464007 | 4/2004 |
| CN | 101443050 A | 5/2009 |

(Continued)

OTHER PUBLICATIONS

Vaz et al. Geographic Atrophy, amdbook.org 2017 [online], [retrieved on Nov. 15, 2021]. Retrieved from the Internet <URL:https://amdbook.org/content/geographic-atrophy-0>, 21 pages.*

(Continued)

*Primary Examiner* — Tracy Vivlemore
(74) *Attorney, Agent, or Firm* — Jon E. Gordon; Haug Partners LLP

(57) ABSTRACT

The present invention relates to methods for treating and preventing ophthalmological disease and disorders, comprising administering Antagonist A or another pharmaceutically acceptable salt thereof, optionally in combination with another treatment, to a subject in need thereof. The present invention also relates to methods for treating and preventing ophthalmological disease and disorders, comprising administering an anti-C5 agent (e.g., ARC1905), optionally in combination with another treatment, to a subject in need thereof.

19 Claims, 23 Drawing Sheets

Specification includes a Sequence Listing.

(56) References Cited

U.S. PATENT DOCUMENTS

| | | |
|---|---|---|
| 5,674,685 A | 10/1997 | Janjic et al. |
| 5,683,867 A | 11/1997 | Biesecker et al. |
| 5,696,249 A | 12/1997 | Gold et al. |
| 5,723,594 A | 3/1998 | Janjic et al. |
| 5,731,144 A | 3/1998 | Toothman et al. |
| 5,731,424 A | 3/1998 | Toothman et al. |
| 5,756,291 A | 5/1998 | Griffin et al. |
| 5,811,533 A | 9/1998 | Gold et al. |
| 5,814,620 A | 9/1998 | Robinson et al. |
| 5,817,785 A | 10/1998 | Gold et al. |
| 5,837,834 A | 11/1998 | Pagratis et al. |
| 5,846,713 A | 12/1998 | Pagratis et al. |
| 5,859,228 A | 1/1999 | Janjic et al. |
| 5,932,462 A | 8/1999 | Harris et al. |
| 5,932,602 A | 8/1999 | Hirth et al. |
| 5,958,691 A | 9/1999 | Pieken et al. |
| 5,990,141 A | 11/1999 | Hirth et al. |
| 6,005,087 A | 12/1999 | Cook et al. |
| 6,011,020 A | 1/2000 | Gold et al. |
| 6,051,698 A | 4/2000 | Janjic et al. |
| 6,054,297 A | 4/2000 | Carter et al. |
| 6,113,906 A | 9/2000 | Greenwald et al. |
| 6,147,204 A | 11/2000 | Gold et al. |
| 6,168,778 B1 | 1/2001 | Janjic et al. |
| 6,207,816 B1 | 3/2001 | Gold et al. |
| 6,229,002 B1 | 5/2001 | Janjic et al. |
| 6,342,219 B1 | 1/2002 | Thorpe et al. |
| 6,342,221 B1 | 1/2002 | Thorpe et al. |
| 6,382,219 B1 | 5/2002 | Jelton |
| 6,395,888 B1 | 5/2002 | Biesecker et al. |
| 6,410,322 B1 | 6/2002 | Robinson |
| 6,416,758 B1 | 7/2002 | Thorpe et al. |
| 6,426,335 B1 | 7/2002 | Janjic et al. |
| 6,448,277 B2 | 9/2002 | Altmann et al. |
| 6,465,188 B1 | 10/2002 | Gold et al. |
| 6,537,988 B2 | 3/2003 | Lee |
| 6,559,126 B2 | 5/2003 | Tournaire et al. |
| 6,566,343 B2 | 5/2003 | Biesecker et al. |
| 6,582,918 B2 | 6/2003 | Janjic et al. |
| 6,632,926 B1 | 10/2003 | Chen et al. |
| 6,699,843 B2 | 3/2004 | Pietras et al. |
| 6,719,750 B2 | 4/2004 | Varner et al. |
| 6,808,719 B2 | 10/2004 | Yaacobi |
| 6,884,879 B1 | 4/2005 | Baca et al. |
| 6,897,294 B2 | 5/2005 | Davis-Smyth et al. |
| 7,060,269 B1 | 6/2006 | Baca et al. |
| 7,070,959 B1 | 7/2006 | Papadopoulos et al. |
| 7,141,375 B2 | 11/2006 | Pietras et al. |
| 7,303,041 B2 | 12/2007 | Stuve |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| 7,354,581 B2 | 4/2008 | Cedarbaum et al. |
| 7,365,166 B2 | 4/2008 | Baca et al. |
| 7,374,757 B2 | 5/2008 | Papadopoulos et al. |
| 7,374,758 B2 | 5/2008 | Papadopoulos et al. |
| 7,459,436 B2 | 12/2008 | Lehmann et al. |
| 7,521,049 B2 | 4/2009 | Wiegand et al. |
| 7,531,173 B2 | 5/2009 | Wiegand et al. |
| 7,531,524 B2 | 5/2009 | Rusconi |
| 7,608,261 B2 | 10/2009 | Furfine et al. |
| 7,723,315 B2 | 5/2010 | Rusconi |
| 7,759,472 B2 | 7/2010 | Shima et al. |
| 7,762,988 B1 | 7/2010 | Vitello |
| 7,807,164 B2 | 10/2010 | Furfine et al. |
| 7,879,993 B2 | 2/2011 | Janjic et al. |
| 7,939,654 B2 | 5/2011 | Janjic et al. |
| 8,039,443 B2 | 10/2011 | Grate et al. |
| 8,092,803 B2 | 1/2012 | Furfine et al. |
| 8,187,597 B2 | 5/2012 | Shima et al. |
| 8,206,707 B2 | 6/2012 | Shima et al. |
| 8,389,489 B2 | 3/2013 | Rusconi |
| 8,481,046 B2 | 7/2013 | Furfine et al. |
| 8,591,885 B2 | 11/2013 | Chang et al. |
| 8,685,397 B2 | 4/2014 | Shima et al. |
| 8,753,625 B2 | 6/2014 | Fung et al. |
| 8,802,107 B2 | 8/2014 | Furfine et al. |
| 8,859,518 B2 | 10/2014 | Rusconi |
| 9,046,513 B2 | 6/2015 | Ghayur et al. |
| 9,340,594 B2 | 5/2016 | Furfine et al. |
| 2002/0032315 A1 | 3/2002 | Baca et al. |
| 2002/0189705 A1 | 12/2002 | Reihl et al. |
| 2003/0036642 A1 | 2/2003 | Janjic et al. |
| 2003/0171320 A1 | 9/2003 | Guyer |
| 2003/0180744 A1 | 9/2003 | Gold et al. |
| 2004/0022727 A1 | 2/2004 | Stanton et al. |
| 2004/0167091 A1 | 8/2004 | Guyer |
| 2004/0180360 A1 | 9/2004 | Wilson et al. |
| 2004/0249130 A1 | 12/2004 | Stanton et al. |
| 2004/0253243 A1 | 12/2004 | Epstein et al. |
| 2004/0253679 A1 | 12/2004 | Epstein et al. |
| 2005/0042273 A1 | 2/2005 | Janjic et al. |
| 2005/0058620 A1 | 3/2005 | Nakamoto et al. |
| 2005/0096257 A1 | 5/2005 | Shima et al. |
| 2005/0124565 A1 | 6/2005 | Diener et al. |
| 2005/0159351 A1 | 7/2005 | Grate et al. |
| 2005/0244462 A1 | 11/2005 | Farooq |
| 2005/0244471 A1 | 11/2005 | Shiah et al. |
| 2005/0244500 A1 | 11/2005 | Whitcup et al. |
| 2005/0288490 A1 | 12/2005 | Nakamoto et al. |
| 2006/0018871 A1 | 1/2006 | Benedict et al. |
| 2006/0073113 A1 | 4/2006 | Nakamoto et al. |
| 2006/0079477 A1 | 4/2006 | Biesecker et al. |
| 2006/0088523 A1 | 4/2006 | Andya et al. |
| 2006/0115450 A1 | 6/2006 | Nakamoto et al. |
| 2006/0167435 A1 | 7/2006 | Adamis et al. |
| 2006/0182783 A1 | 8/2006 | Hughes et al. |
| 2006/0229273 A1 | 10/2006 | Gold et al. |
| 2006/0233860 A1 | 10/2006 | Chang et al. |
| 2007/0021327 A1 | 1/2007 | Pietras et al. |
| 2007/0027101 A1 | 2/2007 | Guyer et al. |
| 2007/0105809 A1 | 5/2007 | Rusconi |
| 2007/0184089 A1 | 8/2007 | Howie et al. |
| 2007/0293432 A1 | 12/2007 | Furfine et al. |
| 2008/0076742 A1 | 3/2008 | Sheibani et al. |
| 2008/0097310 A1 | 4/2008 | Buehler et al. |
| 2008/0145406 A1 | 6/2008 | Asgharian et al. |
| 2008/0152654 A1 | 6/2008 | Reich |
| 2008/0207883 A1 | 8/2008 | Janjic et al. |
| 2008/0286334 A1 | 11/2008 | Shiah et al. |
| 2008/0305115 A1 | 12/2008 | Tice et al. |
| 2009/0053138 A1 | 2/2009 | Preiss et al. |
| 2009/0075342 A1 | 3/2009 | Cload et al. |
| 2009/0269356 A1 | 10/2009 | Epstein et al. |
| 2010/0111942 A1 | 5/2010 | Shima et al. |
| 2010/0119522 A1 | 5/2010 | Shima et al. |
| 2010/0129364 A1 | 5/2010 | Shima et al. |
| 2011/0200593 A1 | 8/2011 | Shima et al. |
| 2012/0087858 A1 | 4/2012 | Ghayur et al. |
| 2012/0100136 A1 | 4/2012 | Patel et al. |
| 2012/0109059 A1 | 5/2012 | Ranalletta et al. |
| 2013/0058951 A1 | 3/2013 | Stoller |
| 2013/0259881 A1 | 10/2013 | Fandl et al. |
| 2013/0274189 A1 | 10/2013 | Furfine et al. |
| 2013/0295102 A1 | 11/2013 | Johnson et al. |
| 2013/0323242 A1 | 12/2013 | Everett et al. |
| 2014/0179621 A1 | 6/2014 | Patel et al. |
| 2014/0193402 A1 | 7/2014 | Wiegand et al. |
| 2014/0242082 A1 | 8/2014 | Shima et al. |
| 2014/0294816 A1 | 10/2014 | Shima et al. |
| 2014/0335078 A1 | 11/2014 | Fung et al. |
| 2015/0017163 A1 | 1/2015 | Patel et al. |
| 2015/0157709 A1 | 6/2015 | Everett et al. |
| 2015/0182623 A1 | 7/2015 | Everett et al. |
| 2015/0202288 A1 | 7/2015 | Shima et al. |
| 2015/0202289 A1 | 7/2015 | Shima et al. |
| 2016/0038589 A1 | 2/2016 | Patel |
| 2016/0264969 A1 | 9/2016 | Patel et al. |

FOREIGN PATENT DOCUMENTS

| | | |
|---|---|---|
| EP | 1660057 | 5/2012 |
| JP | 2009-529058 | 8/2009 |
| JP | 2012-525415 A | 10/2012 |

(56) References Cited

FOREIGN PATENT DOCUMENTS

| WO | WO 95/16032 | 6/1995 |
|---|---|---|
| WO | WO 96/27006 | 9/1996 |
| WO | WO 96/30046 | 10/1996 |
| WO | WO 96/38579 | 12/1996 |
| WO | WO 98/18480 | 5/1998 |
| WO | WO 98/45331 A2 | 10/1998 |
| WO | WO 98/45331 A3 | 12/1998 |
| WO | WO 99/31119 | 6/1999 |
| WO | WO 99/41271 | 8/1999 |
| WO | WO 00/64946 | 11/2000 |
| WO | WO 2001/027264 | 4/2001 |
| WO | WO 2001/087351 | 11/2001 |
| WO | WO 2003/013541 | 2/2003 |
| WO | WO 2003/020276 | 3/2003 |
| WO | WO 2003/025019 | 3/2003 |
| WO | WO 2003/039404 | 5/2003 |
| WO | WO 2004/005282 | 1/2004 |
| WO | WO 2004/050899 | 6/2004 |
| WO | WO 2004/094614 | 11/2004 |
| WO | WO 2005/000890 | 1/2005 |
| WO | WO 2005/000895 | 1/2005 |
| WO | WO 2005/014814 | 2/2005 |
| WO | WO 2005/020972 | 3/2005 |
| WO | WO 2006/050498 | 5/2006 |
| WO | WO 2007/035621 | 3/2007 |
| WO | WO 2007/056227 | 5/2007 |
| WO | WO 2007/103549 | 9/2007 |
| WO | WO 2007/149334 | 12/2007 |
| WO | WO 2010/127029 | 11/2010 |
| WO | WO 2013/093762 | 6/2013 |
| WO | WO 2013/149086 | 10/2013 |
| WO | WO 2013/181495 | 12/2013 |
| WO | WO 2013/181495 A2 | 12/2013 |
| WO | WO 2014/109999 | 7/2014 |
| WO | WO 2015/006734 | 1/2015 |
| WO | WO 2016/025313 | 2/2016 |

OTHER PUBLICATIONS

Anonymous: "NCT01089517 on Jun. 15, 2012: ClinicalTrials.gov Archive", Jun. 15, 2012 (Jun. 15, 2012), XP055341978, Retrieved from the Internet: URL:https://clinicaltrials.gov/archive/NCT01089517/2012_06_15.
Carla Lucia Esposito et al.: "New Insight into Clinical Development of Nucleic Acid Aptamers", Discovery Medicine, vol. 11, No. 61, Jun. 30, 2011 (Jun. 30, 2011), pp. 487-496, XP055341843.
Laura Cerchia et al.: "Coupling Aptamers to Short Interfering RNAs as Therapeutics", Pharmaceuticals, vol. 4, No. 12, Dec. 27, 2011 (Dec. 27, 2011), pp. 1434-1449, XP055082625.
Jaffe Glenn J. et al.: "A Phase 1 Study of Intravitreous E10030 in Combination with Ranibizumab in Neovascular Age-Related Macular Degeneration", Ophthalmology, vol. 123, No. 1, 2016, pp. 78-85, XP029364125.
Kanji Takahashi et al., Treatment Guidelines for Age-Related Macular Degeneration, Nippon Ganka Gakkai Zasshi, Dec. 10, 2012, vol. 116, No. 12, pp. 1150-1155.
Miho Nozaki et al., Drusen Complement Components C3a and C5a Promote Choroidal Neovascularization, PNAS, Feb. 14, 2006, vol. 103, No. 7, p. 2328-2333.
Office Action for U.S. Appl. No. 14/598,365, dated Sep. 15, 2016, 27 pages.
Office Action for U.S. Appl. No. 14/610,332, dated Sep. 15, 2016, 23 pages.
Abdollahi, A. et al., "Inhibition of platelet-derived growth factor signaling attenuates pulmonary fibrosis," The Journal of Experimental Medicine, vol. 201, No. 6, Mar. 21, 2005, 925-935.
Arevalo, J. F. et al., "Tractional retinal detachment following intravitreal bevacizumab (Avastin) in patients with severe proliferative diabetic retinopathy," Br. J. Ophthalmol. 2008;92:213-216.
Armulik, A. et al., "Endothelial/Pericyte Interactions," Circ. Res. 2005;97(6):512-523.
Arnold, J. J. et al., "Age related macular degeneration," BMJ 2000;321(7263):741-744.
Barikian, A. et al., "Induction With Intravitreal Bevacizumab Every Two Weeks in the Management of Neovascular Age-Related Macular Degeneration," Am J Ophthalmol 2015;159:131-137.
Boor, P. et al., "PDGF and the progression of renal disease," Nephrol Dial Transplant (2014) 29:(1)i45-i54.
Busbee, B. G. et al., "Twelve-Month Efficacy and Safety of 0.5 mg or 2.0 mg Ranibizumab in Patients with Subfoveal Neovascular Age-related Macular Degeneration," Ophthalmology 2013;120(5):1046-1056.
Caballero, S. et al., "Anti-sphingosine-1-phosphate monoclonal antibodies inhibit angiogenesis and sub-retinal fibrosis in a murine model of laserinduced choroidal neovascularization," Exp Eye Res. Mar. 2009 ; 88(3):367-377. doi:10.1016/j.exer.2008.07.012.
Campochiaro, P. A. et al., "Platelet-Derived Growth Factor is Chemotactic for Human Retinal Pigment Epithelial Cells," Arch. Ophthalmol., 103(4):576-579 (Apr. 1985).
Day, J. C., "Population Projections of the United States, by Age, Sex, Race, and Hispanic Orgin: 1993-2050," U.S. Bureau of the Census, Current Population Reports, P25-1104, U.S. Department of Commerce, U.S. Government Printing Office, Washington, DC (Nov. 1993), 133 pages.
DeLuca, C. et al., "Imatinib mesylate (gleevec) induced unilateral optic disc edema," Optom Vis Sci., 89(10):e16-e22 (Oct. 2012).
Dvorak, H. F. et al., "Vascular Permeability Factor/Vascular Endothelial Growth Factor, Microvascular Hyperpermeability, and Angiogenesis," American Journal of Pathology, vol. 146, No. 5, 1029-1039 (May 1995).
Green, W. R. et al., "Age related macular degeneration histopathologic studies. The 1992 Lorenz E. Zimmerman Lecture," Ophthalmology 1993; 100:1519-1535.
Grossniklaus, H. E. et al., "Histopathologic and Ultrastructural Features of Surgically Excised Subfoveal Choroidal Neovascular Lesions," Arch Ophthalmol. 2005;123(7):914-921.
Grunwald, J. E. et al., "Risk of Geographic Atrophy in the Comparison of Age-related Macular Degeneration Treatments Trials," Ophthalmology 2014;121(1):150-161.
Hellerbrand, C., "Hepatic stellate cells—the pericytes in the liver," Pflugers Arch—Eur J Physiol (2013) 465(6):775-778.
Hinton, D. R. et al., "Apoptosis in surgically excised choroidal neovascular membranes in age-related macular degeneration," Arch Ophthalmol., 116(2):203-209 (1998).
Hwang, J. C. et al., "Development of Subretinal Fibrosis After Anti-VEGF Treatment in Neovascular Age-Related Macular Degeneration," Ophthalmic Surgery, Lasers & Imaging (Oct. 2009), 6 pages, doi: 10.3928/15428877-20100924-01.
Ishikawa, K. et al., "Molecular mechanisms of subretinal fibrosis in age-related macular degeneration," Experimental Eye Research, 142:19-25 (2016).
Iwayama, T. et al., "Involvement of PDGF in Fibrosis and Scleroderma: Recent Insights from Animal Models and Potential Therapeutic Opportunities," Curr Rheumatol Rep (2013) 15(2):304, 6 pages.
Jain, R. K., "Normalizing tumor vasculature with anti-angiogenic therapy: A new paradigm for combination therapy," Nature Medicine, 7(9):987-989 (Sep. 2001).
Jo, Y-J et al., "Establishment of a New Animal Model of Focal Subretinal Fibrosis That Resembles Disciform Lesion in Advanced Age-Related Macular Degeneration," Invest Ophthalmol Vis Sci. 2011;52:6089-6095. DOI:10.1167/iovs.10-5189.
Kang, H. M. et al., "Subfoveal Choroidal Thickness as a Potential Predictor of Visual Outcome and Treatment Response After Intravitreal Ranibizumab Injections for Typical Exudative Age-Related Macular Degeneration," Am J Ophthalmol 2014;157:1013-1021.
Keck, P. J. et al., "Vascular permeability factor, an endothelial cell mitogen related to PDGF," Science, 1989; 246(4935):1309-1312.
Kent, D. et al., "Choroidal neovascularization: a wound healing perspective," Molecular Vision 2003; 9:747-755.
LeBleu, V. S. et al., "Blockade of PDGF receptor signaling reduces myofibroblast number and attenuates renal fibrosis," Kidney International (2011) 80(11):1119-1121.

(56) References Cited

OTHER PUBLICATIONS

Leibowitz, H. M. et al., "The Framingham Eye Study monograph: An ophthalmological and epidemiological study of cataract, glaucoma, diabetic retinopathy, macular degeneration, and visual acuity in a general population of 2631 adults, 1973-1975," Surv Ophthalmol, 1980;24(Suppl), 335-610.

Lim, L. S. et al., "Age-related macular degeneration," Lancet, 2012; 379:1728-1738.

Liu, Y. et al., "Inhibition of PDGF, TGF-b, and Abl signaling and reduction of liver fibrosis by the small molecule Bcr-Abl tyrosine kinase antagonist Nilotinib," Journal of Hepatology, 2011; 55(3):612-625.

Nishioka, Y. et al., "Targeting platelet-derived growth factor as a therapeutic approach in pulmonary fibrosis," J. Med. Invest. 60(3-4):175-183 (Aug. 2013).

Pauleikhoff, D., "Neovascular age-related macular degeneration," Retina, 25:1065-1084 (2005).

Savage, D. G. et al., "Imatinib mesylate—a new oral targeted therapy," N. Engl. J. Med. Feb. 2002;346(9):683-693.

Seppa, H. et al., "Platelet-derived Growth Factor is Chemotactic for Fibroblasts," The Journal of Cell Biology, 92(2):584-588 (Feb. 1982).

Sjoblom, T. et al., "Growth inhibition of dermatofibrosarcoma protuberans tumors by the platelet-derived growth factor receptor antagonist STI571 through induction of apoptosis," Cancer Res 61(15):5778-5783 (2001).

Van Geest, R. J. et al., "A shift in the balance of vascular endothelial growth factor and connective tissue growth factor by bevacizumab causes the angiofibrotic switch in proliferative diabetic retinopathy," Br J Ophthalmol 2012;96:587e590. doi:10.1136/bjophthalmol-2011-301005.

Wieman, T. J. et al., "Efficacy and Safely of a Topical Gel Formulation of Recombinant Human Platelet-Derived Growth Factor-BB (Becaplermin) in Patients With Chronic Neuropathic Diabetic Ulcers," Diabetes Care, 21(5):822-827 (May 1998).

Woodcock, H. V. et al., "Reducing lung function decline in patients with idiopathic pulmonary fibrosis: potential of nintedanib," Drug Design, Development and Therapy, 2013; 7:503-510.

Dugel, P. U. et al., "Anti-VEGF resistance in neovascular AMD: Role of PDGF antagonism," Investigative Ophthalmology & Visual Science, 56(7):2826 (Jun. 2015), ARVO Annual Meeting Abstract.

Singh, R. P. et al., "A single-arm, investigator-initiated study of the efficacy, safety and tolerability of intravitreal aflibercept injection in subjects with exudative age-related macular degeneration, previously treated with ranibizumab or bevacizumab: 6-month interim analysis," Br. J. Ophthalmol. 98:i22-i27 (2014).

Supplementary European Search Report for European Application No. 13796692.5, dated Oct. 26, 2016, 16 pages.

Office Action for U.S. Appl. No. 14/522,360, dated Dec. 9, 2016, 23 pages.

Supplementary European Search Report for European Application No. 14823713.4, dated Feb. 13, 2017, 9 pages.

ClinicalTrials.gov Archive [online], "View of NCT01089517 on Jun. 15, 2012," A Phase 2, Randomized, Double-Masked, Controlled Trial to Establish the Safety and Efficacy of Intravitreous Injections of E10030 (Anti-PDGF Pegylated Aptamer) Given in Combination With Lucentis in Subjects with Neovascular Age-Related Macular Degeneration, Retrieved from the Internet: URL: <https://clinicaltrials.gov/archive/NCT01089517/2012_06_15,> [Retrieved on Feb. 3, 2017], 3 pages.

Burgess, W. H. et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 111(5):2129-2138 (1990).

Cerchia, L. et al., "Coupling aptamers to short interfering RNAs as therapeutics," Pharmaceuticals, 4(12):1434-1449 (Dec. 2011).

Esposito, C. L. et al., "New insight into clinical development of nucleic acid aptamers," Discovery Medicine, 11(61):487-496 (Jun. 2011).

Greer, S. et al., "Studies on depurination of DNA by heat," J. Mol. Biol. 1962, 4:123-141.

Guiotto, A. et al., "Anchimeric assistance effect on regioselective hydrolysis of branched PEGs: a mechanistic investigation," Bioorganic & Medicinal Chemistry, 12:5031-5037 (2004).

Heier, J. S. et al., "The 1-year results of CLEAR-IT 2, a phase 2 study of vascular endothelial growth factor trap-eye dosed as-needed after 12-week fixed dosing," Ophthalmology, 118(6):1098-1106 (Mar. 2011).

Jaffe, G. J. et al., "Dual Antagonism of PDGF and VEGF in Neovascular Age-Related Macular Degeneration. A Phase IIb, Multicenter, Randomized Controlled Trial," Ophthalmology, pp. 1-11, 2016.

Jaffe, G. J. et al., "A Phase 1 study of intravitreous E10030 in combination with ranibizumab in neovascular age-related macular degeneration," Ophthalmology, 123(1):78-85 (2016).

Krotz, A. H. et al., "Synthesis of Antisense Oligonucleotides with Minimum Depurination," Nucleosides, Nucleotides and Nucleic Acids, 22(2):129-134 (2003).

Lazar, E. et al., "Transforming growth factor alpha: mutation of aspartic acid 47 and leucine 48 results in different biological activities," Molecular and Cellular Biology, 8(3):1247-1252 (1988).

Lindahl, T. et al., "Rate of depurination of native deoxyribonucleic acid," Biochemistry, 11(19):3610-3618 (1972).

Macugen (pegaptanib sodium injection) package insert (Dec. 2011), 2 pages.

Marguet, E. et al., "DNA stability at temperatures typical for hyperthermophiles," Nucleic Acids Research, 22(9):1681-1686 (1994).

Marguet, E. et al., "Protection of DNA by salts against thermodegradation at temperatures typical for hyperthermophiles," Extremophiles 1998, 2:115-122.

Ophthotech, "Ophthotech announces results from pivotal phase 3 trials of Fovista in wet age-related macular degeneration," Conference call and webcast, Dec. 12, 2016, 3 pages.

Perez-Santonja, J. J. et al., "Inhibition of corneal neovascularization by topical bevacizumab (Anti-VEGF) and sunitinib (Anti-VEGF and Anti-PDGF) in an animal model," American Journal of Ophthalmology, 150(4):519-528.e1 (Oct. 2010).

Roger, M. et al., "Selective heat inactivation of pneumococcal transforming deoxyribonucleate," Biochemistry, vol. 47:653-669 (1961).

Stewart, M. W. et al., "Aflibercept (VEGF trap-eye): the newest anti-VEGF drug," British Journal of Ophthalmology, 96(9):1157-1158 (Sep. 2012).

Suzuki, T. et al., "Mechanistic studies on depurination and apurinic site chain breakage in oligodeoxyribonucleotides," Nucleic Acids Research, 22(23):4997-5003 (1994).

Wells, J. A. et al., "Aflibercept, bevacizumab, or ranibizumab for diabetic macular edema. Two-year results from a comparative effectiveness randomized clinical trial," Ophthalmology, 123(6):1351-1359 (Jun. 2016).

Office Action for U.S. Appl. No. 10/926,806, dated Oct. 1, 2009, 13 pages.

Office Action for U.S. Appl. No. 10/926,806, dated May 27, 2009, 19 pages.

Office Action for U.S. Appl. No. 10/926,806, dated Sep. 30, 2008, 37 pages.

Office Action for U.S. Appl. No. 10/926,806, dated Jan. 24, 2008, 30 pages.

Office Action for U.S. Appl. No. 10/926,806, dated May 7, 2007, 18 pages.

International Search Report and Written Opinion for International Application No. PCT/US2004/027612, dated Sep. 19, 2005, 23 pages.

International Preliminary Report on Patentability for International Application No. PCT/US2004/027612, dated Aug. 27, 2006, 10 pages.

European Search Report for European Application No. 10013061, dated Dec. 7, 2010, 8 pages.

Office Action for U.S. Appl. No. 12/465,051, dated Sep. 28, 2011, 19 pages.

Office Action for U.S. Appl. No. 12/465,051, dated Jan. 19, 2011, 16 pages.

(56) References Cited

OTHER PUBLICATIONS

Office Action for U.S. Appl. No. 12/564,863, dated Jul. 13, 2011, 19 pages.
Office Action for U.S. Appl. No. 12/641,270, dated Sep. 6, 2011, 29 pages.
Office Action for U.S. Appl. No. 12/641,270, dated Jan. 31, 2011, 28 pages.
Office Action for U.S. Appl. No. 12/987,508, dated Aug. 16, 2011, 26 pages.
Office Action for U.S. Appl. No. 12/987,508, dated Dec. 13, 2011, 18 pages.
Office Action for U.S. Appl. No. 14/186,149, dated Aug. 1, 2014, 20 pages.
Office Action for U.S. Appl. No. 14/303,973, dated Jul. 24, 2014, 27 pages.
Supplementary European Search Report and Opinion for European Application No. 10770279.7, dated Feb. 19, 2013, 6 pages.
Office Action for U.S. Appl. No. 13/284,221, dated Jun. 15, 2012, 16 pages.
Office Action for U.S. Appl. No. 13/284,221, dated Feb. 11, 2013, 12 pages.
International Search Report and Written Opinion for International Application No. PCT/US2010/032816, dated Sep. 17, 2010, 11 pages.
International Preliminary Report on Patentability for International Application No. PCT/US2010/032816, dated Nov. 1, 2011, 7 pages.
Supplementary European Search Report for European Application No. 16150606.8, dated May 11, 2016, 9 pages.
Office Action for U.S. Appl. No. 13/963,872, dated Apr. 21, 2015, 17 pages.
Supplementary Partial European Search Report for European Application No. 13796692.5, dated Feb. 23, 2016, 8 pages.
Office Action for U.S. Appl. No. 13/797,821, dated Apr. 23, 2014, 17 pages.
International Search Report and Written Opinion for International Application No. PCT/US2013/043536, dated Dec. 20, 2013, 15 pages.
International Preliminary Report on Patentability for International Application No. PCT/US2013/043536, dated Dec. 2, 2014, 11 pages.
Office Action for U.S. Appl. No. 14/554,894, dated Apr. 21, 2016, 15 pages.
International Search Report and Written Opinion for International Application No. PCT/US2014/046416, dated Dec. 10, 2014, 10 pages.
International Search Report and Written Opinion for International Application No. PCT/US2014/052400, dated Feb. 6, 2015, 10 pages.
International Search Report and Written Opinion for International Application No. PCT/US2015/044196, dated Nov. 3, 2015, 10 pages.
A Phase 1, Safety, Tolerability and Pharmacokinetic Profile of Intravitreous Injections of E10030 (Anti-PDGF Pegylated Aptamer) in Subjects With Neovascular Age-Related Macular Degeneration, First Received on Dec. 4, 2007, ClinicalTrials.gov [online], [Retrieved on Jan. 18, 2012]. Retrieved from the Internet: <URL: http://clinicaltrials.gov/ct2/show/NCT00569140>, 5 pages.
A Safety and Efficacy Study of E10030 (Anti-PDGF Pegylated Aptamer) Plus Lucentis for Neovascular Age-Related Macular Degeneration, First Received on Mar. 12, 2010, ClinicalTrials.gov [online], [Retrieved on Jan. 18, 2012]. Retrieved from the Internet: <URL: http://clinicaltrials.gov/show/NCT01089517>, 6 pages.
Abrams, T. J. et al., "SU11248 inhibits KIT and platelet-derived growth factor receptor β in preclinical models of human small cell lung cancer," Molecular Cancer Therapeutics, 2(5):471-478 (2003).
Abramsson, A. et al., "Analysis of mural cell recruitment to tumor vessels," Circulation, 105:112-117 (2002).
Adamis, A. P. et al., "Inhibition of vascular endothelial growth factor prevents retinal ischemia-associated iris neovascularization in a nonhuman primate," Arch. Ophthalmol., 114:66-71 (1996).

Adamis, A. P. et al., "The role of vascular endothelial growth factor in ocular health and disease," Retina, 25:111-118 (2005).
Akiyama, H. et al., "Intraocular injection of an aptamer that binds PDGF-B: a potential treatment for proliferative retinopathies," Journal of Cellular Physiology, 207:407-412 (2006).
Amano, S. et al., "Requirement for vascular endothelial growth factor in wound- and inflammation related corneal neovascularization," Invest. Ophthalmol. Vis. Sci., 39:18-22 (1998).
Andrae, J. et al., "Role of platelet-derived growth factors in physiology and medicine," Genes & Development, 22(10):1276-1312 (2008).
Arakelyan, L. et al., "A computer algorithm describing the process of vessel formation and maturation, and its use for predicting the effects of anti-angiogenic and anti-maturation therapy on vascular tumor growth," Angiogenesis, 5(3):203-214 (2002).
Avastin (Bevacizumab), Labeling Text, Genentech, Inc. (Feb. 26, 2004), 27 pages.
Balasubramaniam, V. et al., "Role of platelet-derived growth factor in vascular remodeling during pulmonary hypertension in the ovine fetus," Am J Physiol Lung Cell Mol Physiol., 284(5):L826-L833 (2003).
Battegay, E. J., "Angiogenesis: mechanistic insights, neovascular diseases, and therapeutic prospects," J. Mol. Med., 73:333-346 (1995).
Benelli, U. et al., "Trapidil inhibits endothelial cell proliferation and angiogenesis in the chick chorioallantoic membrane and in the rat cornea," Journal of Ocular Pharmacology and Therapeutics, 11(2):157-166 (1995).
Benjamin, L. E. et al, "A plasticity window for blood vessel remodelling is defined by pericyte coverage of the preformed endothelial network and is regulated by PDGF-B and VEGF," Development, 125(9):1591-1598 (1998).
Benjamin, L. E. et al., "Selective ablation of immature blood vessels in established human tumors follows vascular endothelial growth factor withdrawal," J. Clin Invest., 103:159-165 (1999).
Bergers, G. et al., "Benefits of targeting both pericytes and endothelial cells in the tumor vasculature with kinase inhibitors," Journal of Clinical Investigation, 111(9):1287-1295 (2003).
Bergers, G. et al., "Tumorigenesis and the angiogenic switch," Nature Reviews Cancer, 3:401-410 (Jun. 2003).
Biesecker, G. et al., "Derivation of RNA aptamer inhibitors of human complement C5," Immunopharmacology, 42(1-3):219-230 (1999).
Biswas, P. et al., "Comparative role of intravitreal ranibizumab versus bevacizumab in choroidal neovascular membrane in age-related macular degeneration," Indian J. Opthalmol., 59(3):191-196 (2011).
Bloch, S. B. et al., "Subfoveal fibrosis in eyes with neovascular age-related macular degeneration treated with intravitreal ranibizumab," Am. J. Ophthalmol., 156:116-124 (2013).
Boyer, D. S., "Combined Inhibition of Platelet Derived (PDGF) and Vascular Endothelial (VEGF) Growth Factors for the Treatment of Neovascular Age-Related Macular Degeneration (NV-AMD)—Results of a Phase 1 Study," [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-...>.
Boyer, D. S., A phase 2b study of Fovista, a platelet derived growth factor (PDGF) inhibitor in combination with a vascular endothelial growth factor (VEGF) inhibitor for neovascular age-related macular degeneratoin (AMD), ARVO 2013 Annual Meeting Abstracts, 280 AMD and Drugs, 618-620 Paper Session, Program No. 2175 (May 6, 2013), 1 page.
Bradley, J. et al., "Combination therapy for the treatment of ocular neovascularization," Angiogenesis, 10(2):141-148 (2007).
Brody, E. N. et al., "Aptamers as therapeutic and diagnostic agents," Reviews in Molecular Biotechnology, 74(1):5-13 (2000).
Brown, D. M. et al., "Ranibizumab versus Verteporfin for Neovascular Age-Related Macular Degeneration," The New England Journal of Medicine, 355(14):1432-1444 (2006).
Brown, L. F. et al., "Vascular permeability factor/vascular endothelial growth factor: a multifunctional angiogenic cytokine," EXS. 79:233-69 (1997).

(56) References Cited

OTHER PUBLICATIONS

Brown, E. B. et al., "In vivo measurement of gene expression, angiogenesis and physiological function in tumors using multiphoton laser scanning microscopy," Nat. Med., 7:864-868 (2001).

Burcovich, B. et al., "Branched polyethylene glycol (bPEG) conjugated antisense oligonucleotides," Nucleosides and Nucleotides, 17(9-11):1567-1570 (1998).

Burke, D. H. et al., "Recombination, RNA evolution, and bifunctional RNA molecules isolated through chimeric SELEX," RNA, 4(9): 1165-1175 (1998).

Campochiaro, P. A., "Retinal and choroidal neovascularization," Journal of Cellular Physiology, 184(3):301-310 (2000).

Campochiaro, P. A. et al., "The pathogenesis of choroidal neovascularization in patients with age-related macular degeneration," Molecular Vision, 5:34-38 (1999).

Campochiaro, P. A., "Pathogenic mechanisms in proliferative vitreoretinopathy," Archives of Ophthalmology, 115(2):237-241 (1997).

Cao, R. et al., "Angiogenesis stimulated by PDGF-CC, a novel member in the PDGF family, involves activation of PDGFR-αα and -αβ receptors," FASEB J, 16(12): 1575-1583 (2002).

Cao, R. et al., "VEGFR1-mediated pericyte ablation links VEGF and PlGF to cancer-associated retinopathy," PNAS, 107(2):856-861 (2010).

Carmeliet, P., "Angiogenesis in health and disease," Nature Medicine, 9(6):653-660 (2003).

Carmeliet, P. et al., "Review Article: Angiogenesis in cancer and other diseases," Nature, 407:249-257 (2000).

Carmeliet, P. et al., "Molecular mechanisms and clinical applications of angiogenesis," Nature, 473(7347):298-307 (2011).

Castellon, R. et al., "Effects of angiogenic growth factor combinations on retinal endothelial cells," Exp. Eye Res., 74(4):523-535 (2002).

Cerchia, L. et al., "Nucleic acid aptamers in cancer medicine," FEBS Letters, 528(1-3):12-16 (2002).

Chalam, K. V. et al., "Anti platelet derived growth factor antibody inhibits retinal pigment epithelial cell induced collagen contraction," IOVS, 39(4):S864 (1998).

Chaudhary, V. et al., "The effect of triamcinolone acetonide as an adjunctive treatment to verteporfin therapy in neovascular age-related macular degeneration: A prospective, randomized, placebo controlled pilot clinical trial," Invest. Ophthalmol. Vis. Sci., 46:E-Abstract 2308 (2005).

Chekenya, M. et al., "The glial precursor proteoglycan, NG2, is expressed on tumour neovasculature by vascular pericytes in human malignant brain tumours," Neuropathol. Appl. Neurobiol., 28:367-380 (2002).

Cochran, J. R. et al., "Domain-level antibody epitope mapping through yeast surface display of epidermal growth factor receptor fragments," Journal of Immunological Methods, 287:147-158 (2004).

Cogburn, L. A. et al, "Growth, metabolic and endocrine responses of broiler cockerels given a daily subcutaneous injection of natural or biosynthetic chicken growth hormone," The Journal of Nutrition, 119(8):1213-1222 (1989).

Cousins, S. W. et al., Patterns of CNV Fluorescein and Indocyanine Green Angiographic Regression Responses After Anti-VEGF Monotherapy or Anti-VEGF Plus Anti-PDGF Combotherapy, [online], Presentation Abstract, May 4, 2009, 2 pages. [Retrieved from the Internet on Mar. 26, 2009.] URL: <http://arvo.abstractsonline.com/Plan/AbstractPrintView.aspx?mID=2281&sKey=f6e4ae6c-...>.

Cullinan-Bove, K. et al., "Vascular endothelial growth factor/Vascular permeability factor expression in the rat uterus: rapid stimulation by estrogen correlates with estrogen-induced increases in uterine capillary permeability and growth," Endocrinology, 133(2):829-837 (1993).

Daniel, E. et al., "Risk of scar in the comparison of age-related macular degeneration treatments trials," Ophthalmology, pp. 1-11 (2013).

Darland, D. C. et al., "Pericyte production of cell-associated VEGF is differentiation-dependent and is associated with endothelial survival," Dev. Biol., 264:275-288 (2003).

Darland, D. C. et al., "Blood vessel maturation: vascular development comes of age," J. Clin. Invest., 103:157-158 (1999).

Database Biosis DN PREV200300143652 & ARVO Annual Meeting Abstract Search and Program Planner, 2002, vol. 2002, pp. Abstract No. 1931, 2 pages.

Davies, D. R. et al., "Unique motifs and hydrophobic interactions shape the binding of modified DNA ligands to protein targets," PNAS, 109(49):19971-19976 (2012).

Davuluri, G. et al., "Activated VEGF receptor shed into the vitreous in eyes with wet AMD: a new class of biomarkers in the vitreous with potential for predicting the treatment timing and monitoring response," Arch. Ophthalmol., 127(5):613-621 (2009).

Dixon, J. A. et al., "VEGF Trap-Eye for the treatment of neovascular age-related macular degeneration," Expert Opinion Investig. Drugs., 18(10):1573-1580 (2009).

Do, D. V. et al.,"An exploratory study of the safety, tolerability and bioactivity of a single intravitreal injection of vascular endothelial growth factor Trap-Eye in patients with diabetic macular oedema," British Journal of Ophthalmology, 93(2):144-149 (2009).

Do, D. V. et al., "Neovascular Age-Related Macular Degeneration," FocalPoints, Clinical Modules for Ophthalmologists, vol. XXVIII, No. 12 (Module 3 of 3), pp. 1-14 (2010).

Dong, A. et al., "Antagonism of PDGF-BB suppresses subretinal neovascularization and enhances the effects of blocking VEGF-A," Angiogenesis, 17(3):553-562 (2013).

Doggrell, S. A., "Pegaptanib: the first antiangiogenic agent approved for neovascular macular degeneration," Expert Opinion Pharmacotherapy, 6(8):1421-1423 (2005).

Drolet et al., "Pharmacokinetics and safety of an anti-vascular endothelial growth factor aptamer (NX1838) following injection into the vitreous humor of rhesus monkeys," Pharm. Res., 17(12):1503-1510 (2000).

Dugel, P. U., "Anti-PDGF combination therapy in neovascular age-related macular degeneration: Results of a phase 2b study," Retina Today, pp. 65-67 and 71 (Mar. 2013).

Dugel, P. U., "Anti-PDGF therapy offers new approach to AMD treatment," Retina Times (2012), 8 pages.

Ebos, J. M. L. et al., "Imatinib mesylate (STI-571) reduces Bcr-Abl-mediated vascular endothelial growth factor secretion in chronic myelogenous leukemia," Molecular Cancer Research, 1(2):89-95 (2002).

Enge, M. et al., "Endothelium-specific platelet-derived growth factor-B ablation mimics diabetic retinopathy," The EMBO Journal, 21(16):4307-4316 (2002).

Erber, R. et al., "Combined inhibition of VEGF- and PDGF-signaling enforces tumor vessel regression by interfering with pericyte-mediated endothelial cell survival mechanisms," The FASEB Journal, 18(2):338-340 (2004).

Ergun, E. et al., "Photodynamic therapy with verteporfin and intravitreal triamcinolone acetonide in the treatment of neovascular age-related macular degeneration," Am. J. Ophthalmol., 142:10-16 (2006).

Everett, R., "Aptamers in Age Related Macular Degeneration: Above and Beyond Anti-VEGF," AAPS Presentation, Jun. 23, 2009, 2 pages.

Everett, R., "E10030, A Pegylated Aptamer Targeting Pericytes: Therapeutic Application for Age-Related Macular Degeneration (AMD)," DIA Presentation, Sep. 23, 2008, 25 pages.

Eyetech Study Group: Preclinical and phase 1A clinical evaluation of an anti-VEGF pegylated aptamer (Eye001) for the treatment of exudative age-related macular degeneration, Retina, 22:143-152 (2002).

Eylea (Aflibercept) Injection, Highlights of Prescribing Information, Regeneron Pharmaceuticals, Inc. (Nov. 18, 2011), 15 pages.

Falcon, B. L. et al., "Aptamers Specifically Targeting PDGF-B Decrease Blood Vessels and Pericytes in Tumors," Presented at the FASEB Experimental Biology, San Diego, CA (2005).

(56) References Cited

OTHER PUBLICATIONS

Falk, M. K. et al., "Four-year treatment results of neovascular age-related macular degeneration with ranibizumab and causes for discontinuation of treatment," Am. J. Ophthalmol., 155(1):89-95.e3 (2013).
Fan, T-P. D. et al., "Controlling the vasculature: angiogenesis, anti-angiogenesis and vascular targeting of gene therapy," Trends Pharmacol. Sci., 16(2):57-66 (1995).
Ferrara, N., "Vascular endothelial growth factor: basic science and clinical progress," Endocr. Rev., 25:581-611 (2004).
Ferris, F. L. et al., "Age-related macular degeneration and blindness due to neovascular maculopathy," Arch. Ophthalmol., 102:1640-1642 (1984).
Floege, J. et al., "Novel approach to specific growth factor inhibition in vivo. Antagonism of platelet-derived growth factor in glomerulonephritis by aptamers," Am J Pathol., 154(1):169-179 (1999).
Folkman, J., "Angiogenesis in cancer, vascular, rheumatoid and other disease," Nature Medicine, 1(1):27-31 (1995).
Foss, A. J. E. et al., "Microvessel count predicts survival in uveal melanoma", Cancer Research, 56(13):2900-2903 (1996).
Friedlander, M., "Fibrosis and diseases of the eye," Journal of Clinical Investigation, 117(3):576-586 (2007).
Fukumura, D. et al., "Tumor induction of VEGF promoter activity in stromal cells," Cell, 94:715-725 (1998).
Gee, M. S. et al., "Tumor vessel development and maturation impose limits on the effectiveness of anti-vascular therapy," Am. J. Pathol., 162:183-193 (2003).
George, D., "Platelet-derived growth factor receptors: a therapeutic target in solid tumors," Seminars in Oncology, 28(5):27-33 (2001).
Gomi, F. et al., "Pharmacological therapy for age-related macular degeneration," Ophthalmology, 46(12):1709-1716 (2004).
Gragoudas, E. S. et al., "Pegaptanib for neovascular age-related macular degeneration," N. Engl. J. Med., 351:2805-2816 (2004).
Green, L. S. et al., "Nuclease-resistant nucleic acid ligands to vascular permeability factor/vascular endothelial growth factor," Chemistry & Biology, 2(10):683-695 (1995).
Greenberg, J. I. et al., "A role for VEGF as a negative regulator of pericyte function and vessel maturation," Nature, 456(7223):809-813 (2008).
Guyer, D. R. et al, "Preclinical and phase 1A clinical evaluation of an anti-VEGF pegylated aptamer (Eye001) for the treatment of exudative age-related macular degeneration," Retina, 22(2):143-152 (2002).
Harris, J. M. et al., "Effect of pegylation on pharmaceuticals," Nature Reviews, 2:214-221 (2003).
Heier, J. S. et al., "Intravitreal aflibercept (VEGF Trap-Eye) in wet age-related macular degeneration," Ophthalmology, 119(12):2537-2548 (2012).
Hellstrom, M. et al., "Role of PDGF-B and PDGFR-beta in recruitment of vascular smooth muscle cells and pericytes during embryonic blood vessel formation in the mouse," Development, 126:3047-3055 (1999).
Hellstrom, M. et al., "Lack of pericytes leads to endothelial hyperplasia and abnormal vascular morphogenesis," J. Cell. Biol., 153:543-553 (2001).
Ishida, S. et al., "VEGF164-mediated inflammation is required for pathological, but not physiological, ischemia-induced retinal neovascularization," J. Exp. Med., 198:483-489 (2003).
Jain, R. K., "Molecular regulation of vessel maturation," Nature Medicine, 9(6):685-693 (2003).
Jain, R. K. et al., "What brings pericytes to tumor vessels?", The Journal of Clinical Investigation, 112(8):1134-1136 (2003).
Jo, N. et al., "Inhibition of platelet-derived growth factor B signaling enhances the efficacy of anti-vascular endothelial growth factor therapy in multiple models of ocular neovascularization," American Journal of Pathology, 168(6):2036-2053 (2006).
Joussen, A. M. et al., "VEGF-dependent conjunctivalization of the corneal surface," Invest. Ophthalmol. Vis. Sci., 44:117-123 (2003).

Kaempf, S. et al., "Effects of bevacizumab (Avastin) on retinal cells in organotypic culture," Invest. Ophthalmol. Vis. Sci., 49(7):3164-3171 (2008).
Kaiser, P. K. et al., "Integrin peptide therapy: The first wet AMD experience," ARVO 2013 Annual Meeting Abstracts, 280 AMD and Drugs, 618-620 Paper Session, Program No. 2177 (May 6, 2013), 2 pages.
Kawada, H. et al., "Multifunctional antioxidants protect cells from mitochondrial dysfunction and ABETA neurotoxicity," ARVO 2013 Annual Meeting Abstracts, 280 AMD and Drugs, 618-620 Paper Session, Program No. 2176 (May 6, 2013), 1 page.
Ke, L. D. et al., "A novel approach to glioma gene therapy: down-regulation of the vascular endothelial growth factor in glioma cells using ribozymes," International Journal of Oncology, 12(6):1391-1396 (1998).
Keane, P. A. et al., "Evaluation of age-related macular degeneration with optical coherence tomography," Survey of Ophthalmology, 57(5):389-414 (2012).
Kinose, F. et al, "Inhibition of retinal and choroidal neovascularization by a novel KDR kinase inhibitor," Molecular Vision, 11:366-373 (2005).
Klein, R. et al., The relationship of age-related maculopathy, cataract, and glaucoma to visual acuity, Invest. Ophthalmol. Vis. Sci., 36:182-191 (1995).
Kliffen, M. et al., "Increased expression of angiogenic growth factors in age-related maculopathy," British Journal of Ophthalmology, 81:154-162 (1997).
Kohno, R. et al., "Histopathology of neovascular tissue from eyes with proliferative diabetic retinopathy after intravitreal bevacizumab injection," Am. J. Ophthalmol., 150(2):223-229.e1 (2010).
Kompella, U. B. et al., "Drug Product Development for the Back of the Eye," Advances in the Pharmaceutical Sciences Series, AAPSPress, Springer (2011), 595 pages.
Koyama, N. et al., "Migratory and proliferative effect of platelet-derived growth factor in rabbit retinal endothelial cells: evidence of an autocrine pathway of platelet-derived growth factor," J. Cell Physiol., 158(1):1-6 (1994).
Krzystolik, M. G. et al., "Prevention of experimental choroidal neovascularization with intravitreal anti-vascular endothelial growth factor antibody fragment," Arch. Ophthalmol., 120:338-346 (2002).
Kudelka, M. R. et al., "Emergence of dual VEGF and PDGF antagonists in the treatment of exudative age-related macular degeneration," Expert Rev. Ophthalmology, 8(5):475-484 (2013).
Kwak, N. et al., "VEGF is major stimulator in model of choroidal neovascularization," Invest. Ophthalmol. Vis. Sci., 41:3158-3164 (2000).
Lai, C-M et al., "Inhibition of corneal neovascularization by recombinant adenovirus mediated antisense VEGF RNA," Exp. Eye Res., 75(6):625-634 (2002).
Lei, H. et al., "Recent developments in our understanding of how platelet-derived growth factor (PDGF) and its receptors contribute to proliferative vitreoretinopathy," Exp. Eye Res., 90(3):376-381 (2010).
Leppanen, O. et al., "Intimal hyperplasia recurs after removal of PDGF-AB and -BB inhibition in the rat carotid artery injury model," Arterioscler Thromb Vase Biol., 20(11):e89-e95 (2000).
Li, V. W. et al., "Microvessel count and cerebrospinal fluid basic fibroblast growth factor in children with brain tumours," The Lancet, 344(8915):82-86 (1994).
Li, Q. et al., "IKK2 inhibition using TPCA-1/PLGA microspheres attenuates the laser induced choroidal neovascularization," ARVO 2013 Annual Meeting Abstracts, 280 AMD and Drugs, 618-620 Paper Session, Program No. 2179 (May 6, 2013), 2 pages.
Lindahl, P. et al., "Pericyte loss and microaneurysm formation in PDGF-B-deficient mice," Science, 277:242-245 (1997).
Lindheimer, M. D., "Unraveling the mysteries of preeclampsia," Am. J. Obstet. Gynecol., 193:3-4 (2005).
Livak, K. J. et al., "Analysis of relative gene expression data using real-time quantitative PCR and the 2(-Delta Delta C(T)) Method," Methods, 25:402-408 (2001).
Lu, C. et al., "Targeting pericytes with a PDGF-B aptamer in human ovarian carcinoma models," Cancer Biol. Ther., 9(3):176-182 (2010).

(56) References Cited

OTHER PUBLICATIONS

Lucentis (ranibizumab injection), Highlights of Prescribing Information, Genentech, Inc. (Jun. 30, 2006), 7 pages.
Magno, A. L. et al., "Development and implementation of an ELISA to detect 'anti-Ranibizumab' immunity in age-related macular degeneration patients," ARVO 2013 Annual Meeting Abstracts, 280 AMD and Drugs, 618-620 Paper Session, Program No. 2181 (May 6, 2013), 2 pages.
Martin, D. F. et al., "Ranibizumab and bevacizumab for treatment of neovascular age-related macular degeneration: two-year results: Comparison of Age-related Macular Degeneration Treatments Trials (CATT) Research Group," Ophthalmology, 119(7):1388-1398 (2012).
Capelle, M. A. H. et al., "High throughput screening of protein formulation stability: Practical considerations," European Journal of Pharmaceutics and Biopharmaceutics, 65:131-148 (2007).
Mayer, G. et al., "Aptamers in Research and Drug Development," Biodrugs, 18(6):351-359 (2004).
McCarty, M. F. et al, "Promises and pitfalls of anti-angiogenic therapy in clinical trials," Trends in Molecular Medicine, 9(2):53-58 (2003).
Monfardini, C. et al., "A Branched Monomethoxypoly(ethylene glycol) for Protein Modification," Bioconjugate Chem., 6:62-69 (1995).
Morescalchi, F. et al., "Proliferative Vitreoretinopathy after Eye Injuries: An Overexpression of Growth Factors and Cytokines Leading to a Retinal Keloid," Mediators of Inflammation, vol. 2013, Article ID 269787, Aug. 26, 2013, 12 pages.
Mori, K. et al., "Inhibition of choroidal neovascularization by intravenous injection of adenoviral vectors expressing secretable endostatin," Am. J. Pathol., 159:313-320 (2001).
Morikawa, S. et al., "Abnormalities in pericytes on blood vessels and endothelial sprouts in tumors," Am. J. Pathol., 160:985-1000 (2002).
Moromizato, Y. et al., "CD18 and ICAM-1-dependent corneal neovascularization and inflammation alter limbal injury," Am. J. Pathol., 157:1277-1281 (2000).
Nakabayashi, M. et al., "HGF/NK4 inhibited VEGF-induced angiogenesis in in vitro cultured endothelial cells and in vivo rabbit model," Diabetologia, 46(1):115-123 (2003).
Ng, E. W. M. et al., "Anti-VEGF aptamer (pegaptanib) therapy for ocular vascular disease," Ann. NY Acad. Sci., 1082:151-171 (2006).
Ng, E. W. M. et al., "Pegaptanib, a targeted anit-VEGF aptamer for ocular vascular disease," Nat. Rev. Drug. Discov., 5(2):123-132 (2006).
Ngo, J. T. et al., "Computational complexity, protein structure prediction, and the levinthal paradox," In the Protein Folding Problem and Tertiary Structure Prediction, Merz, Jr. et al. (eds.), Brikhauser Boston, pp. 492-495 (1994).
Nguyen, Q. D. et al., "A phase I trial of an IV-administered vascular endothelial growth factor trap for treatment in patients with choroidal neovascularization due to age-related macular degeneration," Ophthalmology, 113(9):1522-1532 (2006).
Ostendorf, T. et al., "Specific antagonism of PDGF prevents renal scarring in experimental glomerulonephritis," J. Am. Soc. Nephrol., 12(5):909-918 (2001).
Ozaki, H. et al., "Blockade of vascular endothelial cell growth factor receptor signaling is sufficient to completely prevent retinal neovascularization," American Journal of Pathology, 156(2):697-707 (2000).
Patel, S., "New innovations in AMD technology may be promising," Retina Today, pp. 24-25 (2008).
Patel, S., "Combination therapy for age-related macular degeneration," Retina, 29:S45-S48 (2009).
Pechan, P. et al., "Novel anti-VEGF chimeric molecules delivered by AAV vectors for inhibition of retinal neovascularization," Gene Therapy, 16(1):10-16 (2009).
Pegaptanib: New drug. In macular degeneration: too many risks for too little benefit, Prescire Int., 15(84):127-129 (abstract, no authors listed) (2006).
Petrukhin, K., "New therapeutic targets in atrophic age-related macular degeneration," Expert Opin. Ther. Targets, 11(5):625-630 (2007).
"Particulate matter in ophthalmic solutions," USP789, U.S. Pharmacopeia, Pharmacopeial Forum, 28(5):1496 (Sep. 2002), 3 pages.
"Particulate matter in injections," USP788, Revision Bulletin, The United States Pharmacopeial Convention (Oct. 1, 2011), 3 pages.
Pierce, E. A. et al., "Vascular endothelial growth factor/vascular permeability factor expression in a mouse model of retinal neovascularization," Proc Natl Acad Sci. USA, 92(3):905-909 (1995).
Pietras, K. et al., "Inhibition of PDGF receptor signaling in tumor stroma enhances antitumor effect of chemotherapy," Cancer Research, 62(19):5476-5484 (2002).
Pietras, K. et al, "Inhibition of platelet-derived growth factor receptors reduces interstitial hypertension and increases transcapillary transport in tumors," Cancer Research, 61(7):2929-2934 (2001).
Pontes de Carvalho, R. A. et al., "Delivery from episcleral exoplants," Invest Ophthalmol Vis Sci., 47(1):4532-4539 (2006).
Rao, L. J. et al., "Neovascular AMD: Treatment beyond anti-VEGF," Mar. 1, 2014, 10 pages.
Rasmussen, A. et al., "A 4-year longitudinal study of 555 patients treated with ranibizumab for neovascular age-related macular degeneration," Ophthalmology, 120(12):2630-2636 (2013).
Riemer, A. B. et al., "Matching of trastuzumab (Herceptin) epitope mimics onto the surface of Her-2/neu-a new method of epitope definition," Molecular Immunology, 42(9):1121-1124 (2005).
Rimmele, M., "Nucleic acid aptamers as tools and drugs: recent developments," ChemBioChem., 4:963-971 (2003).
Ritter, M. R. et al., "Three-dimensional in vivo imaging of the mouse intraocular vasculature during development and disease," Invest Ophthalmol Vis Sci., 46(9):3021-3026 (2005).
Robinson, G. S. et al., "Oligodeoxynucleotides inhibit retinal neovascularization in a murine model of proliferative retinopathy," Proc. Natl. Acad. Sci. USA, 93:4851-4856 (1996).
Rodrigues, E. B. et al., "Therapeutic monoclonal antibodies in ophthalmology," Progress in Retinal and Eye Research, 28(2):117-144 (2009).
Rofagha, S. et al., "Seven-year outcomes in ranibizumab-treated patients in anchor, marina, and horizon," Ophthalmology, pp. 1-8 (2013).
Rofagha, S. et al., "Seven-year outcomes in ranibizumab-treated patients in Anchor, Marina, and Horizon: a multicenter cohort study (Seven-Up)," Ophthalmology, 120(11):2292-2299 (2013).
Rosenfeld, P. J. et al., "Ranibizumab for Neovascular Age-Related Macular Degeneration," The New England Journal of Medicine, 355(14):1419-1431 (2006).
Ruckman, J. et al., "2'-Fluoropyrimidine RNA-based aptamers to the 165-amino acid form of vascular endothelial growth factor (VEGF$_{165}$). Inhibition of receptor binding and VEGF-induced vascular permeability through interactions requiring the exon 7-encoded domain," J. Biol. Chem., 273(32):20556-20567 (1998).
Ruhrberg, C. et al., "Spatially restricted patterning cues provided by heparin-binding VEGF—A control blood vessel branching morphogenesis," Genes Dev., 16:2684-2698 (2002).
Ruiz-Ederra, J. et al., "Aquaporin-1 independent microvessel proliferation in a neonatal mouse model of oxygen-induced retinopathy," Invest Ophthalmol Vis Sci., 48(10):4802-4810 (2007).
Saishin, Y. et al, "The kinase inhibitor PKC412 suppresses epiretinal membrane formation and retinal detachment in mice with proliferative retinopathies," Invest Ophthalmol Vis Sci, 44(8):3656-3662 (2003).
Sano, H. et aI., "Study on PDGF receptor β pathway in glomerular formation in neonate mice," Annals New York Acad. Sci., 947:303-305 (2001).
Schmidt-Erfurth, U. et al., "Intravitreal aflibercept injection for neovascular age-related macular degeneration," Ophthalmology, p. 1-9 (2013).
Schraermeyer, U. et al., "Effects of intravitreally injected ranibizumab and aflibercept on retina and choroid of monkey eyes," ARVO 2013 Annual Meeting Abstracts, 280 AMD and Drugs, 618-620 Paper Session, Program No. 2180 (May 6, 2013), 1 page.

(56) References Cited

OTHER PUBLICATIONS

Semeraro, F. et al., "Aflibercept in wetAMD: specific role and optimal use," Drug Design, Development and Therapy, 7:711-722 (2013).
Senger, D. R. et al., "Vascular permeability factor (VPF, VEGF) in tumor biology," Cancer and Metastasis Reviews, 12(3-4):303-324 (1993).
Sennino, B. et al., "Sequential loss of tumor vessel pericytes and endothelial cells after inhibition of platelet-derived growth factor B by selective aptamer AX102," Cancer Research, 67(15):7358-7367 (2007).
Shami, M. et al., "The use of antisense DNA against the receptors for platelet derived growth factor, fibroblast growth factor, and phosphoinositol-3-kinase in vitro and to block PVR in a rabbit model using human pigment epithelial cells," IOVS, 39(4):S580 (1998).
Shawver, L. K. et al., "Smart drugs: tyrosine kinase inhibitors in cancer therapy," Cancer Cell, 1(2):117-123 (2002).
Silva, R. et al., "The Secure study: long-term safety of ranibizumab 0.5 mg in neovascular age-related macular degeneration," Ophthalmology, 120(1):130-139 (2013).
Sims, D. E., "The pericyte—a review," Tissue Cell, 18:153-174 (1986).
Singer, M. A. et al., "Horizon: An open-label extension trial of ranibizumab for choroidal neovascularization secondary to age-related macular degeneration," Ophthalmology, pp. 1-9 (2012).
Singh, R. et al., "Topical Pazopanib for the treatment of previously untreated choroidal neovascularization due to age-related macular degeneration," ARVO 2013 Annual Meeting Abstracts, 280 AMD and Drugs, 618-620 Paper Session, Program No. 2178 (May 6, 2013), 1 page.
Skolnick, J. et al, "From genes to protein structure and function: novel applications of computational approaches in the genomic era," Trends in Biotechnol., 18(1):34-39 (2000).
SOMAmer Technical Note, SomaLogic, Inc., SSM017, Rev. 1, DCN 13-084 (2013), 2 pages.
Sorbera, L. A. et al., "Pegaptanib Sodium," Drugs of the Future, 27(9):841 (2002).
Stahl, A. et al., "The mouse retina as an angiogenesis model," Invest. Ophthalmol. Vis. Sci., 51(6):2813-2826 (2010).
Steffensmeier, A. C. G. et al, "Vitreous injections of pegaptanib sodium triggering allergic reactions," Am J Ophthalmology, 143(3):512-513 (2007).
Stewart, M. W., "PDGF: Ophthalmology's next great target," Expert Review of Ophthalmology, 8(6):527-537 (2013).
Stockmann, C. et al., "Deletion of vascular endothelial growth factor in myeloid cells accelerates tumorigenesis," Nature, 456:814-819 (2008).
Stryer et al., In: Biochemistry, pp. 86 and 92, Third Edition, W. H. Freeman and Company, New York (1988).
Submacular Surgery Trials Research Group, "Histopathologic and ultrastructural features of surgically excised subfoveal choroidal neovascular lesions. Submacular Surgery Trials Report No. 7," Arch. Ophthalmol., 123:914-921 (2005).
Sundberg, C. et al., "Stable expression of angiopoietin-1 and other markers by cultured pericytes: phenotypic similarities to a subpopulation of cells in maturing vessels during later stages of angiogenesis in vivo," Lab. Invest., 82:387-401 (2002).
Tahiri-Alaoui, A. et al., "High affinity nucleic acid aptamers for streptavidin incorporated into bi-specific capture ligands," Nucleic Acids Research, 30(10):e45 (2002), 9 pages.
Thomas, K. A., "Vascular endothelial growth factor, a potent and selective angiogenic agent," The Journal of Biological Chemistry, 271(2):603-606 (1996).
Tobe, T. et al., "Targeted disruption of the FGF2 gene does not prevent choroidal neovascularization in a murine model," American Journal of Pathology, 153(5):1641-1646 (1998).
Tol, J. et al., "Chemotherapy, bevacizumab, and cetuximab in metastatic colorectal cancer," New England Journal of Medicine, 360(6):563-572 (2009).
Uemura, A. et al., "Recombinant angiopoietin-1 restores higher-order architecture of growing blood vessels in mice in the absence of mural cells," J. Clin. Invest., 110:1619-1628 (2002).
Wallace, R. B. et al, "Oligonucleotide probes for the screening of recombinant DNA libraries," Methods in Enzymology, 152:432-439 (1987).
Warne, N. W., "Development of high concentration protein biopharmaceuticals: The use of platform approaches in formulation development," European Journal of Pharmaceutics and Biopharmaceutics, 78(2):208-212(2011).
Weidner, N. et al., "Tumor angiogenesis correlates with metastasis in invasive prostate carcinoma", Am J Pathol., 143(2):401-409 (1993).
Weidner, N. et al., "Tumor angiogenesis: a new significant and independent prognostic indicator in early-stage breast carcinoma," J. Natl Cancer Inst., 84(24):1875-1887 (1992).
West, H. et al., "Stabilization of the retinal vascular network by reciprocal feedback between blood vessels and astrocytes," Development, 132:1855-1862 (2005).
Wilkinson-Berka, J. L. et al., "Inhibition of platelet-derived growth factor promotes pericyte loss and angiogenesis in ischemic retinopathy," American Journal of Pathology, 164(4):1263-1273 (2004).
Willett, C. G. et al., "Direct evidence that the VEGF-specific antibody bevacizumab has antivascular effects in human rectal cancer," Nat Med., 10(2):145-147 (2004).
Winkler, F. et al., "Kinetics of vascular normalization by VEGFR2 blockade governs brain tumor response to radiation: Role of oxygenation, angiopoietin-1, and matrix metalloproteinases," Cancer Cell, 6(6):553-563 (2004).
Witte, L. et al., "Monoclonal antibodies targeting the VEGF receptor-2 (Flk1/KDR) as an anti-angiogenic therapeutic strategy," Cancer and Metastasis Reviews, 17:155-161 (1998).
Wood, J. M., "Inhibition of vascular endothelial growth factor (VEGF) as a novel approach for cancer therapy," Medicina (Buenos Aires), 60(2):41-47 (2000).
Writing Committee for the UK Age-Related Macular Degeneration EMR Users Group, The neovascular age-related macular degeneration database: multicenter study of 92 976 ranibizumab injections: report 1: visual acuity, Ophthalmology, 121(5):1092-1101 (2014).
Yoshida, S. et al., "Involvement of interleukin-8, vascular endothelial growth factor, and basic fibroblast growth factor in tumor necrosis factor alpha-dependent angiogenesis," Molecular and Cellular Biology, 17(7):4015-4023 (1997).
Younes, C. K. et al, "Labelled oligonucleotides as radiopharmaceuticals: pitfalls, problems and perspectives," Current Pharmaceutical Design, 8(16):1451-1466 (2002).
Yu, L. et al., "Interaction between bevacizumab and murine VEGF-A: a reassessment," Investigative Ophthalmology & Visual Science, 49(2):522-527 (2008).
Zhang, M. et al., "Recombinant anti-vascular endothelial growth factor fusion protein efficiently suppresses choridal neovasularization in monkeys," Molecular Vision, 14:37-49 (2008).
Zhang, L. et al., "Vector-based RNAi, a novel tool for isoform-specific knock-down of VEGF and anti-angiogenesis gene therapy of cancer," Biochemical and Biophysical Research Communications, 303(4):1169-1178 (2003).
Zhang, W. et al., "A monoclonal antibody that blocks VEGF binding to VEGFR2 (KDR/Flk-1) inhibits vascular expression of Flk-1 and tumor growth in an orthotopic human breast cancer model," Angiogenesis, 5(1-2):35-44 (2002).
Zhang, Y. et al., "Tissue oxygen levels control astrocyte movement and differentiation in developing retina," Brain Res. Dev. Brain Res., 118:135-145 (1999).
Zhu, Z. et al., "Inhibition of Tumor Growth and Metastasis by Targeting Tumor-Associated Angiogenesis with Antagonists to the Receptors of Vascular Endothelial Growth Factor," Investigational New Drugs, 17:195-212 (1999).
Zondor, S. D. et al., "Bevacizumab: an angiogenesis inhibitor with efficacy in colorectal and other malignancies," Ann. Pharmacother., 38:1258-1264 (2004).
Folkman, J. et al., "Angiogenesis," Minireview, The Journal of Biological Chemistry, 267(16): 10931-10934 (Jun. 1992).

(56) References Cited

OTHER PUBLICATIONS

Supplementary European Search Report issued in corresponding European Application No. 14823713.4 dated Feb. 13, 2017.
Office Action issued in corresponding Japanese Application No. 2016-525821 dated Mar. 29, 2018.
Office Action issued in corresponding Chinese Application No. 201480039516.5 dated Apr. 9, 2018.
Examination Report issued in corresponding Australian Application No. 2014286996 dated Mar. 12, 2019.
Office Action issued in corresponding Japanese Application No. 2018-124310 dated May 9, 2019.
A Phase I Study of ARC1905 (Anti-C5 Aptamer) in Subjects with Dry Age-Related Macular Degeneration, NCT00950638, published on clinicaltrials. gov URL://clinicaltrials.gov/ct2/show/study/NCT00950638_andhttps://clinicaltrials.gov/ct2/history/NCT009540638?, Last retrieved Feb. 24, 2021, first published on Aug. 3, 2009 according to ClinicalTrials.Gov.
Anonymous: "History of Changes for Study: NCT00950638," Sep. 4, 2012 (Sep. 4, 2012), XP055668318, Retrieved from the Internet: URL:https://clinicaltrials.gov/ct2/history/NCT00950638?V5=View#StudyPageTop [retrieved on Feb. 23, 2020].
R.S. Apte, "Targeting Complement Factor 5 in Neovascular Age-Related Macular Degeneration (NV-AMD)—Results of a Phase I Study," Apr. 1, 2009 (Apr. 1, 2009), XP55668326, *Investigative Ophthalmology & Visual*, vol. 50, No. 13, Retrieved from the Internet: URL:https://iovs.arvojournals.org/article.aspx?articleid=2367197 [retrieved on Feb. 13, 2020].
Matt Hasson: Combined complement inhibitor, anti-VEGF may be safe for treatment of wet AMD, Jul. 10, 2010 (Jul. 10, 2010), XP55668328, Retrieved from the Internet: URL:https://www.healio.com/ophthalmology/retina-vitreous/news/print/ocular-surgery-news/{9e987b6a-24c1-4099-8d8b-0b3e32266956}/combined-complement-inhibitor-anti-vegf-may-be-safe-for-treatment-of-wet-amd [retrieved on Feb. 13, 2020].
Ella Leung et al: "Update on current and future novel therapies for dry age-related macular degeneration," Expert Review of Clinical Pharmacology Nov. 1, 2014 Expert Reviews Ltd. GBR, vol. 6, No. 5, Sep. 10, 2013 (Sep. 10, 2013), pp. 565-579, XP055331168, UK.
Ni Zhang et al: "Emerging Pharmacologic Therapies for Wet Age-Related Macular Degeneration," Ophthalmologica, Karger, Basel, CH, vol. 223, No. 6, Jan. 1, 2009 (Jan. 1, 2009), pp. 401-410, XP009164747.
"An Animal Model of Age-related Macular Degeneration in Senescent Macrophage Recruitment Impaired Mice," Investigative Ophthalmology & Visual Science, May 2001, vol. 44, Issue 13, No. 1718.
European Search Report dated Feb. 21, 2020 in corresponding European Application No. EP 19192389.5.
Examination Report No. 1 dated Mar. 1, 2021 issued in corresponding Australian Application No. 2020201824.
First Examiner's Report dated Sep. 24, 2020 issued in corresponding Canadian Application No. 2,915,255.
First Office Action dated Dec. 28, 2020 in corresponding Chinese Application No. 201910114391.2.
Retina Today, pp. 52-55, Oct. 2010.
Office Action dated Dec. 22, 2021 issued in corresponding Korean Patent Application No. 10-2016-7003175.

\* cited by examiner

FIG. 1A
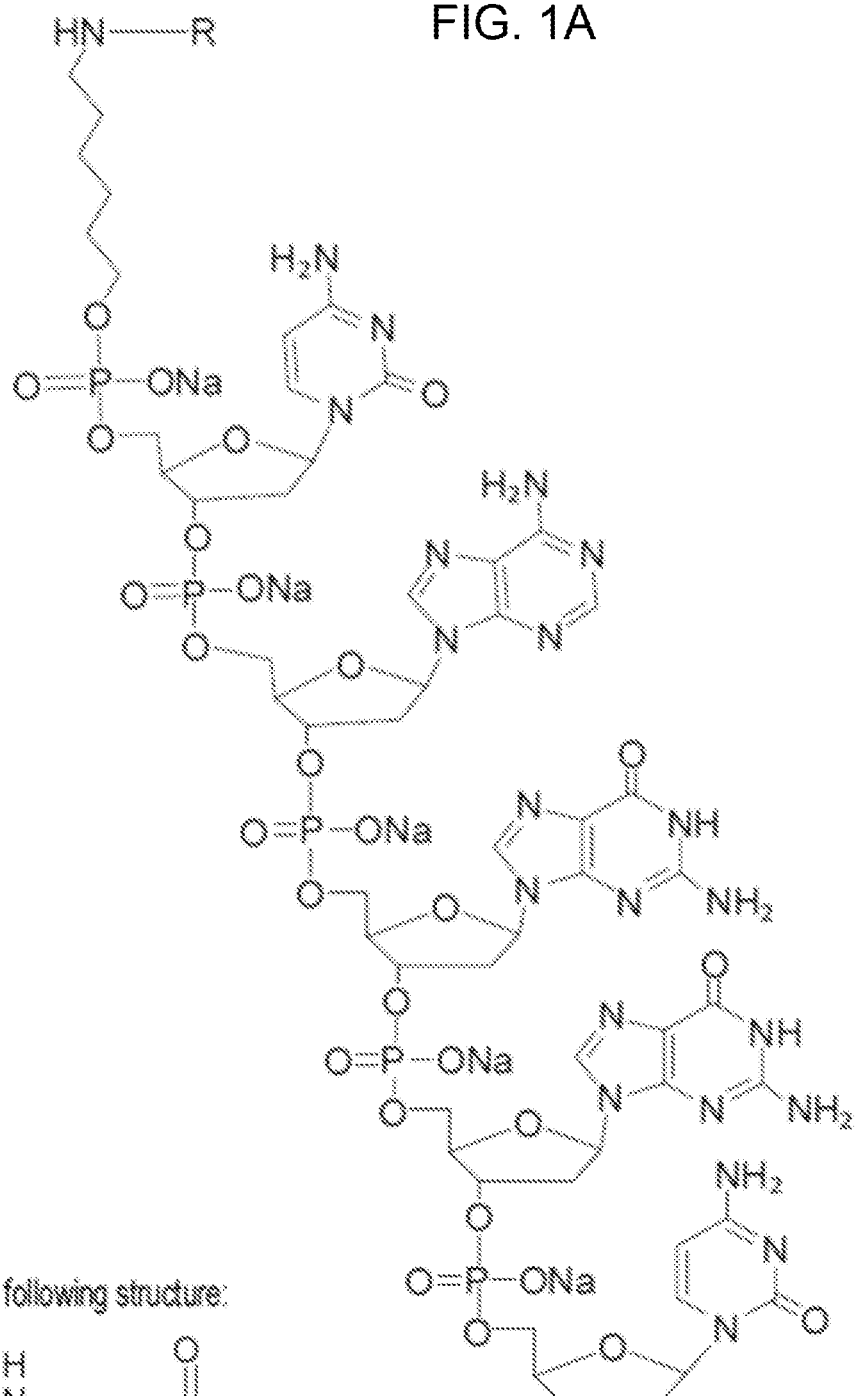
where R represents the following structure:
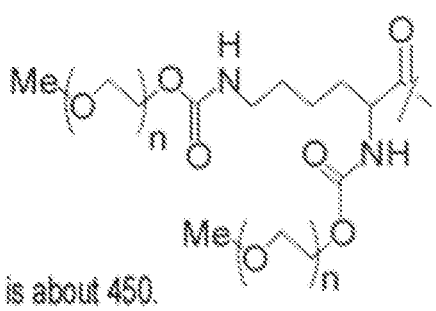
and n is about 450.

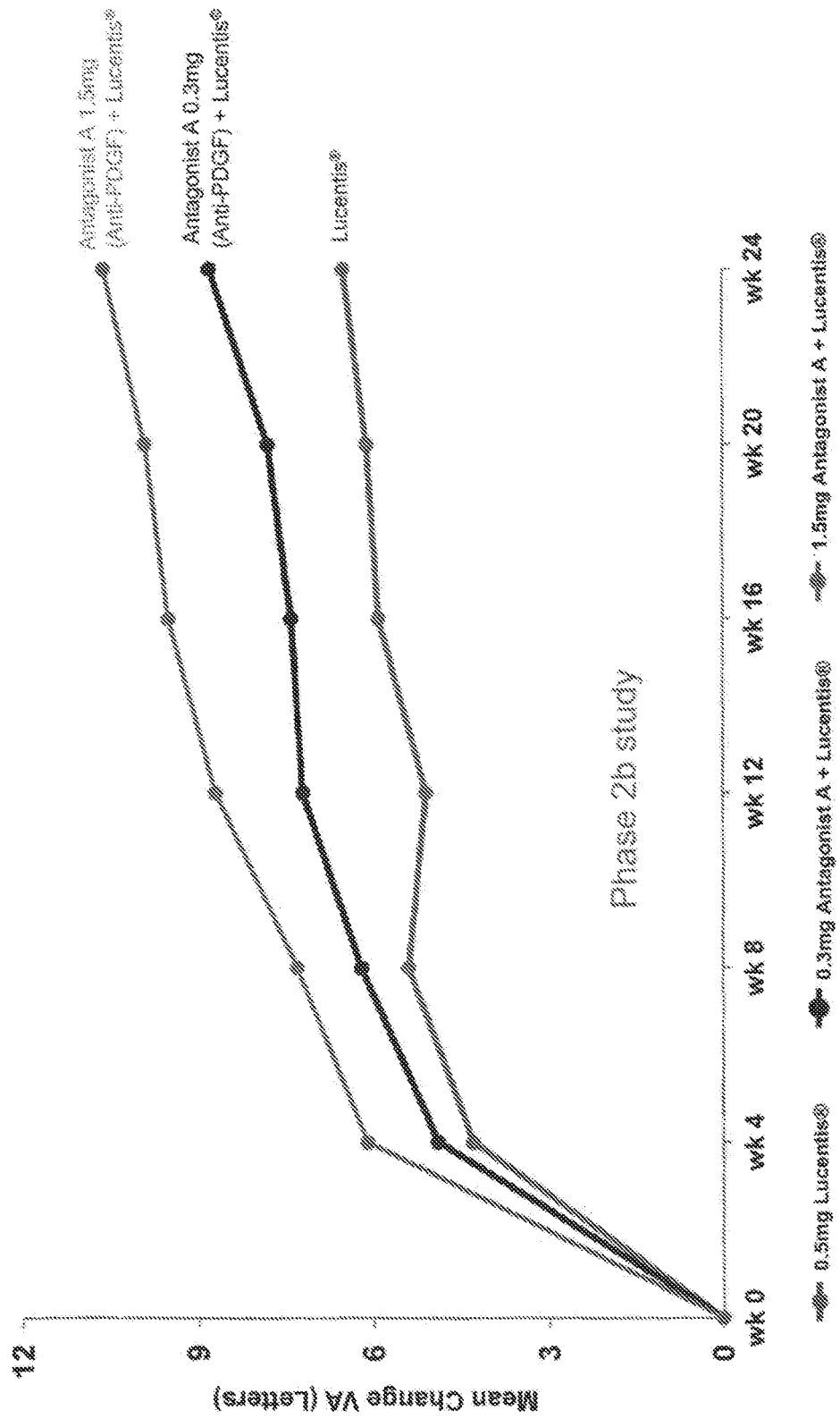

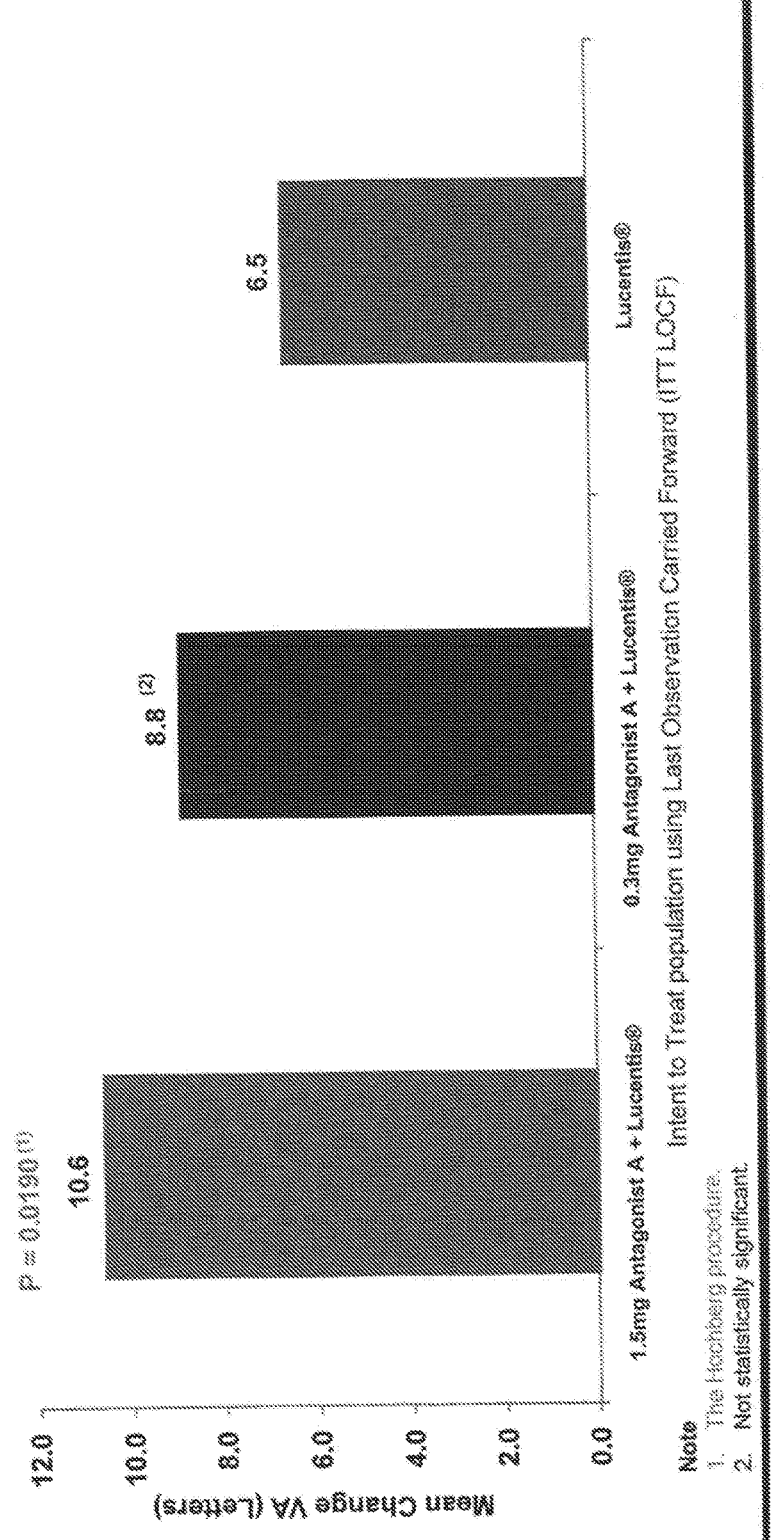

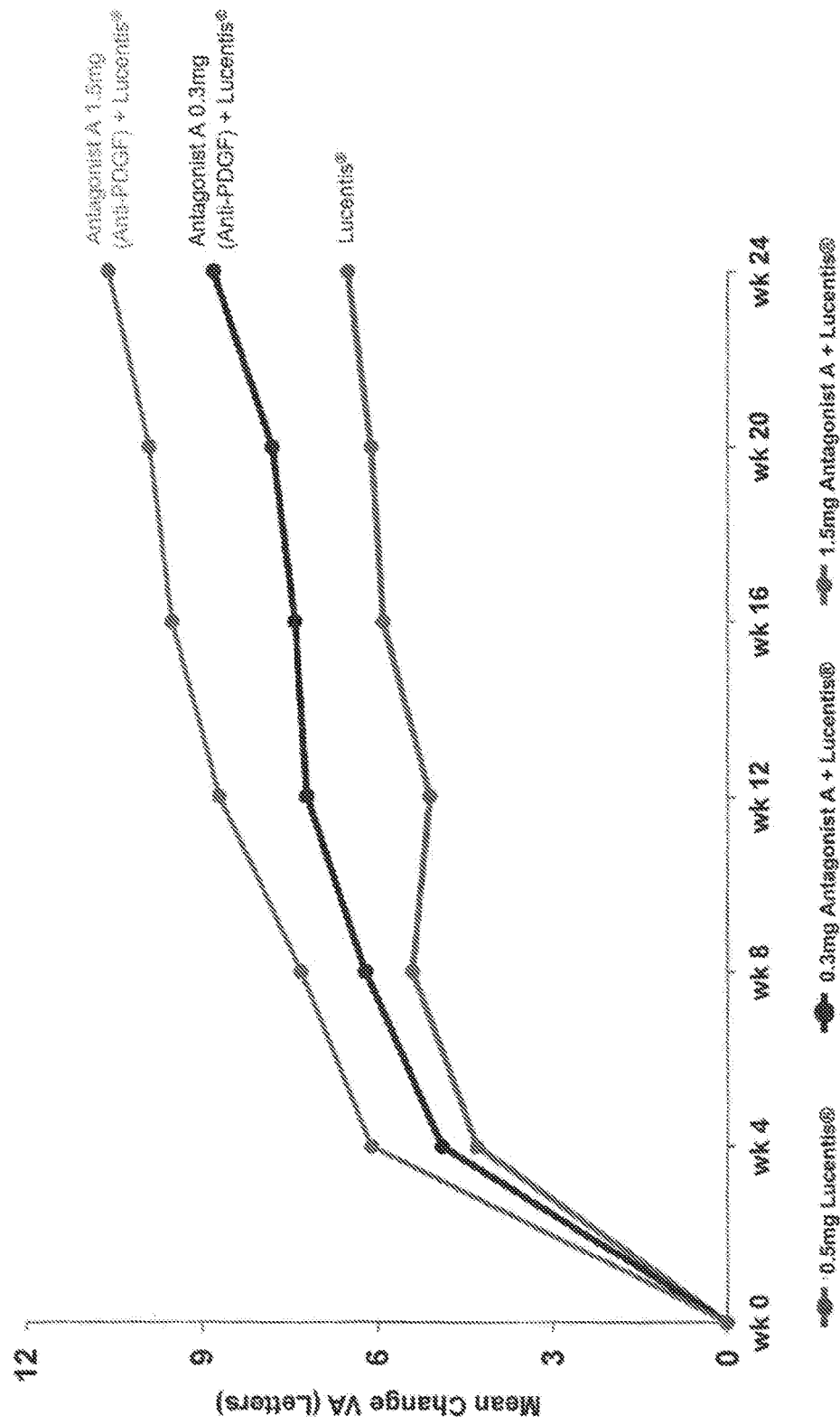

Increased Efficacy Independent of Baseline Lesion Size

Increased Efficacy Independent of Baseline Vision

Antagonist A Combination Group had Greater Proportion of Patients With Significant Visual Gain Antagonist A Combination Group had Fewer Patients With Visual Loss Improved Final Visual Acuity Outcome in Antagonist A 1.5 mg
Combination Arm: 20/40 or Better Improved Final Visual Acuity Outcome in Antagonist A 1.5 mg Combination Arm: 20/25 or Better Improved Final Visual Acuity Outcome in Antagonist A 1.5 mg Combination Arm: 20/200 or Worse Increased Reduction in CNV Size in Small and Large Baseline CNV in Antaognist A (1.5 mg) Combination Arm Increased Reduction in CNV Size in Small and Large Baseline CNV in Antaognist A (1.5 mg) Combination Arm

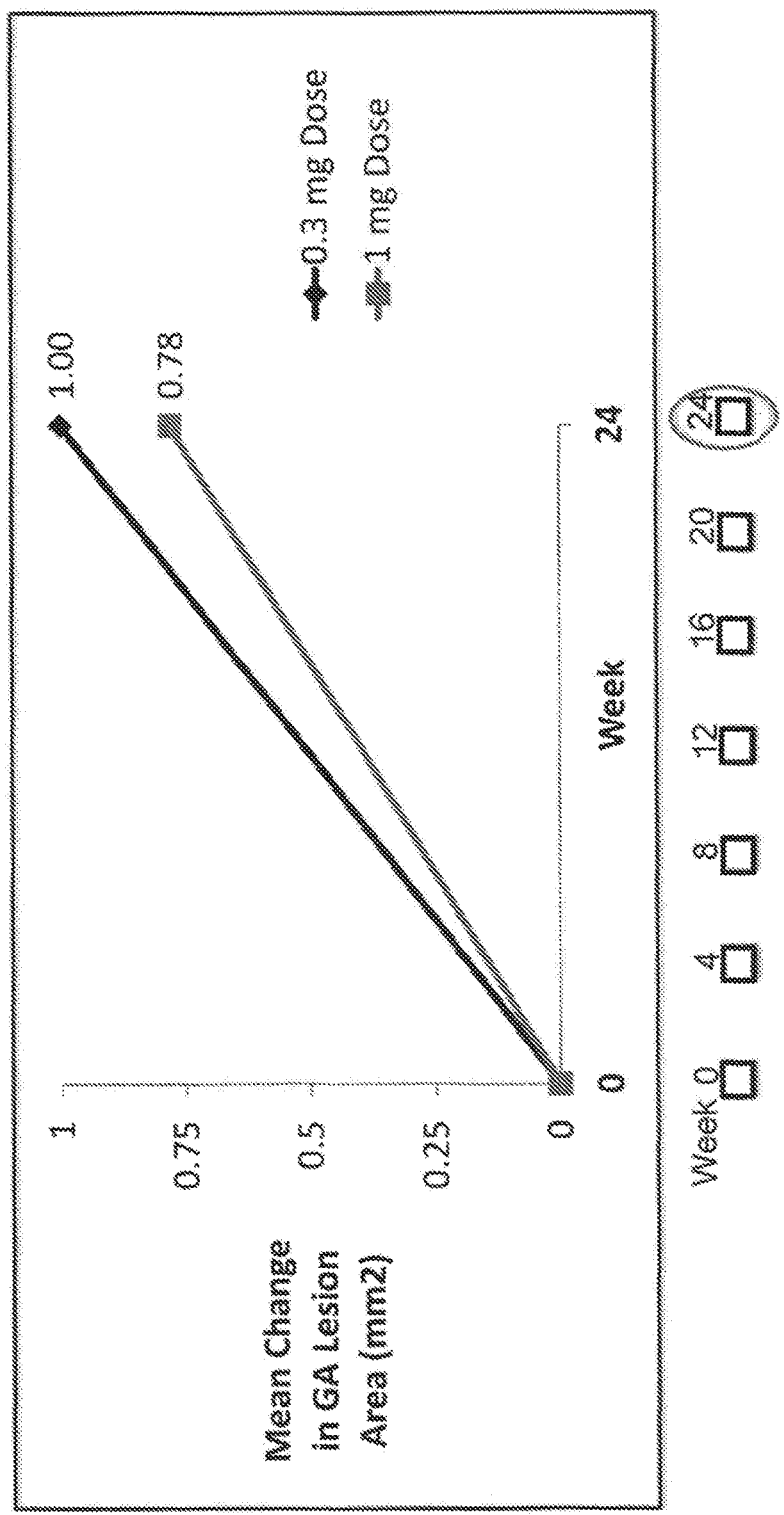

METHODS FOR TREATING OR PREVENTING OPHTHALMOLOGICAL CONDITIONS

CROSS REFERENCE TO RELATED APPLICATIONS

This application is a continuation of U.S. application Ser. No. 16/434,018, filed Jun. 19, 2019, which is a continuation of U.S. application Ser. No. 14/329,702, filed Jul. 11, 20114, which claims the benefit of U.S. provisional application nos. 61/845,938, filed Jul. 12, 2013, 61/845,935, filed Jul. 12, 2013, 61/845,936, filed Jul. 12, 2013, 61/866,502, filed Aug. 15, 2013, 61/866,503, filed Aug. 15, 2013, 61/866,507, filed Aug. 15, 2013, 61/911,854, filed Dec. 4, 2013, 61/911,860, filed Dec. 4, 2013, 61/911,894, filed Dec. 4, 2013, 61/926,812, filed Jan. 13, 2014, 61/926,825, filed Jan. 13, 2014, 61/926,848, filed Jan. 13, 2014, 61/931,116, filed Jan. 24, 2014, 61/931,125, filed Jan. 24, 2014, and 61/931,135, filed Jan. 24, 2014, each of which is incorporated by reference herein in its entirety.

SEQUENCE LISTING

The Sequence Listing associated with this application is provided in text format in lieu of a paper copy, and is hereby incorporated by reference into the specification. The name of the text file containing the Sequence Listing is OPHT_012_06US_SeqList_ST25.txt. The text file is about 372 KB, was created on Jul. 10, 2014, and is being submitted electronically via EFS-Web.

FIELD OF THE INVENTION

This invention relates to methods and compositions useful for the treatment or prevention of an ophthalmological disease or disorder, comprising administration of an effective amount of Antagonist A or another pharmaceutically acceptable salt thereof.

BACKGROUND OF THE INVENTION

Various disorders of the eye are characterized, caused by, or result in choroidal, retinal or iris neovascularization or retinal edema. One of these disorders is macular degeneration. Age-related macular degeneration (AMD) is a disease that affects approximately one in ten Americans over the age of 65. One type of AMD, "wet-AMD," accounts only for approximately 10% of age-related macular degeneration cases but results in approximately 90% of cases of legal blindness from macular degeneration in the elderly. Another disorder of the eye is diabetic retinopathy. Diabetic retinopathy can affect up to 80% of all patients having diabetes for 10 years or more and is the third leading cause of adult blindness, accounting for almost 7% of blindness in the USA. Other disorders include hypertensive retinopathy, central serous chorioretinopathy, cystoid macular edema, Coats disease and ocular or adnexal neoplasms such as choroidal hemangioma, retinal pigment epithelial carcinoma, retinal vein occlusions and intraocular lymphoma.

Therefore, although advances in the understanding of the molecular events accompanying neovascularization have been made, there exists a need to utilize this understanding to develop improved methods for treating or preventing neovascular diseases disorders, including ocular neovascular diseases and disorders such as the neovascularization that occurs with AMD, diabetic retinopathy, and retinal vein occlusions.

SUMMARY OF THE INVENTION

The present invention relates to methods and compositions useful for the treatment or prevention of an ophthalmological disease or disorder.

The present invention provides a method for treating or preventing wet age-related macular degeneration (wet AMD), comprising administering to a subject in need thereof (a) Antagonist A or another pharmaceutically acceptable salt thereof and (b) an VEGF antagonist, wherein (a) and (b) are administered in an amount that is effective for treating or preventing wet AMD, and wherein the administering occurs once every month, ±about seven days, for a first administration period of at least 3 consecutive months, followed by administering (a) and (b) for a second administration period at a frequency of at least every other month ±about seven days beginning at two months ±about seven days after the day of the last month of the first administration period on which (a) and (b) are administered.

Also provided herein is a method for treating or preventing sub-retinal fibrosis, comprising administering to a subject in need thereof (a) Antagonist A or another pharmaceutically acceptable salt thereof in an amount that is effective for treating or preventing sub-retinal fibrosis.

A method for treating or preventing von Hippel-Lindau (VHL) disease, comprising administering to a subject in need thereof. Antagonist A or another pharmaceutically acceptable salt thereof in an amount that is effective for treating or preventing VHL disease is also provided herein.

BRIEF DESCRIPTION OF THE DRAWINGS

Reference is made to the following detailed description, which sets forth illustrative embodiments and the accompanying drawings of which:

FIGS. 1A-F show the chemical structure of Antagonist A, wherein the 5' end of its aptamer (SEQ ID NO: 1) is modified with $Me(OCH_2CH_2)_nOC(O)NH(CH_2)_4CH(NHC(O)O(CH_2CH_2O)_nMe)C(O)NH(CH_2)_6$—, where n is about 450. The designations ⒷⒻ indicate a continuation from a previous panel.

FIG. 2 shows a graph depicting the mean change in visual acuity in wet AMD patients in a phase 2b clinical trial, who were treated with 0.5 mg of Lucentis® alone or with 0.5 mg of Lucentis® and either 1.5 mg of Antagonist A or 0.3 mg of Antagonist A.

FIG. 3 shows a bar graph showing comparative visual-acuity benefit in wet AMD patients with treatment with 0.5 mg of Lucentis® and either 1.5 mg or 0.3 mg of Antagonist A as compared to treatment with Lucentis® monotherapy (0.5 mg).

FIG. 4 shows a graph depicting the early and sustained visual-acuity improvement over time in wet AMD patients treated with Lucentis® monotherapy (0.5 mg) or with 0.5 mg of Lucentis® and either 1.5 mg of Antagonist or 0.3 mg of Antagonist A.

FIG. 5A shows the mean change in visual acuity for patients in each of the indicated baseline lesion quartiles.

FIG. 7A shows the percentage of patients who demonstrated a visual acuity of 20/40 or better; FIG. 7B shows the percentage of patients who demonstrated a visual acuity of 20/25 or better; and FIG. 7C shows the percentage of patients who demonstrated a visual acuity of 20/200 or worse.

FIG. 8A shows the results in all patients, and FIG. 8B shows the results in patients with a visual outcome >3-lines.

FIG. 9 shows a graph depicting the mean change in geographic atrophy (GA) lesion area in dry AMD patients measured at 24 weeks in patients treated with either a 0.3 mg or 1 mg dose of ARC1905 monthly from weeks 0 to 24 in a phase 2a trial.

DETAILED DESCRIPTION OF THE INVENTION

Figure 1B:
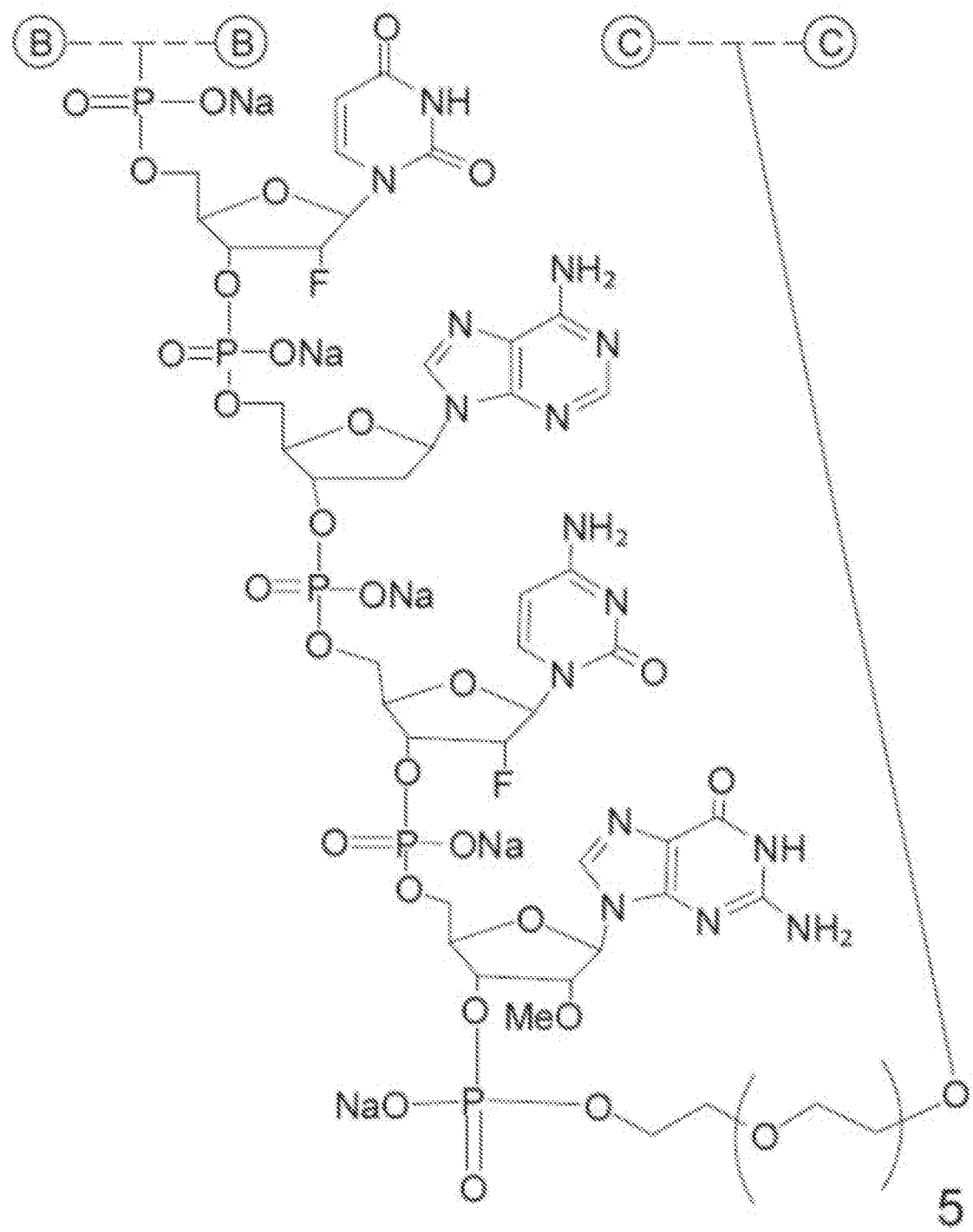
Figure 1C:
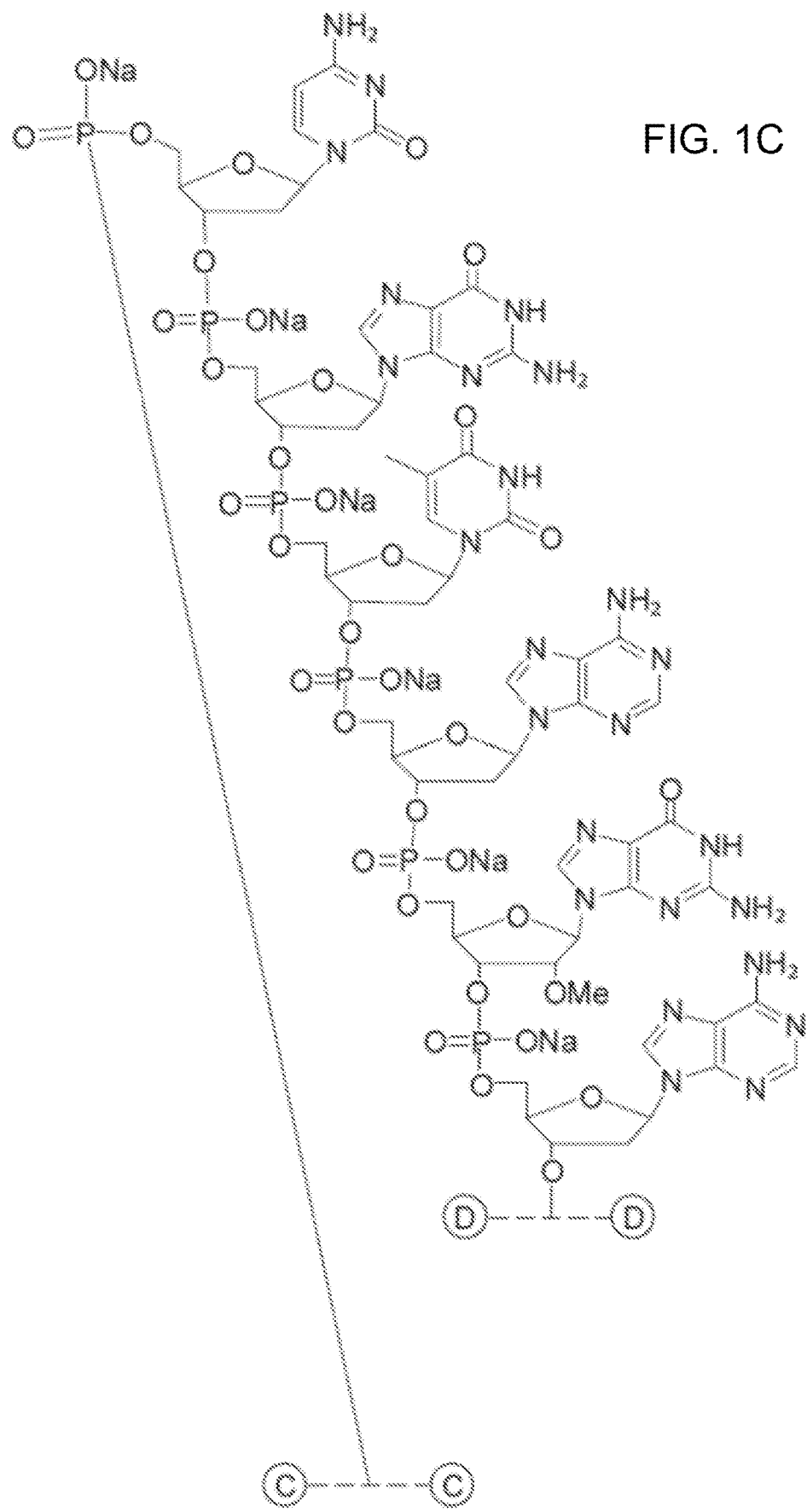
Figure 1D:
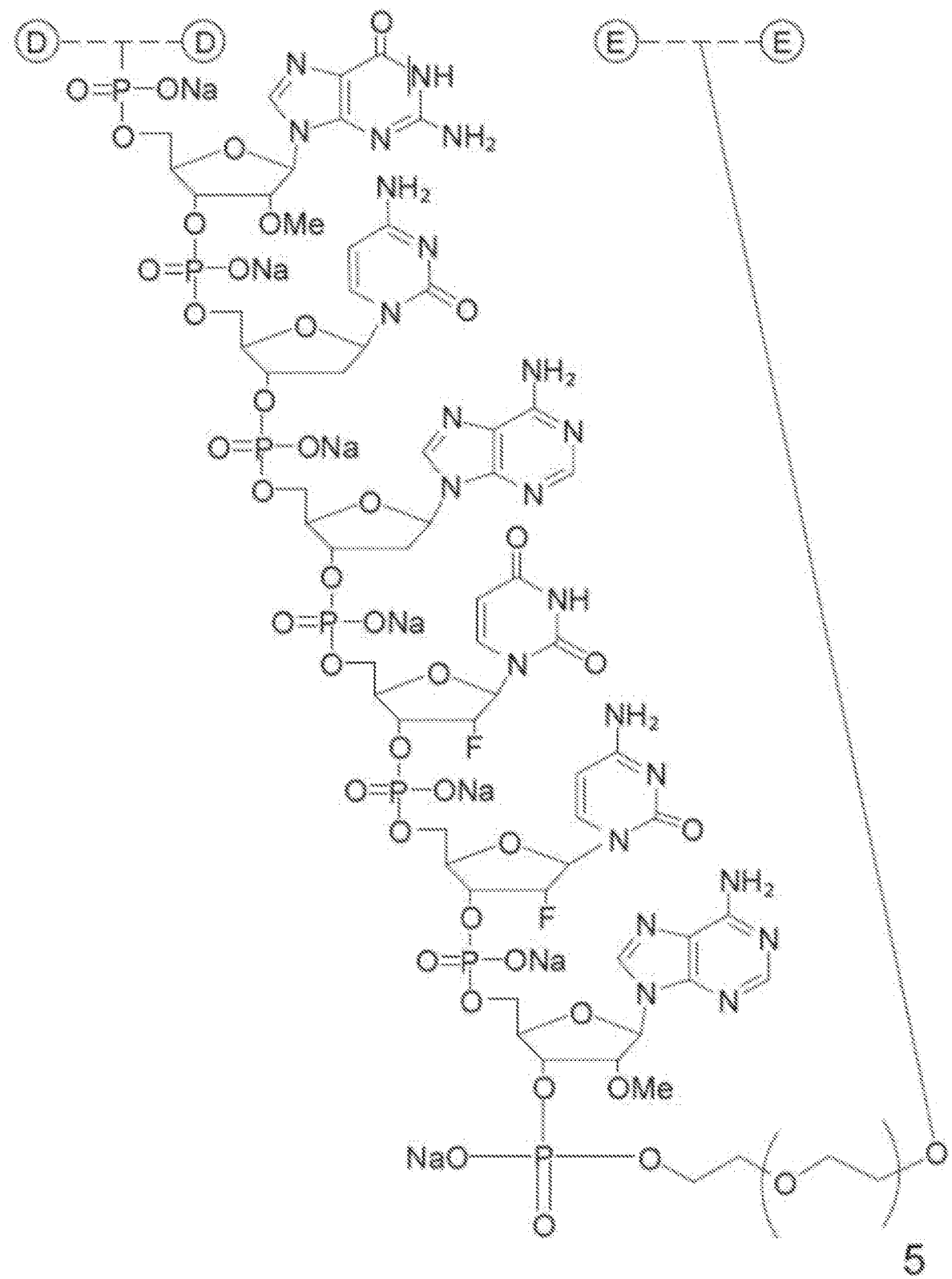
Figure 1E:
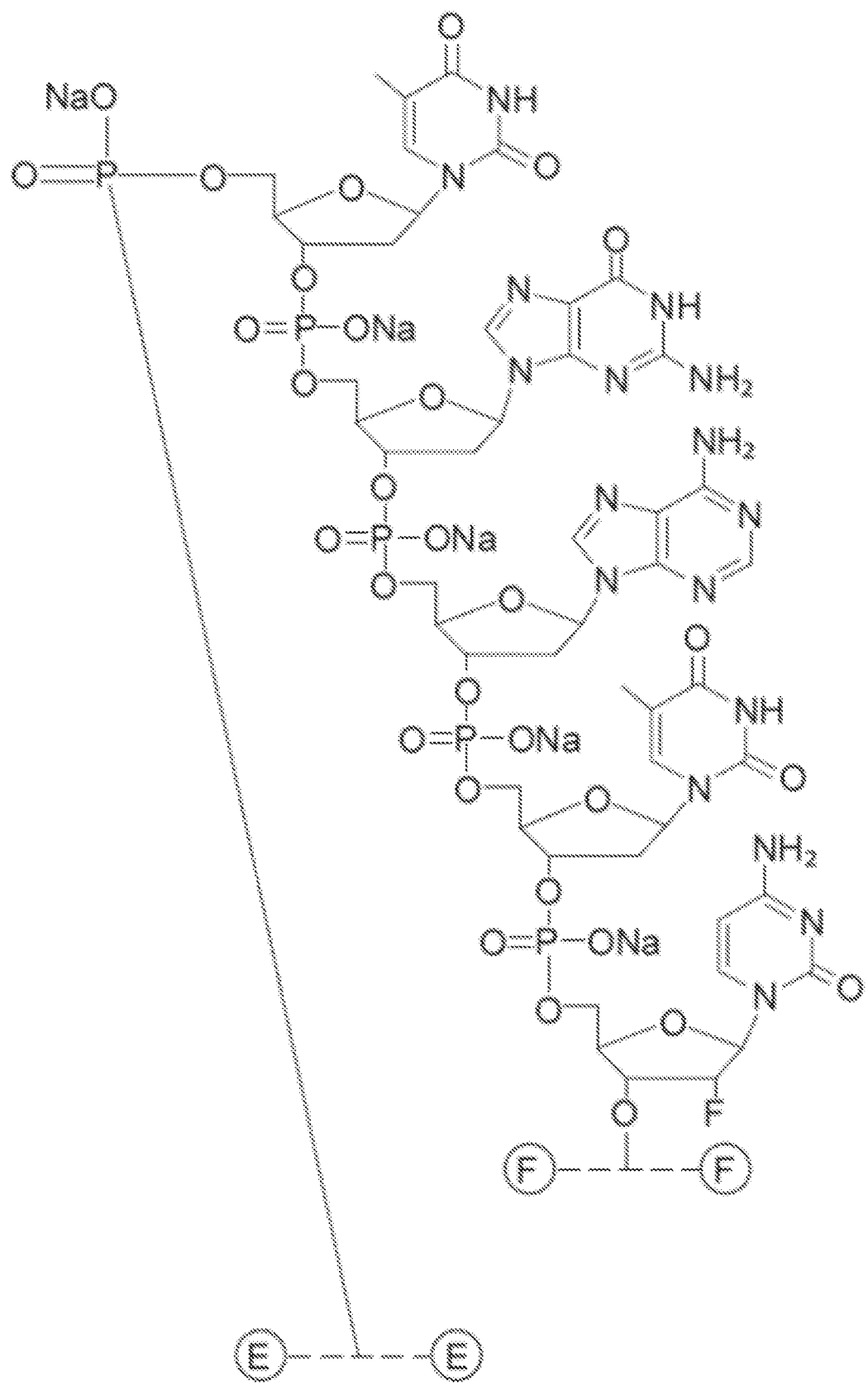
Figure 1F:
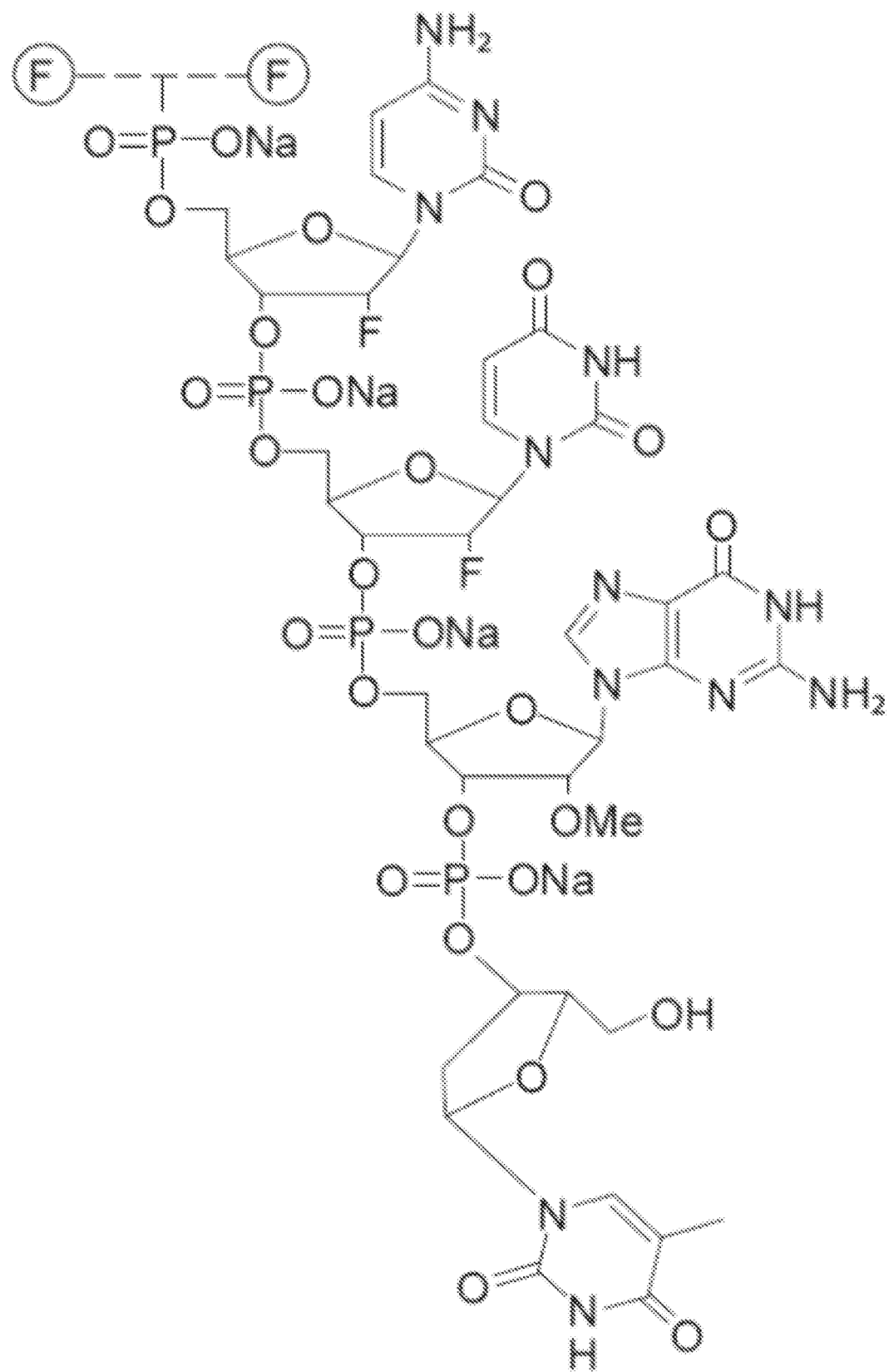

In certain aspects, the present invention provides new and improved methods and compositions for treating and preventing ophthalmological diseases and disorders, including, e.g., new uses, combination therapies, treatment and dosing regimens, and coformulations.

In one aspect, the invention provides methods for treating or preventing an ophthalmological disease or disorder, comprising administering to a subject in need thereof an effective amount of Antagonist A or another pharmaceutically acceptable salt thereof. In particular embodiments, the subject is administered Antagonist A or another pharmaceutically acceptable salt thereof and not administered an anti-C5 agent. In some embodiments, the subject is administered Antagonist A or another pharmaceutically acceptable salt thereof and not administered a VEGF antagonist.

In particular embodiments, the Antagonist A or another pharmaceutically acceptable salt thereof is administered in combination with a VEGF antagonist. In one embodiment, Antagonist A or another pharmaceutically acceptable salt thereof is administered in combination with ranibizumab, bevacizumab, aflibercept, pegaptanib sodium, or ESBA1008.

In particular embodiments, the Antagonist A or another pharmaceutically acceptable salt thereof is administered in combination with a VEGF antagonist and an anti-C5 agent. In one embodiment, Antagonist A or another pharmaceutically acceptable salt thereof is administered in combination with a VEGF antagonist (e.g., ranibizumab, bevacizumab, aflibercept, pegaptanib sodium, or ESBA1008), and ARC1905.

The invention also provides treatment regimens, including treatment and dosing regimens, related to the coadministration of Antagonist A or another pharmaceutically acceptable salt thereof and a VEGF antagonist, optionally also in combination with an anti-C5 agent.

In further embodiments, another agent (e.g., an agent that is not Antagonist A, VEGF antagonist or an anti-C5 agent) that is useful for treating or preventing an ophthalmological disease or disorder is administered. In some embodiments, the methods comprise administering one or more (e.g., two) VEGF antagonists and/or one or more (e.g., two) anti-C5 agents to the subject in need thereof.

In another aspect, the invention provides methods for treating or preventing an ophthalmological disease or disorder, comprising administering to a subject in need thereof an effective amount of an anti-C5 agent (e.g., ARC1905). In particular embodiments, the subject is not administered Antagonist A or another pharmaceutically acceptable salt thereof. In some embodiments, the subject is not administered a VEGF antagonist.

In addition, the invention provides coformulations that comprise Antagonist A or another pharmaceutically acceptable salt thereof and a VEGF antagonist. In certain embodiments, the coformulations further comprise an anti-C5 agent. In certain embodiments, the coformulations are pharmaceutically compositions comprising an effective amount of Antagonist A or another pharmaceutically acceptable salt thereof and VEGF antagonist, and a pharmaceutically acceptable carrier or vehicle. In certain embodiments, the coformulations are pharmaceutically compositions comprising an effective amount of Antagonist A or another pharmaceutically acceptable salt thereof, VEGF antagonist, and anti-C5 agent, and a pharmaceutically acceptable carrier or vehicle.

In one embodiment, the present invention provides methods for treating or preventing an ophthalmological disease or disorder, comprising administering to a subject in need thereof. Antagonist A or another pharmaceutically acceptable salt thereof and optionally a VEGF antagonist, wherein the methods further comprise performing a surgery to treat the ophthalmological disease or disorder and/or administration of an anti-C5 agent.

Definitions and Abbreviations

As used herein, the following terms and phrases shall have the meanings set forth below. Unless defined otherwise, all technical and scientific terms used herein have the same meaning as commonly understood to one of skill in the art to which this invention belongs.

The term "about" when used in connection with a referenced numeric indication means the referenced numeric indication plus or minus up to 10% of that referenced numeric indication. For example, "about 100" means from 90 to 110 and "about six" means from 5.4 to 6.6.

The term "antagonist" refers to an agent that inhibits, either partially or fully, the activity or production of a target molecule. In particular, the term "antagonist," as applied selectively herein, means an agent capable of decreasing levels of gene expression, mRNA levels, protein levels or protein activity of the target molecule. Illustrative forms of antagonists include, for example, proteins, polypeptides, peptides (such as cyclic peptides), antibodies or antibody fragments, peptide mimetics, nucleic acid molecules, antisense molecules, ribozymes, aptamers, RNAi molecules, and small organic molecules. Illustrative non-limiting mechanisms of antagonist inhibition include repression of ligand synthesis and/or stability (e.g., using, antisense, ribozymes or RNAi compositions targeting the ligand gene/nucleic acid), blocking of binding of the ligand to its cognate receptor (e.g., using anti-ligand aptamers, antibodies or a soluble, decoy cognate receptor), repression of receptor synthesis and/or stability (e.g., using, antisense, ribozymes or RNAi compositions targeting the ligand receptor gene/nucleic acid), blocking of the binding of the receptor to its cognate receptor (e.g., using receptor antibodies) and blocking of the activation of the receptor by its cognate ligand (e.g., using receptor tyrosine kinase inhibitors). In addition, the antagonist may directly or indirectly inhibit the target molecule.

The term "antibody fragment" includes a portion of an antibody that is an antigen binding fragment or single chains thereof. An antibody fragment can be a synthetically or genetically engineered polypeptide. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those in the art, and the fragments can be screened for utility in the same manner as whole antibodies.

The term "aptamer" refers to a peptide or nucleic acid that has an inhibitory effect on a target. Inhibition of the target by the aptamer can occur by binding of the target, by catalytically altering the target, by reacting with the target in a way which modifies the target or the functional activity of the target, by ionically or covalently attaching to the target as in a suicide inhibitor or by facilitating the reaction between the target and another molecule. Aptamers can be peptides, ribonucleotides, deoxyribonucleotides, other nucleic acids or a mixture of the different types of nucleic acids. Aptamers can comprise one or more modified amino acid, bases, sugars, polyethylene glycol spacers or phosphate backbone units as described in further detail herein.

A nucleotide sequence is "complementary" to another nucleotide sequence if each of the bases of the two sequences matches, i.e., are capable of forming Watson Crick base pairs. The complement of a nucleic acid strand can be the complement of a coding strand or the complement of a non-coding strand.

The phrase "conserved residue" refers to an amino acid of a group of amino acids having particular common properties. A functional way to define common properties among individual amino acids is to analyze the normalized frequencies of amino acid changes among corresponding proteins of homologous organisms. According to such analyses, groups of amino acids may be characterized where amino acids within a group exchange preferentially with each other, and therefore resemble each other most in their impact on the overall protein structure (Schulz, G. E. and R. H. Schirmer, *Principles of Protein Structure*, Springer-Verlag). Examples of amino acid groups defined in this manner include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

Members of each of the above groups are conserved residues.

The term "label" includes, but is not limited to, a radioactive isotope, a fluorophore, a chemiluminescent moiety, an enzyme, an enzyme substrate, an enzyme cofactor, an enzyme inhibitor, a dye, a metal ion, a ligand (e.g., biotin or a hapten) and the like. Examples of fluorophore labels include fluorescein, rhodamine, dansyl, umbelliferone, Texas red, luminol, NADPH, alpha-beta-galactosidase and horseradish peroxidase.

The term "nucleic acid" refers to a polynucleotide such as deoxyribonucleic acid (DNA) or ribonucleic acid (RNA). The term also includes analogs of RNA or DNA made from nucleotide analogs, and, as applicable to the embodiment being described, single (sense or antisense) and double-stranded polynucleotides, ESTs, chromosomes, cDNAs, mRNAs, and rRNAs.

The terms "RNA interference," "RNAi," "miRNA," and "siRNA" refer to any method by which expression of a gene or gene product is decreased by introducing into a target cell one or more double-stranded RNAs, which are homologous to a gene of interest (particularly to the messenger RNA of the gene of interest, e.g., PDGF or VEGF).

The term "neovascularization" refers to new blood vessel formation in abnormal tissue or in abnormal positions.

The term "angiogenesis" refers to formation of new blood vessels in normal or in abnormal tissue or positions.

The term "ophthalmological disease" includes diseases of the eye and the ocular adnexa.

The term "ocular neovascular disorder" refers to an ocular disorder characterized by neovascularization. In one embodiment, the ocular neovascular disorder is a disorder other than cancer. Examples of ocular neovascular disorders include diabetic retinopathy and age-related macular degeneration.

The term "mammal" includes a human, monkey, cow, hog, sheep, horse, dog, cat, rabbit, rat and mouse. In certain embodiments, a subject is a mammal.

The term "PDGF" refers to a platelet-derived growth factor that regulates cell growth or division. As used herein, the term "PDGF" includes the various subtypes of PDGF including PDGF-B (see SEQ ID NOS: 2 (nucleic acid) and 3 (polypeptide)), PDGF-A (see SEQ ID NOS: 4 (nucleic acid) and 5 (polypeptide), PDGF-C (see SEQ ID NOS: 6 (nucleic acid) and 7 (polypeptide)), PDGF-D, variants 1 (see SEQ ID NOS: 8 (nucleic acid) and 9 (polypeptide)) and 2 (see SEQ ID NOS: 10 (nucleic acid) and 11 (polypeptide)), and dimerized forms thereof, including PDGF-AA, PDGF-AB, PDGF-BB, PDGF-CC, and PDGF-DD. Platelet derived growth factors includes homo- or heterodimers of A-chain (PDGF-A) and B-chain (PDGF-B) that exert their action via binding to and dimerization of two related receptor tyrosine kinase platelet-derived growth factor cell surface receptors (i.e., PDGFRs), PDGFR-α (see SEQ ID NOS: 12 (nucleic acid) and 13 (polypeptide)) and PDGFR-β (see SEQ ID NOS: 14 (nucleic acid) and 15 (polypeptide)). In addition, PDGF-C and PDGF-D, two additional protease-activated ligands for the PDGFR complexes, have been identified (Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47). Due to the different ligand binding specificities of the PDGFRs, it is known that PDGFR-α/α binds PDGF-AA, PDGF-BB, PDGF-AB, and PDGF-CC; PDGFR-β/β binds PDGF-BB and PDGF-DD; whereas PDGFR-α/β binds PDGF-AB, PDGF-BB, PDGF-CC, and PDGF-DD (Betsholtz et al., (2001) *BioEssays* 23: 494-507). As used herein, the term "PDGF" also refers to those members of the class of growth factors that induce DNA synthesis and mitogenesis through the binding and activation of a PDGFR on a responsive cell type. PDGFs can effect, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; and potent vasoconstrictor activity. The term "PDGF" can be used to refer to a "PDGF" polypeptide, a "PDGF" encoding gene or nucleic acid, or a dimerized form thereof.

The term "PDGF-A" refers to an A chain polypeptide of PDGF or its corresponding encoding gene or nucleic acid.

The term "PDGF-B" refers to a B chain polypeptide of PDGF or its corresponding encoding gene or nucleic acid.

The term "PDGF-C" refers to a C chain polypeptide of PDGF or its corresponding encoding gene or nucleic acid.

The term "PDGF-D" refers to a D chain polypeptide of PDGF or its corresponding encoding gene or nucleic acid, including variants 1 and 2 of the D chain polypeptide of PDGF.

The term "PDGF-AA" refers to a dimer having two PDGF-A chain polypeptides.

The term "PDGF-AB" refers to a dimer having one PDGF-A chain polypeptide and one PDGF-B chain polypeptide.

The term "PDGF-BB" refers to a dimer having two PDGF-B chain polypeptides.

The term "PDGF-CC" refers to a dimer having two PDGF-C chain polypeptides.

The term "PDGF-DD" refers to a dimer having two PDGF-D chain polypeptides.

The term "VEGF" refers to a vascular endothelial growth factor that induces angiogenesis or an angiogenic process. As used herein, the term "VEGF" includes the various subtypes of VEGF (also known as vascular permeability factor (VPF) and VEGF-A) (see SEQ ID NOS: 16 (nucleic acid) and 17 (polypeptide)) that arise by, e.g., alternative splicing of the VEGF-A/VPF gene including $VEGF_{121}$, $VEGF_{165}$ and $VEGF_{189}$. Further, as used herein, the term "VEGF" includes VEGF-related angiogenic factors such as PIGF (placenta growth factor), VEGF-B, VEGF-C, VEGF-D and VEGF-E, which act through a cognate VEFG receptor (i.e., VEGFR) to induce angiogenesis or an angiogenic process. The term "VEGF" includes any member of the class of growth factors that binds to a VEGF receptor such as VEGFR-1 (Flt-1) (see SEQ ID NOS: 18 (nucleic acid) and 19 (polypeptide)), VEGFR-2 (KDR/Flk-1) (see SEQ ID NOS: 20 (nucleic acid) and 21 (polypeptide)), or VEGFR-3 (FLT-4). The term "VEGF" can be used to refer to a "VEGF" polypeptide or a "VEGF" encoding gene or nucleic acid.

The term "PDGF antagonist" refers to an agent that reduces, or inhibits, either partially or fully, the activity or production of a PDGF. In certain embodiments, the PDGF antagonist inhibits one or more of PDGF-A, PDGF-B, PDGF-C and PDGF-D. In certain embodiments, the PDGF antagonist inhibits one or more of PDGF-A, PDGF-B, and PDGF-C. In some embodiments, the PDGF antagonist inhibits a dimerized form of PDGF, such as PDGF-AA, PDGF-AB, PDGF-BB, PDGF-CC, and PDGF-DD. In certain embodiments, the PDGF antagonist inhibits PDGF-BB. In other embodiments, the PDGF antagonist inhibits PDGF-AB. A PDGF antagonist can directly or indirectly reduce or inhibit the activity or production of a specific PDGF such as PDGF-B. Furthermore, "PDGF antagonists" consistent with the above definition of "antagonist," include agents that act on a PDGF ligand or its cognate receptor so as to reduce or inhibit a PDGF-associated receptor signal. Examples of "PDGF antagonists" include antisense molecules, ribozymes or RNAi that target a PDGF nucleic acid; anti-PDGF aptamers, anti-PDGF antibodies to PDGF itself or its receptor, or soluble PDGF receptor decoys that prevent binding of a PDGF to its cognate receptor; antisense molecules, ribozymes or RNAi that target a cognate PDGF receptor (PDGFR) nucleic acid; anti-PDGFR aptamers or anti-PDGFR antibodies that bind to a cognate PDGFR receptor; and PDGFR tyrosine kinase inhibitors.

The term "VEGF antagonist" refers to an agent that reduces, or inhibits, either partially or fully, the activity or production of a VEGF. In certain embodiments, the VEGF antagonist inhibits one or more of VEGF-A, VEGF-B, VEGF-C and VEGF-D. A VEGF antagonist can directly or indirectly reduce or inhibit the activity or production of a specific VEGF such as $VEGF_{165}$. Furthermore, "VEGF antagonists" consistent with the above definition of "antagonist," include agents that act on either a VEGF ligand or its cognate receptor so as to reduce or inhibit a VEGF-associated receptor signal. Examples of "VEGF antagonists" include antisense molecules, ribozymes or RNAi that target a VEGF nucleic acid; anti-VEGF aptamers, anti-VEGF antibodies to VEGF itself or its receptor, or soluble VEGF receptor decoys that prevent binding of a VEGF to its cognate receptor; antisense molecules, ribozymes, or RNAi that target a cognate VEGF receptor (VEGFR) nucleic acid; anti-VEGFR aptamers or anti-VEGFR antibodies that bind to a cognate VEGFR receptor; and VEGFR tyrosine kinase inhibitors. In certain embodiments, the VEGF antagonist is a peptide, e.g., a peptide comprising three or more amino acid residues. In certain embodiments, the VEGF antagonist is a bicyclic peptide.

The term "effective amount" when used in connection with an active agent, refers to an amount of the active agent, e.g., a PDGF antagonist, a VEGF antagonist or an anti-C5 agent, alone or in combination with another active agent, that is useful to treat or prevent an ophthalmological disease or disorder. The "effective amount" can vary depending upon the mode of administration, specific locus of the ophthalmological disease or disorder, the age, body weight, and general health of the subject. The effective amount of two or more active agents is the combined amount of the active agents that is useful for treating or preventing an ophthalmological disease or disorder, even if the amount of one of the agents, in the absence of one or more of the other agents, is ineffective to treat or prevent the ophthalmological disease or disorder.

A "variant" of polypeptide X refers to a polypeptide having the amino acid sequence of polypeptide X in which is altered in one or more amino acid residues. The variant can have "conservative" changes, wherein a substituted amino acid has similar structural or chemical properties (e.g., replacement of leucine with isoleucine). More rarely, a variant can have "nonconservative" changes (e.g., replacement of glycine with tryptophan). Analogous minor variations may also include amino acid deletions or insertions, or both. Guidance in determining which amino acid residues may be substituted, inserted, or deleted without eliminating biological or immunological activity can be determined using computer programs well known in the art, for example, LASERGENE software (DNASTAR).

The term "variant," when used in the context of a polynucleotide sequence, can encompass a polynucleotide sequence related to that of gene or the coding sequence thereof. This definition also includes, for example, "allelic," "splice," "species," or "polymorphic" variants. A splice variant can have significant identity to a reference molecule, but will generally have a greater or lesser number of polynucleotides due to alternative splicing of exons during mRNA processing. The corresponding polypeptide can possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species.

The term "anti-C5 agent" refers to an agent that reduces, or inhibits, either partially or fully, the activity or production of a C5 complement protein or a variant thereof. An anti-C5 agent can directly or indirectly reduce or inhibit the activity or production of a C5 complement protein or variant thereof. An anti-C5 agent can reduce or inhibit the conversion of C5 complement protein into its component polypeptides C5a and C5b. Anti-C5 agents can also reduce or inhibit the activity or production of C5a and/or C5b. Examples of "anti-C5 agents" include antisense molecules, ribozymes or RNAi that target a C5 nucleic acid; anti-C5 aptamers including anti-C5a and anti-C5b aptamers, anti-C5 antibodies directed against C5, C5a, C5b, or C5b-9, or soluble C5 receptor decoys that prevent binding of a C5 complement protein or variant or fragment thereof (e.g., C5a or C5b) to a binding partner or receptor.

Agents Useful for Treatment or Prevention of an Opthalmological Disease or Disorder Antagonist A Antagonist A is a PEGylated, anti-PDGF aptamer having the sequence CAGGCUACGC GTAGAGCAUC ATGATCCUGT (SEQ ID NO: 1) (see Example 3 of US Patent Application Publication No. 20050096257, incorporated herein by reference in its entirety) having 2'-fluoro-2'-deoxyuridine at positions 6, 19 and 28; 2'-fluoro-2'-deoxycytidine at positions 8, 20, 26, and 27; 2'-O-Methyl-2'-deoxyguanosine at positions 9, 14, 16, and 29; 2'-O-Methyl-2'-deoxyadenosine at position 21; an inverted orientation T (i.e., 3'-3'-linked) at position 30; and two heaxethyleneglycol phosphoramidite linkages that join together the $9^{th}$ and $10^{th}$ nucleotides and $21^{st}$ and $22^{nd}$ nucleotides via phosphodiester linkages between the linker and the respective nucleotides.

The chemical name of Antagonist A is [(monomethoxy 20K polyethylene glycol carbamoyl-N2-) (monomethoxy 20K polyethylene glycol carbamoyl-N6-)]-lysine-amido-6-hexandilyl-(1-5')-2'-deoxycytidylyl-(3'-5')-2'-deoxyadenylyl-(3'-5')-2'-deoxyguanylyl-(3'-5')- 2'-deoxyguanylyl-(3'-5)-2'-deoxycytidylyl-(3'-5)-2'-deoxy-2'-fluorouridylyl-(3'-5')-2'-deoxyadenylyl-(3'-5)-2'-deoxy-2'-fluorocytidylyl-(3'-5)-2'-deoxy-2'-methoxyguanylyl-(3'-1)-PO₃-hexa (ethyloxy)-(18-5)-2'-deoxycytidylyl-(3'-5')-2'-deoxyguanylyl-(3'-5')- thymidylyl-(3'-5)-2'-deoxyadenylyl-(3'-5')-2'-deoxy-2'-methoxyguanylyl-(3'-5)-2'-deoxyadenylyl-(3'-5)-2'-deoxy-2'-methoxyguanylyl-(3'-5)-2'-deoxycytidylyl-(3'-5)-2'-deoxyadenylyl-(3'-5)-2'-deoxy-2'-fluorouridylyl-(3'-5)-2'-deoxy-2'-fluorocytidylyl-(3'-5)-2'-deoxy-2'-methoxyadenylyl-(3'-1)-PO₃-hexa(ethyloxy)-(18-5)-thymidylyl-(3'-5)-2'-deoxyguanylyl-(3'-5)-2'-deoxyadenylyl-(3'-5)-thymidylyl-(3'-5)-2'-deoxy-2'-fluorocytidylyl-(3'-5)-2'-deoxy-2'-fluorocytidylyl-(3'-5)-2'-deoxy-2'-fluorouridylyl-(3'-5)-2'-deoxy-2'-methoxyguanylyl-(3'-3)-thymidine.

The structure of Antagonist A is shown in FIG. 1.

The sequence of Antagonist A is:

5'-[mPEG2 40 kD]-[HN—(CH₂)₆O] CAGGCU$_f$AC$_f$G$_m$ [PO₃(CH₂CH₂O)₆] CGTAG$_m$AG$_m$CAU$_f$C$_f$A$_m$ [PO₃(CH₂CH₂O)₆]TGATC$_f$C$_f$U$_f$G$_m$-[3T]-3', whose aptamer sequence is set forth in (SEQ ID NO: 1), where [3T] refers to an inverted thymidine nucleotide that is attached to the 3' end of the oligonucleotide at the 3' position on the ribose sugar, and [mPEG2 40 kD] represents two 20 kD polyethylene glycol (PEG) polymer chains, in one embodiment two about 20 kD PEG polymer chains, that are covalently attached to the two amino groups of a lysine residue via carbamate linkages. This moiety is in turn linked with the oligonucleotide via the amino linker described below.

[HN—(CH₂)₆O] represents a bifunctional α-hydroxy-w-amino linker that is covalently attached to the PEG polymer via an amide bond. The linker is attached to the oligonucleotide at the 5'-end of Antagonist A by a phosphodiester linkage.

[PO₃(CH₂CH₂O)₆] represents the hexaethylene glycol (HEX) moieties that join segments of the oligonucleotide via phosphodiester linkages. Antagonist A has two HEX linkages that join together the $9^{th}$ and $10^{th}$ nucleotides and $21^{st}$ and $22^{nd}$ nucleotides via phosphodiester linkages between the linker and the respective nucleotides.

C, A, G, and T represent the single letter code for the 2'-deoxy derivatives of cytosine, adenosine, guanosine, and thymidine nucleic acids, respectively. Antagonist A has four 2'-deoxyribocytosine, six 2'-deoxyriboadenosine, four 2'-deoxyriboguanosine, and four 2'-deoxyribothymidine.

$G_m$ and $A_m$ represent 2'-methoxy substituted forms of guanosine and adenosine, respectively. Antagonist A has four 2'-methoxyguanosines and one 2'-methoxyadenosine. $C_f$ and $U_f$ represent the 2'-fluoro substituted forms of cytosine and uridine, respectively. Antagonist A has four 2'-fluorocytosines and three 2'-fluorouridines.

The phosphodiester linkages in the oligonucleotide, with the exception of the 3'-terminus, connect the 5'- and 3'-oxygens of the ribose ring with standard nucleoside phosphodiester linkages. The phosphodiester linkage between the 3'-terminal thymidine and the penultimate $G_m$ links their respective 3'-oxygens, which is referred to as the 3',3'-cap.

Antagonist A has a molecular weight from 40,000 to 60,000 Daltons, in one embodiment from about 40,000 to about 60,000 Daltons, and can be colorless to slightly yellow in solution. Antagonist A can be present in a solution of monobasic sodium phosphate monohydrate and dibasic sodium phosphate heptahydrate as buffering agents and sodium chloride as a tonicity adjuster. Antagonist A is a hydrophilic polymer. The Antagonist A is soluble in water and in phosphate-buffered saline (PBS), as assessed by visual inspection, to at least 50 mg (based on oligonucleotide weight)/mL solution.

Antagonist A can be synthesized using an iterative chemical synthesis procedure to produce the oligonucleotide portion, which is then covalently bonded to a pegylation reagent, as further described in Example 4 of US Patent Publication NO. 2012/0100136.

Antagonist A is a persodium salt. Other pharmaceutically acceptable salts, however, of Antagonist are useful in the compositions and methods disclosed herein.

VEGF Antagonists

In some embodiments, the VEGF antagonist is ranibizumab (commercially available under the trademark Lucentis® (Genentech, San Francisco, Calif.); see FIG. 1 of U.S. Pat. No. 7,060,269 for the heavy chain and light chain variable region sequences), bevacizumab (commercially available under the trademark Avastin® (Genentech, San Francisco, Calif.); see FIG. 1 of U.S. Pat. No. 6,054,297 for the heavy chain and light chain variable region sequences), aflibercept (commercially available under the trademark Eylea® (Regeneron, Tarrytown, N.Y.), KH902 VEGF receptor-Fc fusion protein (see Zhang et al. (2008) Mol Vis. 14:37-49), 2C3 antibody (see U.S. Pat. No. 6,342,221, Column 8, lines 48-67, Column 9, lines 1-21), ORA102 (available from Ora Bio, Ltd.), pegaptanib (e.g., pegaptanib sodium; commercially available under the trademark Macugen® (Valeant Pharmaceuticals, Bridgewater, N.J.; see FIG. 1 of U.S. Pat. No. 6,051,698)), bevasiranib (see Dejneka et al. (2008) Mol Vis. 14:997-1005), SIRNA-027 (Shen et al. (2006) Gene Ther. 13:225-34), decursin (see U.S. Pat. No. 6,525,089 (Column 3, lines 5-16)), decursinol (see Ahn et al. (1997) Planta Med. 63:360-1), picropodophyllin (see Economou (2008) Investigative Ophthalmology & Visual Science. 49:2620-6), guggulsterone (see Kim et al. (2008) Oncol. Rep. 20:1321-7), PLG101 (see Ahmadi and Lim (2008) Expert Opin Pharmacother. 9:3045-52), PLG201 (see Ahmadi and Lim (2008)), eicosanoid LXA4 (see Baker et al (2009) J Immun. 182:3819-26), PTK787 (commercially available under the trademark Vitalanib™; see Barakat and Kaiser (2009) Expert Opin Investig Drugs 18:637-46), pazopanib (see Takahashi et al. (2009) Arch Ophthalmol. 127:494-9), axitinib (see Hu-Lowe et al. (2008) Clin Cancer Res. 14:7272-83), CDDO-Me (see Sogno et al. (2009) Recent Results Cancer Res. 181:209-12), CDDO-Imm (see Sogno et al. (2009)), shikonin (see Hisa et al. (1998) Anticancer Res. 18:783-90), beta-hydroxyisovaleryl-shikonin (see Hisa et al. (1998)), ganglioside GM3 (Chung et al. (2009) Glycobio. 19:229-39), DC101 antibody (see U.S. Pat. No. 6,448,077, Column 2, lines 61-65), Mab25 antibody (see U.S. Pat. No. 6,448,077, Column 2, lines 61-65), Mab73 antibody (see U.S. Pat. No. 6,448,077, Column 2, lines 61-65), 4A5 antibody (see U.S. Pat. No. 6,383,484, Column 12, lines 50-54), 4E10 antibody (see U.S. Pat. No. 6,383,484, Column 10, lines 66-67, Column 11, lines 1-2), 5F12 antibody (see U.S. Pat. No. 6,383,484, Column 10, lines 62-65), VA01 antibody (see U.S. Pat. No. 5,730,977, Column 6, lines 26-30), BL2 antibody (U.S. Pat. No. 5,730,977, Column 6, lines 30-32), VEGF-related protein (see U.S. Pat. No. 6,451,764, FIG. 1), sFLT01 (see Pechan et al. (2009) Gene Ther. 16:10-6), sFLT02 (see Pechan et al. (2009)), Peptide B3 (see Lacal et al. (2008) Eur J Cancer 44:1914-21), TG100801 (see Palanki et al. (2008) J Med Chem. 51:1546-59), sorafenib (commercially available under the trademark Nexavar™; see Kernt et al. (2008) Acta Ophthalmol. 86:456-8), G6-31 antibody (see Crawford et al. (2009) Cancer Cell 15:21-34), ESBA1008 (see U.S. Pat. No. 8,349,322), tivozanib (see U.S. Pat. No. 6,821,987, incorporated by reference in its entirety; Campas et al. (2009) Drugs Fut 2009, 34(10): 793), or a pharmaceutically acceptable salt thereof.

In another embodiment, the VEGF antagonist is an antibody or an antibody fragment which binds to an epitope VEGF-A (SEQ ID NO: 22) or VEGF-B (SEQ ID NO: 23), or any portion of the epitopes. In one embodiment, the VEGF antagonist is an antibody or antibody fragment that binds to one or more of an epitope of VEGF (e.g., SEQ ID NOS: 22 and 23). In another embodiment, the VEGF antagonist is an antibody or an antibody fragment which binds to an epitope of VEGF, such as an epitope of VEGF-A, VEGF-B, VEGF-C, VEGF-D, or VEGF-E. In some embodiments, the VEGF antagonist binds to an epitope of VEGF such that binding of VEGF and VEGFR are inhibited. In one embodiment, the epitope encompasses a component of the three dimensional structure of VEGF that is displayed, such that the epitope is exposed on the surface of the folded VEGF molecule. In one embodiment, the epitope is a linear amino acid sequence from VEGF.

In some embodiments, an inhibitory antibody directed against VEGF is known in the art, e.g., those described in U.S. Pat. Nos. 6,524,583, 6,451,764 (VRP antibodies), 6,448,077, 6,416,758, 6,403,088 (to VEGF-C), 6,383,484 (to VEGF-D), 6,342,221 (anti-VEGF antibodies), 6,342,219 6,331,301 (VEGF-B antibodies), and 5,730,977, and PCT publications WO96/30046, WO 97/44453, and WO 98/45331, the contents of which are incorporated by reference in their entirety.

Other non-antibody VEGF antagonists include antibody mimetics (e.g., Affibody® molecules, affilins, affitins, anticalins, avimers, Kunitz domain peptides, and monobodies) with VEGF antagonist activity. This includes recombinant binding proteins comprising an ankyrin repeat domain that binds VEGF-A and prevents it from binding to VEGFR-2. One example is MP0112, also known as AGN 150998 (DARPin®). The ankyrin binding domain may have an amino acid sequence of SEQ ID NO: 97.

Recombinant binding proteins comprising an ankyrin repeat domain that binds VEGF-A and prevents it from binding to VEGFR-2 are described in more detail in WO2010/060748 and WO2011/135067.

Further specific antibody mimetics with VEGF antagonist activity are the 40 kD pegylated anticalin PRS-050 and the monobody angiocept (CT-322).

The aforementioned non-antibody VEGF antagonist may be modified to further improve their pharmacokinetic properties or bioavailability. For example, a non-antibody VEGF antagonist may be chemically modified (e.g., pegylated) to extend its in vivo half-life. Alternatively or in addition, it may be modified by glycosylation or the addition of further glycosylation sites not present in the protein sequence of the natural protein from which the VEGF antagonist was derived.

Other non-antibody VEGF antagonist immunoadhesin currently in pre-clinical development is a recombinant human soluble VEGF receptor fusion protein similar to VEGF-trap containing extracellular ligand-binding domains 3 and 4 from VEGFR2/KDR, and domain 2 from VEGFR1/Flt-1; these domains are fused to a human IgG Fc protein fragment (Li et al., 2011 Molecular Vision 17:797-803). This antagonist binds to isoforms VEGF-A, VEGF-B and VEGF-C. The molecule is prepared using two different production processes resulting in different glycosylation patterns on the final proteins. The two glycoforms are referred to as KH902 (conbercept) and KH906. The fusion protein can have the amino acid sequence of SEQ ID NO: 98 and, like VEGF-trap, can be present as a dimer. This fusion protein and related molecules are further characterized in EP1767546.

Anti-C5 Agents

In certain embodiments, the anti-C5 agent modulates a function of a C5 complement protein or a variant thereof. In some embodiments, the anti-C5 agent inhibits a function of C5 complement protein or a variant thereof. In one embodiment, the function inhibited by the anti-C5 agent is C5 complement protein cleavage.

A C5 complement protein variant as used herein encompasses a variant that performs substantially the same function as a C5 complement protein function. A C5 complement protein variant in some embodiments comprises substantially the same structure and in some embodiments comprises at least 80% sequence identity, in some embodiments at least 90% sequence identity, and in some embodiments at least 95% sequence identity to the amino acid sequence of the C5 complement protein comprising the amino acid sequence SEQ ID NO: 24.

In some embodiments, the anti-C5 agent is selected from a nucleic acid molecule, an aptamer, an antisense molecule, an RNAi molecule, a protein, a peptide, a cyclic peptide, an antibody or antibody fragment, a sugar, a polymer, or a small molecule. In certain embodiments, the anti-C5 agent is an anti-C5 agent described in PCT Patent Application Publication No. WO 2007/103549.

In particular embodiments, the anti-C5 agent is an anti-C5 aptamer. Aptamers are nucleic acid molecules having specific binding affinity to molecules through interactions other than classic Watson-Crick base pairing. Aptamers, like peptides generated by phage display or monoclonal antibodies ("mAbs"), are capable of specifically binding to selected targets and modulating the target's activity, e.g., through binding aptamers may block their target's ability to function. The aptamers may be unpegylated or pegylated. In particular embodiments, the aptamers may contain one or more 2' sugar modifications, such as 2'-O-alkyl (e.g., 2'-O-methyl or 2'-O-methoxyethyl) or 2'-fluoro modifications.

Illustrative C5 specific aptamers include the aptamers disclosed in PCT Publication No. WO 2007/103549, which is incorporated by reference in its entirety. Illustrative C5 specific aptamers include the aptamers ARC185 (SEQ ID NO: 25), ARC186 (SEQ ID NO: 26), ARC188 (SEQ ID NO: 27), ARC189 (SEQ ID NO: 28), ARC243 (SEQ ID NO: 29), ARC244 (SEQ ID NO: 30), ARC250 (SEQ ID NO: 31), ARC296 (SEQ ID NO: 32), ARC297 (SEQ ID NO: 33), ARC330 (SEQ ID NO: 34), ARC331 (SEQ ID NO: 35), ARC332 (SEQ ID NO: 36), ARC333 (SEQ ID NO: 37), ARC334 (SEQ ID NO: 38), ARC411 (SEQ ID NO: 39), ARC412 (SEQ ID NO: 40), ARC413 (SEQ ID NO: 41), ARC414 (SEQ ID NO: 42), ARC415 (SEQ ID NO: 43), ARC416 (SEQ ID NO: 44), ARC417 (SEQ ID NO: 45), ARC418 (SEQ ID NO: 46), ARC419 (SEQ ID NO: 47), ARC420 (SEQ ID NO: 48), ARC421 (SEQ ID NO: 49), ARC422 (SEQ ID NO: 50), ARC423 (SEQ ID NO: 51), ARC424 (SEQ ID NO: 52), ARC425 (SEQ ID NO: 53), ARC426 (SEQ ID NO: 54), ARC427 (SEQ ID NO: 55), ARC428 (SEQ ID NO: 56), ARC429 (SEQ ID NO: 57), ARC430 (SEQ ID NO: 58), ARC431 (SEQ ID NO: 59), ARC432 (SEQ ID NO: 60), ARC433 (SEQ ID NO: 61), ARC434 (SEQ ID NO: 62), ARC435 (SEQ ID NO: 63), ARC436 (SEQ ID NO: 64), ARC437 (SEQ ID NO: 65), ARC438 (SEQ ID NO: 66), ARC439 (SEQ ID NO: 67), ARC440 (SEQ ID NO: 68), ARC457 (SEQ ID NO: 69), ARC458 (SEQ ID NO: 70), ARC459 (SEQ ID NO: 71), ARC473 (SEQ ID NO: 72), ARC522 (SEQ ID NO: 73), ARC523 (SEQ ID NO: 74), ARC524 (SEQ ID NO: 75), ARC525 (SEQ ID NO: 76), ARC532 (SEQ ID NO: 77), ARC543 (SEQ ID NO: 78), ARC544 (SEQ ID NO: 79), ARC550 (SEQ ID NO: 80), ARC551 (SEQ ID NO: 81), ARC552 (SEQ ID NO: 82), ARC553 (SEQ ID NO: 83), ARC554 (SEQ ID NO: 84), ARC657 (SEQ ID NO: 85), ARC658 (SEQ ID NO: 86), ARC672 (SEQ ID NO: 87), ARC706 (SEQ ID NO: 88), ARC913 (SEQ ID NO: 89), ARC874 (SEQ ID NO: 90), ARC954 (SEQ ID NO: 91), ARC1537 (SEQ ID NO: 92), ARC1730 (SEQ ID NO: 93), or a pharmaceutically acceptable salt thereof.

In some embodiments, the anti-C5 agent is an aptamer with SEQ ID NO: 94, 95, or 96.

In a particular embodiment, the anti-C5 agent is a C5 specific aptamer comprising the nucleotide sequence of SEQ ID NO: 26 conjugated to a polyethylene glycol moiety via a linker. In some embodiments, the polyethylene glycol moiety has a molecular weight greater than about 10 kDa, particularly a molecular weight of about 20 kDa, more particularly about 30 kDa and more particularly about 40 kDa. In some embodiments, the polyethylene glycol moiety is conjugated via a linker to the 5' end of the aptamer. In some embodiments, the PEG conjugated to the 5' end of is a PEG of about 40 kDa molecular weight. In particular embodiments the about 40 kDa PEG is a branched PEG. In some embodiments the branched about 40 kDa PEG is 1,3-bis(mPEG-[about 20 kDa])-propyl-2-(4'-butamide). In other embodiments the branched about 40 kDa PEG is 2,3-bis(mPEG-[about 20 kDa])-propyl-1-carbamoyl.

In a particular embodiment, the C5 specific aptamer is a compound, ARC187, having the structure set forth below:

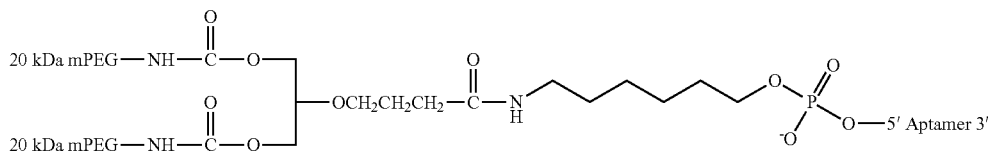

or a pharmaceutically acceptable salt thereof, where Aptamer=fCmGfCfCGfCmGmGfUfCfUfCmAmGmGfCGf CfUmGmAmGfUfCfUmGmAmGf UfUfUAfCf CfUmGfCmG-3T (SEQ ID NO: 26)

wherein fC and fU=2'-fluoro nucleotides, and mG and mA=2'-OMe nucleotides and all other nucleotides are 2'-OH and where 3T indicates an inverted deoxy thymidine. In some embodiments, each 20 kDa mPEG of the above structure has a molecular weight of about 20 kDa.

In another particular embodiment, the C5 specific aptamer is a compound, ARC1905, having the structure set forth below:

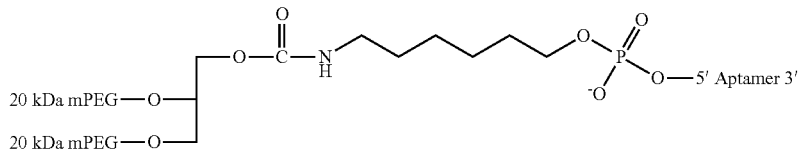

or a pharmaceutically acceptable salt thereof, where Aptamer=fCmGfCfCGfCmGmGfUfCfUfCmAmGmGfCGf CfUmGmAmGfUfCfUmGmAmGfUfUfUAfCf CfUmGfCmG-3T (SEQ ID NO: 26)

wherein fC and fU=2'-fluoro nucleotides, and mG and mA=2'-OMe nucleotides and all other nucleotides are 2'-OH and where 3T indicates and inverted deoxy thymidine. In some embodiments, each 20 kDa mPEG of the above structure has a molecular weight of about 20 kDa.

In other embodiments, the anti-C5 agent is an antisense oligonucleotide or ribozyme targeted to C5 that effects C5 inhibition by inhibiting protein translation from the messenger RNA or by targeting degradation of the corresponding C5 mRNA.

In still other embodiments, the anti-C5 agent is an anti-C5 RNA interference (RNAi) construct. Certain double stranded oligonucleotides useful to effect RNAi against C5 complement protein are less than 30 base pairs in length and may comprise about 25, 24, 23, 22, 21, 20, 19, 18 or 17 base pairs of ribonucleic acid and comprise a sequence with substantial sequence identity to the mRNA sequence of complement C5 protein, particularly human complement C5 protein. Optionally, the dsRNA oligonucleotides may include 3' overhang ends. Non-limiting illustrative 2-nucleotide 3' overhangs are composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., (2001) Nature, 411: 494-8).

Other Agents for Treatment or Prevention of an Ophthalmological Disease or Disorder In another embodiment, another agent useful for treating or preventing an ophthalmological disease or disorder is volociximab or a pharmaceutically acceptable salt thereof (Ramakrishnan et al. (2008) J Exp Ther Oncol. 5:273-86, which is hereby incorporated by reference in its entirety).

In some embodiments, a plurality of aptamers can be associated with a single Non-Immunogenic, High Molecular Weight Compound, such as Polyalkylene Glycol or PEG, or a Lipophilic Compound, such as a glycerolipid. The aptamers can all be to one target or to different targets. In embodiments where a compound comprises more than one PDGF aptamer, there can be an increase in avidity due to multiple binding interactions with a target, such as PDGF or VEGF. In yet further embodiments, a plurality of Polyalkylene Glycol, PEG, glycerol lipid molecules can be attached to each other. In these embodiments, one or more aptamers can be associated with each Polyalkylene Glycol, PEG, or glycerol lipid. This can result in an increase in avidity of each aptamer to its target. In addition, in embodiments where there are aptamers to PDGF or aptamers to PDGF and different Targets associated with Polyalkylene Glycol, PEG, or glycerol lipid, a drug can also be associated with, e.g., covalently bonded to, Polyalkylene Glycol, PEG, or glycerol lipid. Thus the compound would provide targeted delivery of the drug, with Polyalkylene Glycol, PEG, or glycerol lipid serving as a Linker, optionally, with one or more additional linkers.

Aptamers can be 5'-capped and/or 3'-capped with a 5'-5' inverted nucleoside cap structure at the 5' end and/or a 3'-3' inverted nucleoside cap structure at the 3' end. In several embodiments, Antagonist A, Antagonist B, Antagonist C, Antagonist D, pegaptanib, bevasiranib and Sirna-027 are 5' or 3' end-capped.

Methods for Treating or Preventing an Ophthalmological Disease or Disorder

The invention provides methods and compositions useful for treating or preventing ophthalmological diseases and disorders, including but not limited to any of the ophthalmological diseases and disorders described herein.

In some embodiments, the methods for treating or preventing an ophthalmological disease or disorder disclosed herein improve retinal attachment success, improve visual acuity, or stabilize vision. In some embodiments, the methods disclosed herein prevent or retard the rate of further vision loss in a subject.

In some embodiments, administration of Antagonist A or another pharmaceutically acceptable salt thereof in combination with a VEGF antagonist or pharmaceutically acceptable salt thereof and/or an anti-C5 agent improves retinal attachment success, improves visual acuity, or stabilizes vision to a degree that is greater than administration of Antagonist A or another pharmaceutically acceptable salt thereof alone, the VEGF antagonist or pharmaceutically acceptable salt thereof alone, or the anti-C5 agent alone. In some embodiments, the administration of Antagonist A or another pharmaceutically acceptable salt thereof and the VEGF antagonist or pharmaceutically acceptable salt thereof, and optionally, an anti-C5 agent, has a synergistic effect in treating or preventing an ophthalmological disease or disorder. For example, the administration of both Antagonist A or another pharmaceutically acceptable salt thereof and a VEGF antagonist or pharmaceutically acceptable salt thereof can improve retinal attachment success, improve visual acuity, or stabilize vision to a degree that is greater than an additive effect of administering both Antagonist A or another pharmaceutically acceptable salt thereof and the VEGF antagonist or pharmaceutically acceptable salt thereof. In some embodiments, administration of Antagonist A, alone or in combination with a VEGF antagonist and/or an anti-C5 agent, according to the methods described herein, e.g., treatment or dosing regimens, improves retinal attachment success, improves visual acuity, or stabilizes vision to a degree that is greater than administration of Antagonist A, alone or in combination with a VEGF antagonist and/or an anti-C5 agent, according to previously described methods.

In particular embodiments, any of the methods and compositions of the present invention are used to treat or prevent an ophthalmological disease or disorder in particular subjects. For example, in certain embodiments, subjects treated according to a method described herein are defined or identified based on their previous treatments for the disease or disorder, specific manifestations of their disease or disorder being treated, and/or other characteristics. In one embodiment, the subject has a defined phenotype or medical history.

Accordingly, any of the methods described herein may further comprise identifying the subject to be treated, such as by determining whether the subject was previously administered a VEGF antagonist for treating or preventing the disease or disorder or whether the subject had previously failed monotherapy with a VEGF antagonist, e.g., by inquiring of the subject or his health care provider, or by reviewing the subject's medical records.

In one embodiment, the subject was previously treated with a VEGF antagonist or anti-VEGF monotherapy for any ocular disease or disorder for which a VEGF antagonist is used, or for any of the ocular diseases or disorders described herein (e.g., wet-type AMD).

In particular embodiments, the methods and compositions described herein are useful for treating or preventing an ophthalmological disease or disorder in a subject who is anti-VEGF resistant, was previously administered or treated with anti-VEGF monotherapy, does not respond or had not responded favorably or adequately to anti-VEGF monotherapy, and/or failed monotherapy with a VEGF antagonist. In some embodiments, a subject who failed monotherapy is anti-VEGF resistant, has complement-mediated inflammation, and/or did not respond adequately to anti-VEGF monotherapy. In one embodiment, the subject who failed monotherapy with a VEGF antagonist is a subject who experienced a poor visual or anatomic outcome after treatment or administration with a VEGF antagonist. In one embodiment, the subject did not exhibit improved vision or exhibited reduced vision following anti-VEGF monotherapy.

In certain embodiments, the subject does not respond or had not responded favorably or adequately to anti-VEGF monotherapy, as determined by the subject's vision loss or by the subject's lack of significant vision gain following anti-VEGF monotherapy. In one embodiment, the subject's lack of significant vision gain following anti-VEGF monotherapy is determined by the subject's loss of ability to read one or more, in some embodiments three or more, and in some embodiments fifteen or more, letters of a standardized chart of vision testing, e.g., the Early Treatment for Diabetic Retinopathy Study Chart ("ETDRS chart"). In some embodiments, the vision testing is as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, Va. 22161; Accession No. PB85 223006/AS; Ferris et al., Am J Ophthalmol 94:91-96, 1982; or Example 4, as described herein. In some embodiments, the vision testing uses one or more charts available from http://www.nei.nih.gov/photo/keyword.asp?conditions=Eye+Charts&match=all, e.g., ETDRS visual acuity Chart 1, 2 and/or R.

In another embodiment, the subject's vision loss following anti-VEGF monotherapy is determined by the subject's loss of ability to read one or more, in some embodiments three or more, letters or lines of a standardized chart of vision testing, e.g., the ETDRS chart, from baseline. In one embodiment, the subject's lack of significant vision gain following anti-VEGF monotherapy is determined by the subject's inability to read an additional one or more, in some embodiment three or more, and in some embodiments fifteen or more, letters of a standardized chart of vision testing, e.g., the ETDRS chart, from baseline. In another embodiment, the subject's lack of significant vision gain following anti-VEGF monotherapy is determined by the subject's inability to read an additional one or more, in some embodiments three or more, lines of a standardized chart of visual testing, e.g., the ETDRS chart, from baseline. In some embodiments, a subject's vision loss or lack of significant vision gain is determined by the subject's visual loss or anatomic signs of poor treatment response, for example, persistent leakage, increased hemorrhage, persistent or increased retinal pigment epithelium (RPE) detachment, signs of neovascular activity, or growth of neovascularization or increased deposition of abnormal matrix or fibrosis. In particular embodiments, a subject's vision loss or lack of significant vision gain is determined at 12 weeks or at 24 weeks following the initiation of treatment.

In certain embodiments, the subject is anti-VEGF-resistant to a VEGF antagonist, e.g., anti-VEGF monotherapy. In one embodiment, a subject is anti-VEGF resistant if the subject was previously administered with a VEGF antagonist, e.g., anti-VEGF monotherapy, that did not result in the treatment or prevention of the ophthalmological disease or disorder; resulted in only a temporary treatment or prevention of the ophthalmological disease or disorder and rendered the subject in further need of treatment or prevention of the ophthalmological disease or disorder; or that resulted in the subject's visual decline and rendered the subject in further need of treatment or prevention of the ophthalmological disease or disorder.

In another embodiment, a subject is anti-VEGF resistant if the subject was previously treated or administered with an anti-VEGF treatment, e.g., anti-VEGF monotherapy, and failed to achieve any visual gain or experienced visual decline. In some embodiments, the subject did not respond adequately to anti-VEGF treatment. In one embodiment, the subject was administered the anti-VEGF treatment for one year or longer. In some such embodiments, the subject is in need of treatment for wet AMD.

Accordingly, the present invention provides methods for treating, preventing, or stabilizing wet AMD in a subject, such as a subject who has failed monotherapy with a VEGF antagonist (e.g., is anti-VEGF resistant, has complement-mediated inflammation, and/or did not respond adequately to anti-VEGF monotherapy). In particular embodiments, the methods comprise determining whether the subject was previously administered or treated with anti-VEGF monotherapy. In certain embodiments, anti-VEGF monotherapy means administration of only one or more VEGF antagonists. In certain embodiments, anti-VEGF monotherapy includes the optional administration of other drugs that are not agents specifically adapted for treating an ophthalmological disease or disorder, e.g, wet AMD.

In certain embodiments, the methods and compositions described herein are useful for treating or preventing an ophthalmological disease or disorder in a subject that is treatment-naïve. In some embodiments, the subject is treatment-naïve if the subject was not previously treated for the ophthalmological disease or disorder. In some embodiments, the subject is treatment-naïve if the subject was not previously administered or treated with a VEGF antagonist or anti-VEGF monotherapy ("anti-VEGF-treatment-naïve"). In particular embodiments, the methods further comprise determining whether the subject was previously treated for the ophthalmological disease or disorder or administered a VEGF antagonist or anti-VEGF monotherapy, e.g., by inquiring of the subject or his or her health care provider, or by reviewing the subject's medical records. In certain embodiments, anti-VEGF monotherapy means administration of only one or more VEGF antagonists. In certain embodiments, anti-VEGF monotherapy includes the optional administration of other drugs that are not agents specifically adapted for treating an ophthalmological disease or disorder, e.g, wet AMD. In some embodiments, the subject is treatment-naïve if the subject was not previously treated for AMD (e.g., wet AMD). In some embodiments, the subject is treatment-naïve if the subject was not previously treated, or has underwent no previous treatment for AMD (e.g., wet AMD) in either eye. In yet other embodiments, the subject is treatment-naïve if the subject was not previously treated, or has underwent no previous treatment, for AMD (e.g., wet AMD; e.g., in either eye) except for one or more oral supplements of vitamins and minerals. In some embodiments, the subject is treatment-naïve if the subject was not previously administered a therapeutic agent used for the treatment of AMD (e.g., wet AMD).

In certain embodiments, the subject has complement-mediated inflammation. In certain embodiments, the subject is anti-VEGF resistant and has complement-mediated inflammation. In certain embodiments, the complement-mediated inflammation is present in an eye of the subject. In certain embodiments, the complement-mediated inflammation results from previous administration with anti-VEGF monotherapy. In other embodiments, the subject has or has been diagnosed with complement-mediated inflammation. In still other embodiments, the subject did not respond adequately to anti-VEGF monotherapy and has or has been diagnosed with complement-mediated inflammation. In certain embodiments, complement-mediated inflammation is diagnosed in the subject using a genetic screening method. Such genetic screening methods are known to those of skill in the art and include, but are not limited to, screening for mutations in complement genes, such as complement factor H (CFH), CFI, CFHR5, and MCP, BF, and C2 genes.

In certain embodiments, the methods and compositions described herein are useful for treating or preventing an ophthalmological disease or disorder in a subject who is newly diagnosed with the ophthalmological disease or disorder. In some embodiments, the subject is newly diagnosed if the subject was not previously diagnosed for the ophthalmological disease or disorder. In some embodiments, the subject is newly diagnosed with age-related macular degeneration. In some embodiments, the subject is newly diagnosed with dry age-related macular degeneration. In some embodiments, the subject is newly diagnosed with wet-type AMD. In particular embodiments, the methods further comprise determining whether the subject was previously diagnosed for the ophthalmological disease or disorder, e.g., by inquiring of the subject or his or her health care provider, or by reviewing the subject's medical records.

In some embodiments of the invention, the methods and compositions described herein are useful for treating or preventing an ophthalmological disease or disorder that is a neovascular disorder. In other embodiments of the invention, the ophthalmological disease or disorder results in retinal edema. Illustrative ophthalmological diseases or disorders that can be treated or prevented are described herein.

Treatment or Prevention of Age-Related Macular Degeneration

In one embodiment, the ophthalmological disease or disorder treated or prevented by any of the methods or compositions described herein is age-related macular degeneration. Vision changes that can be associated with macular degeneration include distortions and/or blind spots (scotoma) detected using an Amsler grid, changes in dark adaptation (diagnostic of rod cell health), changes in color interpretation (diagnostic of cone cell health), or a decrease in visual acuity. Examples of age-related macular degeneration are nonneovascular (also known as "dry") and neovascular (also known as "wet" or "exudative") macular degeneration.

In one embodiment, the dry age-related macular degeneration is associated with the formation of drusen. In one embodiment, treating or preventing dry macular degeneration encompasses treating or preventing an abnormality of the retinal pigment epithelium and/or underlying vasculature, known as choriocapilaries. Examples of abnormalities of the retinal pigment epithelium include geographic atrophy, non-geographic atrophy, focal hypopigmentation, and focal hyperpigmentation. In another embodiment, treating or preventing wet age-related macular degeneration encompasses treating or preventing choroidal neovascularization or pigment epithelial detachment.

In one embodiment, the invention provides methods for treating or preventing wet age-related macular degeneration. Another aspect of the present invention is methods for treating, preventing, or inhibiting a choroidal neovascular complex in a subject, e.g., inhibiting the formation or growth of a choroidal neovascular complex.

In another aspect of the invention, the invention provides methods for treating or preventing choroidal neovascularization in a subject. In some embodiments, the choroidal neovascularization is subfoveal choroidal neovascularization. In some embodiments, the subfoveal choroidal neovascularization is due to age-related macular degeneration. In one embodiment, the subfoveal choroidal neovascularization is secondary to exudative type AMD. In other embodiments, the subfoveal choroidal neovascularization is present in subjects who have exudative type AMD, and in other embodiments, subfoveal choroidal neovascularization is present in subjects who do not have exudative type AMD. In some embodiments, the subfoveal choroidal neovascularization is secondary to inflammatory, traumatic, myopic, idiopathic or neoplastic afflictions of the macula.

In some embodiments, wet age-related macular degeneration is classified according to the appearance of its choroidal neovascularization (CNV), into classic, occult or mixed (classic and occult) CNV types, as determined by an angiography, known as fluorescence angiography. Classic, occult or mixed (classic and occult) CNV classification can be based on the time, intensity and level of definition of dye appearance, and leakage from the CNV, as assessed by the fluorescein angiography. In some embodiments, the subject has classic CNV (e.g., pure classic) or mixed CNV (predominantly or minimally classic CNV). In some embodiments, the subject has occult CNV (e.g., pure occult CNV).

The administration of Antagonist A or another pharmaceutically acceptable salt thereof and the VEGF antagonist and/or anti-C5 agent can have a synergistic effect in treating or preventing classic CNV or occult CNV. For example, administration of both Antagonist A or another pharmaceutically acceptable salt thereof and the VEGF antagonist can improve visual acuity or stabilize vision to a degree that is greater than an additive effect of both Antagonist A or another pharmaceutically acceptable salt thereof and the VEGF antagonist. In another example, administration of both Antagonist A or another pharmaceutically acceptable salt thereof and the VEGF antagonist can reduce CNV or inhibit the growth of CNV to a greater degree than administration of Antagonist A or another pharmaceutically acceptable salt thereof or the VEGF antagonist. In some embodiments, administration of both Antagonist A or another pharmaceutically acceptable salt thereof and the VEGF antagonist can reduce CNV in a shorter timeframe or with a lower dosage amount or frequency, as compared to the timeframe or dosage amount with administration of Antagonist A or another pharmaceutically acceptable salt thereof or the VEGF antagonist. In some embodiments, administration of both Antagonist A or another pharmaceutically acceptable salt thereof and the VEGF antagonist can reduce CNV or inhibit the growth of CNV to a greater degree than an additive effect of both Antagonist A or another pharmaceutically acceptable salt thereof and the VEGF antagonist. In some embodiments, administration of both Antagonist A or another pharmaceutically acceptable salt thereof and the VEGF antagonist can reduce CNV in a shorter timeframe or with a lower dosage amount or frequency, as compared to an additive timeframe, dosage amount or frequency with administration of both Antagonist A or another pharmaceutically acceptable salt thereof and the VEGF antagonist.

In one embodiment, the present invention provides methods for treating, preventing, or stabilizing non-exudative type ("dry type") AMD. In one embodiment, Antagonist A or another pharmaceutically acceptable salt thereof, an anti-C5 agent, the combination of Antagonist A or another pharmaceutically acceptable salt thereof and an anti-C5 agent, or the combination of an anti-C5 agent and a VEGF antagonist is administered in an amount effective to maintain about the same level of drusen or reduce the level of drusen (e.g., amount, size, number, area and/or morphology) (e.g., size, number, area and/or morphology) as compared to the subject's drusen level prior to administration of Antagonist A or another pharmaceutically acceptable salt thereof, the anti-C5 agent, the combination of Antagonist A or another pharmaceutically acceptable salt thereof and the anti-C5 agent, or or the combination of an anti-C5 agent and a VEGF antagonist, respectively. In a particular embodiment, the level of drusen is reduced by at least or about 5%, at least or about 10%, at least or about 20%, at least or about 30%, at least or about 40%, or at least or about 50%.

In some embodiments, Antagonist A or another pharmaceutically acceptable salt thereof, an anti-C5 agent, the combination of Antagonist A or another pharmaceutically acceptable salt thereof and the anti-C5 agent, or the combination of the anti-C5 agent and a VEGF antagonist is administered in an amount effective to inhibit, slow, or prevent the progression of non-exudative type AMD to geographic atrophy (GA). GA is an advanced form of non-exudative type AMD. In other embodiments, the Antagonist A or another pharmaceutically acceptable salt thereof and/or the anti-C5 agent or a pharmaceutically acceptable salt thereof is administered in an amount effective to reduce the growth or area of a GA lesion over time as compared to that in a subject not receiving Antagonist A or another pharmaceutically acceptable salt thereof and/or the anti-C5 agent. In other embodiments, the anti-C5 agent or a pharmaceutically acceptable salt thereof and a VEGF antagonist is administered in an amount effective to reduce the growth or area of a GA lesion over time as compared to that in a subject not receiving the anti-C5 agent and/or the VEGF antagonist. In a particular embodiment, the change in area or growth of the geographic atrophy lesion over time is reduced by at least or about 5%, at least or about 10%, at least or about 20%, at least or about 30%, at least or about 40%, or at least or about 50%. Methods of identifying and assessing the size of geographic lesions are known to those of skill in the art and include autofluorescence imaging and optical coherence tomography.

In particular embodiments, a subject in whom non-exudative AMD converts to exudative AMD, e.g., when new blood vessels invade the overlying retina, is treated. The present invention further provides methods for treating, preventing, or stabilizing drusen retinopathy secondary to complement-mediated immune disorders, including drusen retinopathy secondary to membranoproliferative glomerulonephritis type II disease. In some embodiments, Antagonist A or another pharmaceutically acceptable salt thereof and/or an anti-C5 agent and/or a VEGF antagonist is administered in an amount effective to reduce retinal drusen in subjects having or having been diagnosed with membranoproliferative glomerulonephritis type II disease or exudative-type AMD as compared to the level of retinal drusen prior to administration of Antagonist A or another pharmaceutically acceptable salt thereof and/or an anti-C5 agent and/or a VEGF antagonist. In certain embodiments, the level of drusen is reduced by at least or about 5%, at least or about 10%, at least or about 20%, at least or about 30%, at least or about 40%, or at least or about 50%.

In one embodiment, the ophthalmological disease or disorder is polypoidal choroidal vasculopathy (PCV), a variant of wet AMD.

Treatment or Prevention of a Condition Associated with Choroidal Neovascularization In one embodiment, the ophthalmological disease or disorder is a condition associated with choroidal neovascularization. Examples of conditions associated with choroidal neovascularization include a degenerative, inflammatory, traumatic or idiopathic condition. Treating or preventing a degenerative disorder associated with choroidal neovascularization also encompasses treating or preventing a heredodegenerative disorder. Examples of heredodegenerative disorders include vitelliform macular dystrophy, fundus flavimaculatus and optic nerve head drusen. Examples of degenerative conditions associated with choroidal neovascularization include myopic degeneration or angioid streaks.

In some embodiments, treating or preventing an inflammatory disorder associated with choroidal neovascularization encompasses treating or preventing ocular histoplasmosis syndrome, multifocal choroiditis, serpininous choroiditis, toxoplasmosis, toxocariasis, rubella, Vogt-Koyanagi-Harada syndrome, Behcet syndrome or sympathetic ophthalmia. In some embodiments, treating or preventing a traumatic disorder associated with choroidal neovascularization encompasses treating or preventing choroidal rupture or a traumatic condition caused by intense photocoagulation.

Treatment or Prevention of Proliferative Retinopathy

One particular aspect of the invention provides methods and compositions for treating or preventing proliferative vitreoretinopathy (PVR). In some embodiments, the PVR is a moderate form. In other embodiments, the PVR is a severe form. In some embodiments, the PVR is a recurrent form. In one embodiment, the subject with PVR also has or had retinal detachment, or the subject has PVR associated with retinal detachment, or PVR related scarring (e.g., scarring resulting from PVR, e.g., retinal scarring). In some embodiments, the PVR is characterized based on the configuration of the retina and the location of the scar tissue, such as in shown in Table 2 (See Lean J, et al. Classification of proliferative vitreoretinopathy used in the silicone study. The Silicone study group. Ophthalmology 1989; 96:765-771). Any of these categories or types of PVR can be treated or prevented according to the present invention.

TABLE 2

Classification of PVR

| Type no. | Type of contraction | Location of PVR | Summary of Clinical Signs |
|---|---|---|---|
| 1 | Focal | Posterior | Starfold |
| 2 | Diffuse | Posterior | Confluent irregular retinal folds in posterior retina; remainder of retina drawn posteriorly; optic disc may not be visible |
| 3 | Sub-retinal | Posterior | "Napkin ring" around disc or "clothesline" elevation of retina |
| 4 | Circumferential | Anterior | Irregular retinal folds in the anterior retina; series of radial folds more posteriorly; peripheral retina within vitreous base stretched inward |
| 5 | Perpendicular | Anterior | Smooth circumferential fold of retina at insertion of posterior hyaloid |
| 6 | Anterior | Anterior | Circumferential fold of retina at insertion of posterior hyaloid pulled forward; trough of peripheral retina anteriorly; ciliary processes stretched with possible hypotony; iris retracted |

The present methods for treating PVR can further comprise administering another agent useful for treating PVR, such as a corticosteriod; antineoplastic drug, such as 5-fluorouracil; colchicine; retinoid; heparin; epidermal growth factor receptor (EGFR) inhibitor, such as gefitinib or erlotinib.

Another aspect of the invention is methods for treating or preventing a proliferative retinopathy, such as one related to PVR (e.g., treating or preventing an ocular manifestation of a proliferative retinopathy), such as proliferative diabetic retinopathy, sickle cell retinopathy, post traumatic retinopathy, hyperviscosity syndromes, Aortic arch syndromes, ocular ischemic syndromes, carotid-cavernous fistula, multiple sclerosis, retinal vasculitis, systemic lupus erythematosus, arteriolitis with SS-A autoantibody, acute multifocal hemorrhagic vasculitis, vasculitis resulting from infection, vasculitis resulting from Behcet's disease, sarcoidosis, coagulopathies, sickling hemoglobinopathies, AC and C-β thalassemia, small vessel hyalinosis, incontinentia pigmenti, Eales' disease, branch retinal artery or vein occlusion, frosted branch angiitis, idiopathic retinal vasculitis, aneurysms, neuroretinitis, retinal embolization, retinopathy of prematurity, Uveitis, pars planitis, acute retinal necrosis, birdshot retinochoroidopathy, long-standing retinal detachment, choroidal melanoma, radiation retinopathy, familial exudative vitreoretinopathy, inherited retinal venous beading, retinoschisis, retinitis pigmentosa, or autosomal dominant vitreoretinochoroidopathy.

Another aspect of the invention is methods for treating or preventing a disease or condition that is a cause that results in proliferative retinopathy or PVR. In one embodiment, post-retinal detachment (e.g., that causes or results in PVR) is treated or prevented. In another embodiment, proliferative diabetic retinopathy (e.g., that causes or results in PVR) or sickle-cell retinopathy (e.g., that causes or results in PVR), as well as scarring caused by one or more of these disorders is treated or prevented.

Treatment or Prevention of Glaucoma

In one embodiment, the opthalmological disease or disorder is glaucoma. In one embodiment the glaucoma is open angle glaucoma, primary open angle glaucoma, secondary open angle glaucoma, closed angle glaucoma, glaucoma that is associated with diabetes, glaucoma that is associated with diabetic retinopathy, angle closure glaucoma, narrow angle glaucoma or acute glaucoma.

Treatment or Prevention of a Neoplasm

In one embodiment, the ophthalmological disease or disorder is a neoplasm. Examples of neoplams include an eyelid tumor, a conjunctival tumor, a choroidal tumor, an iris tumor, an optic nerve tumor, a retinal tumor, an infiltrative intraocular tumor or an orbital tumor. Examples of an eyelid tumor include basal cell carcinoma, squamous carcinoma, sebaceous carcinoma, malignant melanoma, capillary hemangioma, hydrocystoma, nevus or seborrheic keratosis. Examples of a conjunctival tumor include conjunctival Kaposi's sarcoma, squamous carcinoma, intraepithelial neoplasia of the conjunctiva, epibular dermoid, lymphoma of the conjunctiva, melanoma, pingueculum, or pterygium. Examples of a choroidal tumor include choroidal nevus, choroidal hemangioma, metastatic choroidal tumor, choroidal osteoma, choroidal melanoma, ciliary body melanoma or nevus of Ota. Examples of an iris tumor include anterior uveal metastasis, iris cyst, iris melanocytoma, iris melanoma, or pearl cyst of the iris. Examples of an optic nerve tumor include optic nerve melanocytoma, optic nerve sheath meningioma, choroidal melanoma affecting the optic nerve, or circumpapillary metastasis with optic neuropathy. Examples of a retinal tumor include retinal pigment epithelial (RPE) hypertrophy, RPE adenoma, RPE carcinoma, retinoblastoma, or hamartoma of the RPE. In some embodiments, the present invention provides methods for inhibiting retinal pigment epithelium (RPE) or glial cells, such as inhibiting the migration of RPE or glial cells. Examples of an infiltrative intraocular tumor include chronic lymphocytic leukemia, infiltrative choroidopathy, or intraocular lymphoma. Examples of an orbital tumor include adenoid cystic carcinoma of the lacrimal gland, cavernous hemangioma of the orbit, lymphangioma of the orbit, orbital mucocele, orbital pseudotumor, orbital rhabdomyosarcoma, periocular hemangioma of childhood, or sclerosing orbital psuedotumor.

Another aspect of the invention is methods for treating or preventing von Hippel-Lindau (VHL) disease (e.g., treating or preventing visual loss associated VHL disease). In some embodiments, VHL disease is characterized by tumors. The tumors may be malignant or benign. In another embodiment, a benign or malignant tumor in the eye (e.g., ocular tumor) or a cyst (e.g., an ocular cyst), associated with VHL is treated or prevented. In some embodiments, the tumors are hemangioblastomas. In some embodiments, the tumors are von Hippel angioma or retinal capillary hemangiomas (e.g., juxtapapillary hemangioma).

In some embodiments, the subject with VHL disease has a deficiency of the protein "pVHL."

In some embodiments, the VHL disease is severe (e.g., a subject with severe VHL disease has a lesion that cannot be effectively treated with a non-pharmacologic modality (e.g., laser or or cryotherapy), for example, as the lesion resides over or adjacent to a significant neural structure (e.g., optic nerve, macula, papillomacular bundle) that can be damaged with laser or cryotherapy).

In some embodiments, the methods for treating or preventing VHL disease comprise treating an ocular or non-ocular manifestation (e.g., benign or malignant neoplasm or cyst of the kidney, adrenal gland, pancreas, brain, spinal cord, inner ear, epididymis, or broad ligament) of VHL.

In some embodiments, the subjected being treated has a family history of VHL disease or one or more of retinal capillary hemangioma (RCH), spinal or cerebellar hemangioblastoma, pheochromocytoma, multiple pancreatic cysts, epididymal or broad ligament cystadenoma, multiple renal cysts, and renal cell carcinoma. In some embodiments, the subject has one or more RCH, spinal and cerebellar hemangioblastoma, pheochromocytoma, multiple pancreatic cysts, epididymal or broad ligament cystadenomas, multiple renal cysts, or renal cell carcinoma before the age of 60 years. In some embodiments, the subject has two or more hemangioblastomas of the retina or brain or a single hemangioblastoma in association with a visceral manifestation, such as kidney or pancreatic cysts; renal cell carcinoma; adrenal or extra-adrenal pheochromocytomas; endolymphatic sac tumors; papillary cystadenomas of the epididymis or broad ligament; or neuroendocrine tumors of the pancreas. In some embodiments, the subject has a disease-causing germline mutation in the VHL gene.

In some embodiments, the subject has RCH that exhibit activity, such as associated intra- or sub-retinal exudation or lipid deposition (which may reflect ongoing vascular incompetence and is not reflective of residual changes following previous treatment or secondary to coexistent retinal traction); increased size of the tumor compared to a previous time point as assessed by fundus photography or fluorescein angiography (FA); associated intra-, sub-, or pre-retinal hemorrhage not secondary to previous treatment, as assessed by fundus photography or FA; appearance of new feeder vessels or greater dilation or tortuosity of existing feeder vessels compared to a previous time point; and/or vitreous cell or haze indicative of vitreous exudation, in the absence of other ocular features potentially responsible for such findings. In some embodiments, the subject has RCH that is not readily treatable using cryotherapy or thermal laser because of its size, posterior location, poor previous response to conventional therapy, or other factors.

In some embodiments, methods or compositions of the invention are used to treat or prevent a complication of VHL, visual dysfunction (e.g., from VHL), or a fibrous complication of VHL (e.g., fibrous meningioma). In certain embodiments, the methods or compositions of the present invention are used to treat a manifestation of VHL as vascular proliferation that comprises fine, superficial, juxtapapillary vessels that are often associated with fibrovascular proliferation and epiretinal membrane formation.

Treatment or Prevention of Scarring or Fibrosis

Another aspect the invention provides methods for treating, inhibiting or preventing scarring or fibrosis (e.g., scarring or fibrosis is under the macular region of the retina). In some embodiments, the scarring is a fibrovascular scar (e.g., in the retina). In some embodiments, the fibrosis is hepatic, pulmonary or renal fibrosis. In some embodiments, the fibrosis is ocular fibrosis. In some embodiments, the fibrosis is sub-retinal fibrosis (e.g., associated with neovascular AMD). In some embodiments, the sub-retinal fibrosis is not associated with neovascular AMD. In some embodiments, the fibrosis is subfoveal fibrosis. In some embodiments, the subfoveal fibrosis is with retinal atrophy. In some embodiments, subfoveal fibrosis or sub-retinal fibrosis develops after administration of a VEGF antagonist, e.g., anti-VEGF monotherapy.

In some embodiments, the scarring results from glaucoma surgery, or follows glaucoma surgery, such as trabeculectomy, filtering surgery (such as partial thickness filtering surgery), glaucoma filtering procedures, minimally invasive glaucoma surgery, glaucoma valve implant surgery, glaucoma seton surgery, glaucoma tube shunt placement, glaucoma stent placement, or combined cataract and glaucoma surgery. In some embodiments, the methods of the present invention are useful to treat or prevent scarring relating to or resulting from glaucoma surgery (e.g., that can result in scar related proliferation). In some embodiments, the scarring is sub-retinal scarring. In some embodiments, the scarring is sub-retinal scarring that occurs following choroidal neovascular regression.

In particular embodiments, methods for treating, inhibiting or preventing sub-retinal fibrosis (e.g., reducing the formation of sub-retinal fibrosis) comprise administering to a subject in need thereof an effective amount of Antagonist A or another pharmaceutically acceptable salt thereof and a VEGF antagonist. In some embodiments, the subject has or is diagnosed with AMD (e.g., wet AMD). In some embodiments, the subject has or is diagnosed with advanced wet AMD.

Treatment or Prevention of Other Ophthalmological Diseases and Disorders

In certain embodiments, the ophthalmological disease or disorder is a cataract (e.g., age-related cataract), diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal sub-retinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment).

In other embodiments, the ophthalmological disease or disorder is sickle cell disease (SCD), anemia, or sickle cell retinopathy (e.g., non-neovascular or non-proliferative ocular manifestations). In some embodiments, vaso-occlusive phenomena or hemolysis associated with SCD is treated or prevented. In some embodiments, ocular manifestations of SCD include vascular occlusions in the conjunctiva, iris, retina, or choroid. Non-neovascular or non-proliferative ocular manifestations can include conjunctival vascular occlusions which transform smooth vessels into comma-shaped fragments, iris atrophy, retinal "salmon patch" hemorrhages, retinal pigmentary changes and other abnormalities of the retinal vasculature, macula, choroid, and optic disc. In some embodiments, neovascularization or the proliferative ocular manifestation involves the growth of abnormal vascular fronds which can lead to vitreous hemorrhage, retinal detachment, epiretinal membranes, resulting in vision loss. In some embodiments, the methods further comprise performing another treatment, such as diathermy, cryotherapy, laser photocoagulation or surgery (e.g., vitrectomy).

In one embodiment, the ophthalmological disease or disorder is a condition associated with peripheral retinal neovascularization. Examples of conditions associated with peripheral retinal neovascularization include ischemic vascular disease, inflammatory disease with possible ischemia, incontinentia pigmenti, retinitis pigmentosa, retinoschisis or chronic retinal detachment.

Examples of ischemic vascular disease include proliferative diabetic retinopathy, branch retinal vein occlusion, branch retinal arteriolar occlusion, carotid cavernous fistula, sickling hemoglobinopathy, non-sickling hemoglobinopathy, IRVAN syndrome (retinal vasculitic disorder characterized by idiopathic retinal vasculitis, an aneurysm, and neuroretinitis), retinal embolization, retinopathy of prematurity, familial exudative vitreoretinopathy, hyperviscosity syndrome, aortic arch syndrome or Eales disease. Examples of sickling hemoglobinopathy include SS hemoglobinopathy and SC hemoglobinopathy. Examples of non-sickling hemoglobinopathy include AC hemoglobinopathy and AS hemoglobinopathy. Examples of hyperviscosity syndrome include leukemia, Waldenstrom macroglobulinemia, multiple myeloma, polycythemia or myeloproliferative disorder.

In some embodiments, treating or preventing an inflammatory disease with possible ischemia encompasses treating or preventing retinal vasculitis associated with systemic disease, retinal vasculitis associated with an infectious agent, uveitis or birdshot retinopathy. Examples of systemic diseases include systemic lupus erythematosis, Behcet's disease, inflammatory bowel disease, sarcoidosis, multiple sclerosis, Wegener's granulomatosis and polyarteritis *nodosa*. Examples of infectious agents include a bacterial agent that is the causative agent for syphilis, tuberculosis, Lyme disease or cat-scratch disease, a virus such as herpesvirus, or a parasite such as *Toxocara canis* or *Toxoplasma gondii*. Examples of uveitis include pars planitis or Fuchs uveitis syndrome.

Compositions for Therapeutic or Prophylactic Administration

Antagonist A or another pharmaceutically acceptable salt thereof, VEGF antagonists, or anti-C5 agents can be administered as a component of a composition that further comprises a pharmaceutically acceptable carrier or vehicle, e.g., a pharmaceutical composition. In certain embodiments, each therapeutic agent is administered to the subject in a separate composition. However, in other embodiments, two or more therapeutic agents may be administered to the subject in the same composition. In one embodiment, a composition of the invention comprises an effective amount of Antagonist A or another pharmaceutically acceptable salt thereof, a VEGF antagonist, and/or an anti-C5 agent and a pharmaceutically acceptable carrier or vehicle. In another embodiment, a composition comprising Antagonist A or another pharmaceutically acceptable salt thereof and another composition comprising a VEGF antagonist are administered. In some embodiments, another composition comprising an anti-C5 agent is administered. In some embodiments, a composition comprising Antagonist A or another pharmaceutically acceptable salt thereof and a VEGF antagonist is administered. In some embodiments, another composition comprising an anti-C5 agent is also administered.

Administration of each antagonist may be by any suitable means that results in an amount of Antagonist A or another pharmaceutically acceptable salt thereof, VEGF antagonist, and/or anti-C5 agent that is effective for the treatment or prevention of an ophthalmological disease or disorder. Each antagonist, for example, can be admixed with a suitable carrier substance, and is generally present in an amount of 1-95% by weight of the total weight of the composition. The composition may be provided in a dosage form that is suitable for ophthalmic, oral, parenteral (e.g., intravenous, intramuscular, subcutaneous), rectal, transdermal, nasal, or inhalant administration. In one embodiment, the composition is in a form that is suitable for injection directly in the eye. The composition may be in form of, e.g., tablets, capsules, pills, powders, granulates, suspensions, emulsions, solutions, gels including hydrogels, pastes, ointments, creams, plasters, delivery devices, suppositories, enemas, injectables, implants, sprays, drops or aerosols. The compositions comprising one or more antagonists can be formulated according to conventional pharmaceutical practice (see, e.g., Remington: *The Science and Practice of Pharmacy*, (20th ed.) ed. A. R. Gennaro, 2000, Lippincott Williams & Wilkins, Philadelphia, Pa. and *Encyclopedia of Pharmaceutical Technology*, eds., J. Swarbrick and J. C. Boylan, 1988-2002, Marcel Dekker, New York).

The compositions are, in one useful aspect, administered parenterally (e.g., by intramuscular, intraperitoneal, intravenous, intraocular, intravitreal, retro-bulbar, subconjunctival, subtenon or subcutaneous injection or implant) or systemically. Formulations for parenteral or systemic administration include sterile aqueous or non-aqueous solutions, suspensions, or emulsions. A variety of aqueous carriers can be used, e.g., water, buffered water, saline, and the like. Examples of other suitable vehicles include polypropylene glycol, polyethylene glycol, vegetable oils, gelatin, hydrogels, hydrogenated naphalenes, and injectable organic esters, such as ethyl oleate. Such formulations may also contain auxiliary substances, such as preserving, wetting, buffering, emulsifying, and/or dispersing agents. Biocompatible, biodegradable lactide polymer, lactide/glycolide copolymer, or polyoxyethylene-polyoxypropylene copolymers may be used to control the release of the active ingredients.

Alternatively, the compositions can be administered by oral ingestion. Compositions intended for oral use can be prepared in solid or liquid forms, according to any method known to the art for the manufacture of pharmaceutical compositions.

Solid dosage forms for oral administration include capsules, tablets, pills, powders, and granules. Generally, these pharmaceutical preparations contain active ingredients admixed with non-toxic pharmaceutically acceptable excipients. These include, for example, inert diluents, such as calcium carbonate, sodium carbonate, lactose, sucrose, glucose, mannitol, cellulose, starch, calcium phosphate, sodium phosphate, kaolin and the like. Binding agents, buffering agents, and/or lubricating agents (e.g., magnesium stearate) may also be used. Tablets and pills can additionally be prepared with enteric coatings. The compositions may optionally contain sweetening, flavoring, coloring, perfuming, and preserving agents in order to provide a more palatable preparation.

Compositions useful for ophthalmic use include tablets comprising one or more antagonists in admixture with a pharmaceutically acceptable excipient. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The antagonists of the present invention may be admixed in a tablet or other vehicle, or may be partitioned. In one example, one antagonist is contained on the inside of the tablet, and the other antagonist is on the outside, such that a substantial portion of the other antagonist is released prior to the release of the contained antagonist. If desired, antagonists in a tablet form may be administered using a drug delivery device (see below).

For example, compositions of the present invention may be administered intraocularly by intravitreal injection into the eye as well as by subconjunctival and subtenon injections. Other routes of administration include transcleral, retrobulbar, intraperitoneal, intramuscular, and intravenous. Alternatively, compositions can be administered using a drug delivery device or an intraocular implant (see below).

In one embodiment, Antagonist A or another pharmaceutically acceptable salt thereof or VEGF antagonist (e.g., ranibizumab, bevacizumab, aflibercept, pegaptanib sodium, or ESBA1008) is administered intravitreally with a 30-gauge or 27-gauge needle. In some embodiments, a 0.5 inch needle is used. In one embodiment, Antagonist A or another pharmaceutically acceptable salt thereof is administered intravitreally with a 30-gauge 0.5 inch needle and a VEGF antagonist (e.g., ranibizumab, bevacizumab, aflibercept, pegaptanib sodium, or ESBA1008) is administered intravitreally with a 27-gauge needle. In some embodiments, 50 μL (1.5 mg in 0.05 mL) of Antagonist A or another pharmaceutically acceptable salt thereof is administered intravitreally with a 30-gauge 0.5 inch needle and 50 μL of a VEGF antagonist (e.g., 0.5 mg of ranibizumab, 1.25 mg of bevacizuamb, or 2.0 mg of aflibercept) is administered intravitreally with a 27-gauge needle.

Liquid dosage forms for oral administration can include pharmaceutically acceptable emulsions, solutions, suspensions, syrups, and soft gelatin capsules. These forms can contain inert diluents commonly used in the art, such as water or an oil medium, and can also include adjuvants, such as wetting agents, emulsifying agents, and suspending agents.

In some instances, the compositions can also be administered topically, for example, by patch or by direct application to a region, such as the epidermis or the eye, susceptible to or affected by a neovascular disorder, or by iontophoresis.

In one embodiment, the compositions can comprise one or more pharmaceutically acceptable excipients. In one embodiment, excipients for compositions that comprise an antagonist include, but are not limited to, buffering agents, nonionic surfactants, preservatives, tonicity agents, sugars, amino acids, and pH-adjusting agents. Suitable buffering agents include, but are not limited to, monobasic sodium phosphate, dibasic sodium phosphate, and sodium acetate. Suitable nonionic surfactants include, but are not limited to, polyoxyethylene sorbitan fatty acid esters such as polysorbate 20 and polysorbate 80. Suitable preservatives include, but are not limited to, benzyl alcohol. Suitable tonicity agents include, but are not limited to sodium chloride, mannitol, and sorbitol. Suitable sugars include, but are not limited to, α,α-trehalose. Suitable amino acids include, but are not limited to glycine and histidine. Suitable pH-adjusting agents include, but are not limited to, hydrochloric acid, acetic acid, and sodium hydroxide. In one embodiment, the pH-adjusting agent or agents are present in an amount effective to provide a pH of about 3 to about 8, about 4 to about 7, about 5 to about 6, about 6 to about 7, or about 7 to about 7.5. In one embodiment, the compositions do not comprise a preservative. In another embodiment, the composition does not comprise an antimicrobial agent. In another embodiment, the composition does not comprise a bacteriostat. Suitable excipients for a VEGF antagonist also include those described in U.S. Pat. No. 7,365,166, the contents of which are herein incorporated by reference in their entirety.

In one embodiment, the composition is in the form of an aqueous solution that is suitable for injection. In one embodiment, a composition is in the form of an aqueous solution that is suitable for injection. In one embodiment, a composition comprises Antagonist A or another pharmaceutically acceptable salt thereof, a buffering agent, a pH-adjusting agent, and water for injection. In another embodiment, a composition comprises Antagonist A or another pharmaceutically acceptable salt thereof, monobasic sodium phosphate, dibasic sodium phosphate, sodium chloride, hydrochloride acid, and sodium hydroxide.

In one embodiment, the composition comprises a VEGF antagonist, a buffering agent, a sugar, a nonionic surfactant, and water for injection. In another embodiment, the composition comprises a VEGF antagonist, monobasic sodium phosphate, dibasic sodium phosphate, α,α-trehalose dehydrate, and polysorbate 20. In one embodiment, the composition comprises a VEGF antagonist, a buffering agent, a pH-adjusting agent, a tonicity agent, and water that is suitable for injection. In another embodiment, the composition comprises a VEGF antagonist, monobasic sodium phosphate, dibasic sodium phosphate, sodium chloride, hydrochloric acid, and sodium hydroxide. In one embodiment, the VEGF antagonist is a pegylated anti-VEGF aptamer, e.g., pegaptanib sodium In another embodiment, the VEGF antagonist is ranibizumab, bevacizumab, aflibercept or ESBA1008. This invention provides the pharmaceutically acceptable salts of the antagonists. An antagonist of the present invention can possess a sufficiently basic functional group, which can react with any of a number of inorganic and organic acids, to form a pharmaceutically acceptable salt. A pharmaceutically-acceptable acid addition salt is formed from a pharmaceutically-acceptable acid, as is well known in the art. Such salts include the pharmaceutically acceptable salts listed in Journal of Pharmaceutical Science, 66, 2-19 (1977) and The Handbook of Pharmaceutical Salts; Properties, Selection, and Use. P. H. Stahl and C. G. Wermuth (ED.s), Verlag, Zurich (Switzerland) 2002, which are hereby incorporated by reference in their entirety.

Examples of a pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts. The term "pharmaceutically acceptable salt" includes a hydrate of a compound of the invention and also refers to a salt of an antagonist of the present invention having an acidic functional group, such as a carboxylic acid functional group or a hydrogen phosphate functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. In one embodiment, the pharmaceutically acceptable salt is a sodium salt. In another embodiment, the pharmaceutically acceptable salt is a persodium salt.

The present invention further provides comprising Antagonist A or another pharmaceutically acceptable salt thereof. In one embodiment, the present compositions comprise about 30.0 mg of Antagonist A or another pharmaceutically acceptable salt thereof, about 0.3 mg of monobasic sodium phosphate monohydrate, about 2.1 mg of dibasic sodium phosphate heptahydrate and about 9.0 mg of sodium chloride per about 1 mL. In some embodiments, hydrochloric acid and/or sodium hydroxide are present as needed to adjust the pH of the composition. In some embodiments, the pH is about pH 5.5 to about pH 7.5 or about pH 6.0.

In some embodiments, the compositions comprise about 3% (w/v) of Antagonist A or another pharmaceutically acceptable salt thereof, about 0.03% (w/v) of monobasic sodium phosphate monohydrate, about 0.2% (w/v) of dibasic sodium phosphate heptahydrate, about 0.9% (w/v) of sodium chloride and about 95.9% (w/v) of water. In some embodiments, hydrochloric acid and/or sodium hydroxide are present as needed to adjust the pH of the composition. In some embodiments, the pH is about pH 5.5 to about pH 7.5 or about pH 6.0.

In certain embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is about 0.002 mg/mL to about 50 mg/mL. In some embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is less than or about 100 mg/mL, less than about 50 mg/mL, less than about 40 mg/mL, less than about 30 mg/mL, less than about 25 mg/mL, less than about 20 mg/mL, less than about 15 mg/mL, less than about 10 mg/mL, or less than about 5 mg/mL. In certain embodiments, the concentration of Antagonist A or another pharmaceutically acceptable salt thereof, a VEGF antagonist (e.g., ranibizumab, bevacizumab, aflibercept, ESBA1008 or pegaptanib sodium), and/or an anti-C5 agent (e.g., ARC1905 or a pharmaceutically acceptable salt thereof) in a composition is about 0.3 mg/mL to about 100 mg/mL, about 0.3 mg/mL to about 50 mg/mL, about 0.3 mg/mL to about 40 mg/mL, about 0.3 mg/mL to about 30 mg/mL, about 0.3 to about 25 mg/mL, about 0.3 mg/mL to about 20 mg/mL, about 0.3 mg/mL to about 15 mg/mL, about 0.3 mg/mL to about 10 mg/mL, about 1 mg/mL to about 100 mg/mL, about 1 mg/mL to about 50 mg/mL, about 1 mg/mL to about 40 mg/mL, about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 5 mg/mL, about 5 mg/mL to about 100 mg/mL, or about 5 mg/mL to about 50 mg/mL.

In certain embodiments, methods of the invention comprise administering Antagonist A and optionally one or both of a VEGF antagonist and an anti-C5 agent as a component of a pharmaceutical composition. In one embodiment, the present invention provides compositions comprising an effective amount of: (a) Antagonist A or another pharmaceutically acceptable salt thereof; and (b) a VEGF antagonist or a pharmaceutically acceptable salt thereof. In certain embodiments, the compositions further comprise an effective amount of an anti-C5 agent or a pharmaceutically acceptable salt thereof. In some embodiments, the compositions stabilize one or more of the Antagonist A or another pharmaceutically acceptable salt thereof, the VEGF antagonist, and the anti-C5 agent. In certain embodiments, the Antagonist A or another pharmaceutically acceptable salt thereof, the VEGF antagonist and/or the anti-C5 agent does not adversely affect the activity of the other active agent(s) present in the composition. In particular embodiments, at least about 90% of one or more of the active agents in the composition, e.g., Antagonist A or another pharmaceutically acceptable salt thereof, VEGF antagonist, or anti-C5 agent, is chemically stable when the composition is stored at a temperature of from about 2.0° C. to about 8.0° C. for at least about twelve weeks.

In particular embodiments, Antagonist A or another pharmaceutically acceptable salt thereof, the VEGF antagonist or the anti-C5 agent is chemically stable when it shows no sign of decomposition or modification resulting in formation of a new chemical entity. In particular embodiments, Antagonist A or another pharmaceutically acceptable salt thereof, the VEGF antagonist or the anti-C5 agent is chemically stable when at least about 50%, at least about 60%, at least about 70%, at least about 80%, at least about 90%, a least about 95%, or at least about 99% of Antagonist A or another pharmaceutically acceptable salt thereof, the VEGF antagonist or the anti-C5 agent shows no sign of decomposition or modification resulting in formation of a new chemical entity, e.g., when stored at a temperature of from about 2.0° C. to about 8.0° C. for at least about twelve weeks.

In certain embodiments, the Antagonist A or another pharmaceutically acceptable salt thereof does not adversely affect the activity of the VEGF antagonist (e.g., ranibizumab, bevacizumab, aflibercept, pegaptanib sodium, or ESBA1008) or the ARC1905 or a pharmaceutically acceptable salt thereof. In certain embodiments, the VEGF antagonist (e.g., ranibizumab, bevacizumab, aflibercept, pegaptanib sodium, or ESBA1008) does not adversely affect the activity of the Antagonist A or another pharmaceutically acceptable salt thereof, or ARC1905 or a pharmaceutically acceptable salt thereof. In certain embodiments, ARC1905 or a pharmaceutically acceptable salt thereof does not adversely affect the activity of the Antagonist A or another pharmaceutically acceptable salt thereof, or the VEGF antagonist (e.g., ranibizumab, bevacizumab, aflibercept, pegaptanib sodium, or ESBA1008).

In particular embodiments, the compositions comprise Antagonist A or another pharmaceutically acceptable salt thereof; and ranibizumab, bevacizumab, aflibercept, pegaptanib sodium or ESBA1008, or a pharmaceutically acceptable salt thereof, and the compositions are physically or chemically stable with respect to both active agents at a particular pH or suitable for parenteral administration. In particular embodiments, the compositions comprise Antagonist A or another pharmaceutically acceptable salt thereof; ranibizumab, bevacizumab, aflibercept, pegaptanib sodium or ESBA1008 or a pharmaceutically acceptable salt thereof; and ARC1905 or a pharmaceutically acceptable salt thereof, and the compositions are physically or chemically stable with respect to all active agents at a particular pH or suitable for parenteral administration. In particular embodiments, a composition is physically stable if at least about 50%, at least about 60%, at least about 70%, at least about 80%, at least about 90%, at least about 95%, or at least about 99% of all active agents, i.e., the Antagonist A or another pharmaceutically acceptable salt thereof, the VEGF antagonist, and the anti-C5 agent (when present) present in the composition show no sign of aggregation, precipitation or denaturation upon visual examination of color or clarity, or as measured by UV light scattering or by size exclusion chromatography (SEC) or differential scanning calorimetry (DSC).

In particular embodiments, the compositions of the invention are considered physically stable if after storage the average number of particles detected does not exceed about 50 particles/mL, where the particles have a diameter >about 10 μm and does not exceed 5 particles/mL, where the particles have a diameter >25 μm, as measured by the Light Obscuration Particle Count Test described in (788) *Particulate Matter in Injections*, Revised Bulletin, Official Oct. 1, 2011, The United States Pharmacopeial Convention.

In particular embodiments, the compositions are considered physically stable if after storage the average number of particles detected does not exceed 50 particles/mL, where the particles have a diameter >10 μm; does not exceed 5 particles/mL, where the particles have a diameter >25 μm; and does not exceed 2 particles/mL, where the particles have a diameter >50 μm, as measured by the microscopic method particle count test described in (788) *Particulate Matter in Injections*, Revised Bulletin, Official Oct. 1, 2011, The United States Pharmacopeial Convention.

In particular embodiments, the compositions comprise Antagonist A or another pharmaceutically acceptable salt thereof, a VEGF antagonist (e.g., ranibizumab, bevacizumab, aflibercept, ESBA1008 or pegaptanib sodium) and, optionally, an anti-C5 agent (e.g., ARC1905 or a pharmaceutically acceptable salt thereof) and are chemically stable for at least eight weeks or at least twelve weeks at 25° C. or for at least twelve weeks or at least sixteen weeks or at least 24 weeks at 4° C. In particular embodiments, at least 80% of each of Antagonist A or another pharmaceutically acceptable salt thereof, VEGF antagonist, and anti-C5 agent (if present) show no sign of decomposition or modification resulting in formation of a new chemical entity under at least one of these conditions.

In particular embodiments, compositions comprise the following: (1) Antagonist A or another pharmaceutically acceptable salt thereof; (2) a VEGF antagonist; optionally, (3) an anti-C5 agent; (4) a buffer; optionally, (5) a tonicity modifier; and, optionally, (6) a surfactant. In specific embodiments of such compositions, the buffer is an acetate, phosphate, Tris or histidine buffer, or a mixture thereof; the tonicity modifier is sodium chloride, mannitol, sorbitol, or trehalose, or a mixture thereof; and the surfactant is polysorbate 20. In various embodiments, Antagonist A or another pharmaceutically acceptable salt thereof is present in compositions of the invention at a concentration of about 0.1 mg/mL to about 200 mg/mL; and the VEGF antagonist is present at a concentration of about 0.1 mg/mL to about 200 mg/mL. When present, the anti-C5 agent is present at a concentration of about 0.1 mg/mL to about 200 mg/mL. The buffer is present at a concentration of about 1 mM to about 200 mM; the tonicity modifier is present at a concentration of about 10 mM to about 200 mM (sodium chloride), about 1% to about 10% (w/v) (sorbitol), or about 1% to about 20% (w/v) (trehalose); and the surfactant, when present, is present at a concentration of about 0.005% to about 0.05% or a concentration of about 0.001% to about 0.05%.

In particular embodiments, the ratio of the concentration (mass of Antagonist A or another pharmaceutically acceptable salt thereof less that of its —R group/volume of composition) of Antagonist A or another pharmaceutically acceptable salt thereof to the concentration (mass/volume of composition) of the VEGF antagonist (e.g., ranibizumab, bevacizumab, aflibercept, pegaptanib sodium, or ESBA1008), ARC1905, or a pharmaceutically acceptable salt thereof, present in the composition is less than, or less than or equal to, 25.0, less than, or less than or equal to, 10.0, less than, or less than or equal to, 9.0, less than, or less than or equal to, 8.0, less than, or less than or equal to, 7.0, less than, or less than or equal to, 6.0, less than, or less than or equal to, 5.0, less than, or less than or equal to, 4.0, less than, or less than or equal to, 3.0, less than, or less than or equal to, 2.0 or less than, or less than or equal to, 1.0. Antagonist A's —R group is depicted in FIG. 1. In particular embodiments, the ratio of the concentration (mass of Antagonist A or another pharmaceutically acceptable salt thereof less that of its —R group/volume of composition) of Antagonist A or another pharmaceutically acceptable salt thereof to the concentration (mass/volume of composition) of the VEGF antagonist (e.g., ranibizumab, bevacizumab, aflibercept, pegaptanib sodium, or ESBA1008), ARC1905, or a pharmaceutically acceptable salt thereof, present in the composition is in the range of about 1 to about 10, about 2 to about 5, about 3 about 4, or about 5. In certain embodiments, the compositions comprise Antagonist A or another pharmaceutically acceptable salt thereof, a VEGF antagonist (e.g., ranibizumab, bevacizumab, aflibercept, pegaptanib sodium, or ESBA1008), and ARC1905 or a pharmaceutically acceptable salt thereof.

In one particular embodiment, the compositions comprise Antagonist A or another pharmaceutically acceptable salt thereof, a VEGF antagonist (e.g., ranibizumab, bevacizumab, aflibercept, ESBA1008, or pegaptanib sodium), and, optionally, an anti-C5 agent (e.g., ARC1905 or a pharmaceutically acceptable salt thereof), wherein the ratio of the concentration of PDGF antagonist to the concentration of VEGF antagonist (and/or anti-C5 agent) is less than 2; and the compositions further comprise sodium chloride at a concentration of about 10 mM to about 200 mM, histidine at a concentration of about 1 mM to about 100 mM, and polysorbate (e.g., polysorbate 20) at a concentration of about 0.005% to about 0.05%, where the pH of the composition is about 5.5 to about 7.0.

In certain embodiments, the compositions comprise one or more of a tonicity modifier, a surfactant, and a buffer suitable to achieve or maintain the particular pH or be suitable for parenteral administration. Appropriate buffers include those described herein as well as others known in the art, such as, e.g., Good's buffers, e.g., IVIES.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a tonicity modifier that is sorbitol or sodium chloride, or mixtures thereof. In certain embodiments, the compositions further comprise an anti-C5 agent (e.g., ARC1905 or a pharmaceutically acceptable salt thereof). In particular embodiments, the tonicity modifier is sorbitol, and the pH of the composition is about 5.0 to about 8.0, about 5.0 to about 7.0, about 6.0 or about 7.0. In particular embodiments, the tonicity modifier is sodium chloride, and the pH of the composition is about 5.0 to about 8.0, about 5.0 to about 7.0, about 5.5 to about 7.5, about 6.0 to about 8.0, about 8.0, about 7.0, or about 6.0. In certain embodiments, the tonicity modifier is sorbitol at about 1% to about 10% (w/v), or about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). In particular embodiments, the tonicity modifier is sodium chloride at a concentration of about 10 mM to about 200 mM, about 50 mM to 200 mM, about 75 mM to about 200 mM, about 50 mM to about 150 mM, about 100 mM, about 110 mM, about 120 mM, about 130 mM about 140 mM or about 150 mM. In one embodiment, the tonicity modifier is sodium chloride at a concentration of about 130 mM. In other embodiments, the tonicity modifier is sodium chloride at a concentration of about 75 mM or about 120 mM. With respect to tonicity modifier concentration, "mM" refers to milimoles of the tonicity modifier per liter of composition.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a buffer capable of achieving or maintaining the pH of the composition within a desired range. In certain embodiments, the compositions further comprise an anti-C5 agent (e.g., ARC1905 or a pharmaceutically acceptable salt thereof). In certain embodiments, the compositions comprise histidine (e.g., L-histidine or a pharmaceutically acceptable salt thereof) or phosphate as a buffer, e.g., sodium phosphate, potassium phosphate, or both. In certain embodiments, the buffer is present at a concentration of about 1 mM to about 200 mM, about 1 mM to about 150 mM, about 1 mM to about 20 mM, about 1 mM to about 10 mM, about 2 mM to about 100 mM, about 2 mM to about 20 mM, about 5 mM to about 20 mM, or about 10 mM. In particular embodiments, the pH of the buffered composition is about 5.0 to about 8.0, about 5.0 to about 7.0, about 5.5 to about 7.5, about 5.5 to about 7.0, or about 6.0. In one embodiment, the buffered composition has a pH of about 5.5 to about 7.0. In certain embodiments, the buffer comprises histidine at a concentration of about 1 mM to about 200 mM, about 1 mM to about 150 mM, about 2 mM to about 100 mM, about 5 mM to about 20 mM, or about 10 mM, and the buffered composition has a pH of about 5.5 to about 7.0, or about 6.0. In one particular embodiment, the buffer comprises histidine at a concentration of about 10 mM and the pH of the histidine-buffered composition is about 6.0. With respect to buffer concentration, "mM" refers to millimoles of buffer (e.g., histidine) per liter of composition.

In certain embodiments, the compositions comprise Antagonist A or another pharmaceutically acceptable salt thereof, a VEGF antagonist (e.g., ranibizumab, bevacizumab, aflibercept, ESBA1008 or pegaptanib sodium), and a buffer that comprises phosphate, alone or in combination with histidine. In certain embodiments, the compositions further comprise an anti-C5 agent (e.g., ARC1905 or a pharmaceutically acceptable salt thereof). The phosphate buffer may be, e.g., a sodium phosphate or potassium phosphate buffer. In certain embodiments, the buffer comprises phosphate at a concentration of about 1 mM to about 200 mM, about 1 mM to about 50 mM, about 2 mM to about 200 mM, about 2 mM to about 50 mM, about 5 mM to about 200 mM, about 5 mM to about 100 mM, about 5 mM to about 50 mM, about 10 mM to about 150 mM, about 10 mM to about 100 mM, about 5 mM, about 10 mM, about 25 mM, or about 50 mM. In particular embodiments, the pH of the buffered composition is about 5.0 to about 8.0, about 6.0 to about 8.0, about 5.5 to about 7.5, about 5.5 to about 7.0, about 6.0, about 7.0, or about 8.0. In one embodiment, the buffer comprises phosphate, and the buffered composition has a pH of about 6.0 to about 8.0. In certain embodiments, the buffer comprises phosphate at a concentration of about 5 mM to about 200 mM, about 5 mM to about 150 mM, about 5 mM to about 100 mM, about 5 mM, about 8 mM, about 10 mM, about 25 mM, or about 50 mM, and the buffered composition has a pH of about 5.5 to about 7.5, about 5.5 to about 7.0, or about 6.0. In one particular embodiment, the buffer comprises phosphate at a concentration of about 10 mM, and the buffered composition has a pH of about 6.2.

In certain embodiments, the compositions comprise Antagonist A or another pharmaceutically acceptable salt thereof), a VEGF antagonist (e.g., ranibizumab, bevacizumab, aflibercept, ESBA1008 or pegaptanib sodium), and a surfactant. In certain embodiments, the compositions further comprise an anti-C5 agent (e.g., ARC1905 or a pharmaceutically acceptable salt thereof). In particular embodiments, the surfactant is polysorbate 20 at a concentration of about 0.001% (w/v) to about 0.05% (w/v), about 0.002% (w/v) to about 0.05% (w/v), about 0.005% (w/v) to about 0.05% (w/v), about 0.01% (w/v) to about 0.05% (w/v), or about 0.02% (w/v).

In one embodiment, the compositions comprise Antagonist A or another pharmaceutically acceptable salt thereof, a VEGF antagonist (e.g., ranibizumab, bevacizumab, aflibercept, ESBA1008 or pegaptanib sodium), histidine, and NaCl. In certain embodiments, the compositions further comprise an anti-C5 agent (e.g., ARC1905 or a pharmaceutically acceptable salt thereof). The composition may further comprise polysorbate.

In certain embodiments, the compositions comprise an effective amount of: (a) about 0.3 mg/mL to about 30 mg/mL of Antagonist A or another pharmaceutically acceptable salt thereof; (b) about 0.5 mg/mL to about 20 mg/mL of a VEGF antagonist (e.g., ranibizumab, bevacizumab, aflibercept, ESBA1008 or pegaptanib sodium); and one or both of: (c) a buffer capable of achieving or maintaining the pH of the compositions at about pH 5.0 to about pH 8.0; and (d) a tonicity modifier. In certain embodiments, the compositions further comprise (e) about 0.3 mg/mL to about 30 mg/mL of an anti-C5 agent (e.g., ARC1905 or a pharmaceutically acceptable salt thereof). In certain embodiments, the buffer is about 1 mM to about 20 mM L-histidine or about 1 mM to about 20 mM sodium phosphate, and the tonicity modifier is about 10 mM to about 200 mM NaCl, about 1% to about 20% (w/v) sorbitol, or about 1% to about 20% (w/v) trehalose. In particular embodiments, the compositions further comprise: (f) about 0.001% (w/v) to about 0.05% (w/v) surfactant.

In certain embodiments, the compositions comprise: (a) about 0.3 mg/mL to about 30 mg/mL of Antagonist A or another pharmaceutically acceptable salt thereof; and (b) about 0.5 mg/mL to about 20 mg/mL of a VEGF antagonist (e.g., ranibizumab, bevacizumab, aflibercept, ESBA1008 or pegaptanib sodium). In certain embodiments, the compositions further comprise (c) about 0.3 mg/mL to about 30 mg/mL of an anti-C5 agent (e.g., ARC1905 or a pharmaceutically acceptable salt thereof). In certain embodiments, any of these the compositions further comprise one or both of: (d) about 1 mM to about 20 mM L-histidine; and (e) about 10 mM to about 200 mM NaCl. In further embodiments, the compositions further comprise: (f) about 0.001% (w/v) to about 0.05% (w/v) surfactant, which is optionally polysorbate. In a particular embodiment, the compositions comprise: (a) about 0.3 mg/mL to about 30 mg/mL of Antagonist A or another pharmaceutically acceptable salt thereof; (b) about 0.5 mg/mL to about 20 mg/mL of a VEGF antagonist (e.g., ranibizumab, bevacizumab, aflibercept, ESBA1008 or pegaptanib sodium); (c) about 1 mM to about 20 mM L-histidine; and (d) about 10 mM to about 200 mM NaCl, wherein the pH of the compositions is about pH 5.0 to about pH 7.0. In certain embodiments, the compositions further comprise (e) about 0.3 mg/mL to about 30 mg/mL of an anti-C5 agent (e.g., ARC1905 or a pharmaceutically acceptable salt thereof). In certain embodiments, the compositions further comprise: (f) about 0.01% (w/v) polysorbate 20.

In certain embodiments, compositions comprise: (a) about 1.0 mg/mL to about 100 mg/mL, or about 5.0 mg/mL to about 50 mg/mL of Antagonist A or another pharmaceutically acceptable salt thereof); and (b) about 1.0 mg/mL to about 50 mg/mL of a VEGF antagonist (e.g., ranibizumab, bevacizumab, aflibercept, ESBA1008 or pegaptanib sodium). In certain embodiments, the compositions further comprise (c) about 1.0 mg/mL to about 100 mg/mL of an anti-C5 agent (e.g., ARC1905 or a pharmaceutically acceptable salt thereof). In other embodiments, any of the compositions further comprise one or both of (d) about 1 mM to about 20 mM L-histidine; and (e) about 10 mM to about 200 mM NaCl. In further embodiments, any of the compositions further comprise: (f) about 0.001% (w/v) to about 0.05% (w/v) surfactant, which is optionally polysorbate.

In certain embodiments, compositions comprise: (a) about 0.3 mg/mL to about 30 mg/mL of Antagonist A or another pharmaceutically acceptable salt thereof); (b) about 0.5 mg/mL to about 20 mg/mL of a VEGF antagonist (e.g., ranibizumab, bevacizumab, aflibercept, ESBA1008 or pegaptanib sodium); and one or both of (c) a buffer capable of achieving or maintaining the pH of the composition to about pH 5.0 to about pH 8.0; and (d) a tonicity modifier. In certain embodiments, the compositions further comprise about 0.3 mg/mL to about 30 mg/mL of an anti-C5 agent (e.g., ARC1905 or a pharmaceutically acceptable salt thereof). In particular embodiments, the buffer, where present, is about 1 mM to about 20 mM L-histidine or about 1 mM to about 20 mM sodium phosphate; and the tonicity modifier, where present, is about 10 mM to about 200 mM NaCl, about 1% to about 20% (w/v) sorbitol, or about 1% to about 20% (w/v) trehalose. In certain embodiments, the buffer is about 1 mM to about 20 mM L-histidine; and the tonicity modifier is about 10 mM to about 200 mM NaCl, wherein the pH of the compositions is about pH 5.0 to about pH 7.0.

Any of the compositions can also comprise a surfactant, e.g., about 0.001% (w/v) to about 0.05% (w/v) surfactant.

In certain embodiments the compositions comprise: (a) about 3 mg/mL to about 90 mg/mL Antagonist A or another pharmaceutically acceptable salt thereof; (b) about 1.0 mg/mL to about 30 mg/mL of a VEGF antagonist (e.g., ranibizumab, bevacizumab, aflibercept, ESBA1008 or pegaptanib sodium); and one or both of (c) a buffer capable of achieving or maintaining the pH of the compositions to about pH 5.0 to about pH 8.0; and (d) a tonicity modifier. In certain embodiments, any of the compositions further comprises (e) about 3 mg/mL to about 90 mg/mL of an anti-C5 agent (e.g., ARC1905 or a pharmaceutically acceptable salt thereof). In particular embodiments, the buffer, where present, comprises about 1 mM to about 100 mM sodium phosphate or about 1.0 mM to about 10 mM histidine.HCl; and the tonicity modifier, where present, is about 0.5% (w/v) to about 10% (w/v) trehalose.

In certain embodiments, a composition of the invention comprises: (a) about 0.3 mg/mL to about 30 mg/mL Antagonist A or another pharmaceutically acceptable salt thereof; (b) about 0.5 mg/mL to about 20 mg/mL ranibizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer is about 1 mM to about 20 mM L-histidine or about 1 mM to about 20 mM sodium phosphate, and the tonicity modifier is about 10 mM to about 200 mM NaCl, about 1% to about 20% (w/v) sorbitol, or about 1% to about 20% (w/v) trehalose. In particular embodiments, the composition of the invention further comprises: (e) about 0.001% (w/v) to about 0.05% (w/v) surfactant. In particular embodiments, the composition further comprises: (f) an anti-C5 agent, another PDGF antagonist, or another VEGF antagonist. In particular embodiments, the anti-C5 agent is ARC 186, ARC 187, or ARC1905, and the other VEGF antagonist is bevacizumab or aflibercept.

In certain embodiments, a composition of the invention comprises: (a) about 0.3 mg/mL to about 30 mg/mL Antagonist A or another pharmaceutically acceptable salt thereof; and (b) about 0.5 mg/mL to about 25 mg/mL bevacizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer is about 5 mM to about 200 mM sodium phosphate or about 5 mM to about 200 mM Tris.HCl, and the tonicity modifier is about 10 mM to about 200 mM NaCl, about 1% to about 20% (w/v) sorbitol, or about 1% to about 20% (w/v) trehalose. In particular embodiments, the composition of the invention further comprises: (e) about 0.001% (w/v) to about 0.05% (w/v) surfactant. In particular embodiments, the composition further comprises: (f) an anti-C5 agent, another PDGF antagonist, and/or another VEGF antagonist. In particular embodiments, the anti-C5 agent is ARC186, ARC187, or ARC1905, and the other VEGF antagonist is ranibizumab or aflibercept.

In certain embodiments, a composition of the invention comprises: (a) about 0.3 mg/mL to about 30 mg/mL Antagonist A or another pharmaceutically acceptable salt thereof; (b) about 5 mg/mL to about 40 mg/mL aflibercept or a pharmaceutically acceptable salt thereof; and one or more of: (c) a buffer capable of achieving or maintaining the pH of the composition at about pH 5.0 to about pH 8.0; (d) a tonicity modifier; and (e) 0 to about 10% (w/v) sucrose. In certain embodiments, the buffer is about 5 mM to about 50 mM phosphate, and the tonicity modifier is about 10 mM to about 200 mM NaCl. In particular embodiments, the composition of the invention further comprises: (f) about 0.001% (w/v) to about 0.05% (w/v) surfactant. In particular embodiments, the composition further comprises: (g) an anti-C5 agent, another PDGF antagonist, and/or another VEGF antagonist. In particular embodiments, the anti-C5 agent is ARC186, ARC187, or ARC1905, and the other VEGF antagonist is ranibizumab or bevacizumab.

In certain embodiments, a composition of the invention comprises: (a) about 3 mg/mL to about 90 mg/mL Antagonist A or another pharmaceutically acceptable salt thereof; (b) about 1.0 mg/mL to about 30 mg/mL ranibizumab or a pharmaceutically acceptable salt thereof; and one or both of: (c) a buffer capable of achieving or maintaining the pH of the composition at about pH 5.0 to about pH 8.0; and (d) a tonicity modifier. In certain embodiments, the buffer comprises about 1 mM to about 100 mM sodium phosphate or about 1.0 mM to about 10 mM histidine.HCl, and the tonicity modifier is about 0.5% (w/v) to about 10% (w/v) trehalose. In particular embodiments, the composition further comprises: (e) an anti-C5 agent, another PDGF antagonist, and/or another VEGF antagonist. In particular embodiments, the anti-C5 agent is ARC186, ARC187, or ARC1905, and the other VEGF antagonist is bevacizumab or aflibercept.

Illustrative compositions include F1-F31, as described in Tables 3 and 4. Illustrative compositions are also described in PCT Application Publication No. WO2013/181495. Any of these compositions may further comprise an anti-C5 agent, such as ARC1905 or a pharmaceutically acceptable salt thereof.

TABLE 3

Composition Matrix for Illustrative Antagonist A: Ranibizumab Compositions

| Comp. | Buffer | pH | Tonicity Modifier | [Ant. A] (mg/mL) | [ran] (mg/mL) | Polysorbate 20 (% w/v) |
|---|---|---|---|---|---|---|
| F1 | 10 mM Sodium Phosphate | 7.3 | 150 mM NaCl | 3 | 0 | 0% |
| F2 | 10 mM Sodium Acetate | 5.0 | 5% (w/v) Sorbitol | 3 | 5 | 0.01% |
| F3 | 10 mM Sodium Acetate | 5.0 | 130 mM NaCl | 3 | 5 | 0.01% |
| F4 | 10 mM Histidine•HCl | 5.5 | 10% (w/v) Trehalose | 0 | 5 | 0.01% |
| F5 | 10 mM Histidine•HCl | 6.0 | 5% (w/v) Sorbitol | 3 | 5 | 0.01% |
| F6 | 10 mM Histidine•HCl | 6.0 | 130 mM NaCl | 3 | 5 | 0.01% |
| F7 | 10 mM Sodium Phosphate | 7.0 | 5% (w/v) Sorbitol | 3 | 5 | 0.01% |
| F8 | 10 mM Sodium Phosphate | 7.0 | 130 mM NaCl | 3 | 5 | 0.01% |
| F9 | 10 mM Tris•HCl | 8.0 | 5% (w/v) Sorbitol | 3 | 5 | 0.01% |
| F10 | 10 mM Tris•HCl | 8.0 | 130 mM NaCl | 3 | 5 | 0.01% |
| F11 | 5 mM Sodium Phosphate + 5 mM Histidine | 6.5 | 75 mM NaCl + 5% (w/v) Trehalose | 3 | 5 | 0.005% |
| F27 | 10 mM Sodium Phosphate | 7.3 | 150 mM NaCl | 30 | 0 | 0% |
| F28 | 10 mM Histidine•HCl | 5.5 | 10% (w/v) Trehalose | 0 | 10 | 0.01% |
| F29 | 10 mM Histidine•HCl | 5.5 | 10% (w/v) Trehalose | 0 | 40 | 0.01% |
| F30 | 5 mM Sodium Phosphate + 5 mM Histidine•HCl | 5.5 | 75 mM NaCl + 5% (w/v) Trehalose | 15 | 5 | 0.005% |
| F31 | 8 mM Sodium Phosphate + 2 mM Histidine•HCl | 5.5 | 120 mM NaCl + 2% (w/v) Trehalose | 24 | 8 | 0.002% |

"Ant. A" is Antagonist A;
"ran." is ranibizumab

TABLE 4

Composition Matrix for Illustrative Antagonist A: Bevacizumab Compositions

| Comp. | Buffer | pH | Tonicity Modifier | Antagonist A Concentration (mg/mL, oligo wt.) | Bevacizumab Concentration (mg/mL) | Surfactant |
|---|---|---|---|---|---|---|
| F12 | 10 mM Phosphate | 7.3 | 150 mM Sodium Chloride | 30 | 0.0 | 0% |
| F13 | 50 mM Acetate | 4 | 5% (w/v) Sorbitol | 3 | 12.5 | 0.02% Polysorbate 20 |
| F14 | 50 mM Acetate | 4 | 130 mM Sodium Chloride | 3 | 12.5 | 0.02% Polysorbate 20 |
| F15 | 50 mM Acetate | 5 | 5% (w/v) Sorbitol | 3 | 12.5 | 0.02% Polysorbate 20 |
| F16 | 50 mM Acetate | 5 | 130 mM Sodium Chloride | 3 | 12.5 | 0.02% Polysorbate 20 |

TABLE 4-continued

Composition Matrix for Illustrative Antagonist A: Bevacizumab Compositions

| Comp. | Buffer | pH | Tonicity Modifier | Antagonist A Concentration (mg/mL, oligo wt.) | Bevacizumab Concentration (mg/mL) | Surfactant |
|---|---|---|---|---|---|---|
| F17 | 50 mM Phosphate | 6 | 5% (w/v) Sorbitol | 3 | 12.5 | 0.02% Polysorbate 20 |
| F18 | 50 mM Phosphate | 6.2 | 6% (w/v) Trehalose | 0 | 12.5 | 0.02% Polysorbate 20 |
| F19 | 50 mM Phosphate | 6 | 130 mM Sodium Chloride | 3 | 12.5 | 0.02% Polysorbate 20 |
| F20 | 50 mM Phosphate | 7 | 5% (w/v) Sorbitol | 3 | 12.5 | 0.02% Polysorbate 20 |
| F21 | 50 mM Phosphate | 7 | 130 mM Sodium Chloride | 3 | 12.5 | 0.02% Polysorbate 20 |
| F22 | 50 mM Tris | 8 | 5% (w/v) Sorbitol | 3 | 12.5 | 0.02% Polysorbate 20 |
| F23 | 50 mM Tris | 8 | 130 mM Sodium Chloride | 3 | 12.5 | 0.02% Polysorbate 20 |
| F24 | 30 mM Phosphate | 6.3 | 75 mM sodium Chloride +3% (w/v) Trehalose | 15 | 12.5 | 0.02% Polysorbate 20 |
| F25 | 10 mM Phosphate | 7.3 | 150 mM Sodium Chloride | 3 | 0.0 | 0% |
| F26 | 30 mM Phosphate | 6.3 | 75 mM sodium Chloride + 3% (w/v) Trehalose | 3 | 12.5 | 0.02% Polysorbate 20 |

Administration and Dosage

The methods or compositions according to the invention can be administered alone or in conjunction with another therapy and can be provided at home, a doctor's office, a clinic, a hospital's outpatient department, or a hospital. Treatment can begin at a hospital so that the doctor can observe the therapy's effects closely and make any adjustments that are needed. The duration of the administration can depend on the type of ophthalmological disease or disorder being treated or prevented, the age and condition of the subject, the stage and type of the subject's disease or disorder, and how the subject responds to the treatment. Additionally, a subject having a greater risk of developing an ophthalmological disease or disorder (e.g., a diabetic patient) can receive treatment to inhibit or delay the onset of symptoms. In one embodiment, the present methods or compositions allow for the administration of a relatively lower dose of each antagonist.

The dosage and frequency of administration of each antagonist can be controlled independently. For example, one antagonist can be administered three times per day, while the other antagonist can be administered once per day. Administration can be performed in on-and-off cycles that include rest periods so that the subject's body has a chance to recover from a side effect, if any. The antagonists can also be present in the same composition.

In other embodiments, Antagonist A or another pharmaceutically acceptable salt thereof and optionally, a VEGF antagonist and/or anti-C5 agent are administered prior to, during, and/or after another treatment. In one embodiment, Antagonist A or another pharmaceutically acceptable salt thereof and the VEGF antagonist and/or anti-C5 agent are administered concurrently, such as in a co-formulation, prior to, during, and/or after the other treatment. In other embodiments, Antagonist A or another pharmaceutically acceptable salt thereof and the VEGF antagonist are administered sequentially, prior to, during, and/or after the other treatment. In some embodiments, Antagonist A or another pharmaceutically acceptable salt thereof is administered prior to the administration of the VEGF antagonist. In other embodiments, Antagonist A or another pharmaceutically acceptable salt thereof is administered subsequent to the administration of the VEGF antagonist. In some embodiments, the other treatment is performing surgery. Examples of other treatment include pneumatic retinopexy, laser retinopexy, scleral buckling, and pars plana vitrectomy (PPV), laser photocoagulation, or cryotherapy.

Administration of a composition disclosed herein with performing another treatment can improve retinal attachment success, improve visual acuity, reduce choroidal neovascularization or stabilize vision to a degree that is greater than performing the other treatment alone. For example, in some embodiments, the administration of both Antagonist A or another pharmaceutically acceptable salt thereof with performing another treatment can improve retinal attachment success, improve visual acuity, or stabilize vision to a degree that is greater than an additive effect of both Antagonist A or another pharmaceutically acceptable salt thereof with performing the other treatment. In some embodiments, the synergistic effect is in reducing the size or growth of a tumor (e.g., in treating or preventing VHL disease, retinal capillary hemangioma, or von Hippel angioma). In some embodiments, the synergistic effect is reducing or inhibiting scarring or fibrosis (e.g., ocular scarring of fibrosis, such as subretinal fibrosis).

Administration of both Antagonist A or another pharmaceutically acceptable salt thereof and the VEGF antagonist can improve retinal attachment success, improve visual acuity, or stabilize vision to a degree that is greater than administration of Antagonist A or another pharmaceutically acceptable salt thereof or the VEGF antagonist. In some embodiments, the administration of Antagonist A or another pharmaceutically acceptable salt thereof and the VEGF antagonist can have a synergistic effect in treating or preventing an ophthalmological disease or disorder. For example, the administration of both Antagonist A or another pharmaceutically acceptable salt thereof and the VEGF antagonist can improve retinal attachment success, improve visual acuity, or stabilize vision to a degree that is greater than an additive effect of administering both Antagonist A or another pharmaceutically acceptable salt thereof and the VEGF antagonist. In some embodiments, the synergistic effect is in reducing the size or growth of a tumor (e.g., in treating or preventing VHL disease, retinal capillary hemangioma, or von Hippel angioma). In some embodiments, the synergistic effect is reducing or inhibiting scarring or fibrosis (e.g., ocular scarring of fibrosis, such as subretinal fibrosis).

In some embodiments, the methods comprise administering Antagonist A or another pharmaceutically acceptable salt thereof, VEGF antagonist and anti-C5 agent, in which two or more of Antagonist A or another pharmaceutically acceptable salt thereof, the VEGF antagonist and the anti-C5 agent are present in the same composition. In certain embodiments, the PDGF antagonist and the VEGF antagonist are present in the same composition; in certain embodiments, Antagonist A or another pharmaceutically acceptable salt thereof and the anti-C5 agent are present in the same composition; and in certain embodiments, the VEGF antagonist and the anti-C5 agent are present in the same composition. In some embodiments, all three of Antagonist A or another pharmaceutically acceptable salt thereof, the VEGF antagonist and the anti-C5 agent are present in the same composition.

In some embodiments, Antagonist A or another pharmaceutically acceptable salt thereof, the VEGF antagonist and the anti-C5 agent are administered sequentially. In one embodiment, Antagonist A or another pharmaceutically acceptable salt thereof is administered prior to the VEGF antagonist or the anti-C5 agent. In one embodiment, the VEGF antagonist is administered prior to Antagonist A or another pharmaceutically acceptable salt thereof or the anti-C5 agent. In one embodiment, the anti-C5 agent is administered prior to the VEGF antagonist or Antagonist A or another pharmaceutically acceptable salt thereof. In one embodiment, Antagonist A or another pharmaceutically acceptable salt thereof is administered prior to the VEGF antagonist and anti-C5 agent. In one embodiment, the VEGF antagonist is administered prior to Antagonist A or another pharmaceutically acceptable salt thereof and the -C5 agent. In one embodiment, the anti-C5 agent is administered prior to the VEGF antagonist and PDGF antagonist.

In certain embodiments, the subject is administered two or more active agents (e.g., Antagonist A or another pharmaceutically acceptable salt thereof and a VEGF antagonist) in a staggered dosing regimen, wherein one or more of the two or more active agents is administered before another one or more of the two or more active agents is administered to the subject.

In certain embodiments, the one or more active agent(s) is administered at least one day before the other one or more active agent(s). Accordingly, in some embodiments the present methods comprise administering on one or more days Antagonist A or another pharmaceutically acceptable salt thereof, one or more VEGF antagonists or one or more anti-C5 agents.

In one embodiment, the order of administration is: Antagonist A or another pharmaceutically acceptable salt thereof, followed by VEGF antagonist, followed by anti-C5 agent. In another embodiment, the order of administration is: Antagonist A or another pharmaceutically acceptable salt thereof, followed by anti-C5 agent, followed by VEGF antagonist. In another embodiment, the order of administration is: VEGF antagonist, followed by anti-C5 agent, followed by Antagonist A or another pharmaceutically acceptable salt thereof. In another embodiment, the order of administration is: VEGF antagonist, followed by Antagonist A or another pharmaceutically acceptable salt thereof, followed by anti-C5 agent. In yet another embodiment the order of administration is: anti-C5 agent, followed by Antagonist A or another pharmaceutically acceptable salt thereof, followed by VEGF antagonist. In another embodiment the order of administration is: anti-C5 agent, followed by VEGF antagonist, followed by PDGF antagonist.

In some embodiments, the Antagonist A or another pharmaceutically acceptable salt thereof and the VEGF antagonist are administered concurrently, and the anti-C5 agent is administered prior to or subsequent to administration of the PDGF antagonist and VEGF antagonist. In some embodiments, Antagonist A or another pharmaceutically acceptable salt thereof and the anti-C5 agent are administered concurrently, and the VEGF antagonist is administered prior to or subsequent to administration of Antagonist A or another pharmaceutically acceptable salt thereof and the VEGF antagonist. In some embodiments, the VEGF antagonist and anti-C5 agent are administered concurrently, and Antagonist A or another pharmaceutically acceptable salt thereof is administered prior to or subsequent to administration of the anti-C5 agent and VEGF antagonist.

In other embodiments, the order of administration is: Antagonist A or another pharmaceutically acceptable salt thereof, followed by VEGF antagonist and anti-C5 agent, wherein the VEGF antagonist and anti-C5 agent are present in the same composition. In another embodiment, the order of administration is: VEGF antagonist, followed by anti-C5 agent and Antagonist A or another pharmaceutically acceptable salt thereof, wherein the anti-C5 agent and PDGF antagonist are present in the same composition. In yet another embodiment the order of administration is: anti-C5 agent, followed by Antagonist A or another pharmaceutically acceptable salt thereof and VEGF antagonist, wherein the PDGF antagonist and VEGF antagonist are present in the same composition.

In still other embodiments, the order of administration is: Antagonist A or another pharmaceutically acceptable salt thereof and VEGF antagonist, wherein Antagonist A or another pharmaceutically acceptable salt thereof and the VEGF antagonist are present in the same composition, followed by anti-C5 agent. In another embodiment, the order of administration is: Antagonist A or another pharmaceutically acceptable salt thereof and anti-C5 agent, wherein Antagonist A or another pharmaceutically acceptable salt thereof and the anti-C5 agent are present in the same composition, followed by VEGF antagonist. In another embodiment, the order of administration is: VEGF antagonist and anti-C5 agent, wherein the VEGF antagonist and anti-C5 agent are present in the same composition, followed by Antagonist A or another pharmaceutically acceptable salt thereof.

For example, Antagonist A or another pharmaceutically acceptable salt thereof can be administered prior to or subsequent to administration of a VEGF antagonist and/or an anti-C5 agent; a VEGF antagonist can be administered prior to or subsequent to administration of Antagonist A or another pharmaceutically acceptable salt thereof and/or anti-C5 agent; or an anti-C5 agent can be administered prior to or subsequent to administration of Antagonist A or another pharmaceutically acceptable salt thereof and/or a VEGF antagonist.

In some embodiments, the present methods comprise administering a first agent prior to administering a second agent. In some embodiments, the present methods comprise administering a first agent prior to administering a second agent and administering the second agent prior to administering a third agent.

In some embodiments, the present methods comprise concurrently administering a first agent and a second agent. In some embodiments, the present methods comprise concurrently administering a first agent and a second agent prior to administering a third agent.

In some embodiments, the present methods comprise administering a first agent prior to concurrently administering a second agent and third agent.

In some embodiments, the present methods comprise concurrently administering a first agent, a second agent and a third agent.

Illustrative groups of first agent, second agent and third agent are set forth below in Tables 5 and 6.

TABLE 5

| Group | First Agent | Second Agent | Third Agent |
|---|---|---|---|
| A | Antagonist A or another pharmaceutically acceptable salt thereof | VEGF antagonist | Anti-C5 Agent |
| B | Antagonist A or another pharmaceutically acceptable salt thereof | Anti-C5 Agent | VEGF antagonist |
| C | VEGF antagonist | Antagonist A or another pharmaceutically acceptable salt thereof | Anti-C5 Agent |
| D | VEGF antagonist | Anti-C5 Agent | Antagonist A or another pharmaceutically acceptable salt thereof |
| E | Anti-C5 Agent | Antagonist A or another pharmaceutically acceptable salt thereof | VEGF antagonist |
| F | Anti-C5 Agent | VEGF antagonist | Antagonist A or another pharmaceutically acceptable salt thereof |

TABLE 6

| Group | First Agent | Second Agent | Third Agent |
|---|---|---|---|
| A | Antagonist A | ranibizumab | ARC1905 |
| B | Antagonist A | bevacizumab | ARC1905 |
| C | Antagonist A | aflibercept | ARC1905 |
| D | Antagonist A | pegaptanib sodium | ARC1905 |
| E | Antagonist A | ESBA1008 | ARC1905 |
| F | Antagonist A | ARC1905 | ranibizumab |
| G | Antagonist A | ARC1905 | bevacizumab |
| H | Antagonist A | ARC1905 | aflibercept |
| I | Antagonist A | ARC1905 | pegaptanib sodium |
| J | Antagonist A | ARC1905 | ESBA1008 |
| K | ranibizumab | Antagonist A | ARC1905 |
| L | bevacizumab | Antagonist A | ARC1905 |
| M | aflibercept | Antagonist A | ARC1905 |
| N | pegaptanib sodium | Antagonist A | ARC1905 |
| O | ESBA1008 | Antagonist A | ARC1905 |
| P | ranibizumab | ARC1905 | Antagonist A |
| Q | bevacizumab | ARC1905 | Antagonist A |
| R | aflibercept | ARC1905 | Antagonist A |
| S | pegaptanib sodium | ARC1905 | Antagonist A |
| T | ESBA1008 | ARC1905 | Antagonist A |
| U | ARC1905 | Antagonist A | ranibizumab |
| V | ARC1905 | Antagonist A | bevacizumab |
| W | ARC1905 | Antagonist A | aflibercept |
| X | ARC1905 | Antagonist A | pegaptanib sodium |
| Y | ARC1905 | Antagonist A | ESBA1008 |
| Z | ARC1905 | ranibizumab | Antagonist A |
| AA | ARC1905 | bevacizumab | Antagonist A |
| AB | ARC1905 | aflibercept | Antagonist A |
| AC | ARC1905 | pegaptanib sodium | Antagonist A |
| AD | ARC1905 | ESBA1008 | Antagonist A |

In some embodiments, the present methods comprise administering Antagonist A or another pharmaceutically acceptable salt thereof and two or more VEGF antagonists. In some embodiments, the present methods comprise administering Antagonist A or another pharmaceutically acceptable salt thereof and two or more anti-C5 agents. In some embodiments, the present methods comprise administering a VEGF antagonist and two or more anti-C5 agents.

In some embodiments, the present methods comprise administering Antagonist A or another pharmaceutically acceptable salt thereof prior to administering two or more VEGF antagonists. In some embodiments, the present methods comprise administering Antagonist A or another pharmaceutically acceptable salt thereof prior to administering a first VEGF antagonist and administering the first VEGF antagonist prior to administering a second VEGF antagonist.

In some embodiments, the present methods comprise concurrently administering Antagonist A or another pharmaceutically acceptable salt thereof and a VEGF antagonist. In some embodiments, the present methods comprise concurrently administering Antagonist A or another pharmaceutically acceptable salt thereof and a first VEGF antagonist prior to administering a second VEGF antagonist.

In some embodiments, the present methods comprise administering Antagonist A or another pharmaceutically acceptable salt thereof prior to concurrently administering a first VEGF antagonist and a second VEGF antagonist.

In some embodiments, the present methods comprise concurrently administering Antagonist A or another pharmaceutically acceptable salt thereof, a first VEGF antagonist and a second VEGF antagonist.

In some embodiments, the present methods comprise administering a VEGF antagonist prior to administering two PDGF antagonists (e.g., Antagonist A or another pharmaceutically acceptable salt thereof and another PDGF antagonist). In some embodiments, the present methods comprise administering a VEGF antagonist prior to administering a first PDGF antagonist and administering the first PDGF antagonist prior to administering a second PDGF antagonist.

In some embodiments, the present methods comprise concurrently administering a VEGF antagonist and Antagonist A or another pharmaceutically acceptable salt thereof. In some embodiments, the present methods comprise concurrently administering a VEGF antagonist and a first PDGF antagonist prior to administering a second PDGF antagonist.

In some embodiments, the present methods comprise administering a VEGF antagonist prior to concurrently administering a first PDGF antagonist and a second PDGF antagonist.

In some embodiments, the present methods comprise concurrently administering a VEGF antagonist, a first PDGF antagonist and a second PDGF antagonist.

In some embodiments, the present methods comprise administering Antagonist A or another pharmaceutically acceptable salt thereof prior to administering two or more anti-C5 agents. In some embodiments, the present methods comprise administering Antagonist A or another pharmaceutically acceptable salt thereof prior to administering a first anti-C5 agent and administering the first anti-C5 agent prior to administering a second anti-C5 agent.

In some embodiments, the present methods comprise concurrently administering Antagonist A or another pharmaceutically acceptable salt thereof and an anti-C5 agent. In some embodiments, the present methods comprise concurrently administering Antagonist A or another pharmaceutically acceptable salt thereof and a first anti-C5 agent prior to administering a second anti-C5 agent.

In some embodiments, the present methods comprise administering Antagonist A or another pharmaceutically acceptable salt thereof prior to concurrently administering a first anti-C5 agent and a second anti-C5 agent.

In some embodiments, the present methods comprise concurrently administering Antagonist A or another pharmaceutically acceptable salt thereof, a first anti-C5 agent and a second anti-C5 agent.

In some embodiments, the present methods comprise administering an anti-C5 agent prior to administering two or more PDGF antagonists. In some embodiments, the present methods comprise administering an anti-C5 agent prior to administering a first PDGF antagonist and administering the first PDGF antagonist prior to administering a second PDGF antagonist.

In some embodiments, the present methods comprise concurrently administering an anti-C5 agent and Antagonist A or another pharmaceutically acceptable salt thereof. In some embodiments, the present methods comprise concurrently administering an anti-C5 agent and a first PDGF antagonist prior to administering a second PDGF antagonist.

In some embodiments, the present methods comprise administering an anti-C5 agent prior to concurrently administering a first PDGF antagonist and a second PDGF antagonist.

In some embodiments, the present methods comprise concurrently administering an anti-C5 agent, a first PDGF antagonist and a second PDGF antagonist.

In some embodiments, the present methods comprise administering a VEGF antagonist prior to administering two or more anti-C5 agents. In some embodiments, the present methods comprise administering a VEGF antagonist prior to administering a first anti-C5 agent and administering the first anti-C5 agent prior to administering a second anti-C5 agent.

In some embodiments, the present methods comprise concurrently administering a VEGF antagonist and an anti-C5 agent. In some embodiments, the present methods comprise concurrently administering a VEGF antagonist and a first anti-C5 agent prior to administering a second anti-C5 agent.

In some embodiments, the present methods comprise administering a VEGF antagonist prior to concurrently administering a first anti-C5 agent and a second anti-C5 agent.

In some embodiments, the present methods comprise concurrently administering a VEGF antagonist, a first anti-C5 agent and a second anti-C5 agent.

In some embodiments, the present methods comprise administering an anti-C5 agent prior to administering two or more VEGF antagonists. In some embodiments, the present methods comprise administering an anti-C5 agent prior to administering a first VEGF antagonist and administering the first VEGF antagonist prior to administering a second VEGF antagonist.

In some embodiments, the present methods comprise concurrently administering an anti-C5 agent and a VEGF antagonist. In some embodiments, the present methods comprise concurrently administering an anti-C5 agent and a first VEGF antagonist prior to administering a second VEGF antagonist.

In some embodiments, the present methods comprise administering an anti-C5 agent prior to concurrently administering a first VEGF antagonist and a second VEGF antagonist.

In some embodiments, the present methods comprise concurrently administering an anti-C5 agent, a first VEGF antagonist and a second VEGF antagonist.

In some embodiments, the first agent and second agent are PDGF antagonists, which can be the same or different. In some embodiment, the first agent and second agent are VEGF antagonists, which can be the same or different. In some embodiments, the first agent and second agent are anti-C5 agents, which can be the same or different.

In some embodiments, the first agent and third agent are PDGF antagonists, which can be the same or different. In some embodiment, the first agent and third agent are VEGF antagonists, which can be the same or different. In some embodiments, the first agent and third agent are anti-C5 agents, which can be the same or different.

In some embodiments, the second agent and third agent are PDGF antagonists, which can be the same or different. In some embodiment, the second agent and third agent are VEGF antagonists, which can be the same or different. In some embodiments, the second agent and third agent are anti-C5 agents, which can be the same or different.

Illustrative groups of first agent, second agent and third agent are set forth below in Tables 7, 8, 9 and 10.

TABLE 7

| Group | First Agent | Second Agent | Third Agent |
|---|---|---|---|
| A | PDGF Antagonist | VEGF antagonist | VEGF antagonist |
| B | VEGF antagonist | PDGF Antagonist | VEGF antagonist |
| C | VEGF antagonist | VEGF antagonist | PDGF Antagonist |
| D | PDGF Antagonist | Anti-C5 Agent | Anti-C5 Agent |
| E | Anti-C5 Agent | PDGF Antagonist | Anti-C5 Agent |
| F | Anti-C5 Agent | Anti-C5 Agent | PDGF Antagonist |
| G | PDGF Antagonist | PDGF Antagonist | VEGF antagonist |
| H | PDGF Antagonist | VEGF antagonist | PDGF Antagonist |
| I | VEGF antagonist | PDGF Antagonist | PDGF Antagonist |
| J | PDGF Antagonist | PDGF Antagonist | Anti-C5 Agent |
| K | PDGF Antagonist | Anti-C5 Agent | PDGF Antagonist |
| L | Anti-C5 Agent | PDGF Antagonist | PDGF Antagonist |

TABLE 8

| Group | First Agent | Second Agent | Third Agent |
|---|---|---|---|
| A | PDGF Antagonist | First VEGF antagonist | Second VEGF antagonist |
| B | First VEGF antagonist | PDGF Antagonist | Second VEGF antagonist |
| C | First VEGF antagonist | Second VEGF antagonist | PDGF Antagonist |
| D | PDGF Antagonist | First Anti-C5 Agent | Second Anti-C5 Agent |
| E | First Anti-C5 Agent | PDGF Antagonist | Second Anti-C5 Agent |
| F | First Anti-C5 Agent | Second Anti-C5 Agent | PDGF Antagonist |
| G | First PDGF Antagonist | Second PDGF Antagonist | VEGF antagonist |
| H | First PDGF Antagonist | VEGF antagonist | Second PDGF Antagonist |
| I | VEGF antagonist | First PDGF Antagonist | Second PDGF Antagonist |

TABLE 8-continued

| Group | First Agent | Second Agent | Third Agent |
|---|---|---|---|
| J | First PDGF Antagonist | Second PDGF Antagonist | Anti-C5 Agent |
| K | First PDGF Antagonist | Anti-C5 Agent | Second PDGF Antagonist |
| L | Anti-C5 Agent | First PDGF Antagonist | Second PDGF Antagonist |

TABLE 9

| Group | First Agent | Second Agent | Third Agent |
|---|---|---|---|
| A | Antagonist A | ranibizumab | Antagonist A |
| B | Antagonist A | ranibizumab | ranibizumab |
| C | Antagonist A | bevacizumab | Antagonist A |
| D | Antagonist A | bevacizumab | bevacizumab |
| E | Antagonist A | aflibercept | Antagonist A |
| F | Antagonist A | aflibercept | aflibercept |
| G | Antagonist A | pegaptanib sodium | Antagonist A |
| H | Antagonist A | pegaptanib sodium | pegaptanib sodium |
| I | Antagonist A | ESBA1008 | Antagonist A |
| J | Antagonist A | ESBA1008 | ESBA1008 |
| K | Antagonist A | ARC1905 | Antagonist A |
| L | Antagonist A | ARC1905 | ARC1905 |
| M | ranibizumab | Antagonist A | ranibizumab |
| N | ranibizumab | Antagonist A | Antagonist A |
| O | bevacizumab | Antagonist A | bevacizumab |
| P | bevacizumab | Antagonist A | Antagonist A |
| Q | aflibercept | Antagonist A | aflibercept |
| R | aflibercept | Antagonist A | Antagonist A |
| S | pegaptanib sodium | Antagonist A | pegaptanib sodium |
| T | pegaptanib sodium | Antagonist A | Antagonist A |
| U | ESBA1008 | Antagonist A | ESBA1008 |
| V | ESBA1008 | Antagonist A | Antagonist A |
| W | ARC1905 | Antagonist A | ARC1905 |
| X | ARC1905 | Antagonist A | Antagonist A |
| Y | ranibizumab | ranibizumab | Antagonist A |
| Z | bevacizumab | bevacizumab | Antagonist A |
| AA | aflibercept | aflibercept | Antagonist A |
| AB | pegaptanib sodium | pegaptanib sodium | Antagonist A |
| AC | ESBA1008 | ESBA1008 | Antagonist A |
| AD | ARC1905 | ARC1905 | Antagonist A |
| AE | ranibizumab | ranibizumab | bevacizumab |
| AF | ranibizumab | bevacizumab | ranibizumab |
| AG | ranibizumab | ranibizumab | aflibercept |
| AH | ranibizumab | aflibercept | ranibizumab |
| AI | ranibizumab | ranibizumab | pegaptanib sodium |
| AJ | ranibizumab | pegaptanib sodium | ranibizumab |
| AK | ranibizumab | ranibizumab | ESBA1008 |
| AL | ranibizumab | ESBA1008 | ranibizumab |
| AM | ranibizumab | ranibizumab | ARC1905 |
| AN | ranibizumab | ARC1905 | ranibizumab |
| AO | bevacizumab | bevacizumab | ranibizumab |
| AP | bevacizumab | ranibizumab | bevacizumab |
| AQ | bevacizumab | bevacizumab | aflibercept |
| AR | bevacizumab | aflibercept | bevacizumab |
| AS | bevacizumab | bevacizumab | pegaptanib sodium |
| AT | bevacizumab | pegaptanib sodium | bevacizumab |
| AU | bevacizumab | bevacizumab | ESBA1008 |
| AV | bevacizumab | ESBA1008 | bevacizumab |
| AW | bevacizumab | bevacizumab | ARC1905 |
| AX | bevacizumab | ARC1905 | bevacizumab |
| AY | aflibercept | aflibercept | ranibizumab |
| AZ | aflibercept | ranibizumab | aflibercept |
| BA | aflibercept | aflibercept | bevacizumab |
| BB | aflibercept | bevacizumab | aflibercept |
| BC | aflibercept | aflibercept | pegaptanib sodium |
| BD | aflibercept | pegaptanib sodium | aflibercept |
| BE | aflibercept | aflibercept | ESBA1008 |
| BF | aflibercept | ESBA1008 | aflibercept |
| BG | aflibercept | aflibercept | ARC1905 |
| BH | aflibercept | ARC1905 | aflibercept |
| BI | pegaptanib sodium | pegaptanib sodium | ranibizumab |
| BJ | pegaptanib sodium | ranibizumab | pegaptanib sodium |
| BK | pegaptanib sodium | pegaptanib sodium | bevacizumab |
| BL | pegaptanib sodium | bevacizumab | pegaptanib sodium |
| BM | pegaptanib sodium | pegaptanib sodium | aflibercept |
| BN | pegaptanib sodium | aflibercept | pegaptanib sodium |
| BO | pegaptanib sodium | pegaptanib sodium | ESBA1008 |
| BP | pegaptanib sodium | ESBA1008 | pegaptanib sodium |
| BQ | pegaptanib sodium | pegaptanib sodium | ARC1905 |
| BR | pegaptanib sodium | ARC1905 | pegaptanib sodium |
| BS | ESBA1008 | ESBA1008 | ranibizumab |
| BT | ESBA1008 | ranibizumab | ESBA1008 |
| BU | ESBA1008 | ESBA1008 | bevacizumab |
| BV | ESBA1008 | bevacizumab | ESBA1008 |
| BW | ESBA1008 | ESBA1008 | aflibercept |
| BX | ESBA1008 | aflibercept | ESBA1008 |
| BY | ESBA1008 | ESBA1008 | pegaptanib sodium |
| BZ | ESBA1008 | pegaptanib sodium | ESBA1008 |
| CA | ESBA1008 | ESBA1008 | ARC1905 |
| CB | ESBA1008 | ARC1905 | ESBA1008 |
| CC | ARC1905 | ARC1905 | ranibizumab |
| CD | ARC1905 | ranibizumab | ARC1905 |
| CE | ARC1905 | ARC1905 | bevacizumab |
| CF | ARC1905 | bevacizumab | ARC1905 |
| CG | ARC1905 | ARC1905 | aflibercept |
| CH | ARC1905 | aflibercept | ARC1905 |
| CI | ARC1905 | ARC1905 | pegaptanib sodium |
| CJ | ARC1905 | pegaptanib sodium | ARC1905 |
| CK | ARC1905 | ARC1905 | ESBA1008 |
| CL | ARC1905 | ESBA1008 | ESBA1008 |

TABLE 10

| Group | First Agent | Second Agent | Third Agent |
|---|---|---|---|
| A | Antagonist A | ranibizumab | bevacizumab |
| B | Antagonist A | ranibizumab | aflibercept |
| C | Antagonist A | ranibizumab | pegaptanib sodium |
| D | Antagonist A | bevacizumab | aflibercept |
| E | Antagonist A | bevacizumab | pegaptanib sodium |
| F | Antagonist A | aflibercept | pegaptanib sodium |
| G | ranibizumab | bevacizumab | Antagonist A |
| H | ranibizumab | aflibercept | Antagonist A |
| I | ranibizumab | pegaptanib sodium | Antagonist A |
| J | bevacizumab | aflibercept | Antagonist A |
| K | bevacizumab | pegaptanib sodium | Antagonist A |
| L | aflibercept | pegaptanib sodium | Antagonist A |
| M | ranibizumab | Antagonist A | bevacizumab |
| N | ranibizumab | Antagonist A | aflibercept |
| O | ranibizumab | Antagonist A | pegaptanib sodium |
| P | bevacizumab | Antagonist A | aflibercept |
| Q | bevacizumab | Antagonist A | pegaptanib sodium |
| R | aflibercept | Antagonist A | pegaptanib sodium |
| S | bevacizumab | ranibizumab | Antagonist A |
| T | aflibercept | ranibizumab | Antagonist A |
| U | pegaptanib sodium | ranibizumab | Antagonist A |
| V | aflibercept | bevacizumab | Antagonist A |
| W | pegaptanib sodium | bevacizumab | Antagonist A |
| X | pegaptanib sodium | aflibercept | Antagonist A |
| Y | bevacizumab | Antagonist A | ranibizumab |
| Z | aflibercept | Antagonist A | ranibizumab |
| AA | pegaptanib sodium | Antagonist A | ranibizumab |
| AB | aflibercept | Antagonist A | bevacizumab |
| AC | pegaptanib sodium | Antagonist A | bevacizumab |
| AD | pegaptanib sodium | Antagonist A | aflibercept |
| AE | Antagonist A | ARC187 | ARC1905 |
| AF | Antagonist A | ARC1905 | ARC187 |
| AG | ARC187 | ARC1905 | Antagonist A |
| AH | ARC1905 | ARC187 | Antagonist A |
| AI | ARC187 | Antagonist A | ARC1905 |
| AJ | ARC1905 | Antagonist A | ARC187 |

In one embodiment, two or more agents are administered concurrently. In one embodiment, the two or more agents administered concurrently are present in the same composition. In another embodiment, the two or more agents administered concurrently are each present in a separate composition.

In certain embodiments, the time period from administration of a first agent to administration of a second agent is at least 1 min, at least 5 min, at least 10 min, at least 15 min, at least 30 min, or at least one hour. In certain embodiments, the time period from administration of a first agent to administration of a second agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of a first agent to administration of a second agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, a second agent is administered within 90 days, 30 days, 10 days, 5 days, 2 days, 1 day, 24 hours, 1 hour, 30 minutes, 10 minutes, 5 minutes or one minute after administration of a second agent.

In certain embodiments, the time period from administration of a second agent to administration of a third agent is at least 1 min, at least 5 min, at least 10 min, at least 15 min, at least 30 min, or at least one hour. In certain embodiments, the time period between administration of a second agent and administration of a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period between administration of a second agent and administration of a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, a third agent is administered within 90 days, 30 days, 10 days, 5 days, 2 days, 1 day, 24 hours, 1 hour, 30 minutes, 10 minutes, 5 minutes or one minute after administration of a second agent.

In certain embodiments, the time period between concurrent administration of a first agent and a second agent and administration of a third agent is at least 1 min, at least 5 min, at least 10 min, at least 15 min, at least 30 min, or at least one hour. In certain embodiments, the time period between concurrent administration of a first agent and a second agent and administration of a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from concurrent administration of a first agent and a second agent to administration of a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, administration of a third agent is within 90 days, 30 days, 10 days, 5 days, 2 days, 1 day, 24 hours, 1 hour, 30 minutes, 10 minutes, 5 minutes or one minute of concurrent administration of a first agent and a second agent.

In certain embodiments, the time period from administration of a first agent to concurrent administration a second agent and a third agent is at least 1 min, at least 5 min, at least 10 min, at least 15 min, at least 30 min, or at least one hour. In certain embodiments, the time period from administration of a first agent to concurrent administration of a second agent and a third agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of a first agent to concurrent administration of a second agent and a third agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min. In certain embodiments, concurrent administration of a second agent and a third agent is within 90 days, 30 days, 10 days, 5 days, 2 days, 1 day, 24 hours, 1 hour, 30 minutes, 10 minutes, 5 minutes or one minute of administration of a first agent.

The administration of two or more, such as three or more, active agents (e.g., Antagonist A or another pharmaceutically acceptable salt thereof, a VEGF antagonist and an anti-C5 agent) can have a synergistic effect in treating or preventing a disease or disorder, e.g., an ophthalmological disease or disorder. For example, administration of Antagonist A or another pharmaceutically acceptable salt thereof, VEGF antagonist and anti-C5 agent (or any two of these active agents) can improve retinal attachment success, improve visual acuity, reduce choroidal neovascularization or stabilize vision to a degree that is greater than an additive effect of the active agents.

In certain embodiments, the invention provides methods for treating or preventing an ophthalmological disease or disorder, comprising administering to a subject in need thereof one or more, in some embodiments two or more or three or more, active agents via an apparatus. In other embodiments, the methods further comprise performing surgery on the subject. In other embodiments, the methods further comprise administering another active agent, such as an antineoplastic drug, including but not limited to any of those described herein. In particular embodiments, the methods further comprise administering another active agent and performing surgery on the subject.

In some embodiments, administration of Antagonist A or another pharmaceutically acceptable salt thereof, and optionally a VEGF antagonist and/or an anti-C5 agent to a subject results in improved vision, such as increased visual acuity. In some embodiments, the subject experienced moderate vision loss, defined as losing 15 letters or more from baseline on ETDRS visual acuity testing, measured at week 24, prior to treatment with Antagonist A or another pharmaceutically acceptable salt thereof.

In some embodiments, visual acuity testing is as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, Va. 22161; Accession No. PB85 223006/AS; Ferris et al., Am J Ophthalmol 94:91-96, 1982; or or Example 4, as described herein. In some embodiments, the visual acuity testing uses one or more charts available from http://www.nei.nih.gov/photo/keyword.asp?conditions=Eye+Charts&match=all, e.g., ETDRS visual acuity Chart 1, 2 and/or R.

In other embodiments, administration of Antagonist A or another pharmaceutically acceptable salt thereof and a VEGF antagonist results in fewer ocular adverse events, a decrease in size of RCH (e.g., measured by fundus photography and FA), a decrease in exudation (measured by fundus photography, OCT, and FA), or a decrease in epiretinal proliferation or retinal traction (assessed by fundus photography), compared to those experienced by a subject who was not administered with Antagonist A or another pharmaceutically acceptable salt thereof. In some embodiments, the subject does not require, and the methods do not comprise, ablative treatment of RCH or ocular surgery.

In some embodiments, administration of Antagonist A or another pharmaceutically acceptable salt thereof, and optionally a VEGF antagonist and/or an anti-C5 agent, to a subject results in improved vision independent of baseline lesion size or baseline vision, compared to vision of a subject who was not administered with Antagonist A or another pharmaceutically acceptable salt thereof, or compared to a subject administered anti-VEGF monotherapy. In some embodiments, administration of Antagonist A or another pharmaceutically acceptable salt thereof, and optionally a VEGF antagonist and/or an anti-C5 agent, to a subject results in the subject having a visual acuity of 20/40 or better, or 20/25 or better vision. In some embodiments, administration of Antagonist A or another pharmaceutically acceptable salt thereof, and optionally a VEGF antagonist and/or an anti-C5 agent to a subject results in an increased reduction in CNV size in the subject, compared to CNV size in a patient who was not administered with Antagonist A or another pharmaceutically acceptable salt thereof, or compared to a subject administered anti-VEGF monotherapy. In some embodiments, administration of Antagonist A or another pharmaceutically acceptable salt thereof, and optionally a VEGF antagonist and/or an anti-C5 agent, to a subject results in a reduction in CNV size (e.g., reduction in disc area (DA) size). In some embodiments, administration of Antagonist A or another pharmaceutically acceptable salt thereof, and optionally a VEGF antagonist and/or an anti-C5 agent to a subject result in an increased reduction in DA in the subject, compared to DA in a patient who was not administered with Antagonist A or another pharmaceutically acceptable salt thereof, or compared to a subject administered anti-VEGF monotherapy. In some embodiments, the increased reduction in CNV size is in subjects with small baseline CNV, e.g., less than or equal to 1.62 DA (disc area). In some embodiments, the increased reduction in CNV size (e.g., in disc area) is in subjects with large baseline CNV, e.g., greater than 1.62 DA. In some embodiments, administration of Antagonist A or another pharmaceutically acceptable salt thereof, and optionally a VEGF antagonist and/or an anti-C5 agent, to a subject results in neovascular regression. In some embodiments, administration of Antagonist A or another pharmaceutically acceptable salt thereof, and optionally a VEGF antagonist and/or an anti-C5 agent, to a subject results in reduced neovascular growth, compared to that occurring in a subject who was not administered with Antagonist A or another pharmaceutically acceptable salt thereof, or compared to a subject administered anti-VEGF monotherapy. In some embodiments, the reduced neovascular growth is anti-fibrosis. In some embodiments, administration of Antagonist A or another pharmaceutically acceptable salt thereof, and optionally a VEGF antagonist and/or an anti-C5 agent, to a subject results in a decrease in or absence of hyper-reflective material, e.g., sub-retinal hyper-reflective material, such as a decrease in the size of sub-retinal hyper-reflective material (SHRM) as evidenced by spectral domain optical coherence tomography (SD-OCT). In some embodiments, administration of Antagonist A or another pharmaceutically acceptable salt thereof, and optionally a VEGF antagonist and/or an anti-C5 agent, to a subject results in an increase in resolution of hyper-reflective material, e.g., sub-retinal hyper-reflective material, such as compared to a subject who was not administered with Antagonist A or another pharmaceutically acceptable salt thereof, or compared to a subject administered a VEGF antagonist, anti-VEGF monotherapy, and/or an anti-C5 agent.

In some embodiments, a subject with improved vision has a greater than 3-line, 4-line or 5-line gain in visual acuity. In one embodiment, a subject's visual acuity is determined using a protocol such as the Early Treatment for Diabetic Retinopathy Study ("ETDRS") or the Age-Related Eye Disease Study ("AREDS") protocol. In some embodiments, visual acuity is measured using a modified ETDRS and/or AREDS protocol, such as the measurement of visual acuity described in Ferris et al., Am J Ophthalmol 94:91-96, 1982. In some embodiments, visual acuity is measured as described in Early Treatment Diabetic Retinopathy Study Research Group (ETDRS), Manual of Operations, Baltimore: ETDRS Coordinating Center, University of Maryland. Available from: National Technical Information Service, 5285 Port Royal Road, Springfield, Va. 22161; Accession No. PB85 223006/AS. In other embodiments, visual acuity testing is measured as described in Example 4 below. In some embodiments, the visual acuity testing uses one or more charts available from http://www.nei.nih.gov/photo/keyword.asp?conditions=Eye+Charts&match=all, e.g., ETDRS visual acuity Chart 1, 2 and/or R.

In one embodiment, a subject's visual acuity is determined by one or more of the following procedures: (1) measurement of best-corrected visual acuity (BCVA) with required manifest refraction; (2) measurement of corrected visual acuity with conditional manifest refraction; or (3) measurement of corrected visual acuity without manifest refraction.

In one embodiment, each of the PDGF and VEGF antagonists is administered in an amount effective to treat or prevent an ophthalmological disease or disorder. The amount of antagonist that is admixed with the carrier materials to produce a single dosage can vary depending upon the subject being treated and the particular mode of administration.

The dosage of each antagonist can depend on several factors including the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used. Furthermore, the exact individual dosages can be adjusted somewhat depending on a variety of factors, including the specific combination of antagonists being administered, the time of administration, the route of administration, the nature of the formulation, the rate of excretion, the particular ophthalmological disease or disorder being treated, the severity of the disorder, and the anatomical location of the neovascular disorder. Some variations in the dosage can be expected.

Generally, when orally administered to a subject, the dosage of an antagonist of the present invention is normally 0.001 mg/kg/day to 100 mg/kg/day, 0.01 mg/kg/day to 50 mg/kg/day, or 0.1 mg/kg/day to 10 mg/kg/day. Generally, when orally administered to a human, the dosage of an antagonist of the present invention is normally 0.001 mg to 300 mg per day, 1 mg to 200 mg per day, or 5 mg to 50 mg per day. Dosages up to 200 mg per day may be necessary. For administration of an antagonist of the present invention by parenteral injection, the dosage is normally 0.1 mg to 250 mg per day, 1 mg to 20 mg per day, or 3 mg to 5 mg per day. Injections may be given up to four times daily. In some embodiments, the dosage of a PDGF or VEGF antagonist for use in the present invention is normally 0.1 mg to 1500 mg per day, or 0.5 mg to 10 mg per day, or 0.5 mg to 5 mg per day. A dosage of up to 3000 mg per day can be administered.

In some embodiments, for administration by parenteral injection of a three active agents (e.g., Antagonist A or another pharmaceutically acceptable salt thereof, VEGF antagonist and an anti-C5 agent or other combination disclosed herein), the dosage of each of the PDGF antagonist, VEGF antagonist and anti-C5 agent, is typically 0.1 mg to 250 mg per day, 1 mg to 20 mg per day, or 3 mg to 5 mg per day. Injections may be given up to four times daily. Generally, when parenterally administered, the dosage of Antagonist A or another pharmaceutically acceptable salt thereof, VEGF antagonist, or anti-C5 agent is typically 0.1 mg to 1500 mg per day, or 0.5 mg to 10 mg per day, or 0.5 mg to 5 mg per day. A dosage of at least up to 3000 mg per day can be administered.

In some embodiments, in which Antagonist A or another pharmaceutically acceptable salt thereof, VEGF antagonist and/or anti-C5 agent are ophthalmologically administered to a human, for example intravitreally, the dosage of each of Antagonist A or another pharmaceutically acceptable salt thereof, VEGF antagonist and anti-C5 agent is typically 0.003 mg to 5.0 mg per eye per administration, or 0.03 mg to 3.0 mg per eye per administration, or 0.1 mg to 1.0 mg per eye per administration. In one embodiment, the dosage of each of Antagonist A or another pharmaceutically acceptable salt thereof, VEGF antagonist and anti-C5 agent is about 0.03 mg, about 0.3 mg, about 0.5 mg, about 1.0 mg, about 1.25 mg, about 1.5 mg, about 2.0 mg or about 3.0 mg per eye. In one embodiment, the dosage Antagonist A or another pharmaceutically acceptable salt thereof is about 0.03 mg, about 0.3 mg, about 0.5 mg, about 1.0 mg, about 1.25 mg, about 1.5 mg, about 2.0 mg, about 3.0 mg, or about 4.0 mg per eye. In another embodiment, the dosage of a VEGF antagonist (e.g., ranibizumab, bevacizumab, aflibercept, ESBA1008 or pegaptanib sodium) is about 0.03 mg, about 0.3 mg, about 0.5 mg, about 1.0 mg, about 1.25 mg, about 1.5 mg, about 1.65 mg, about 2.0 mg, about 3.0 mg, or about 4.0 mg per eye. In another embodiment, the dosage of the anti-C5 agent (e.g., ARC1905 or a pharmaceutically acceptable salt thereof) is about 0.03 mg, about 0.3 mg, about 0.5 mg, about 1.0 mg, about 1.25 mg, about 1.5 mg, about 1.65 mg, about 2.0 mg, about 3.0 mg, or about 4.0 per eye.

In certain embodiments where a subject is administered both Antagonist A or another pharmaceutically acceptable salt thereof and a VEGF antagonist, and optionally an anti-C5 agent, the dosage of Antagonist A or another pharmaceutically acceptable salt thereof) is about 1.5 mg, and the dosage of the VEGF antagonist (e.g., ranibizumab) is about 0.5 mg. In certain embodiments where a subject is administered both Antagonist A or another pharmaceutically acceptable salt thereof and a VEGF antagonist, the dosage of Antagonist A or another pharmaceutically acceptable salt thereof is about 3.0 mg, and the dosage of the VEGF antagonist (e.g., ranibizumab) is about 0.5 mg. In certain embodiments, a subject is administered both Antagonist A or another pharmaceutically acceptable salt thereof and a VEGF antagonist, wherein the dosage of Antagonist A or another pharmaceutically acceptable salt thereof) is about 1.5 mg, and the dosage of the VEGF antagonist (e.g., bevacizumab) is about 1.25 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist (e.g., bevacizumab) is about 1.25 mg. In certain embodiments, a subject is administered both Antagonist A or another pharmaceutically acceptable salt thereof and a VEGF antagonist, wherein the dosage of Antagonist A or another pharmaceutically acceptable salt thereof is about 1.5 mg, and the dosage of the VEGF antagonist (e.g., aflibercept) is about 2.0 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist (e.g., aflibercept) is about 2.0 mg. In certain embodiments, a subject is administered both Antagonist A or another pharmaceutically acceptable salt thereof and a VEGF antagonist, wherein the dosage of Antagonist A or another pharmaceutically acceptable salt thereof is about 1.5 mg, and the dosage of the VEGF antagonist, e.g., pegaptanib sodium, is about 1.65 mg. In certain embodiments, a subject is administered both Antagonist A or another pharmaceutically acceptable salt thereof and a VEGF antagonist, wherein the dosage of Antagonist A or another pharmaceutically acceptable salt thereof is about 3.0 mg, and the dosage of the VEGF antagonist, e.g., pegaptanib sodium, is about 1.65 mg.

The dosage can range from about 0.01 mL to about 0.2 mL administered per eye, or about 0.03 mL to about 0.15 mL administered per eye, or about 0.05 mL to about 0.10 mL administered per eye.

Antagonist A or a pharmaceutically acceptable salt thereof can be delivered intravitreally at up to about 30 mg/ml with injection volumes up to 100 µL.

Illustrative Antagonist A/VEGF antagonist combination pairs and their dosages are set forth in Table 11:

TABLE 11

| Combination No. | PDGF Antagonist | VEGF Antagonist |
|---|---|---|
| 1 | Antagonist A (about 1.5 mg) | ranibizumab (about 0.5 mg) |
| 2 | Antagonist A (about 3.0 mg) | ranibizumab (about 0.5 mg) |
| 3 | Antagonist A (about 1.5 mg) | bevacizumab (about 1.25 mg) |
| 4 | Antagonist A (about 3.0 mg) | bevacizumab (about 1.25 mg) |
| 5 | Antagonist A (about 1.5 mg) | aflibercept (about 2.0 mg) |
| 6 | Antagonist A (about 3.0 mg) | aflibercept (about 2.0 mg) |
| 7 | Antagonist A (about 3.0 mg) | pegaptanib sodium (about 1.65 mg) |
| 8 | Antagonist A (about 3.0 mg) | pegaptanib sodium (about 1.65 mg) |

In particular embodiments wherein the subject is administered an anti-C5 agent in combination with Antagonist A or another pharmaceutically acceptable salt thereof and the VEGF antagonist, the anti-C5 agent may be administered at a dosage of about 0.03 mg, about 0.3 mg, about 0.5 mg, about 1.0 mg, about 1.25 mg, about 1.5 mg, about 2.0 mg or about 3.0 mg per eye.

In certain embodiments, ocular dosages of compositions comprising anti-C5 aptamers, such as ARC1905 and ARC187, or a pharmaceutically acceptable salt thereof, can range from about 0.01 mg to about 5 mg/eye or from about 0.1 mg to about 3 mg/eye. For instance, ocular dosages of compositions comprising ARC1905, ARC187, or a pharmaceutically acceptable salt thereof may be about 0.01 mg, about 0.03 mg, about 0.05 mg, about 0.1 mg, about 0.3 mg, about 0.5 mg, about 1 mg, about 1.5 mg, about 2 mg, about 2.5 mg, about 3 mg, about 3.5 mg, about 4 mg, about 4.5 mg, or about 5 mg. Such dosages may be administered ocularly, for example by intravitreal injection, weekly, biweekly, monthly, or quarterly, optionally by a sustained release device or formulation. In some embodiments, the anti-C5 aptamers (e.g., ARC1905, ARC187, or a pharmaceutically acceptable salt thereof) can be administered in multiple injections (e.g., intravitreal injections) over a period of months separated by varying time intervals. In certain such embodiments, initial injections received early in the treatment regimen are separated by a shorter interval than injections received later in the treatment regimen. For instance, one dosage regimen, particularly useful in methods for treating, preventing, or stabilizing AMD (e.g., non-exudative type AMD or geographic atrophy), comprises administering initial injections at the start of treatment (e.g., first two, three, four, or five injections) of anti-C5 aptamer (e.g., ARC1905, ARC187, or a pharmaceutically acceptable salt thereof) on a monthly basis and administering subsequent injections at longer intervals (e.g., every three, four, five, or six months). By way of example, the first three injections of anti-C5 aptamer are administered to a subject every month, whereas the fourth and fifth injections are administered three or four months after the previous injection. Intervals between injections of anti-C5 aptamer may be adjusted based on the subject's response to treatment as measured, for example, by change in geographic atrophy lesion size or improvement or stabilization of visual acuity.

In some embodiments, an anti-C5 aptamer is administered to a subject with a VEGF antagonist, wherein the dosage of the anti-C5 aptamer is about 0.03 mg, and the dosage of the VEGF antagonist, e.g., ranibizumab, is about 0.5 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., ranibizumab, is about 0.5 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., ranibizumab, is about 0.5 mg.

In some embodiments, an anti-C5 aptamer is administered to a subject with a VEGF antagonist, wherein the dosage of the anti-C5 aptamer is about 0.03 mg, and the dosage of the VEGF antagonist, e.g., bevacizumab, is about 1.25 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., bevacizumab, is about 1.25 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., bevacizumab, is about 1.25 mg.

In some embodiments, an anti-C5 aptamer is administered to a subject with a VEGF antagonist, wherein the dosage of the anti-C5 aptamer is about 0.03 mg, and the dosage of the VEGF antagonist, e.g., aflibercept, is about 2.0 mg. In certain embodiments, a subject is administered both an anti-C5 aptamer and a VEGF antagonist, wherein the dosage of the anti-C5 aptamer is about 1.0 mg, and the dosage of the VEGF antagonist, e.g., aflibercept, is about 2.0 mg. In certain embodiments, a subject is administered both an anti-C5 aptamer and a VEGF antagonist, wherein the dosage of the anti-C5 aptamer is about 2.0 mg, and the dosage of the VEGF antagonist, e.g., aflibercept, is about 2.0 mg.

Administration of each antagonist can, independently, be one to four times daily or one to four times per month or one to six times per year or once every two, three, four or five years. Administration can be for the duration of one day or one month, two months, three months, six months, one year, two years, three years, and may even be for the life of the patient. In one embodiment, the administration is performed once a month for three months. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

In addition to treating pre-existing ophthalmological diseases and disorders, the compositions can be administered prophylactically in order to prevent or slow the onset of these disease and disorders. The term "prevent" encompasses inhibiting or delaying the onset or progression of a disease or disorder. In prophylactic applications, the composition can be administered to a patient susceptible to or otherwise at risk of a particular ophthalmological disease or disorder.

In one embodiment, Antagonist A or another pharmaceutically acceptable salt thereof and the VEGF antagonist are administered to a subject in need of treatment therewith, typically in the form of an injectable pharmaceutical composition. Antagonist A or another pharmaceutically acceptable salt thereof and VEGF antagonist can be administered either in separate compositions or in a pharmaceutical composition comprising both the PDGF antagonist and VEGF antagonist. The administration can be by injection, for example by intraocular injection, or by using a drug delivery device. Parenteral, systemic, or transdermal administration is also within the scope of the invention. The administration of Antagonist A or another pharmaceutically acceptable salt thereof and the VEGF antagonist can be sequential in time or concurrent. When administered sequentially, the administration of each can be by the same or different route. In one embodiment, Antagonist A or another pharmaceutically acceptable salt thereof is administered within 90 days, 30 days, 10 days, 5 days, 24 hours, 1 hour, 30 minutes, 10 minutes, 5 minutes or one minute of administration of a VEGF antagonist. Where Antagonist A or another pharmaceutically acceptable salt thereof is administered prior to the VEGF antagonist, the VEGF antagonist is administered within a time and in an amount such that the total amount of Antagonist A or another pharmaceutically acceptable salt thereof and VEGF antagonist is effective to treat or prevent an ophthalmological disease or disorder. Where the VEGF antagonist is administered prior to Antagonist A or another pharmaceutically acceptable salt thereof, Antagonist A or another pharmaceutically acceptable salt thereof is administered within a time and in an amount such that the total amount of Antagonist A or another pharmaceutically acceptable salt thereof and VEGF antagonist is effective to treat or prevent an ophthalmological disease or disorder.

In one embodiment, Antagonist A or another pharmaceutically acceptable salt thereof or VEGF antagonist (e.g., ranibizumab, bevacizumab, pegaptanib sodium, ESBA1008 or aflibercept) is administered intravitreally with a 30-gauge or 27-gauge needle. In some embodiments, a 0.5 inch needle is used. In one embodiment, Antagonist A or another pharmaceutically acceptable salt thereof is administered intravitreally with a 30-gauge 0.5 inch needle and a VEGF antagonist (e.g., ranibizumab, bevacizumab, pegaptanib sodium, ESBA1008 or aflibercept) is administered intravitreally with a 27-gauge needle. In some embodiments, 50 µL (1.5 mg in 0.05 mL) of Antagonist A or another pharmaceutically acceptable salt thereof is administered intravitreally with a 30-gauge 0.5 inch needle and 50 µL (0.5 mg in 0.05 mL) of a VEGF antagonist (e.g., ranibizumab, bevacizumab, pegaptanib sodium or aflibercept) is administered intravitreally with a 27-gauge needle.

In certain embodiments where Antagonist A or another pharmaceutically acceptable salt thereof such as Antagonist A or another pharmaceutically acceptable salt thereof is used in combination with a VEGF antagonist, such as ranibizumab, bevacizumab, ESBA1008, pegaptanib sodium or aflibercept, one of these two agents is first administered to the subject, and then the other agent is administered to the subject. In particular embodiments, the two agents are both administered to the same eye of the subject. In particular embodiments, the two agents are both administered to both eyes of the subject. The two agents may be administered to an eye in either order, i.e., Antagonist A or another pharmaceutically acceptable salt thereof may be administered first, and then the VEGF antagonist administered, or the VEGF antagonist may be administered first, and then Antagonist A or another pharmaceutically acceptable salt thereof administered. The agent administered second may be administered immediately following administration of the agent administered first, or the agent administered second may be administered after a time period following administration of the agent administered first.

In certain embodiments, the time period from administration of the first agent to administration of the second agent is at least 1 min, at least 5 min, at least 10 min, at least 15 min, at least 30 min, or at least one hour. In certain embodiments, the time period from administration of the first agent to administration of the second agent is between 1 min and 2 hours, between 5 min and 2 hours, between 10 min and 2 hours, between 15 min and 2 hours, between 30 min and 2 hours, between 45 min and 2 hours, between 1 hour and 2 hours, or between 30 min and 1 hour. In certain embodiments, the time period from administration of the first agent to administration of the second agent is about 1 min, about 2 min, about 3 min, about 5 min, about 10 min, about 15 min, about 20 min, about 25 min, about 30 min, about 35 min, about 40 min, about 45 min, about 50 min, about 55 min, about 60 min, about 90 min, or about 120 min.

In certain embodiments, the present invention provides methods for treating or preventing any of the ophthalmological diseases described herein, comprising providing to a subject in need thereof. Antagonist A or another pharmaceutically acceptable salt thereof at a first time point, and providing to the subject a VEGF antagonist, e.g., aflibercept, bevacizumab, ranibizumab, ESBA1008, or pegaptanib sodium, at a second time point, wherein the amount of time between the first time point and the second time point is about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days.

In certain embodiments, Antagonist A or another pharmaceutically acceptable salt thereof and the VEGF antagonist are administered intravitreally. In certain embodiments, about 1.5 mg or 3.0 mg of Antagonist A or another pharmaceutically acceptable salt thereof to an eye, and about 0.5 mg, about 1.25 mg, about 1.65 mg, or about 2.0 mg of the VEGF antagonist is administered to an eye. In some embodiments, the VEGF antagonist is administered intravitreally about 30 minutes after Antagonist A or another pharmaceutically acceptable salt thereof is administered intravitreally. In some embodiments, Antagonist A or another pharmaceutically acceptable salt thereof is administered intravitreally about 30 minutes after the VEGF antagonist is administered intravitreally.

In one embodiment, a VEGF antagonist is administered to at least one eye of the subject, about 1 hour is allowed to elapse following administration of the VEGF antagonist, and then Antagonist A or another pharmaceutically acceptable salt thereof is administered to the same eye. In one embodiment, Antagonist A or another pharmaceutically acceptable salt thereof is administered to at least one eye of the subject, about 1 hour is allowed to lapse following administration of the PDGF antagonist, and then a VEGF antagonist is administered to the same eye.

In certain embodiments, the PDGF antagonist and the VEGF antagonist are administered to each eye in a total combined volume of less than or about 50 µL, less than or about 60 µL, less than or about 70 µL, less than or about 80 µL, less than or about 90 µL, less than or about 100 µL, less than or about 120 µL, less than or about 150 µL, or less than or about 200 µL.

In certain embodiments, Antagonist A or another pharmaceutically acceptable salt thereof, VEGF antagonist and anti-C5 agent are administered intraocularly, e.g., intravitreally. In particular embodiments, Antagonist A or another pharmaceutically acceptable salt thereof, VEGF antagonist and anti-C5 agent are administered to the mammal via a single injection, e.g., a single intraocular or intravitreal injection. In particular embodiments, Antagonist A or another pharmaceutically acceptable salt thereof, VEGF antagonist and anti-C5 agent are administered sequentially. In certain embodiments, two or more of Antagonist A or another pharmaceutically acceptable salt thereof, a VEGF antagonist and an anti-C5 agent are administered at the same time, e.g., in the same composition. In particular embodiments, one of Antagonist A or another pharmaceutically acceptable salt thereof, a VEGF antagonist and an anti-C5 agent is administered, and within about 30 seconds, one or two of others are subsequently administered. In particular embodiments, all three of Antagonist A or another pharmaceutically acceptable salt thereof, a VEGF antagonist and an anti-C5 agent are administered within about 30 seconds or one minute of each other. In other embodiments, one of Antagonist A or another pharmaceutically acceptable salt thereof, a VEGF antagonist and an anti-C5 agent is administered, and one or both of the others are administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In other embodiments, one or two of Antagonist A or another pharmaceutically acceptable salt thereof, VEGF antagonist and anti-C5 agent are administered, and the other is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In certain embodiments, one of the PDGF antagonist, VEGF antagonist and anti-C5 agent is administered; and another is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later; and the remaining one is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In certain embodiments wherein two of Antagonist A or another pharmaceutically acceptable salt thereof, VEGF antagonist and anti-C5 agent are present in the same composition, the composition is administered and the PDGF antagonist, VEGF antagonist or anti-C5 agent that is not present in the composition is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later. In other embodiments wherein two of Antagonist A or another pharmaceutically acceptable salt thereof, VEGF antagonist and anti-C5 agent are present in the same composition, Antagonist A or another pharmaceutically acceptable salt thereof, VEGF antagonist or anti-C5 agent that is not present in the composition is administered, and the composition is administered about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours, about 36 hours, about 48 hours, about three days, about four days, about five days, about six days, or about seven days later.

In certain embodiments, Antagonist A or another pharmaceutically acceptable salt thereof, e.g., Antagonist A or another pharmaceutically acceptable salt thereof, is administered about every 24 hours for two or more, three or more, four or more, five or more, six or more, or seven or more days, and a VEGF antagonist, e.g., aflibercept, bevacizumab, ESBA1008, pegaptanib sodium or ranimizumab, is administered about 48 hours following the first administration of Antagonist A or another pharmaceutically acceptable salt thereof. In certain embodiments, Antagonist A or another pharmaceutically acceptable salt thereof is administered on each of four successive days, i.e., day 1, day 2, day 3 and day 4, and the VEGF antagonist (e.g., bevacizumab, ranicizumab, ESBA1008, pegaptanib sodium or aflibercept) is administered on the third day, i.e., day 3. In particular embodiments, a composition comprising Antagonist A or another pharmaceutically acceptable salt thereof, e.g., Antagonist A or another pharmaceutically acceptable salt thereof, is administered to a subject, and a composition comprising a VEGF antagonist is administered to the subject about forty-eight hours later.

In one embodiment, about 50 mg/kg of Antagonist A or another pharmaceutically acceptable salt thereof (e.g., Antagonist A or another pharmaceutically acceptable salt thereof) is administered, e.g., intraperitoneally, on day 1, day 2, day 3 and day 4, and about 1 mg/kg of a VEGF antagonist (e.g., bevacizumab, ranibizumab, ESBA1008, pegaptanib sodium, or aflibercept) is administered on day 3. In one embodiment, about 50 mg/kg of Antagonist A or another pharmaceutically acceptable salt thereof (e.g., Antagonist A or another pharmaceutically acceptable salt thereof) is administered on day 1, day 2, day 3 and day 4, and about 5 mg/kg of a VEGF antagonist (e.g., bevacizumab, ranibizumab, ESBA1008, pegaptanib sodium, or aflibercept) is administered on day 3.

In one embodiment, about 50 mg/kg of Antagonist A or another pharmaceutically acceptable salt thereof is administered on day 1, day 2, day 3 and day 4, and about 1 mg/kg of aflibercept is administered on day 3. In one embodiment, about 50 mg/kg of Antagonist A or another pharmaceutically acceptable salt thereof is administered on day 1, day 2, day 3 and day 4, and about 5 mg/kg of aflibercept is administered on day 3.

In one embodiment, about 0.03 mg, about 0.3 mg, about 0.5 mg, about 1.0 mg, about 1.5 mg or about 3.0 mg of Antagonist A or another pharmaceutically acceptable salt thereof (e.g., Antagonist A or another pharmaceutically acceptable salt thereof) is administered intravitreally on day 1, day 2, day 3 and day 4, and about 0.5 mg, about 1.0 mg, about 1.5 mg, about 1.65 mg, about 3.0 mg, or about 4.0 mg of a VEGF antagonist (e.g., bevacizumab, ranibizumab, ESBA1008, pegaptanib sodium, or aflibercept) is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 0.5 mg of ranibizumab is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 1.25 mg of bevacizumab is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 2.0 mg of aflibercept is administered intravitreally on day 3. In one embodiment, about 0.3 mg or about 1.5 mg of Antagonist A or another pharmaceutically acceptable salt thereof is administered intravitreally on day 1, day 2, day 3 and day 4, and about 1.65 mg of pegaptanib sodium is administered intravitreally on day 3.

In some embodiments, Antagonist A or another pharmaceutically acceptable salt thereof and VEGF antagonist are administered every four weeks or every 30 days, for six treatments. In some embodiments, the VEGF antagonist is ranibizumab. In some embodiments, 0.3 mg of Antagonist A or another pharmaceutically acceptable salt thereof and 0.5 mg of ranibizumab are administered every four weeks or every 30 days, for six treatments. In some embodiments, 1.5 mg of Antagonist A or another pharmaceutically acceptable salt thereof and 0.5 mg of ranibizumab are administered every four weeks or every 30 days, for six treatments.

In some embodiments, 0.3 mg of Antagonist A or another pharmaceutically acceptable salt thereof and 1.25 mg of bevacizumab, 2.0 mg of aflibercept, or 1.65 mg of pegaptanib sodium are administered every four weeks or every 30 days, for six treatments. In some embodiments, 1.5 mg of Antagonist A or another pharmaceutically acceptable salt thereof and 1.25 mg of bevacizumab, 2.0 mg of aflibercept, or 1.65 mg of pegaptanib sodium are administered every four weeks or every 30 days, for six treatments.

In some embodiments, the methods comprise administering Antagonist A or another pharmaceutically acceptable salt thereof, bevacizumab and aflibercept. In some embodiments, the methods comprise administering Antagonist A or another pharmaceutically acceptable salt thereof, bevacizumab and aflibercept every four weeks or every 30 days, for six treatments. In some embodiments, the methods comprise administering 1.5 mg of Antagonist A or another pharmaceutically acceptable salt thereof, 1.25 mg of bevacizumab, and 2 mg of aflibercept. In some embodiments, the methods comprise administering 1.5 mg of Antagonist A or another pharmaceutically acceptable salt thereof, 1.25 mg of bevacizumab, and 2 mg of aflibercept every four weeks or every 30 days, for six treatments.

In some embodiments, the methods comprise administering to a subject in need thereof (a) Antagonist A or another pharmaceutically acceptable salt thereof and (b) an VEGF antagonist, wherein (a) and (b) are administered in an amount that is effective for treating or preventing an ocular condition (e.g., wet AMD), and wherein the administering occurs once every month, ±about seven days, for 12 consecutive months.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for a first 12 consecutive months, and immediately thereafter once every two months, ±about seven days, for a second 12 consecutive months, commencing on the second month of the second 12 consecutive months.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for 24 consecutive months is also provided herein.

In some embodiments, the methods comprise administering to a subject in need thereof (a) Antagonist A or another pharmaceutically acceptable salt thereof and (b) an VEGF antagonist, wherein: (a) and (b) are administered in an amount that is effective for treating or preventing an ocular condition (e.g., wet AMD); and the administering occurs once every month, ±about seven days, for three consecutive months, and immediately thereafter once every two months, ±about seven days, for 12 consecutive months, commencing on the second month of the 12 consecutive months.

In some embodiments, the methods comprise continuous treatment, continuous and discontinuous treatments, and/or retreatments, e.g., for the treatment or preventing of wet-type AMD or subfoveal neovascular AMD. In some embodiments, continuous treatment comprises administering to Antagonist A or another pharmaceutically acceptable salt thereof and an anti-VEGF agent monthly (±7 days) for at least 1, 2, 3, 4, 5, 6, 7, 8, 9, 10, 11, or 12 consecutive months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the methods further comprise measuring the subject's visual acuity. In some embodiments, the subject's visual acuity is measured once every month, ±about seven days. In some embodiments, visual acuity is stable when it is stable for three consecutive months. In some embodiments, visual acuity is stable when at each of the last two of the three consecutive months, visual acuity is within 5 ETDRS letters (better or worse) of the subject's visual acuity at the first of the three consecutive months (i.e., the month immediately preceding the first of the two consecutive following months).

In some embodiments, a subject is administered in accordance with the present methods until the subject's visual acuity is stable. In some embodiments, a subject is administered in accordance with the present methods until the subject's visual acuity is stable for three consecutive months. In some embodiments, a subject is administered in accordance with the present methods until the subject's visual acuity at each of the last two of the three consecutive months is ≤a five-ETDRS-letter difference from the subject's visual acuity of the first of the three consecutive months. In some embodiments, a subject is administered in accordance with the present methods until the subject experiences no new or significant intraretinal or sub-retinal hemorrhage, or no increase of ≥50 µm in foveal intraretinal fluid. In some embodiments, a subject is administered in accordance with the present methods until the subject's visual acuity measured at each of the last two of the three consecutive months is ≤a five-ETDRS-letter difference from the subject's visual acuity of the first of the three consecutive months, and the subject experiences no new or significant intraretinal or sub-retinal hemorrhage, and no increase of ≥50 µm in foveal intraretinal fluid.

In some embodiments, discontinuous treatment is administered after continuous treatment, in which discontinuous treatment is based on a physician's discretion, and the subject has stabilized vision as determined by ≤a five-ETDRS-letter difference in the subject's visual acuity after continuous and discontinuous treatment.

In some embodiments, subjects with a loss of visual acuity of >5 ETDRS letters from the previous monthly assessment, new and significant intraretinal or sub-retinal hemorrhage, and/or an increase of ≥50 µm in foveal intraretinal fluid are retreated.

In some embodiments, the continuous method comprises administering Antagonist A or another pharmaceutically acceptable salt thereof and a VEGF antagonist in an amount that is effective for treating or preventing wet AMD, wherein the administering occurs once every month, ±about seven days, for 12 consecutive months. In some embodiments, the methods further comprise measuring the subject's visual acuity at one month, ±about seven days, immediately following the 12 consecutive months, wherein the subject's visual acuity measured on the twelfth of the 12 consecutive months and the one month immediately following the 12 consecutive months is ≤a five-ETDRS-letter difference in the subject's visual acuity measured on the eleventh of the 12 consecutive months.

In some embodiments, the methods further comprise measuring the subject's visual acuity once every month, ±about seven days, on each of an additional 11 consecutive months. In some embodiments, the subject's visual acuity measured on any two consecutive months of the additional 11 consecutive months is ≤a five-ETDRS-letter difference in the subject's visual acuity measured on a month immediately preceding the two consecutive months.

In some embodiments, the subject's visual acuity measured on the twelfth of the 12 consecutive months and the one month immediately following the 12 consecutive months is not ≤a five-ETDRS-letter difference in the subject's visual acuity measured on the eleventh of the 12 consecutive months and the subject is retreated. In some embodiments, retreatment comprises administering to the patient on the one month immediately following the 12 consecutive months Antagonist A or another pharmaceutically acceptable salt thereof and a VEGF antagonist in an amount that is effective for treating or preventing wet AMD, measuring the patient's visual acuity on a month, ±about seven days, immediately following the one month immediately following the 12 consecutive months, and administering to the subject on each immediately following month Antagonist A or another pharmaceutically acceptable salt thereof and a VEGF antagonist in an amount that is effective for treating or preventing wet AMD, until the subject's visual acuity on any two consecutive following months is ≤a five-ETDRS-letter difference in the subject's visual acuity measured on a month immediately preceding the first of the two consecutive following months. In some embodiments, the total number of months does not exceed 24.

In some embodiments, wherein the subject's visual acuity measured on the one month immediately following the 12 consecutive months is not ≤a five-ETDRS-letter difference in the subject's visual acuity measured on the twelfth of the 12 consecutive months and is not solely attributable to newly diagnosed foveal atrophy or worsening ocular media opacity, the method further comprises administering to the subject on the one month immediately following the 12 consecutive months Antagonist A or another pharmaceutically acceptable salt thereof and a VEGF antagonist in an amount that is effective for treating or preventing wet AMD; and administering to the subject on each immediately following month (a) and (b) in an amount that is effective for treating or preventing wet AMD, until the subject's visual acuity measured on any two consecutive following months is ≤a five-ETDRS-letter difference in the subject's visual acuity measured on a month immediately preceding the first of the two consecutive following months. In some embodiments, the total number of months does not exceed 24.

In some embodiments, wherein the subject presents intraretinal or sub-retinal hemorrhage or a ≥50 µm increase in foveal intraretinal fluid at one month, ±about seven days, immediately following the 12 consecutive months, the method further comprises administering to the subject on the one month immediately following the 12 consecutive months Antagonist A or another pharmaceutically acceptable salt thereof an a VEGF antagonist in an amount that is effective for treating or preventing wet AMD; and administering to the subject on each immediately following month (a) and (b) in an amount that is effective for treating or preventing wet AMD, until the subject's visual acuity measured on any two consecutive following months is ≤a five-ETDRS-letter difference in the subject's visual acuity measured on a month immediately preceding the first of the two consecutive following months. In some embodiments, the total number of months does not exceed 24.

Also provided herein is a method comprising administering Antagonist A or another pharmaceutically acceptable salt thereof and a VEGF antagonist intravitreally once every month, ±about seven days, for a first 12 consecutive months, and immediately thereafter once every two months, ±about seven days, for a second 12 consecutive months, commencing on the second month of the second 12 consecutive months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the method further comprises measuring the subject's visual acuity once every month, ±about seven days, during the first 12 consecutive months and second 12 consecutive months. In some embodiments, the subject's visual acuity measured on any one of the first, third, fifth, seven, ninth and eleventh months of the second consecutive 12 months decreased at least five ETDRS letters relative to the patient's visual acuity measured on the month immediately preceding the first, third, fifth, seven, ninth or eleventh month of the second consecutive 12 months.

In some embodiments, the methods further comprises administering to the subject an amount of Antagonist A or a pharmaceutically acceptable salt thereof and a VEGF antagonist effective for treating or preventing wet AMD on the month in which the subject's visual acuity measured the decrease of at least five ETDRS letters relative to the patient's visual acuity measured on the immediately preceding month.

In some embodiments, the method further comprises administering Antagonist A or a pharmaceutically acceptable salt thereof and a VEGF antagonist on any one of the first, third, fifth, seven, ninth and eleventh months of the second consecutive 12 months.

In some embodiments, the decrease in visual acuity is attributed to solely newly diagnosed foveal atrophy or opacified ocular media.

In some embodiments, the subject presents intraretinal or sub-retinal hemorrhage or a ≥50 µm increase in foveal intraretinal fluid on any one of the first, third, fifth, seven, ninth and eleventh months of the second consecutive 12 months.

In some embodiments, the method further comprises administering Antagonist A or a pharmaceutically acceptable salt thereof and a VEGF antagonist on month in which the subject presents intraretinal or sub-retinal hemorrhage or a ≥50 μm increase in foveal intraretinal fluid.

Also provided herein is a method comprising administering Antagonist A or another pharmaceutically acceptable salt thereof and a VEGF antagonist intravitreally once every month, ±about seven days, for 24 consecutive months. In other embodiments, Antagonist A or another pharmaceutically acceptable salt thereof and a VEGF antagonist are administered intravitreally once a month for three months and then every other month for the next 21 months. In some embodiments, Antagonist A or a pharmaceutically acceptable salt thereof is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours of administration of the VEGF antagonist. In some embodiments, the VEGF antagonist is administered prior to administration of Antagonist A or a pharmaceutically acceptable salt thereof. In other embodiments, Antagonist A or a pharmaceutically acceptable salt thereof is administered prior to administration of the VEGF antagonist. In some embodiments, Antagonist A or a pharmaceutically acceptable salt thereof and a VEGF antagonist are administered as a co-formulation. In some embodiments, the amount of Antagonist A or a pharmaceutically acceptable salt thereof administered is about 1.5 mg/eye and the amount of VEGF antagonist administered is about 0.5 mg/eye (e.g., ranibizumab), about 1.25 mg/eye (e.g., bevacizumab), about 1.65 mg/eye (e.g., pegaptanib sodium), or about 2.0 mg/eye (e.g., aflibercept).

In some embodiments, the methods comprise administering to a subject in need thereof (a) Antagonist A or another pharmaceutically acceptable salt thereof and (b) an VEGF antagonist, wherein (a) and (b) are administered in an amount that is effective for treating or preventing an ophthalmological disease or disorder (e.g., wet AMD), and wherein the administering occurs once every month, ±about seven days, for a first administration period of at least 3 consecutive months, followed by administering (a) and (b) for a second administration period at a frequency of at least every other month ±about seven days beginning at two months ±about seven days after the day of the last month of the first administration period on which (a) and (b) are administered. In some embodiments, the first administration period is for at least 6 consecutive months. In some embodiments, the VEGF antagonist is ranibizumab or bevacizumab, wherein (a) and (b) are administered at a frequency of once every month ±about seven days during the second administration period and wherein the second administration period is at least about nine months.

In some embodiments, the methods further comprise measuring the subject's visual acuity on a day that is prior to and within about one month of administration of (a) and (b). In some embodiments, the methods further comprise administering to the subject (a) and (b) in an amount that is effective for treating or preventing an an ophthalmological disease or disorder (e.g., wet AMD), until the subject's visual acuity on any two consecutive following months is ≤a five-ETDRS-letter difference in the subject's visual acuity measured on a month immediately preceding the first of the two consecutive following months.

In some embodiments, the method further comprise administering to the subject (a) and (b) every other month in an amount that is effective for treating or preventing an an ophthalmological disease or disorder (e.g., wet AMD), until the subject's visual acuity on any two consecutive visual acuity assessments is not ≤a five-ETDRS-letter difference in the subject's visual acuity measured on a visual acuity assessment immediately preceding the first of the two consecutive visual acuity assessments.

In other embodiments, the methods further comprise administering to the subject (a) and (b) every month in an amount that is effective for treating or preventing an an ophthalmological disease or disorder (e.g., wet AMD), until the subject's visual acuity on any two consecutive following months is ≤a five-ETDRS-letter difference in the subject's visual acuity measured on a month immediately preceding the first of the two consecutive following months.

In some embodiments, the methods comprise administering to a subject in need thereof (a) Antagonist A or another pharmaceutically acceptable salt thereof and (b) aflibercept, wherein (a) and (b) are administered in an amount that is effective for treating or preventing an ophthalmological disease or disorder (e.g., wet AMD), and wherein the administering occurs once every month, ±about seven days, for a first administration period of at least 3 consecutive months, followed by administering (a) and (b) for a second administration period at a frequency of at least every other month ±about seven days beginning at two months ±about seven days after the day of the last month of the first administration period on which (a) and (b) are administered.

In some embodiments, the subject has intraretinal or sub-retinal hemorrhage or a ≥50 μm increase in foveal intraretinal fluid at one month, ±about seven days, immediately following the second administration period. In some embodiments, the methods further comprise administering to the subject on each month ±about seven days, beginning on the month that immediately follows the second administration period (a) and (b) in an amount that is effective for treating or preventing wet AMD, until the subject's visual acuity measured on any two consecutive months that follow the 12 consecutive months is ≤a five-ETDRS-letter difference in the subject's visual acuity measured on a month immediately preceding the first of the two consecutive months.

In some embodiments, the total number of months of treatment does not exceed 24.

Pharmaceutical compositions according to the invention may be formulated to release Antagonist A or another pharmaceutically acceptable salt thereof, a VEGF antagonist, or an anti-C5 agent, substantially immediately upon administration or at any predetermined time period after administration, using controlled release formulations. For example, a pharmaceutical composition can be provided in sustained-release form. The use of immediate or sustained release compositions depends on the nature of the condition being treated. If the condition consists of an acute disorder, treatment with an immediate release form can be utilized over a prolonged release composition. For certain preventative or long-term treatments, a sustained released composition can also be appropriate.

Administration of one or both of the antagonists of, or an anti-C5 agent, in controlled release formulations can be useful where the antagonist, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of degradation or metabolism of the therapeutic antagonist. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes. Methods for preparing such sustained or controlled release formulations are well known in the art.

Antagonist A or another pharmaceutically acceptable salt thereof, the VEGF antagonist, or the anti-C5 agent can also be delivered using a drug-delivery device such as an implant. Such implants can be biodegradable and/or biocompatible, or can be non-biodegradable. The implants can be permeable to Antagonist A or another pharmaceutically acceptable salt thereof, the VEGF antagonist, or the anti-C5 agent. Ophthalmic drug delivery devices can be inserted into a chamber of the eye, such as the anterior or posterior chamber or can be implanted in or on the sclera, choroidal space, or an avascularized region exterior to the vitreous. In one embodiment, the implant can be positioned over an avascular region, such as on the sclera, so as to allow for transcleral diffusion of Antagonist A or another pharmaceutically acceptable salt thereof, the VEGF antagonist, or the anti-C5 agent to the desired site of treatment, e.g., the intraocular space and macula of the eye. Furthermore, the site of transcleral diffusion can be proximal to a site of neovascularization such as a site proximal to the macula. Suitable drug delivery devices are described, for example, in U.S. Publication Nos. 2008/0286334; 2008/0145406; 2007/0184089; 2006/0233860; 2005/0244500; 2005/0244471; and 2005/0244462, and U.S. Pat. Nos. 6,808,719 and 5,322,691, the contents of each of which is herein incorporated by reference in its entirety.

In one embodiment, the implant comprises Antagonist A or another pharmaceutically acceptable salt thereof and/or VEGF antagonist dispersed in a biodegradable polymer matrix. The matrix can comprise PLGA (polylactic acid-polyglycolic acid copolymer), an ester-end capped polymer, an acid end-capped polymer, or a mixture thereof. In another embodiment, the implant comprises Antagonist A or another pharmaceutically acceptable salt thereof and/or a VEGF antagonist, a surfactant, and lipophilic compound. The lipophilic compound can be present in an amount of about 80-99% by weight of the implant. Suitable lipophilic compounds include, but are not limited to, glyceryl palmitostearate, diethylene glycol monostearate, propylene glycol monostearate, glyceryl monostearate, glyceryl monolinoleate, glyceryl monooleate, glyceryl monopalmitate, glyceryl monolaurate, glyceryl dilaurate, glyceryl monomyristate, glyceryl dimyristate, glyceryl monopalmitate, glyceryl dipalmitate, glyceryl monostearate, glyceryl distearate, glyceryl monooleate, glyceryl dioleate, glyceryl monolinoleate, glyceryl dilinoleate, glyceryl monoarachidate, glyceryl diarachidate, glyceryl monobehenate, glyceryl dibehenate, and mixtures thereof. In another embodiment, the implant comprises Antagonist A or another pharmaceutically acceptable salt thereof and/or a VEGF antagonist housed within a hollow sleeve. The PDGF antagonist or VEGF antagonist, or both, are delivered to the eye by inserting the sleeve into the eye, releasing the implant from the sleeve into the eye, and then removing the sleeve from the eye. An example of this delivery device is described in U.S. Publication No. 2005/0244462, which is hereby incorporated by reference in its entirety.

In one embodiment, the implant is a flexible ocular insert device adapted for the controlled sustained release of Antagonist A or another pharmaceutically acceptable salt thereof and/or a VEGF antagonist into the eye. In one embodiment, the device includes an elongated body of a polymeric material in the form of a rod or tube containing Antagonist A or another pharmaceutically acceptable salt thereof, VEGF antagonist or both, and with at least two anchoring protrusions extending radially outwardly from the body. The device may have a length of at least 8 mm and the diameter of its body portion including the protrusions does not exceed 1.9 mm. The sustained release mechanism can, for example, be by diffusion or by osmosis or bioerosion. The insert device can be inserted into the upper or lower formix of the eye so as to be independent of movement of the eye by virtue of the formix anatomy. The protrusions can be of various shapes such as, for example, ribs, screw threads, dimples or bumps, truncated cone-shaped segments or winding braid segments. In a further embodiment, the polymeric material for the body is selected as one which swells in a liquid environment. Thus a device of smaller initial size can be employed. The insert device can be of a size and configuration such that, upon insertion into the upper or lower formix, the device remains out of the field of vision so as to be well retained in place and imperceptible by a recipient over a prolonged period of use. The device can be retained in the upper or lower formix for 7 to 14 days or longer. An example of this device is described in U.S. Pat. No. 5,322,691, which is hereby incorporated by reference in its entirety.

Kits

The invention relates to kits comprising one or more pharmaceutical compositions and instructions for use. At least two antagonists can be formulated together or in separate compositions and in individual dosage amounts. The antagonists are also useful when formulated as pharmaceutically acceptable salts. In one embodiment, the kits comprise a composition comprising Antagonist A or another pharmaceutically acceptable salt thereof and a pharmaceutically acceptable carrier or vehicle and another composition comprising a VEGF antagonist and a pharmaceutically acceptable carrier or vehicle. In another embodiment, the kits comprise a composition comprising a VEGF antagonist, Antagonist A or another pharmaceutically acceptable salt thereof and a pharmaceutically acceptable carrier or vehicle. Each of the kits' compositions can be contained in a container. In some embodiments, the kits comprise an anti-C5 agent.

The kits can comprise (1) an amount of Antagonist A or another pharmaceutically acceptable salt thereof and a pharmaceutically acceptable carrier, vehicle, or diluent in a first unit dosage form; (2) an amount of a VEGF antagonist and a pharmaceutically acceptable carrier, vehicle, or diluent in a second unit dosage form; and (3) a container. The container can be used to separate components and include, for example, a divided bottle or a divided foil packet. The separate antagonist compositions may also, if desired, be contained within a single, undivided container. In some embodiments, the kits comprise an anti-C5 agent.

The kits can also comprise directions for the administration of the antagonists. The kits are particularly advantageous when the separate components are administered in different dosage forms, are administered at different dosage levels, or when titration of the individual antagonists is desired.

EXAMPLES

Example 1: Antagonist A and Ranibizumab Combination Therapy for Treating Subfoveal Neovascular Lesions Secondary to Neovascular Age-Related Macular Degeneration (NVAMD)

In this study, 449 subjects with subfoveal neovascular lesions secondary to NVAMD received six monthly intravitreous injections of Antagonist A given in combination with ranibizumab (administered as Lucentis®, commercially available from Genentech, South San Francisco, Calif.). Antagonist A was injected as the formulation shown in Table 12. The primary efficacy endpoint in the study was the mean change in visual acuity from baseline at the week 24 visit. As pre-specified in the analysis plan, the Hochberg procedure (Hochberg, Y. (1988). A sharper Bonferroni procedure for multiple tests of significance. *Biometrika*. 75, 800-802) was employed to account for multiple dose comparisons.

The subjects were randomized in a 1:1:1 ratio to the groups shown in Table 13.

change of visual acuity gain compared to ranibizumab monotherapy from baseline to 24 weeks (10.6 ETDRS letters at week 24, compared to 6.5 letters, p=0.019, representing a 62% additional benefit). (FIG. 3) Subjects treated with Lucentis® and either 1.5 mg or 0.3 mg Antagonist A showed a 62% comparative benefit from baseline compared to treatment with Lucentis® alone.

In addition, the mean change in vision over time demonstrated the benefit of combination therapy at each measured time point over 24 weeks. (FIG. 4) That benefit was sustained during the study and demonstrated increasing differentiation of the curves at study closure.

Figure 5A:
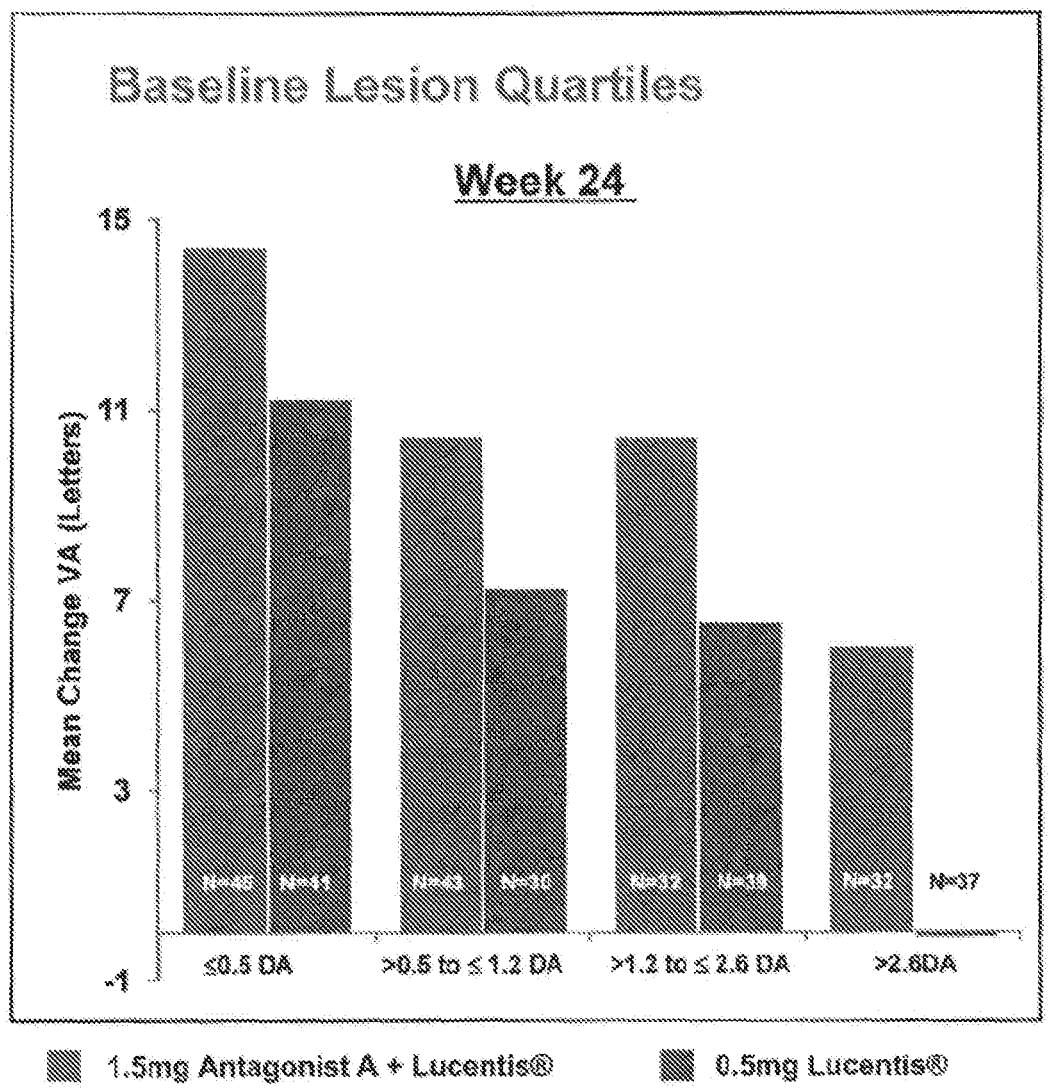
FIGS. 5A and 5A provide bar graphs showing that the increased efficacy of treatment with 0.5 mg of Lucentis® and either 1.5 mg or 0.3 mg of Antagonist A as compared to treatment with Lucentis® monotherapy (0.5 mg) in patients with wet AMD is independent of baseline lesion size or baseline vision.
Figure 5B:
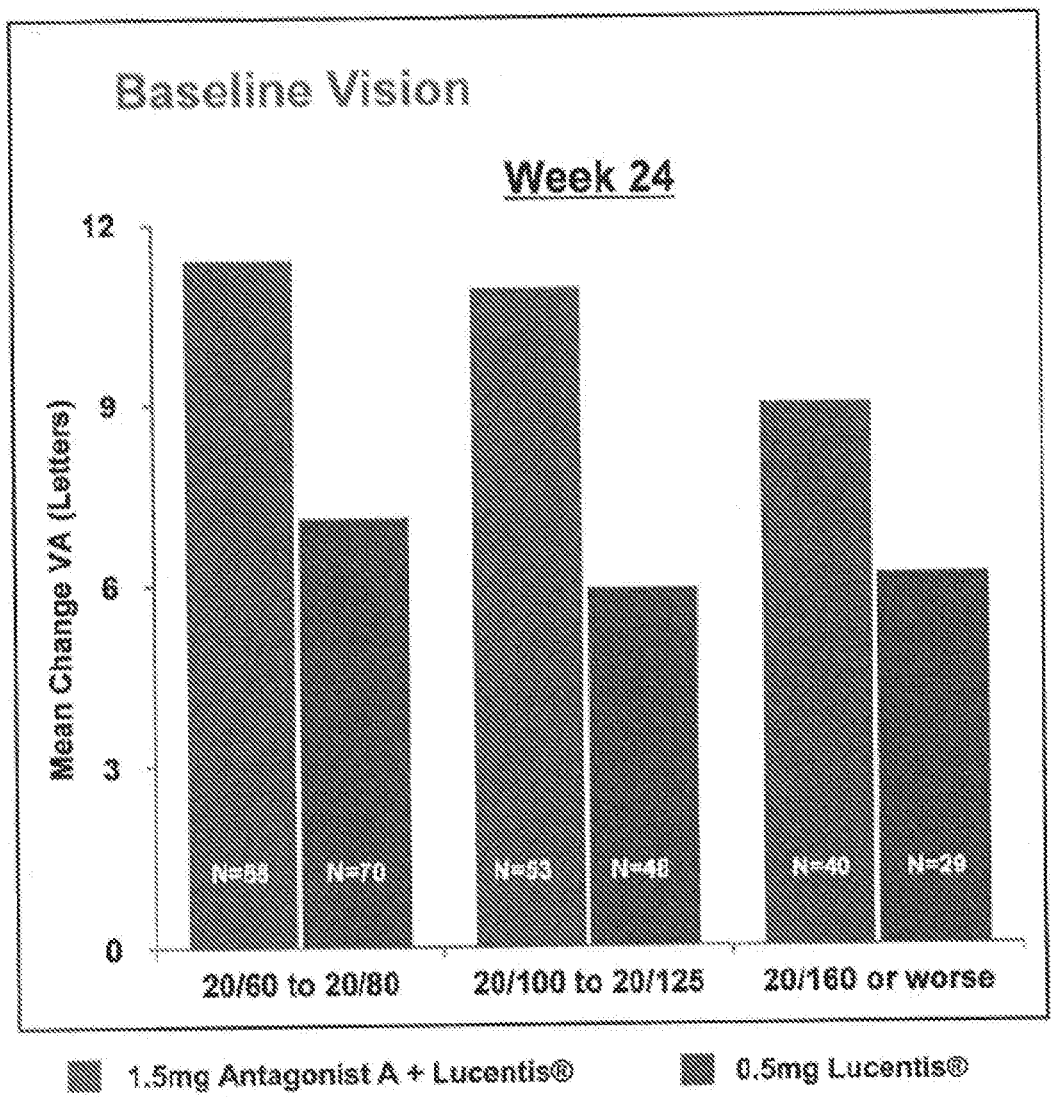
FIG. 5B shows the mean change in visual acuity for patients with the indicated baseline vision.

Treatment with 0.5 mg of Lucentis® and either 1.5 mg or 0.3 mg Antagonist A in wet AMD patients also had increased efficacy as compared to patients treated with Lucentis® alone, independent of baseline lesion size or vision. (FIGS. 5A and 5B)

Figure 6A:
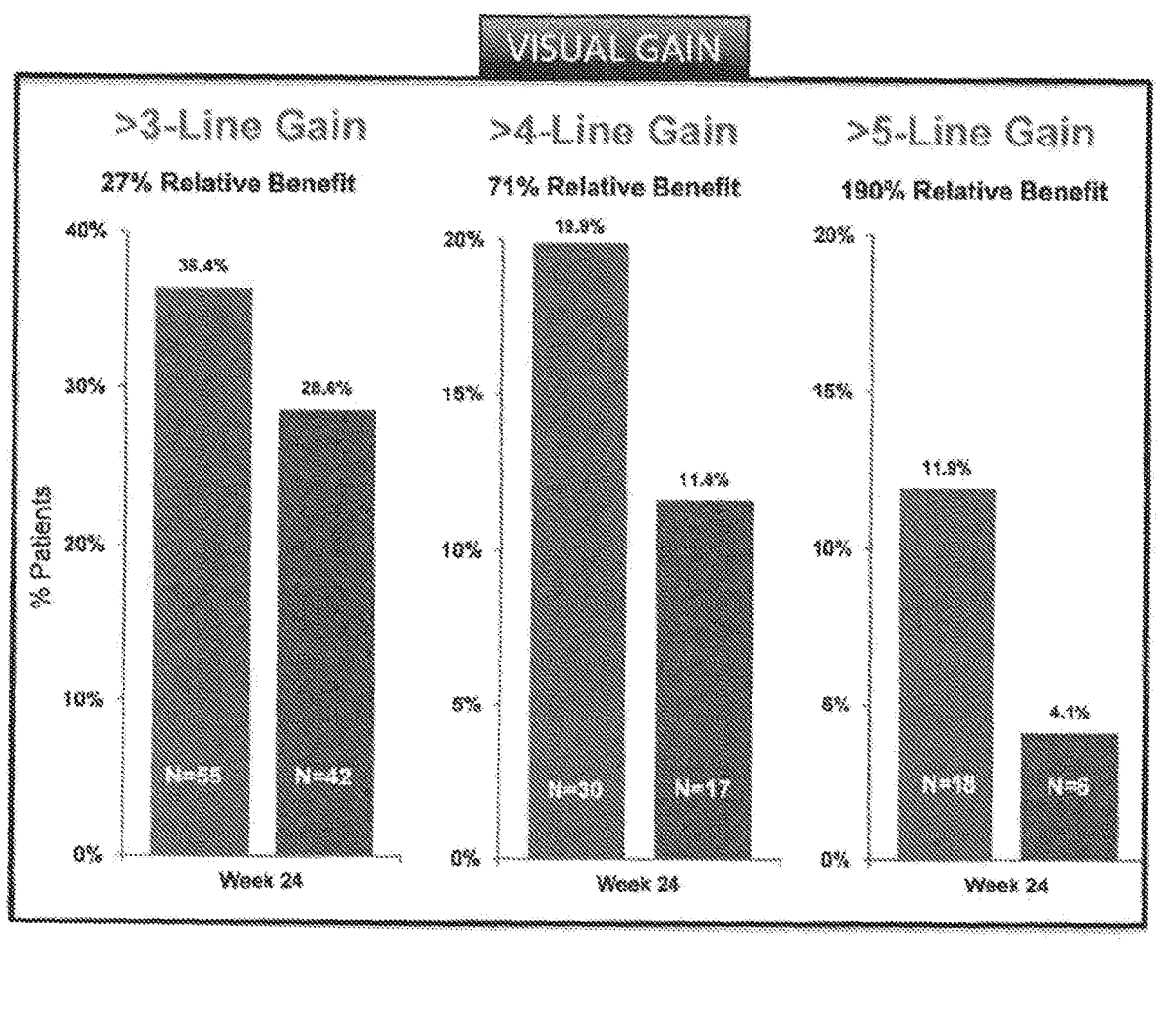
FIGS. 6A and 6B provide bar graphs showing that the cohort of patients treated with a combination of 0.5 mg of Lucentis® and 1.5 mg of Antagonist A included a greater proportion of patients with significant visual gain (FIG. 6A) and fewer patients with visual loss (FIG. 6B) as compared to the cohort of patients with treated Lucentis® monotherapy (0.5 mg).

A greater percentage of subjects in the Combination Therapy (1.5 mg) group achieved enhanced visual outcomes compared to those in the Ranibizumab Monotherapy group with respect to multiple treatment endpoints at week 24, as shown in FIG. 6A, and Table 14.

TABLE 12

Antagonist A Formulation

| Name of Ingredient | Reference to Standards | Function | 30 mg/mL Solution Composition | Percent (w/v) |
|---|---|---|---|---|
| Antagonist A | In-house standard | Drug substance | 30.0 mg | 3% |
| Monobasic Sodium Phosphate Monohydrate | USP/Ph. Eur | pH buffering agent | 0.3 mg | 0.03% |
| Dibasic Sodium Phosphate Heptahydrate | USP/Ph. Eur | pH buffering agent | 2.1 mg | 0.2% |
| Sodium Chloride | USP/Ph. Eur | Tonicity adjuster | 9.0 mg | 0.9% |
| Hydrochloric Acid | NF/Ph. Eur | pH adjuster | As needed | |
| Sodium Hydroxide | NF/Ph. Eur | pH adjuster | As needed | |
| Water for Injection | USP/Ph. Eur | Diluent | q.s. | 95.9% |
| Nitrogen | NF/Ph. Eur | Inert gas overlay | — | — |
| Total Volume | | | 1 ml | |
| Volume in Final Drug Product Presentation | | | 230 microliters | |

TABLE 13

Antagonist A and Ranibizumab Combination Therapy for Subfoveal Neovascular Lesions Secondary to NVAMD Treatment Groups

| Group No. | Group Name | Treatment Regimen |
|---|---|---|
| 1 | Combination Therapy (0.3 mg) | Subjects were administered 0.3 mg/eye of Antagonist A and 0.5 mg/eye of Lucentis ® |
| 2 | Combination Therapy (1.5 mg) | Subjects were administered 1.5 mg/eye of Antagonist A and 0.5 mg/eye of Lucentis ® |
| 3 | Ranibizumab Monotherapy | Subjects were administered Antagonist A Sham and 0.5 mg/eye of Lucentis ® |

Combination therapy proved superior in terms of mean visual gain when compared to eyes that were treated with anti-VEGF monotherapy. Subjects treated with Lucentis® and either 1.5 mg/eye or 0.3 mg/eye Antagonist A showed an increase in visual acuity compared with those treated with Lucentis® alone (FIG. 2). The combination of 1.5 mg/eye of Antagonist A and 0.5 mg of Lucentis® met the pre-specified, alpha protected primary endpoint of superiority in mean

TABLE 14

Percentage of Subjects in the Combination Therapy (1.5 mg) Group and Ranibizumab Monotherapy Group with Visual Acuity Improvement

| | Percentage of Patients | |
|---|---|---|
| Treatment Endpoint | Combination Therapy (1.5 mg) | Ranibizumab Monotherapy |
| >3-lines of visual acuity improvement | 36.4% | 28.6% |
| >4-lines of visual acuity improvement | 19.9% | 11.6% |
| >5-lines of visual acuity improvement | 11.9% | 4.1% |
| ≥20/40 vision after treatment | 37.0% | 31.9% |
| ≥20/25 vision after treatment | 12.3% | 5.6% |

Figure 6B:
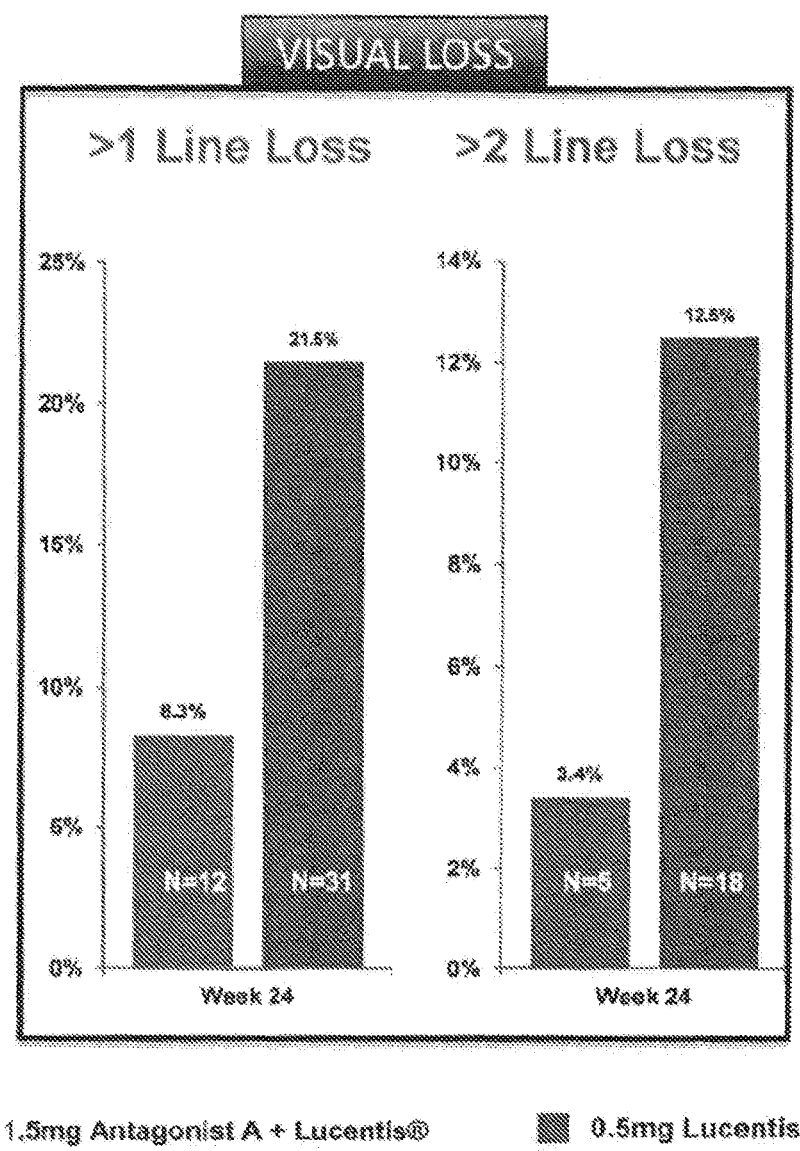

Moreover, fewer subjects in the Combination Therapy (1.5 mg) group demonstrated a loss of visual acuity as compared to the number of subjects in the Ranibizumab Monotherapy group at week 24, as shown in FIG. 6B and Table 15.

TABLE 15

Percentage of Subjects in the Combination Therapy (1.5 mg) Group and Ranibizumab Monotherapy Group with Visual Acuity Loss

| Treatment Endpoint | Percentage of Patients | |
|---|---|---|
| | Combination Therapy (1.5 mg) | Ranibizumab Monotherapy |
| ≥1-lines of visual acuity loss | 8.3% | 21.5% |
| ≥2-lines of visual acuity loss | 3.4% | 12.5% |
| ≤20/125 vision after treatment | 19.2% | 27.8% |
| ≤20/200 vision after treatment | 10.3% | 13.9% |

Figure 7A:
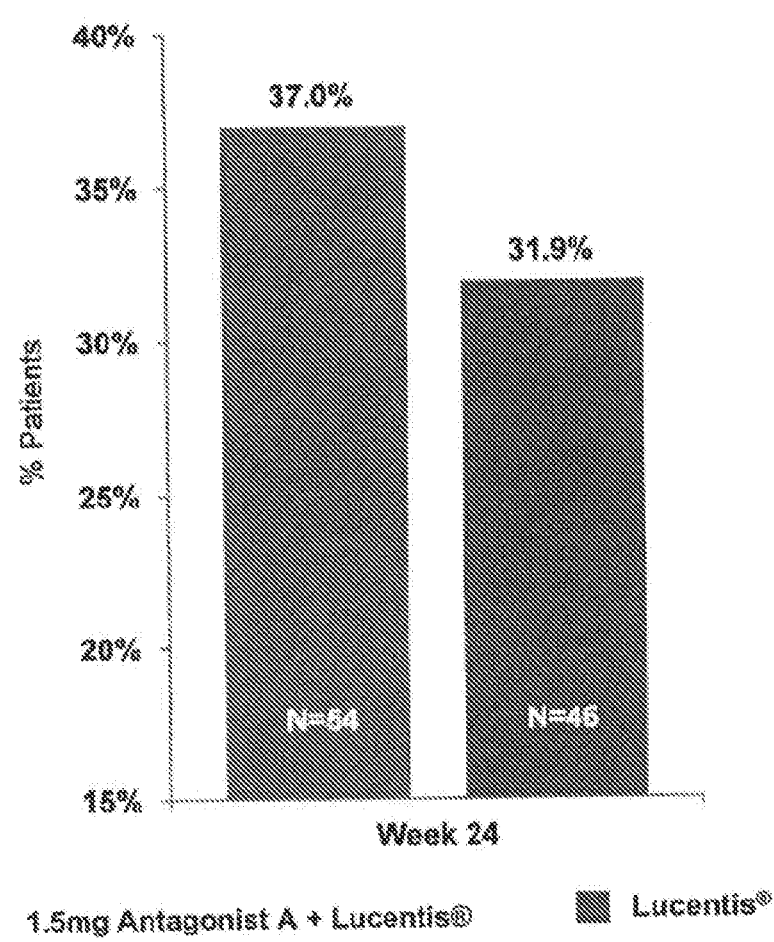
FIGS. 7A-C provide bar graphs showing that patients treated with 0.5 mg of Lucentis® and 1.5 mg of Antagonist A exhibited a greater mean improvement in final visual acuity as compared to patients treated with Lucentis® monotherapy (0.5 mg).
Figure 7B:
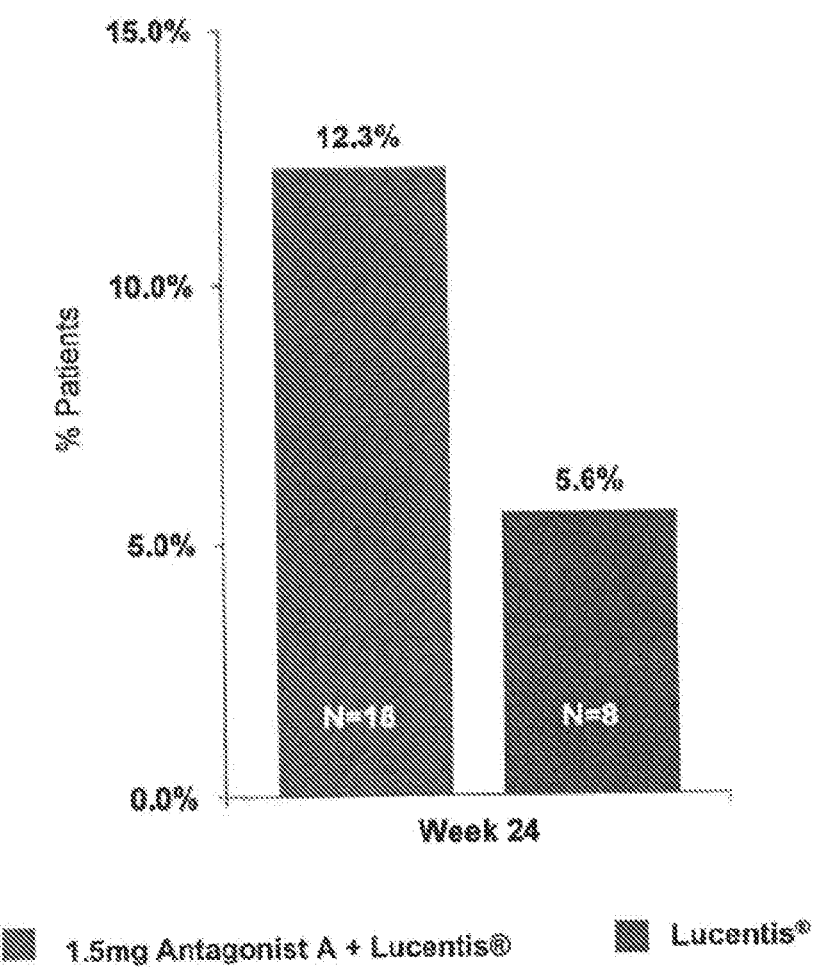
Figure 7C:
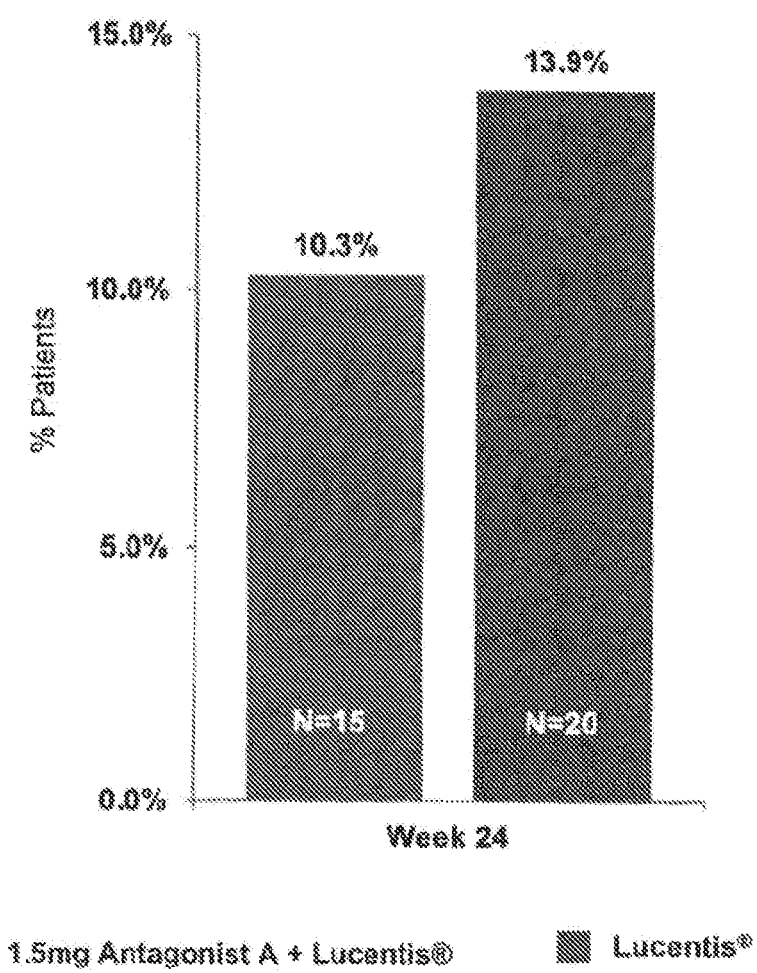
Figure 8A:
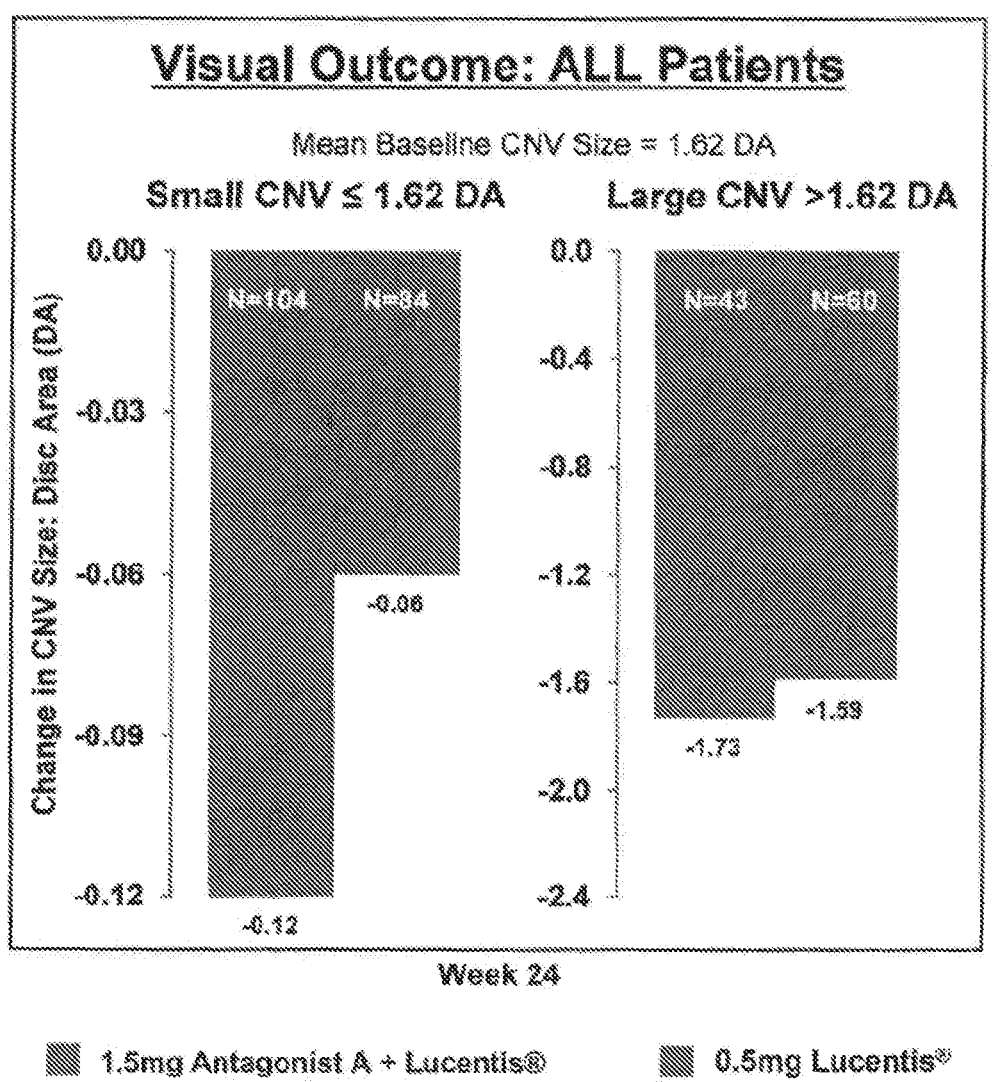
FIGS. 8A and 8B provide bar graphs showing increased reduction in choroidal neovascularization (CNV) lesion size in small and large baseline CNV lesions in wet AMD patients treated with both 0.5 mg of Lucentis® and 1.5 mg of Antagonist A as compared to patients treated with Lucentis® monotherapy (0.5 mg).
Figure 8B:
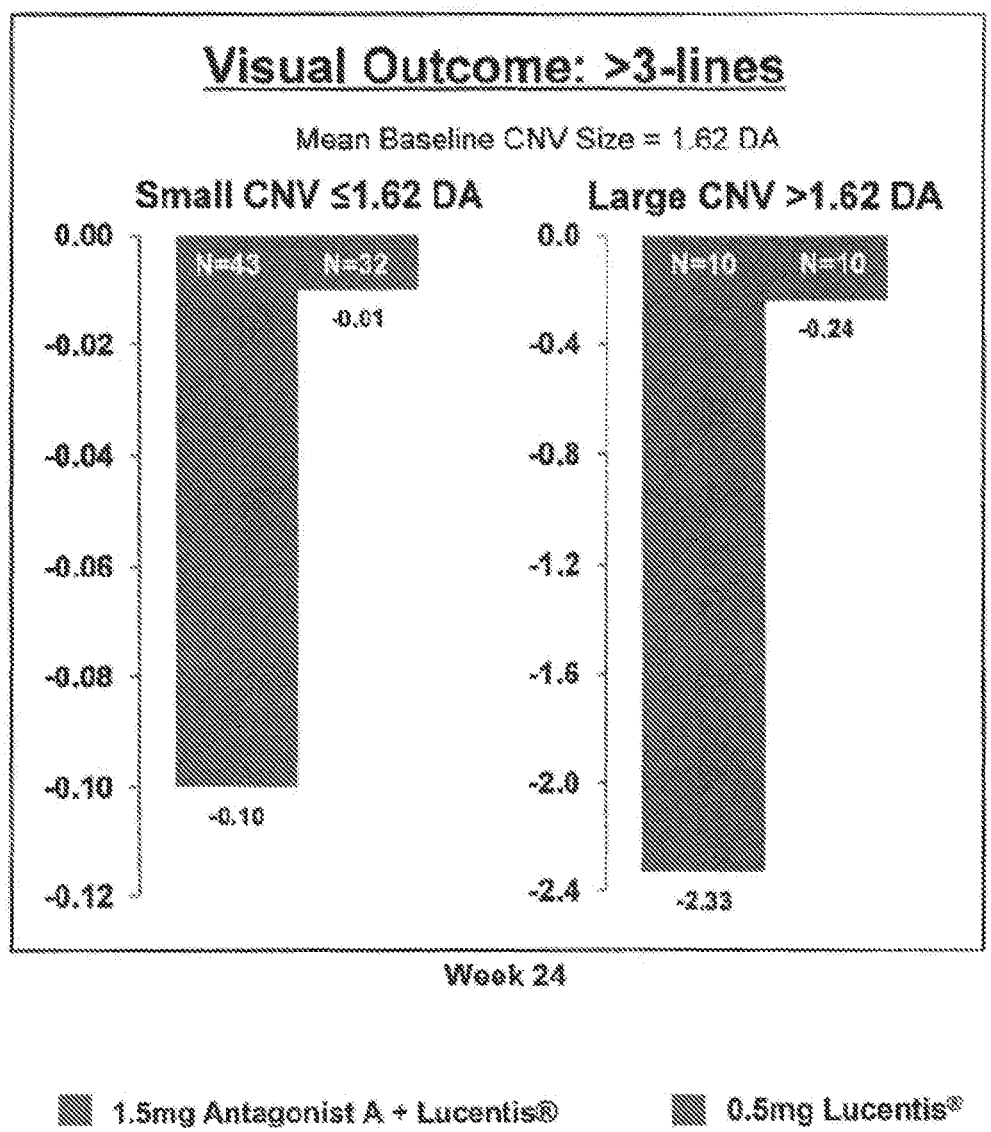

Subjects treated with Lucentis® and 1.5 mg Antagonist A showed improved final visual acuity compared to patients treated with Lucentis® monotherapy. (FIG. 7) Subjects in the Combination Therapy (1.5 mg) group also showed increased reduction in CNV size in small and large baseline CNV as compared to subjects in the Ranibizumab Monotherapy group (FIGS. 8A and 8B).

Combination therapy was well tolerated. There were no events of endophthalmitis, retinal detachment, retinal tear or iatrogenic traumatic cataract after a total of 4431 intravitreal injections (1776 administrations of Antagonist A and 2655 administrations of Lucentis®). As expected, mean intraocular pressure (IOP) increased after each intravitreal injection consistent with a volume effect. However, mean IOP in all arms returned to pre-injection levels at the next visit, including at the end of the study. The systemic safety profile of combination therapy was similar to that of ranibizumab monotherapy.

The results of the trial show statistically significant superior efficacy of the combination treatment with Antagonist A and ranibizumab over Lucentis® (ranibizumab) monotherapy for the treatment of wet AMD.

Example 2: ARC1905 for the Treatment of Wet AMD

Forty-three patients with subfoveal neovascular AMD received six monthly administrations of ARC1905 (0.3 mg/eye, 1 mg/eye or 2 mg/eye) in combination with Lucentis. The mean change in visual acuity at week 24 was an increase of +13.6, +11.7 and +15.3 letters at the doses of 0.3 mg, 1 mg and 2 mg, respectively. Furthermore, 46%, 47% and 60% of patients gained 3 or more lines of visual acuity at the doses of 0.3 mg, 1 mg, and 2 mg, respectively.

Example 3: ARC1905 for the Treatment and Prevention of Dry AMD

Figure 10:
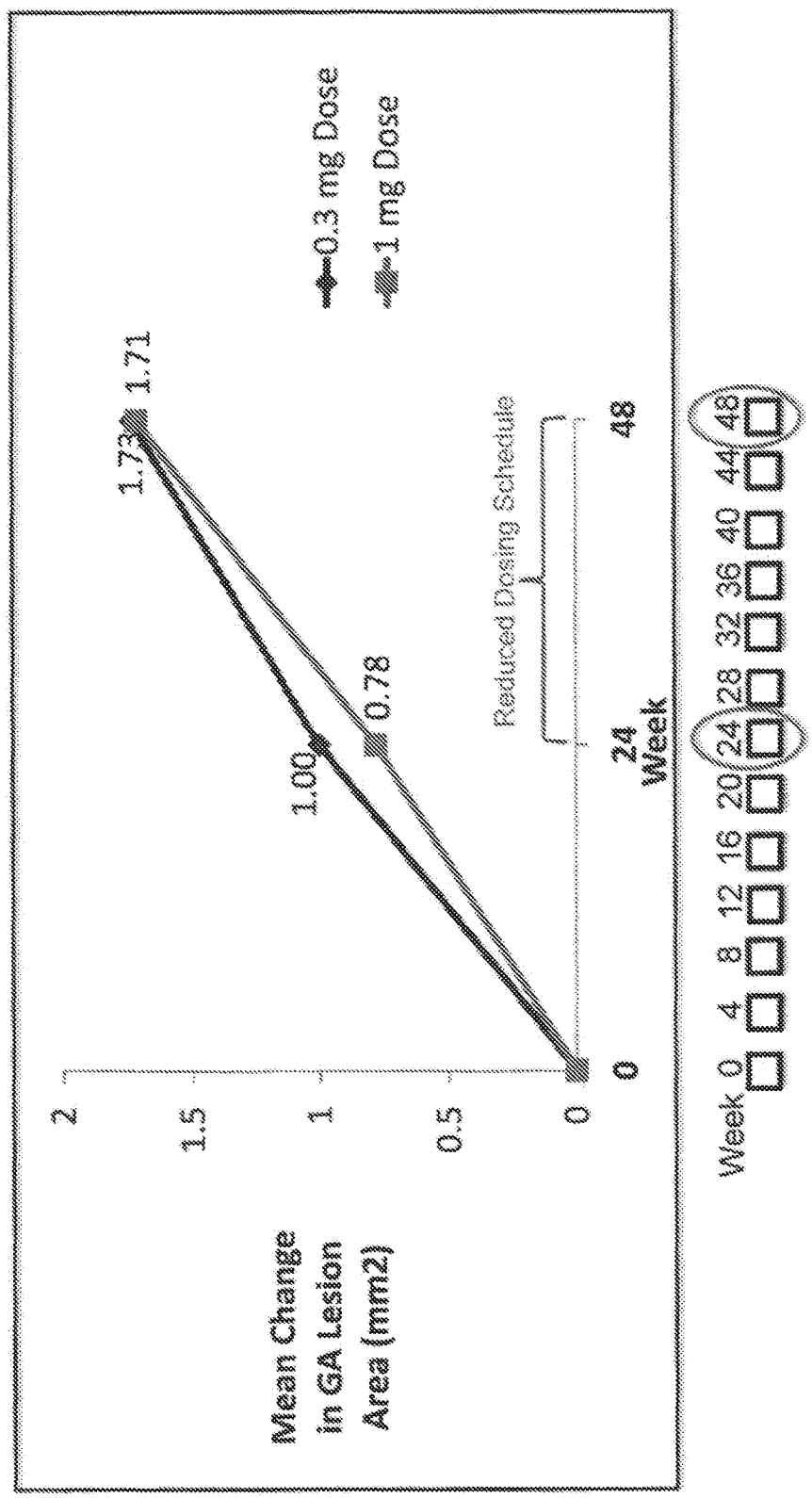
FIG. 10 shows a graph depicting the mean change in GA lesion area in dry AMD patients measured at 24 weeks and 48 weeks in patients treated with either a 0.3 mg or 1 mg dose of ARC1905 monthly from weeks 0 to 48 in a phase 2a trial.

Forty-seven patients with dry AMD were enrolled to receive five intravitreal injections of either 0.3 mg/eye or 1.0 mg/eye of ARC1905 over a 36-week treatment period. FIG. 9 shows the mean change in geographic atrophy (GA) lesion area in dry AMD patients measured at week 24 in patients treated with either 0.3 mg or 1.0 mg doses of ARC1905 at weeks 0, 4, and 8. FIG. 10 shows the mean change in GA lesion in dry AMD patients measured at week 24 and week 48 in patients treated with either 0.3 mg or 1.0 mg doses of ARC1905 at weeks 0, 4, 8, 24, and 36. The results show a dose-dependent reduction in growth of the GA lesion, indicating ARC1905 can slow the progression of GA in non-exudative type AMD patients Example 4: Visual Acuity Testing Using ETDRS Chart Best-corrected visual acuity is measured using standard charts, lighting, and procedures. Best correction is determined by careful refraction at that visit.

Figure 11:
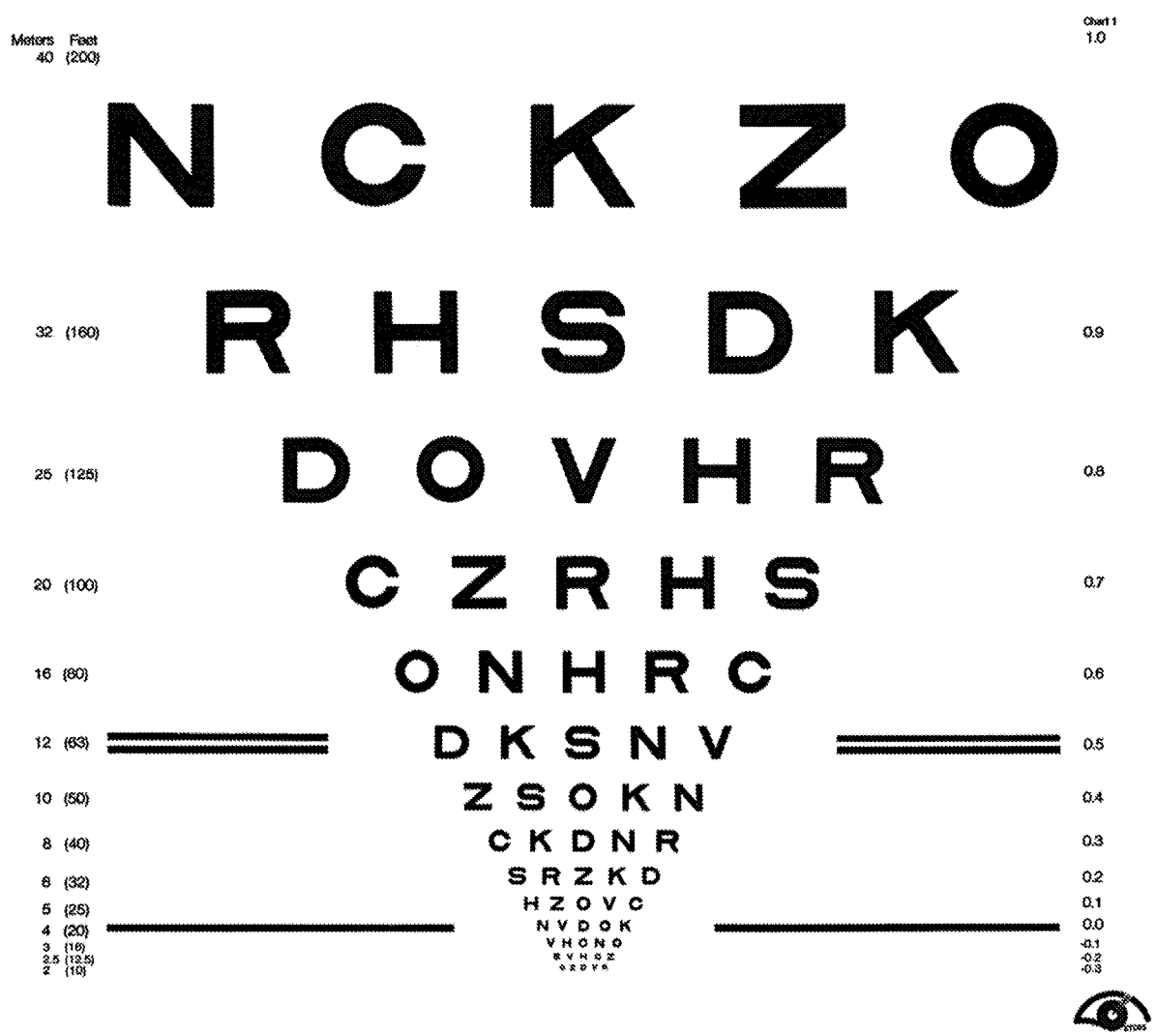
FIG. 11 shows Early Treatment for Diabetic Retinopathy Study ("ETDRS") Chart 1.
Figure 12:
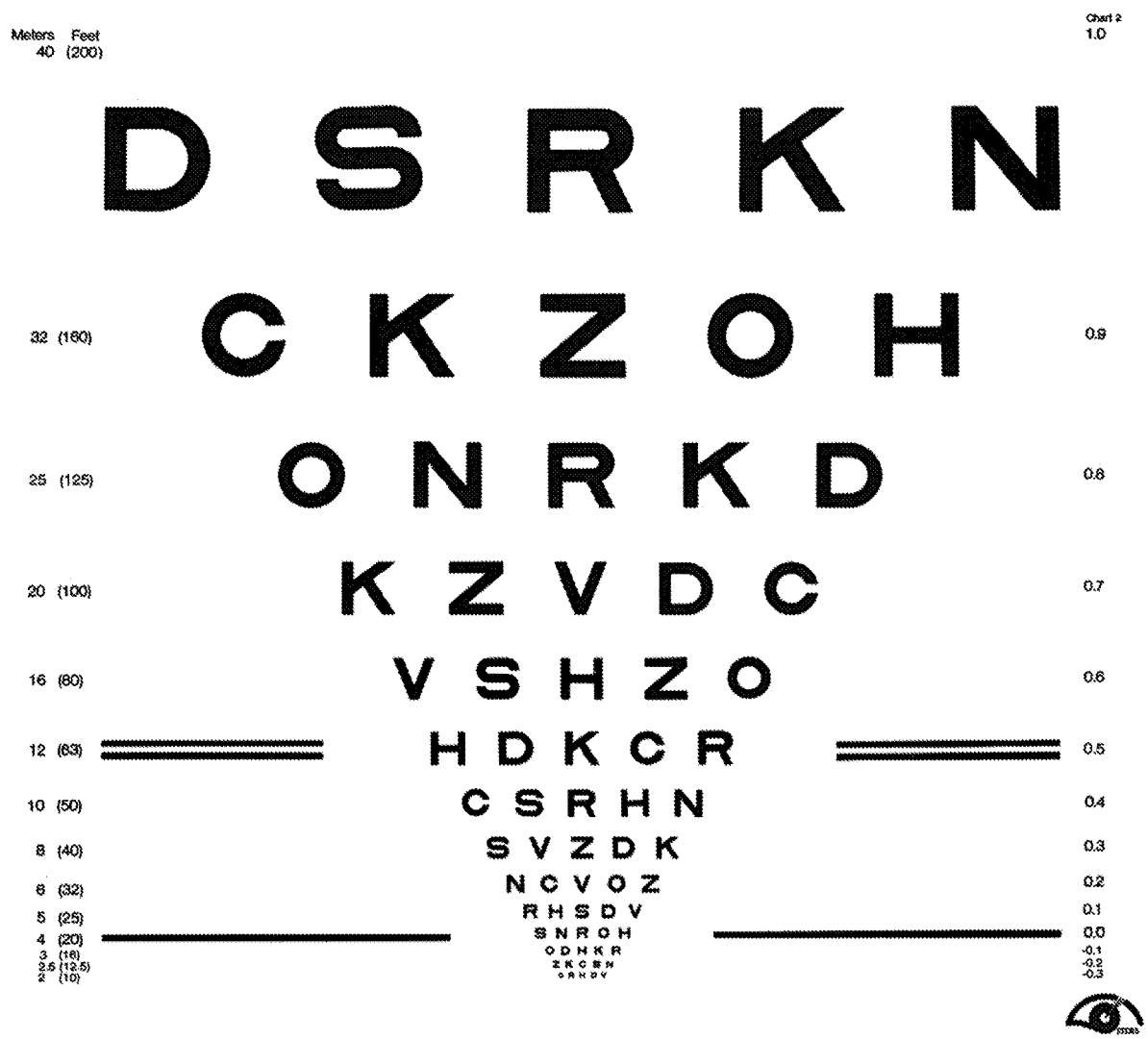
FIG. 12 shows Early Treatment for Diabetic Retinopathy Study ("ETDRS") Chart 2.
Figure 13:
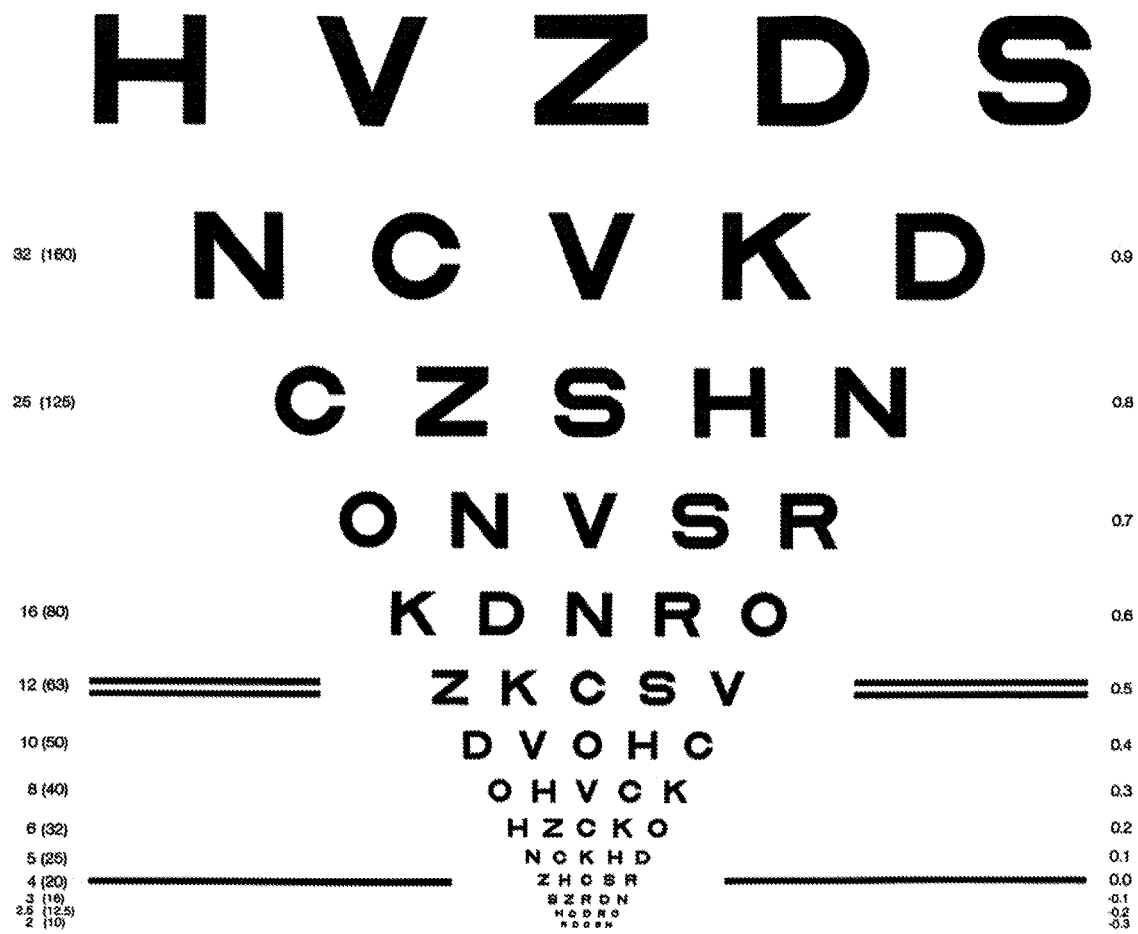
FIG. 13 shows Early Treatment for Diabetic Retinopathy Study ("ETDRS") Chart R.

Chart 1 (FIG. 11) is used for testing the visual acuity of the right eye. Chart 2 (FIG. 12) is used for testing the left eye. Chart R (FIG. 13) is used for testing refraction. Subjects do not see any of the charts before the examination.

A distance of 4 meters is between the subject's eyes and the visual acuity chart. With the box light off, not more than 15 foot-candles of light (161.4 Lux) fall on the center of the chart. To measure the amount of light, the room is set up for visual acuity testing, but with the box light off. The light meter is placed at the fourth line from the top of the chart, with its back against the chart and the reading is taken. If more than one lane is available for testing visual acuity, the visual acuity of an individual subject should be measured in the same lane at each visit. If different lanes are used to test visual acuity, they each meet the same standards.

Retroilluminated ETDRS charts are used. The illuminator box is either wall-mounted or mounted on a stand (available from Lighthouse Low Vision Services). The light box is mounted at a height such that the top of the third row letter is 49±2 inches from the floor.

The visual acuity light box is equipped with two 20-watt fluorescent tubes (available from General Electric Cool Daylight) and a ballast which partially covers the tubes. Because the illumination of fluorescent tubes generally diminishes by 5 percent during the first 100 hours and by another 5 percent during the next 2000 hours, new tubes are kept on for 4 days (96 hours) continuously, and replaced once a year.

A sticker is placed on the back of the light box, indicating the date on which the present tubes were installed. A spare set of burned in bulbs is available.

Each tube is partly covered by a 14-inch fenestrated sleeve, which is open in the back. This serves as a baffle to reduce illumination. Each sleeve is centered on the tube with the opening towards the back.

All eyes are tested at 4 meters first, even if the refraction was performed at 1 meter. The subject is seated comfortably directly in front of the chart so that the eyes remain at the 4 meter distance. Testing begins with the right eye. The subject's left eye is occluded. A folded tissue or eye pad lightly taped over the eye behind the trial frame serves as an effective occluder that allows eccentric fixation without inadvertent use of the covered eye. After testing the right eye, occlusion of the right eye is done before Chart 2 is put up for testing the left eye.

The lens correction from the subjective refraction is in the trial frame worn by the subject.

The subject is asked to read the letters slowly, approximately one letter per second. The subject is told that only one chance is given to read each letter on the chart. If the subject is unsure about the identity of the letter, then the subject is encouraged to guess.

The subject begins by reading the top line of the chart and continue reading every letter on each smaller line, from left to right on each line. The examiner circles every correct letter read and totals each line and the whole column (0 if no letters are correct) on the data collection form. An X is put through letters read incorrectly. Letters, for which no guess was attempted, are not circled. When a subject reaches a level where he/she cannot guess, the examiner may stop the test provided that the subject has made errors on previous guesses, which is a clear indication that the best visual acuity has been obtained.

When a subject cannot read at least 20 letters on the chart at 4.0 meters, the subject is tested at 1.0 meter. The distance from the subject to the chart should be measured again using the rigid one meter stick. The distance is measured from the outer canthus to the center of the fourth letter (right eye) or the second letter (left eye) of the third line of the chart. The spherical correction in the trial frame should be changed by adding +0.75 to correct for the closer test distance. The subject may fixate eccentrically or turn or shake his/her head to improve visual acuity. If this is done, the examiner ensures that the fellow eye remains occluded both centrally and peripherally and that the subject does not move forward in the chair. Particular care should be taken to ensure the subject does not move forward when testing at 1 meter. The subject is reminded to blink.

The examiner does not tell the subject if a letter was identified correctly. The subject may be encouraged by neutral comments, such as "good", "next", and "OK".

The examiner does not stand close to the chart during testing. The examiner's attention is focused on the subject and the data collection form. If the subject has difficulty locating the next line to read, the examiner may go up to the chart and point to the next line to be read, and then moves away from the chart.

When it is possible to measure the visual acuity of the eye at 4.0 meters (i.e., 20 or more letters read at 4 meters), the visual acuity score for that eye is recorded as the number of letters correct plus 30. The subject gets credit for the 30 1M letters even though they did not have to read them. Otherwise, the visual acuity score is the number of letters read correctly at 1.0 meter plus the number, if any, read at 4M. If no letters are read correctly at either 4.0 meters or 1 meter, then the visual acuity score is recorded as 0.

INCORPORATION BY REFERENCE

All publications and patent applications disclosed in this specification are herein incorporated by reference to the same extent as if each individual publication or patent application was specifically and individually indicated to be incorporated by reference.

What is claimed is:

1. A method of treating geographic atrophy in a human subject in need thereof, the method comprising administering via intravitreal injection to said subject about 2 mg/eye of a pegylated aptamer in an amount sufficient to reduce growth of a lesion associated with geographic atrophy in the subject, wherein the aptamer comprises the sequence
fCmGfCfCGfCmGmGfUfCfUfC-
mAmGmGfCGfCfUmGmAmGf UfCfUmGmAmGfU-
fUfUAfCfCfUmGfCmG-3T (SEQ ID NO:26),
wherein fC and fU=2' fluoro nucleotides, mG and mA=2'-OMe nucleotides, all other nucleotides are 2'-OH, and 3T indicates an inverted deoxythymidine, or a salt thereof, and
wherein the pegylated aptamer is administered to the subject biweekly, monthly, or quarterly.

2. The method according to claim 1, wherein the pegylated aptamer is provided as a pegylated moiety conjugated to the aptamer via a linker.

3. The method according to claim 2, wherein the pegylated moiety is conjugated to the 5' end of the aptamer.

4. The method according to claim 2, wherein the pegylated moiety is a branched PEG.

5. The method according to claim 2, wherein the pegylated moiety has a molecular weight greater than about 10 kDA.

6. The method according to claim 2, wherein the pegylated moiety has a molecular weight of about 40 kDa.

7. The method according to claim 1, wherein the pegylated moiety has the following structure:

8. The method according to claim 1, wherein the growth of the GA lesion in the subject in need thereof is reduced by at least 10%, as compared to a subject who is not administered the anti-C5 agent.

9. The method according to claim 1, wherein the anti-C5 agent is administered monthly.

10. The method according to claim 9, wherein the anti-C5 agent is administered monthly for three injections, and the fourth and fifth injections are administered three or four months after the third injection.

11. The method according to claim 1, wherein the anti-C5 agent is administered bimonthly.

12. The method according to claim 1, wherein the anti-C5 agent is administered quarterly.

13. The method according to claim 1, wherein the growth of the GA lesion in the subject in need thereof is reduced by at least 20% as compared to a subject who is not administered the anti-C5 agent.

14. The method according to claim 1, wherein the growth of the GA lesion in the subject in need thereof is reduced by at least 30% as compared to a subject who is not administered the anti-C5 agent.

15. The method according to claim 1, wherein the growth of the GA lesion in the subject in need thereof is reduced by at least 40% as compared to a subject who is not administered the anti-C5 agent.

16. The method according to claim 1, wherein the growth of the GA lesion in the subject in need thereof is reduced by at least 50% as compared to a subject who is not administered the anti-C5 agent.

17. The method according to claim 1, wherein growth of the lesion is assessed using autofluorescence imaging or optical coherence tomography.

18. A method of treating geographic atrophy in a human subject in need thereof, the method comprising administering via intravitreal injection to said subject about 2 mg/eye of a pegylated aptamer in an amount sufficient to reduce growth of a lesion associated with geographic atrophy in the subject, wherein the aptamer comprises the sequence
fCmGfCfCGfCmGmGfUfCfUfC-
   mAmGmGfCGfCfUmGmAmGf UfCfUmGmAmGfU-
   fUfUAfCfCfUmGfCmG-3T (SEQ ID NO:26),
wherein fC and fU=2' fluoro nucleotides, mG and mA=2'-OMe nucleotides, all other nucleotides are 2'-OH, and 3T indicates an inverted deoxythymidine, or a salt thereof, and
wherein the pegylated aptamer is administered to the subject biweekly, monthly, or quarterly,
wherein the pegylated moiety is a branched PEG and has a molecular weight greater than about 10 kDA, and
wherein the growth of the GA lesion in the subject in need thereof is reduced by at least 30% as compared to a subject who is not administered the anti-C5 agent.

19. A method of treating geographic atrophy in a human subject in need thereof, the method comprising administering via intravitreal injection to said subject about 2 mg/eye of a pegylated aptamer in an amount sufficient to reduce growth of a lesion associated with geographic atrophy in the subject, wherein the aptamer comprises the sequence
fCmGfCfCGfCmGmGfUfCfUfC-
   mAmGmGfCGfCfUmGmAmGf UfCfUmGmAmGfU-
   fUfUAfCfCfUmGfCmG-3T (SEQ ID NO:26),
wherein fC and fU=2' fluoro nucleotides, mG and mA=2'-OMe nucleotides, all other nucleotides are 2'-OH, and 3T indicates an inverted deoxythymidine, or a salt thereof, and
wherein the pegylated aptamer is administered to the subject biweekly, monthly, or quarterly,
wherein the pegylated moiety is a branched PEG and has a molecular weight greater than about 10 kDA, and
wherein the growth of the GA lesion in the subject in need thereof is reduced by at least 40% as compared to a subject who is not administered the anti-C5 agent.

* * * * *

UNITED STATES PATENT AND TRADEMARK OFFICE
CERTIFICATE OF CORRECTION

| | |
|---|---|
| PATENT NO. | : 11,273,171 B2 |
| APPLICATION NO. | : 17/346556 |
| DATED | : March 15, 2022 |
| INVENTOR(S) | : Samir Patel et al. |

It is certified that error appears in the above-identified patent and that said Letters Patent is hereby corrected as shown below:

In the Claims

In Claim 1, Column 445, Line 53, delete "geographic atrophy" and insert -- geographic atrophy (GA) --.

In Claim 7, Column 446, Lines 66–67, delete "pegylated moiety" and insert -- pegylated aptamer --.

In Claim 8, Column 447, Line 13, delete "anti-C5 agent" and insert -- pegylated aptamer --.

In Claim 9, Column 447, Lines 14–15, delete "anti-C5 agent" and insert -- pegylated aptamer --.

In Claim 10, Column 447, Lines 16–17, delete "anti-C5 agent" and insert -- pegylated aptamer --.

In Claim 11, Column 447, Lines 20–21, delete "anti-C5 agent" and insert -- pegylated aptamer --.

In Claim 12, Column 447, Lines 22–23, delete "anti-C5 agent" and insert -- pegylated aptamer --.

In Claim 13, Column 447, Line 27, delete "anti-C5 agent" and insert -- pegylated aptamer --.

In Claim 14, Column 447, Line 31, delete "anti-C5 agent" and insert -- pegylated aptamer --.

In Claim 15, Column 447, Line 35, delete "anti-C5 agent" and insert -- pegylated aptamer --.

In Claim 16, Column 447, Line 39, delete "anti-C5 agent" and insert -- pegylated aptamer --.

In Claim 18, Column 448, Line 11, immediately after the "," that immediately follows the word "subject", insert -- wherein the pegylated aptamer comprises an aptamer and a pegylated moiety, --.

Signed and Sealed this
Third Day of October, 2023

Katherine Kelly Vidal
*Director of the United States Patent and Trademark Office*

In Claim 19, Column 448, Line 31, immediately after the "," that immediately follows the word "subject", insert -- wherein the pegylated aptamer comprises an aptamer and a pegylated moiety, --.

In Claim 19, Column 448, Line 45, delete "anti-C5 agent" and insert -- pegylated aptamer --.

SEQUENCE LISTING

```
<160> NUMBER OF SEQ ID NOS: 98

<210> SEQ ID NO 1
<211> LENGTH: 30
<212> TYPE: DNA
<213> ORGANISM: Artificial Sequence
<220> FEATURE:
<223> OTHER INFORMATION: Synthetic anti-PDGF aptamer
<220> FEATURE:
<221> NAME/KEY: misc_feature
<222> LOCATION: (1)..(1)
<223> OTHER INFORMATION: May be modified with two 20 kD polyethylene
      glycol polymer chains that are covalently attached to the two
      amino groups of a lysine residue via carbamate linkages
<220> FEATURE:
<221> NAME/KEY: misc_feature
<222> LOCATION: (1)..(1)
<223> OTHER INFORMATION: May be modified with a bifunctional alpha-
      hydroxy-omega-amino linker covalently attached to the polyethylene
      glycol polymer chains via an amide bond
<220> FEATURE:
<221> NAME/KEY: misc_feature
<222> LOCATION: (6)..(6)
<223> OTHER INFORMATION: May be 2'-fluoro-2'-deoxyuridine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (9)..(10)
<223> OTHER INFORMATION: May be linked via hexaethylene glycol moieties
      via phosphodiester linkages
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
```

```
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (21)..(22)
<223> OTHER INFORMATION: May be linked via hexaethylene glycol moieties
      via phosphodiester linkages
<220> FEATURE:
<221> NAME/KEY: misc_feature
<222> LOCATION: (26)..(27)
<223> OTHER INFORMATION: May be 2'-fluoro-2'-deoxycytidine
<220> FEATURE:
<221> NAME/KEY: misc_feature
<222> LOCATION: (28)..(28)
<223> OTHER INFORMATION: May be 2'-fluoro-2'-deoxyuridine
<220> FEATURE:
<221> NAME/KEY: misc_feature
<222> LOCATION: (29)..(29)
<223> OTHER INFORMATION: May be 2'-O-Methyl-2'-deoxyguanosine
<220> FEATURE:
<221> NAME/KEY: misc_feature
<222> LOCATION: (30)..(30)
<223> OTHER INFORMATION: May be an inverted orientation T (3'-3'-linked)

<400> SEQUENCE: 1
caggcuacgc gtagagcauc atgatccugt                                      30

<210> SEQ ID NO 2
<211> LENGTH: 2137
<212> TYPE: DNA
<213> ORGANISM: Homo sapiens

<400> SEQUENCE: 2
ccctgcctgc ctccctgcgc acccgcagcc tccccgctg cctccctagg gctcccctcc       60
ggccgccagc gcccattttt cattccctag atagagatac tttgcgcgca cacacataca    120
tacgcgcgca aaaggaaaa aaaaaaaaaa aagcccaccc tccagcctcg ctgcaaagag     180
aaaaccggag cagccgcagc tcgcagctcg cagcccgcag cccgcagagg acgcccagag    240
cggcgagcgg gcgggcagac ggaccgacgg actcgcgccg cgtccacctg tcggccgggc    300
ccagccgagc gcgcagcggg cacgccgcgc gcgcggagca gccgtgcccg ccgcccgggc    360
ccgccgccag ggcgcacacg ctcccgcccc cctacccggc ccgggcggga gtttgcacct    420
ctccctgccc gggtgctcga gctgccgttg caaagccaac tttggaaaaa gttttttggg    480
ggagacttgg gccttgaggt gcccagctcc gcgctttccg attttggggg cctttccaga    540
aaatgttgca aaaagctaa gccggcgggc agaggaaaac gcctgtagcc ggcgagtgaa     600
gacgaaccat cgactgccgt gttccttttc ctcttggagg ttggagtccc ctgggcgccc    660
ccacacggct agacgcctcg gctggttcgc gacgcagccc ccggccgtg gatgctgcac     720 tcgggctcgg gatccgccca ggtagcggcc tcggacccag gtcctgcgcc caggtcctcc    780 cctgccccc agcgacggag ccggggccgg gggcggcggc gccgggggca tgcgggtgag     840
ccgcggctgc agaggcctga gcgcctgatc gccgcggacc cgagccgagc ccacccccct    900
ccccagcccc ccaccctggc cgcggggcg gcgcgctcga tctacgcgtt cggggccccg     960
cggggccggg cccggagtcg gcatgaatcg ctgctgggcg ctcttcctgt ctctctgctg   1020
```

-continued

| | |
|---|---|
| ctacctgcgt ctggtcagcg ccgagggggga ccccattccc gaggagcttt atgagatgct | 1080 |
| gagtgaccac tcgatccgct cctttgatga tctccaacgc ctgctgcacg agaccccgg | 1140 |
| agaggaagat ggggccgagt tggacctgaa catgacccgc tcccactctg gaggcgagct | 1200 |
| ggagagcttg gctcgtggaa gaaggagcct gggttccctg accattgctg agccggccat | 1260 |
| gatcgccgag tgcaagacgc gcaccgaggt gttcgagatc tcccggcgcc tcatagaccg | 1320 |
| caccaacgcc aacttcctgg tgtggccgcc ctgtgtggag gtgcagcgct gctccggctg | 1380 |
| ctgcaacaac cgcaacgtgc agtgccgccc cacccaggtg cagctgcgac ctgtccaggt | 1440 |
| gagaaagatc gagattgtgc ggaagaagcc aatctttaag aaggccacgg tgacgctgga | 1500 |
| agaccacctg gcatgcaagt gtgagacagt ggcagctgca cggcctgtga cccgaagccc | 1560 |
| gggggggttcc caggagcagc gagccaaaac gccccaaact cgggtgacca ttcggacggt | 1620 |
| gcgagtccgc cggccccca agggcaagca ccggaaattc aagcacacgc atgacaagac | 1680 |
| ggcactgaag gagacccttg agcctaggg gcatcggcag gagagtgtgt gggcagggtt | 1740 |
| atttaatatg gtatttgctg tattgccccc atggggcctt ggagtagata atattgtttc | 1800 |
| cctcgtccgt ctgtctcgat gcctgattcg gacggccaat ggtgcctccc ccacccctcc | 1860 |
| acgtgtccgt ccaccctctcc atcagcgggt ctcctcccag cggcctccgg ctcttgccca | 1920 |
| gcagctcaag aagaaaaaga aggactgaac tccatcgcca tcttcttccc ttaactccaa | 1980 |
| gaacttggga taagagtgtg agagagactg atggggtcgc tctttggggg aaacgggttc | 2040 |
| cttcccctgc acctggcctg ggccacacct gagcgctgtg gactgtcctg aggagccctg | 2100 |
| aggacctctc agcatagcct gcctgatccc tgaaccc | 2137 |

<210> SEQ ID NO 3
<211> LENGTH: 241
<212> TYPE: PRT
<213> ORGANISM: Homo sapiens

<400> SEQUENCE: 3

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

```
Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225             230                 235                 240

Ala

<210> SEQ ID NO 4
<211> LENGTH: 2305
<212> TYPE: DNA
<213> ORGANISM: Homo sapiens

<400> SEQUENCE: 4
ttcttggggc tgatgtccgc aaatatgcag aattaccggc cgggtcgctc ctgaagccag      60
cgcggggagc gagcgcggcg gcggccagca ccgggaacgc accgaggaag aagcccagcc     120
cccgccctcc gccccttccg tccccacccc ctacccggcg gccaggagg ctccccggct      180 gcggcgcgca ctccctgttt ctcctcctcc tggctggcg tgcctgcctc tccgcactca      240
ctgctcgccg gcgccgtcc gccagctccg tgctccccgc gccaccctcc tccgggccgc      300
gctccctaag ggatggtact gaatttcgcc gccacaggag accggctgga gcgcccgccc      360
cgcgcctcgc ctctcctccg agcagccagc gcctcgggac gcgatgagga ccttggcttg      420
cctgctgctc ctcggctgcg gatacctcgc ccatgttctg gccgaggaag ccgagatccc      480
ccgcgaggtg atcgagaggc tggcccgcag tcagatccac agcatccggg acctccagcg      540
actcctggag atagactccg tagggagtga ggattctttg gacaccagcc tgagagctca      600
cggggtccac gccactaagc atgtgcccga gaagcggccc ctgcccattc ggaggaagag      660
aagcatcgag gaagctgtcc ccgctgtctg caagaccagg acggtcattt acgagattcc      720
tcggagtcag gtcgacccca cgtccgccaa cttcctgatc tggccccccgt gcgtggaggt      780 gaaacgctgc accggctgct gcaacacgag cagtgtcaag tgccagccct cccgcgtcca      840
ccaccgcagc gtcaaggtgg ccaaggtgga atacgtcagg aagaagccaa aattaaaga       900 agtccaggtg aggttagagg gcatttggag gtgcgcctgc gcgaccacaa gcctgaatcc      960
ggattatcgg gaagaggaca cggatgtgag gtgaggatga ccgcagccc tttcctggga     1020 catggatgta catggcgtgt acattcctg aacctactat gtacggtgct ttattgccag      1080
tgtgcggtct ttgttctcct ccgtgaaaaa ctgtgtccga gaacactcgg gagaacaaag     1140
agacagtgca catttgttta atgtgacatc aaagcaagta ttgtagcact cggtgaagca     1200
gtaagaagct tccttgtcaa aaagagagag agagagagag agagagaaaa caaaaccaca     1260
aatgacaaaa acaaaacgga ctcacaaaaa tatctaaact cgatgagatg gagggtcgcc     1320
ccgtgggatg gaagtgcaga ggtctcagca gactggattt ctgtccgggt ggtcacaggt     1380
gcttttttgc cgaggatgca gagcctgctt tgggaacgac tccagagggg tgctggtggg     1440
ctctgcaggg cccgcaggaa gcaggaatgt cttggaaacc gccacgcgaa ctttagaaac     1500
cacacctcct cgctgtagta tttaagccca tacagaaacc ttcctgagag ccttaagtgg     1560
tttttttttt tgtttttgtt ttgtttttt ttttttgtt tttttttttt tttttttttt      1620
ttacaccata aagtgattat taagcttcct tttactcttt ggctagcttt ttttttttt      1680 tttttttttt ttttttttaa ttatctcttg gatgacattt acaccgataa cacacaggct     1740
```

```
gctgtaactg tcaggacagt gcgacggtat ttttcctagc aagatgcaaa ctaatgagat   1800
gtattaaaat aaacatggta tacctaccta tgcatcattt cctaaatgtt tctggctttg   1860
tgtttctccc ttaccctgct ttatttgtta atttaagcca ttttgaaaga actatgcgtc   1920
aaccaatcgt acgccgtccc tgcggcacct gccccagagc ccgtttgtgg ctgagtgaca   1980
acttgttccc cgcagtgcac acctagaatg ctgtgttccc acgcggcacg tgagatgcat   2040
tgccgcttct gtctgtgttg ttggtgtgcc ctggtgccgt ggtggcggtc actccctctg   2100
ctgccagtgt ttggacagaa cccaaattct ttatttttgg taagatattg tgctttacct   2160
gtattaacag aaatgtgtgt gtgtggtttg ttttttttgta aaggtgaagt ttgtatgttt   2220
acctaatatt acctgttttg tatacctgag agcctgctat gttcttcttt tgttgatcca   2280
aaattaaaaa aaaaatacca ccaac                                         2305

<210> SEQ ID NO 5
<211> LENGTH: 196
<212> TYPE: PRT
<213> ORGANISM: Homo sapiens

<400> SEQUENCE: 5

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
        50                  55                  60

Ala His Gly Val His Ala Thr Lys His Val Pro Glu Lys Arg Pro Leu
    65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
    145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
                180                 185                 190

Thr Asp Val Arg
        195

<210> SEQ ID NO 6
<211> LENGTH: 3018
<212> TYPE: DNA
<213> ORGANISM: Homo sapiens

<400> SEQUENCE: 6
gcccggagag ccgcatctat tggcagcttt gttattgatc agaaactgct cgccgccgac     60
ttggcttcca gtctggctgc gggcaaccct tgagttttcg cctctgtcct gtcccccgaa    120
```

```
ctgacaggtg ctcccagcaa cttgctgggg acttctcgcc gctccccgc gtccccaccc      180 cctcattcct ccctcgcctt cacccccacc cccaccactt cgccacagct caggatttgt      240
ttaaaccttg ggaaactggt tcaggtccag gttttgcttt gatccttttc aaaaactgga      300
gacacagaag agggctctag gaaaaagttt tggatgggga tatgtggaaa ctaccctgcg      360
attctctgct gccagagcag gctcggcgct tccaccccag tgcagccttc ccctggcggt      420
ggtgaaagag actcgggagt cgctgcttcc aaagtgcccg ccgtgagtga gctctcaccc      480
cagtcagcca aatgagcctc ttcgggcttc tcctgctgac atctgccctg ccggccaga      540 gacagggggac tcaggcggaa tccaacctga gtagtaaatt ccagtttcc agcaacaagg     600 aacagaacgg agtacaagat cctcagcatg agagaattat tactgtgtct actaatggaa      660
gtattcacag cccaaggttt cctcatactt atccaagaaa tacggtcttg gtatggagat      720
tagtagcagt agaggaaaat gtatggatac aacttacgtt tgatgaaaga tttgggcttg      780
aagacccaga gatgacata tgcaagtatg attttgtaga agttgaggaa cccagtgatg       840
gaactatatt agggcgctgg tgtggttctg gtactgtacc aggaaaacag atttctaaag      900
gaaatcaaat taggataaga tttgtatctg atgaatattt tccttctgaa ccagggttct      960
gcatccacta caacattgtc atgccacaat tcacagaagc tgtgagtcct tcagtgctac     1020 cccttcagc tttgccactg gacctgctta ataatgctat aactgccttt agtaccttgg      1080 aagacttat tcgatatctt gaaccagaga gatggcagtt ggacttagaa gatctatata     1140
ggccaacttg gcaacttctt ggcaaggctt ttgtttttgg aagaaaatcc agagtggtgg     1200
atctgaacct tctaacagag gaggtaagat tatacagctg cacacctcgt aacttctcag     1260
tgtccataag ggaagaacta agagaaccg ataccatttt ctggccaggt tgtctcctgg      1320
ttaaacgctg tggtgggaac tgtgcctgtt gtctccacaa ttgcaatgaa tgtcaatgtg     1380
tcccaagcaa agttactaaa aaataccacg aggtccttca gttgagacca agaccggtg     1440 tcagggggatt gcacaaatca ctcaccgacg tggccctgga gcaccatgag gagtgtgact    1500
gtgtgtgcag agggagcaca ggaggatagc cgcatcacca ccagcagctc ttgcccagag    1560
ctgtgcagtg cagtggctga ttctattaga gaacgtatgc gttatctcca tccttaatct    1620
cagttgtttg cttcaaggac cttttcatctt caggatttac agtgcattct gaaagaggag   1680
acatcaaaca gaattaggag ttgtgcaaca gctcttttga gaggaggcct aaaggacagg    1740
agaaaaggtc ttcaatcgtg gaaagaaaat taaatgttgt attaaataga tcaccagcta   1800
gtttcagagt taccatgtac gtattccact agctgggttc tgtatttcag ttctttcgat     1860
acggcttagg gtaatgtcag tacaggaaaa aaactgtgca agtgagcacc tgattccgtt    1920
gccttgctta actctaaagc tccatgtcct gggcctaaaa tcgtataaaa tctgattttt     1980
tttttttttt tttgctcata ttcacatatg taaaccagaa cattctatgt actacaaacc   2040
tggtttttaa aaaggaacta tgttgctatg aattaaactt gtgtcgtgct gataggacag    2100
actggatttt tcatatttct tattaaaatt tctgccattt agaagaagag aactacattc    2160
atggtttgga agagataaac ctgaaaagaa gagtggcctt atcttcactt tatcgataag   2220
tcagtttatt tgtttcattg tgtacatttt tatattctcc ttttgacatt ataactgttg    2280
gcttttctaa tcttgttaaa tatatctatt tttaccaaag gtatttaata ttcttttta     2340 tgacaactta gatcaactat ttttagcttg gtaaattttt ctaaacacaa ttgttatagc    2400
cagaggaaca aagatgatat aaaatattgt tgctctgaca aaaatacatg tatttcattc    2460
```

-continued

```
tcgtatggtg ctagagttag attaatctgc attttaaaaa actgaattgg aatagaattg    2520
gtaagttgca aagactttt  gaaataatt  aaattatcat atcttccatt cctgttattg    2580
gagatgaaaa taaaaagcaa cttatgaaag tagacattca gatccagcca ttactaacct    2640
attccttttt tggggaaatc tgagcctagc tcagaaaaac ataaagcacc ttgaaaaaga    2700
cttggcagct tcctgataaa gcgtgctgtg ctgtgcagta ggaacacatc ctatttattg    2760
tgatgttgtg gttttattat cttaaactct gttccataca cttgtataaa tacatggata    2820
tttttatgta cagaagtatg tctcttaacc agttcactta ttgtactctg gcaatttaaa    2880
agaaaatcag taaatatttt tgcttgtaaa atgcttaata tcgtgcctag gttatgtggt    2940
gactatttga atcaaaaatg tattgaatca tcaaataaaa gaatgtggct attttgggga    3000
gaaaattaaa aaaaaaaa                                                  3018
```

<210> SEQ ID NO 7
<211> LENGTH: 345
<212> TYPE: PRT
<213> ORGANISM: Homo sapiens

<400> SEQUENCE: 7

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270
```

```
Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
                340                 345

<210> SEQ ID NO 8
<211> LENGTH: 3997
<212> TYPE: DNA
<213> ORGANISM: Homo sapiens

<400> SEQUENCE: 8
tctcaggggc cgcggccggg gctggagaac gctgctgctc cgctcgcctg ccccgctaga      60
ttcggcgctg cccgcccccct gcagcctgtg ctgcagctgc cggccaccgg agggggcgaa    120
caaacaaacg tcaacctgtt gtttgtcccg tcaccattta tcagctcagc accacaagga    180
agtgcggcac ccacacgcgc tcggaaagtt cagcatgcag gaagtttggg gagagctcgg    240
cgattagcac agcgacccgg gccagcgcag ggcgagcgca ggcggcgaga gcgcagggcg    300
gcgcggcgtc ggtcccggga gcagaacccg gcttttcctt ggagcgacgc tgtctctagt    360
cgctgatccc aaatgcaccg gctcatcttt gtctacactc taatctgcgc aaacttttgc    420
agctgtcggg acacttctgc aaccccgcag agcgcatcca tcaaagcttt gcgcaacgcc    480
aacctcaggc gagatgagag caatcaccctc acagacttgt accgaagaga tgagaccatc    540
caggtgaaag gaaacggcta cgtgcagagt cctagattcc gaacagctca ccccaggaac    600
ctgctcctga catggcggct tcactctcag gagaatacac ggatacagct agtgtttgac    660
aatcagtttg gattagagga agcagaaaat gatatctgta ggtatgattt tgtggaagtt    720
gaagatatat ccgaaaccag taccattatt agaggacgat ggtgtggaca caaggaagtt    780
cctccaagga taaaatcaag aacgaaccaa attaaaatca cattcaagtc cgatgactac    840
tttgtggcta aacctggatt caagatttat tattctttgc tggaagattt ccaacccgca    900
gcagcttcag agaccaactg gaatctgtca caagctcta tttcaggggt atcctataac    960
tctccatcag taacggatcc cactctgatt gcggatgctc tggacaaaaa aattgcagaa   1020
tttgatacag tggaagatct gctcaagtac ttcaatccag agtcatggca agaagatctc   1080
gagaatatgt atctggacac ccctcggtat cgaggcaggt cataccatga ccggaagtca   1140
aaagttgacc tggataggct caatgatgat gccaagcgtt acagttgcac tcccaggaat   1200
tactcggtca atataagaga agagctgaag ttggccaatg tggtcttctt ccacgttgc   1260 ctcctcgtgc agcgctgtgg aggaaattgt ggctgtggaa ctgtcaactg gaggtcctgc   1320
acatgcaatt cagggaaaac cgtgaaaaag tatcatgagg tattacagtt tgagcctggc   1380
cacatcaaga ggaggggtag agctaagacc atggctctag ttgacatcca gttggatcac   1440
catgaacgat gtgattgtat ctgcagctca agaccacctc gataagagaa tgtgcacatc   1500
cttacattaa gcctgaaaga acctttagtt taaggagggt gagataagag acccttttcc   1560
taccagcaac caaacttact actagcctgc aatgcaatga acacaagtgg ttgctgagtc   1620
tcagccttgc tttgttaatg ccatggcaag tagaaaggta tatcatcaac ttctatacct   1680
```

```
aagaatatag gattgcattt aataatagtg tttgaggtta tatatgcaca aacacacaca   1740
gaaatatatt catgtctatg tgtatataga tcaaatgttt tttttggtat atataaccag   1800
gtacaccaga gcttacatat gtttgagtta gactcttaaa atcctttgcc aaaataaggg   1860
atggtcaaat atatgaaaca tgtcttttaga aaatttagga gataaattta tttttaaatt   1920
ttgaaacaca aaacaatttt gaatcttgct ctcttaaaga aagcatcttg tatattaaaa   1980
atcaaaagat gaggctttct tacatataca tcttagttga ttattaaaaa aggaaaaata   2040
tggtttccag agaaaaggcc aatacctaag catttttcc atgagaagca ctgcatactt   2100
acctatgtgg actataataa cctgtctcca aaaccatgcc ataataatat aagtgcttta   2160
gaaattaaat cattgtgttt tttatgcatt ttgctgaggc atgcttattc atttaacacc   2220
tatctcaaaa acttacttag aaggttttt attatagtcc tacaaaagac aatgtataag   2280
ctgtaacaga attttgaatt gttttctctt gcaaaacccc tccacaaaag caaatccttt   2340
caagaatggc atgggcattc tgtatgaacc tttccagatg gtgttcagtg aaagatgtgg   2400
gtagttgaga acttaaaaag tgaacattga aacatcgacg taactggaaa ttaggtggga   2460
tatttgatag gatccatatc taataatgga ttcgaactct ccaaactaca ccaattaatt   2520
taatgtatct tgcttttgtg ttcccgtctt tttgaaatat agacatggat ttataatggc   2580
attttatatt tggcaggcca tcatagatta tttacaacct aaaagctttt gtgtatcaaa   2640
aaaatcacat tttattaatg taaatttcta atcgtatact tgctcactgt tctgatttcc   2700
tgtttctgaa ccaagtaaaa tcagtcctag aggctatggt tcttaatcta tggagcttgc   2760
tttaagaagc cagttgtcaa ttgtggtaac acaagtttgg ccctgctgtc ctactgttta   2820
atagaaaact gttttacatt ggttaatggt atttagagta atttttttctc tctgcctcct   2880 ttgtgtctgt tttaaaggag actaactcca ggagtaggaa atgattcatc atcctccaaa   2940
gcaagaggct taagagagaa acaccgaaat tcagatagct cagggactgc taacagagaa   3000
ctacattttt cttattgcct tgaaagttaa aaggaaagca gatttcttca gtgactttgt   3060
ggtcctacta actacaacca gtttgggtga cagggctggt aaagtcccag tgttagatga   3120
gtgacctaaa tatacttaga tttctaagta tggtgctctc aggtccaagt tcaactattc   3180
ttaagcagtg caattcttcc cagttatttg agatgaaaga tctctgctta ttgaagatgt   3240
accttctaaa actttcctaa aagtgtctga tgttttact caagagggga gtggtaaaat   3300
taaatactct attgttcaat tctctaaaat cccagaacac aatcagaaat agctcaggca   3360
gacactaata attaagaacg ctcttcctct tcataactgc tttgcaagtt tcctgtgaaa   3420
acatcagttt cctgtaccaa agtcaaaatg aacgttacat cactctaacc tgaacagctc   3480
acaatgtagc tgtaaatata aaaaatgaga gtgttctacc cagttttcaa taaaccttcc   3540
aggctgcaat aaccagcaag gttttcagtt aaagccctat ctgcacttt tatttattag   3600 ctgaaatgta agcaggcata ttcactcact tttctttgcc tttcctgaga gttttattaa   3660
aacttctccc ttggttacct gttatctttt gcacttctaa catgtagcca ataaatctat   3720
ttgatagcca tcaaaggaat aaaaagctgg ccgtacaaat tacatttcaa aacaaaccct   3780
aataaatcca catttccgca tggctcattc acctggaata atgccttta ttgaatatgt   3840 tcttataggg caaaacactt tcataagtag agttttttat gtttttttgtc atatcggtaa   3900 catgcagctt tttcctctca tagcatttttc tatagcgaat gtaatatgcc tcttatcttc   3960
atgaaaaata aatattgctt ttgaacaaaa ctaaaaa                            3997
```

<210> SEQ ID NO 9
<211> LENGTH: 370
<212> TYPE: PRT
<213> ORGANISM: Homo sapiens

<400> SEQUENCE: 9

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
    275                 280                 285

Asn Val Val Phe Phe Pro Arg Cys Leu Leu Val Gln Arg Cys Gly Gly
290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
    355                 360                 365

Pro Arg
    370

<210> SEQ ID NO 10
<211> LENGTH: 3979
<212> TYPE: DNA
<213> ORGANISM: Homo sapiens

<400> SEQUENCE: 10

```
tctcagggc cgcggccggg gctggagaac gctgctgctc cgctcgcctg ccccgctaga      60
ttcggcgctg cccgcccct gcagcctgtg ctgcagctgc cggccaccgg agggggcgaa     120
caaacaaacg tcaacctgtt gtttgtcccg tcaccattta tcagctcagc accacaagga     180
agtgcggcac ccacacgcgc tcggaaagtt cagcatgcag aagtttggg gagagctcgg      240
cgattagcac agcgacccgg gccagcgcag ggcgagcgca ggcggcgaga gcgcagggcg     300
gcgcggcgtc ggtcccggga gcagaacccg gcttttcctt ggagcgacgc tgtctctagt     360
cgctgatccc aaatgcaccg gctcatcttt gtctacactc taatctgcgc aaacttttgc     420
agctgtcggg acacttctgc aaccccgcag agcgcatcca tcaaagcttt gcgcaacgcc     480
aacctcaggc gagatgactt gtaccgaaga gatgagacca tccaggtgaa aggaaacggc     540
tacgtgcaga gtcctagatt cccgaacagc tacccccagga acctgctcct gacatggcgg     600
cttcactctc aggagaatac acggatacag ctagtgtttg acaatcagtt tggattagag     660
gaagcagaaa atgatatctg taggtatgat tttgtggaag ttgaagatat atccgaaacc     720
agtaccatta ttagaggacg atggtgtgga cacaaggaag ttcctccaag gataaaatca     780
agaacgaacc aaattaaaat cacattcaag tccgatgact actttgtggc taaacctgga     840
ttcaagattt attattcttt gctggaagat ttccaaccc gcagcagctt cagagaccaac     900
tgggaatctg tcacaagctc tatttcaggg gtatcctata actctccatc agtaacggat     960
cccactctga ttgcggatgc tctggacaaa aaaattgcag aatttgatac agtggaagat    1020
ctgctcaagt acttcaatcc agagtcatgg caagaagatc ttgagaatat gtatctggac    1080
accccctcggt atcgaggcag gtcataccat gaccggaagt caaaagttga cctggatagg    1140
ctcaatgatg atgccaagcg ttacagttgc actcccagga attactcggt caatataaga    1200
gaagagctga agttggccaa tgtggtcttc tttccacgtt gcctcctcgt gcagcgctgt    1260
ggaggaaatt gtggctgtgg aactgtcaac tggaggtcct gcacatgcaa ttcagggaaa    1320
accgtgaaaa agtatcatga ggtattacag tttgagcctg gccacatcaa gaggaggggt    1380
agagctaaga ccatggctct agttgacatc cagttggatc accatgaacg atgtgattgt    1440
atctgcagct caagaccacc tcgataagag aatgtgcaca tccttacatt aagcctgaaa    1500
gaacctttag tttaaggagg gtgagataag agacccttt cctaccagca accaaactta    1560
ctactagcct gcaatgcaat gaacacaagt ggttgctgag tctcagcctt gctttgttaa    1620
tgccatggca agtagaaagg tatatcatca acttctatac ctaagaatat aggattgcat    1680
ttaataatag tgtttgaggt tatatatgca caaacacaca cagaaatata ttcatgtcta    1740
tgtgtatata gatcaaatgt tttttttggt atatataacc aggtacacca gagcttacat    1800
atgtttgagt tagactctta aaatcctttg ccaaaataag ggatggtcaa atatatgaaa    1860
catgtcttta gaaatttag gagataaatt tattttaaa ttttgaaaca caaacaatt    1920
ttgaatcttg ctctcttaaa gaaagcatct tgtatattaa aaatcaaaag atgaggcttt    1980
cttacatata catcttagtt gattattaaa aaaggaaaaa tatggtttcc agagaaaagg    2040
ccaataccta agcattttt ccatgagaag cactgcatac ttacctatgt ggactataat    2100
aacctgtctc caaaccatg ccataataat ataagtgctt tagaaattaa atcattgtgt    2160
```

```
ttttatgca ttttgctgag gcatgcttat tcatttaaca cctatctcaa aaacttactt    2220
agaaggtttt ttattatagt cctacaaaag acaatgtata agctgtaaca gaattttgaa    2280
ttgttttcct ttgcaaaacc cctccacaaa agcaaatcct ttcaagaatg gcatgggcat    2340
tctgtatgaa cctttccaga tggtgttcag tgaaagatgt gggtagttga aacttaaaa    2400 agtgaacatt gaaacatcga cgtaactgga aattaggtgg gatatttgat aggatccata    2460
tctaataatg gattcgaact ctccaaacta caccaattaa tttaatgtat cttgcttttg    2520
tgttcccgtc ttttgaaat atagacatgg atttataatg gcattttata tttggcaggc    2580
catcatagat tatttacaac ctaaaagctt ttgtgtatca aaaaatcac attttattaa    2640 tgtaaatttc taatcgtata cttgctcact gttctgattt cctgtttctg aaccaagtaa    2700
aatcagtcct agaggctatg gttcttaatc tatggagctt gctttaagaa gccagttgtc    2760
aattgtggta acacaagttt ggccctgctg tcctactgtt taatagaaaa ctgttttaca    2820
ttggttaatg gtatttagag taatttttc tctctgcctc ctttgtgtct gtttaaagg    2880 agactaactc caggagtagg aaatgattca tcatcctcca aagcaagagg cttaagagag    2940
aaacaccgaa attcagatag ctcagggact gctaacagag aactacattt ttcttattgc    3000
cttgaaagtt aaaaggaaag cagatttctt cagtgacttt gtggtcctac taactacaac    3060
cagtttgggt gacagggctg gtaaagtccc agtgttagat gagtgaccta aatatactta    3120
gatttctaag tatggtgctc tcaggtccaa gttcaactat tcttaagcag tgcaattctt    3180
cccagttatt tgagatgaaa gatctctgct tattgaagat gtaccttcta aaactttcct    3240
aaaagtgtct gatgttttta ctcaagaggg gagtggtaaa attaaatact ctattgttca    3300
attctctaaa atcccagaac acaatcgaaa atagctcagg cagacactaa taattaagaa    3360
cgctcttcct cttcataact gctttgcaag tttcctgtga aaacatcagt ttcctgtacc    3420
aaagtcaaaa tgaacgttac atcactctaa cctgaacagc tcacaatgta gctgtaaata    3480 taaaaatga gagtgttcta cccagttttc aataaaccat ccaggctgca ataaccagca    3540
aggttttcag ttaaagccct atctgcactt tttatttatt agctgaaatg taagcaggca    3600
tattcactca cttttctttg cctttcctga gagttttatt aaaacttctc ccttggttac    3660
ctgttatctt ttgcacttct aacatgtagc aataaatct atttgatagc catcaaagga    3720
ataaaaagct ggccgtacaa attacatttc aaaacaaacc ctaataaatc cacatttccg    3780
catggctcat tcacctggaa taatgccttt tattgaatat gttcttatag ggcaaaacac    3840
tttcataagt agagtttttt atgttttttg tcatatcggt aacatgcagc ttttcctct    3900 catagcattt tctatagcga atgtaatatg cctcttatct tcatgaaaaa taaatattgc    3960
ttttgaacaa aactaaaaa                                                 3979
```

<210> SEQ ID NO 11
<211> LENGTH: 364
<212> TYPE: PRT
<213> ORGANISM: Homo sapiens

<400> SEQUENCE: 11

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Asp Leu Tyr Arg Arg Asp Glu
        35                  40                  45

Thr Ile Gln Val Lys Gly Asn Gly Tyr Val Gln Ser Pro Arg Phe Pro
    50                  55                  60

Asn Ser Tyr Pro Arg Asn Leu Leu Leu Thr Trp Arg Leu His Ser Gln
65                  70                  75                  80

Glu Asn Thr Arg Ile Gln Leu Val Phe Asp Asn Gln Phe Gly Leu Glu
                85                  90                  95

Glu Ala Glu Asn Asp Ile Cys Arg Tyr Asp Phe Val Glu Val Glu Asp
            100                 105                 110

Ile Ser Glu Thr Ser Thr Ile Ile Arg Gly Arg Trp Cys Gly His Lys
        115                 120                 125

Glu Val Pro Pro Arg Ile Lys Ser Arg Thr Asn Gln Ile Lys Ile Thr
    130                 135                 140

Phe Lys Ser Asp Asp Tyr Phe Val Ala Lys Pro Gly Phe Lys Ile Tyr
145                 150                 155                 160

Tyr Ser Leu Leu Glu Asp Phe Gln Pro Ala Ala Ala Ser Glu Thr Asn
                165                 170                 175

Trp Glu Ser Val Thr Ser Ser Ile Ser Gly Val Ser Tyr Asn Ser Pro
            180                 185                 190

Ser Val Thr Asp Pro Thr Leu Ile Ala Asp Ala Leu Asp Lys Lys Ile
        195                 200                 205

Ala Glu Phe Asp Thr Val Glu Asp Leu Leu Lys Tyr Phe Asn Pro Glu
    210                 215                 220

Ser Trp Gln Glu Asp Leu Glu Asn Met Tyr Leu Asp Thr Pro Arg Tyr
225                 230                 235                 240

Arg Gly Arg Ser Tyr His Asp Arg Lys Ser Lys Val Asp Leu Asp Arg
                245                 250                 255

Leu Asn Asp Asp Ala Lys Arg Tyr Ser Cys Thr Pro Arg Asn Tyr Ser
            260                 265                 270

Val Asn Ile Arg Glu Glu Leu Lys Leu Ala Asn Val Val Phe Phe Pro
        275                 280                 285

Arg Cys Leu Leu Val Gln Arg Cys Gly Gly Asn Cys Gly Cys Gly Thr
    290                 295                 300

Val Asn Trp Arg Ser Cys Thr Cys Asn Ser Gly Lys Thr Val Lys Lys
305                 310                 315                 320

Tyr His Glu Val Leu Gln Phe Glu Pro Gly His Ile Lys Arg Arg Gly
                325                 330                 335

Arg Ala Lys Thr Met Ala Leu Val Asp Ile Gln Leu Asp His His Glu
            340                 345                 350

Arg Cys Asp Cys Ile Cys Ser Ser Arg Pro Pro Arg
        355                 360

<210> SEQ ID NO 12
<211> LENGTH: 6574
<212> TYPE: DNA
<213> ORGANISM: Homo sapiens

<400> SEQUENCE: 12
aagagcaaaa agcgaaggcg caatctggac actgggagat tcggagcgca gggagtttga      60
gagaaacttt tattttgaag agaccaaggt tgagggggg cttatttcct gacagctatt      120
tacttagagc aaatgattag ttttagaagg atggactata acattgaatc aattacaaaa      180
cgcggttttt gagcccatta ctgttggagc tacaggaga gaaacagagg aggagactgc      240
aagagatcat tggaggccgt gggcacgctc tttactccat gtgtgggaca ttcattgcgg      300

```
aataacatcg aggagaagt tcccagagc tatggggact tcccatccgg cgttcctggt    360
cttaggctgt cttctcacag ggctgagcct aatcctctgc cagctttcat taccctctat    420
ccttccaaat gaaatgaaa aggttgtgca gctgaattca tccttttctc tgagatgctt    480
tggggagagt gaagtgagct ggcagtaccc catgtctgaa gaagagagct ccgatgtgga    540
aatcagaaat gaagaaaaca acagcggcct ttttgtgacg gtcttggaag tgagcagtgc    600
ctcggcggcc cacacagggt tgtacacttg ctattacaac cacactcaga cagaagagaa    660
tgagcttgaa ggcaggcaca tttacatcta tgtgccagac ccagatgtag cctttgtacc    720
tctaggaatg acggattatt tagtcatcgt ggaggatgat gattctgcca ttataccttg    780
tcgcacaact gatcccgaga ctcctgtaac cttacacaac agtgaggggg tggtacctgc    840
ctcctacgac agcagacagg gctttaatgg gaccttcact gtagggccct atatctgtga    900
ggccaccgtc aaaggaaaga agttccagac catcccattt aatgtttatg ctttaaaagc    960
aacatcagag ctggatctag aaatggaagc tcttaaaacc gtgtataagt caggggaaac   1020
gattgtggtc acctgtgctg tttttaacaa tgaggtggtt gaccttcaat ggacttaccc   1080
tggagaagtg aaaggcaaag gcatcacaat gctggaagaa atcaaagtcc catccatcaa   1140
attggtgtac actttgacgg tccccgaggc cacggtgaaa gacagtggag attacgaatg   1200
tgctgcccgc caggctacca gggaggtcaa agaaatgaag aaagtcacta tttctgtcca   1260
tgagaaaggt ttcattgaaa tcaaacccac cttcagccag ttggaagctg tcaacctgca   1320
tgaagtcaaa cattttgttg tagaggtgcg ggcctaccca cctcccagga tatcctggct   1380
gaaaaacaat ctgactctga ttgaaaatct cactgagatc accactgatg tggaaaagat   1440
tcaggaaata aggtatcgaa gcaaattaaa gctgatccgt gctaaggaag aagacagtgg   1500
ccattatact attgtagctc aaaatgaaga tgctgtgaag agctatactt ttgaactgtt   1560
aactcaagtt ccttcatcca ttctggactt ggtcgatgat caccatggct caactggggg   1620
acagacggtg aggtgcacag ctgaaggcac gccgcttcct gatattgagt ggatgatatg   1680
caaagatatt aagaaatgta ataatgaaac ttcctggact attttggcca acaatgtctc   1740
aaacatcatc acggagatcc actcccgaga caggagtacc gtggagggcc gtgtgacttt   1800
cgccaaagtg gaggagacca tcgccgtgcg atgcctggct aagaatctcc ttggagctga   1860
gaaccgagag ctgaagctgg tggctcccac cctgcgttct gaactcacgg tggctgctgc   1920
agtcctggtg ctgttggtga ttgtgatcat ctcacttatt gtcctggttg tcatttggaa   1980
acagaaaccg aggtatgaaa ttcgctggag ggtcattgaa tcaatcagcc cagatggaca   2040
tgaatatatt tatgtggacc cgatgcagct gccttatgac tcaagatggg agtttccaag   2100
agatggacta gtgcttggtc gggtcttggg gtctggagcg tttgggaagg tggttgaagg   2160
aacagcctat ggattaagcc ggtcccaacc tgtcatgaaa gttgcagtga agatgctaaa   2220
acccacggcc agatccagtg aaaaacaagc tctcatgtct gaactgaaga taatgactca   2280
cctggggcca catttgaaca ttgtaaactt gctgggagcc tgcaccaagt caggccccat   2340
ttacatcatc acagagtatt gcttctatgg agatttggtc aactatttgc ataagaatag   2400
ggatagcttc ctgagccacc acccagagaa gccaaagaaa gagctggata tctttggatt   2460
gaaccctgct gatgaaagca cacggagcta tgttatttta tcttttgaaa acaatggtga   2520
ctacatggac atgaagcagg ctgatactac acagtatgtc cccatgctag aaaggaaaga   2580
ggtttctaaa tattccgaca tccagagatc actctatgat cgtccagcct catataagaa   2640
gaaatctatg ttagactcag aagtcaaaaa cctcctttca gatgataact cagaaggcct   2700
```

| | |
|---|---|
| tactttattg gatttgttga gcttcaccta tcaagttgcc cgaggaatgg agtttttggc | 2760 |
| ttcaaaaaat tgtgtccacc gtgatctggc tgctcgcaac gtcctcctgg cacaaggaaa | 2820 |
| aattgtgaag atctgtgact ttggcctggc cagagacatc atgcatgatt cgaactatgt | 2880 |
| gtcgaaaggc agtacctttc tgcccgtgaa gtggatggct cctgagagca tctttgacaa | 2940 |
| cctctacacc acactgagtg atgtctggtc ttatggcatt ctgctctggg agatcttttc | 3000 |
| ccttggtggc accccttacc ccggcatgat ggtggattct actttctaca ataagatcaa | 3060 |
| gagtgggtac cggatggcca agcctgacca cgctaccagt gaagtctacg agatcatggt | 3120 |
| gaaatgctgg aacagtgagc cggagaagag accctccttt taccacctga gtgagattgt | 3180 |
| ggagaatctg ctgcctggac aatataaaaa gagttatgaa aaaattcacc tggacttcct | 3240 |
| gaagagtgac catcctgctg tggcacgcat gcgtgtggac tcagacaatg catacattgg | 3300 |
| tgtcacctac aaaaacgagg aagacaagct gaaggactgg gagggtggtc tggatgagca | 3360 |
| gagactgagc gctgacagtg gctacatcat tcctctgcct gacattgacc ctgtccctga | 3420 |
| ggaggaggac ctgggcaaga ggaacagaca cagctcgcag acctctgaag agagtgccat | 3480 |
| tgagacgggt tccagcagtt ccaccttcat caagagagag gacgagacca ttgaagacat | 3540 |
| cgacatgatg gatgacatcg gcatagactc ttcagacctg gtggaagaca gcttcctgta | 3600 |
| actggcggat tcgaggggtt ccttccactt ctggggccac ctctggatcc cgttcagaaa | 3660 |
| accactttat tgcaatgcag aggttgagag gaggacttgg ttgatgttta aagagaagtt | 3720 |
| cccagccaag ggcctcgggg agcgttctaa atatgaatga atgggatatt ttgaaatgaa | 3780 |
| ctttgtcagt gttgcctctt gcaatgcctc agtagcatct cagtggtgtg tgaagtttgg | 3840 |
| agatagatgg ataagggaat aataggccac agaaggtgaa ctttgtgctt caaggacatt | 3900 |
| ggtgagagtc caacagacac aatttatact gcgacagaac ttcagcattg taattatgta | 3960 |
| aataactcta accaaggctg tgtttagatt gtattaacta tcttctttgg acttctgaag | 4020 |
| agaccactca atccatccat gtacttccct cttgaaacct gatgtcagct gctgttgaac | 4080 |
| ttttttaaaga agtgcatgaa aaaccatttt tgaaccttaa aaggtactgg tactatagca | 4140 |
| ttttgctatc ttttttagtg ttaaagagat aaagaataat aattaaccaa ccttgtttaa | 4200 |
| tagatttggg tcatttagaa gcctgacaac tcattttcat attgtaatct atgtttataa | 4260 |
| tactactact gttatcagta atgctaaatg tgtaataatg taacatgatt tccctccaga | 4320 |
| gaaagcacaa tttaaaacaa tccttactaa gtaggtgatg agtttgacag ttttttgacat | 4380 |
| ttatattaaa taacatgttt ctctataaag tatggtaata gctttagtga attaaattta | 4440 |
| gttgagcata gagaacaaag taaaagtagt gttgtccagg aagtcagaat ttttaactgt | 4500 |
| actgaatagg ttccccaatc catcgtatta aaaaacaatt aactgccctc tgaaataatg | 4560 |
| ggattagaaa caaacaaaac tcttaagtcc taaaagttct caatgtagag gcataaacct | 4620 |
| gtgctgaaca taacttctca tgtatattac ccaatggaaa atataatgat cagcaaaaag | 4680 |
| actggatttg cagaagtttt ttttttttttt ttcttcatgc ctgatgaaag ctttggcgac | 4740 |
| cccaatatat gtattttttg aatctatgaa cctgaaaagg gtcagaagga tgcccagaca | 4800 |
| tcagcctcct tctttcaccc cttacccccaa agagaaagag tttgaaactc gagaccataa | 4860 |
| agatattctt tagtggaggc tggatgtgca ttagcctgga tcctcagttc tcaaatgtgt | 4920 |
| gtggcagcca ggatgactag atcctggggtt tccatccttg agattctgaa gtatgaagtc | 4980 |
| tgagggaaac cagagtctgt attttctaa actccctggc tgttctgatc ggccagtttt | 5040 |

-continued

```
cggaaacact gacttaggtt tcaggaagtt gccatgggaa acaaataatt tgaactttgg      5100
aacagggttg gcattcaacc acgcaggaag cctactattt aaatccttgg cttcaggtta      5160
gtgacattta atgccatcta gctagcaatt gcgaccttaa tttaactttc cagtcttagc      5220
tgaggctgag aaagctaaag tttggttttg acaggttttc caaaagtaaa gatgctactt      5280
cccactgtat gggggagatt gaactttccc cgtctcccgt cttctgcctc ccactccata      5340
ccccgccaag gaaaggcatg tacaaaaatt atgcaattca gtgttccaag tctctgtgta      5400
accagctcag tgttttggtg gaaaaaacat tttaagtttt actgataatt tgaggttaga      5460
tgggaggatg aattgtcaca tctatccaca ctgtcaaaca ggttggtgtg ggttcattgg      5520
cattctttgc aatactgctt aattgctgat accatatgaa tgaaacatgg gctgtgatta      5580
ctgcaatcac tgtgctatcg gcagatgatg cttggaaga tgcagaagca ataataaagt       5640
acttgactac ctactggtgt aatctcaatg caagccccaa ctttcttatc caacttttc       5700
atagtaagtg cgaagactga gccagattgg ccaattaaaa acgaaaacct gactaggttc      5760
tgtagagcca attagacttg aaatacgttt gtgtttctag aatcacagct caagcattct      5820
gtttatcgct cactctccct tgtacagcct tattttgttg gtgctttgca ttttgatatt      5880
gctgtgagcc ttgcatgaca tcatgaggcc ggatgaaact tctcagtcca gcagtttcca      5940
gtcctaacaa atgctcccac ctgaatttgt atatgactgc atttgtgtgt gtgtgtgtgt      6000
tttcagcaaa ttccagattt gtttccttt ggcctcctgc aaagtctcca gaagaaaatt       6060
tgccaatctt tcctactttc tattttatg atgacaatca agccggcct gagaaacact        6120
atttgtgact ttttaaacga ttagtgatgt ccttaaaatg tggtctgcca atctgtacaa      6180
aatggtccta ttttttgtgaa gagggacata agataaaatg atgttataca tcaatatgta    6240
tatatgtatt tctatataga cttggagaat actgccaaaa catttatgac aagctgtatc     6300
actgccttcg tttatatttt tttaactgtg ataatcccca caggcacatt aactgttgca     6360
cttttgaatg tccaaaattt atattttaga aataataaaa agaaagatac ttacatgttc     6420
ccaaaacaat ggtgtggtga atgtgtgaga aaaactaact tgatagggtc taccaataca     6480
aaatgtatta cgaatgcccc tgttcatgtt tttgttttaa aacgtgtaaa tgaagatctt    6540
tatatttcaa taaatgatat ataatttaaa gtta                                  6574
```

<210> SEQ ID NO 13
<211> LENGTH: 1089
<212> TYPE: PRT
<213> ORGANISM: Homo sapiens

<400> SEQUENCE: 13

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
```

```
            100                 105                 110
Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525
```

```
Ala Ala Val Leu Val Leu Val Ile Val Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940
```

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
        980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro
    1010                1015                1020

Asp Ile Asp Pro Val Pro Glu Glu Asp Leu Gly Lys Arg Asn
    1025                1030                1035

Arg His Ser Ser Gln Thr Ser Glu Glu Ser Ala Ile Glu Thr Gly
    1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu
    1070                1075                1080

Val Glu Asp Ser Phe Leu
    1085

<210> SEQ ID NO 14
<211> LENGTH: 5718
<212> TYPE: DNA
<213> ORGANISM: Homo sapiens

<400> SEQUENCE: 14
ctcctgaggc tgccagcagc cagcagtgac tgcccgccct atctgggacc caggatcgct     60
ctgtgagcaa cttggagcca gagaggagat caacaaggag gaggagagag ccggcccctc    120
agccctgctg cccagcagca gcctgtgctc gccctgccca acgcagacag ccagacccag    180
ggcggcccct ctggcggctc tgctcctccc gaaggatgct ggggagtgaa ggcgaagctg    240
ggccgctcct ctcccctaca gcagcccccct tcctccatcc ctctgttctc ctgagccttc    300
aggagcctgc accagtcctg cctgtccttc tactcagctg ttaccactc tgggaccagc    360
agtctttctg ataactggga gagggcagta aggaggactt cctggagggg gtgactgtcc    420
agagcctgga actgtgccca caccagaagc catcagcagc aaggacacca tgcggcttcc    480
gggtgcgatg ccagctctgg ccctcaaagg cgagctgctg ttgctgtctc tcctgttact    540
tctggaacca cagatctctc agggcctggt cgtcacaccc ccggggccag agcttgtcct    600
caatgtctcc agcaccttcg ttctgacctg ctcgggttca gctccggtgg tgtgggaacg    660
gatgtcccag gagccccac aggaaatggc caaggcccag gatggcacct ctcccagcgt    720
gctcacactg accaacctca ctgggctaga cacgggagaa tactttgca cccacaatga    780
ctcccgtgga ctgagaccg atgagcggaa acggctctac atctttgtgc cagatcccac    840
cgtgggcttc ctccctaatg atgccgagga actattcatc tttctcacgg aaataactga    900
gatcaccatt ccatgccgag taacagaccc acagctggtg gtgacactgc acgagaagaa    960
agggacgttg cactgcctg tcccctatga tcaccaacgt ggcttttctg gtatctttga   1020
ggacagaagc tacatctgca aaaccaccat tggggacagg gaggtggatt ctgatgccta   1080
ctatgtctac agactccagg tgtcatccat caacgtctct gtgaacgcag tgcagactgt   1140
ggtccgccag ggtgagaaca tcaccctcat gtgcattgtg atcgggaatg aggtggtcaa   1200
cttcgagtgg acataccccc gcaaagaaag tgggcggctg gtggagccgg tgactgactt   1260

```
cctcttggat atgccttacc acatccgctc catcctgcac atccccagtg ccgagttaga   1320
agactcgggg acctacacct gcaatgtgac ggagagtgtg aatgaccatc aggatgaaaa   1380
ggccatcaac atcaccgtgg ttgagagcgg ctacgtgcgg ctcctgggag aggtgggcac   1440
actacaattt gctgagctgc atcggagccg gacactgcag gtagtgttcg aggcctaccc   1500
accgcccact gtcctgtggt tcaaagacaa ccgcaccctg ggcgactcca gcgctggcga   1560
aatcgccctg tccacgcgca acgtgtcgga gacccggtat gtgtcagagc tgacactggt   1620
tcgcgtgaag gtggcagagg ctggccacta ccatgcggg ccttccatg aggatgctga   1680
ggtccagctc tccttccagc tacagatcaa tgtccctgtc cgagtgctgg agctaagtga   1740
gagccaccct gacagtgggg aacagacagt ccgctgtcgt ggccggggca tgccccagcc   1800
gaacatcatc tggtctgcct gcagagacct caaaaggtgt ccacgtgagc tgccgcccac   1860
gctgctgggg aacagttccg aagaggagag ccagctggag actaacgtga cgtactggga   1920
ggaggagcag gagtttgagg tggtgagcac actgcgtctg cagcacgtgg atcgccact   1980
gtcggtgcgc tgcacgctgc gcaacgctgt gggccaggac acgcaggagg tcatcgtggt   2040
gccacactcc ttgccctta aggtggtggt gatctcagcc atcctggccc tggtggtgct   2100
caccatcatc tcccttatca tcctcatcat gctttggcag aagaagccac gttacgagat   2160
ccgatggaag gtgattgagt ctgtgagctc tgacggccat gagtacatct acgtggaccc   2220
catgcagctg ccctatgact ccacgtggga gctgccgcgg gaccagcttg tgctgggacg   2280
caccctcggc tctggggcct ttgggcaggt ggtggaggcc acggctcatg gcctgagcca   2340
ttctcaggcc acgatgaaag tggccgtcaa gatgcttaaa tccacagccc gcagcagtga   2400
gaagcaagcc cttatgtcgg agctgaagat catgagtcac cttgggcccc acctgaacgt   2460
ggtcaacctg ttgggggcct gcaccaaagg aggacccatc tatatcatca ctgagtactg   2520
ccgctacgga gacctggtgg actacctgca ccgcaacaaa cacaccttcc tgcagcacca   2580
ctccgacaag cgccgcccgc ccagcgcgga gctctacagc aatgctctgc ccgttgggct   2640
cccctgccc agccatgtgt ccttgaccgg ggagagcgac ggtggctaca tggacatgag   2700
caaggacgag tcggtggact atgtgcccat gctggacatg aaaggagacg tcaaatatgc   2760
agacatcgag tcctccaact acatggcccc ttacgataac tacgttccct ctgcccctga   2820
gaggacctgc cgagcaactt tgatcaacga gtctccagtg ctaagctaca tggacctcgt   2880
gggcttcagc taccaggtgg ccaatggcat ggagtttctg gcctccaaga actgcgtcca   2940
cagagacctg gcggctagga acgtgctcat ctgtgaaggc aagctggtca agatctgtga   3000
ctttggcctg gctcgagaca tcatgcggga ctcgaattac atctccaaag gcagcacctt   3060
tttgcccttta aagtggatgg ctccggagag catcttcaac agcctctaca ccaccctgag   3120
cgacgtgtgg tccttcggga tcctgctctg ggagatcttc accttgggtg gcacccctta   3180
cccagagctg cccatgaacg agcagttcta caatgccatc aaacgggtt accgcatggc   3240
ccagcctgcc catgcctccg acgagatcta tgagatcatg cagaagtgct gggaagagaa   3300
gtttgagatt cggccccct tctcccagct ggtgctgctt ctcgagagac tgttgggcga   3360
aggttacaaa aagaagtacc agcaggtgga tgaggagttt ctgaggagtg accacccagc   3420
catccttcgg tcccaggccc gcttgcctgg gttccatggc ctccgatctc ccctggacac   3480
cagctccgtc ctctatactg ccgtgcagcc caatgagggt gacaacgact atatcatccc   3540
cctgcctgac cccaaacccg aggttgctga cgagggccca ctggagggtt ccccagcct   3600
```

| | |
|---|---|
| agccagctcc accctgaatg aagtcaacac ctcctcaacc atctcctgtg acagcccct | 3660 |
| ggagccccag gacgaaccag agccagagcc ccagcttgag ctccaggtgg agccggagcc | 3720 |
| agagctggaa cagttgccgg attcggggtg ccctgcgcct cgggcggaag cagaggatag | 3780 |
| cttcctgtag ggggctggcc cctaccctgc cctgcctgaa gctcccccc tgccagcacc | 3840 |
| cagcatctcc tggcctggcc tgaccgggct tcctgtcagc caggctgccc ttatcagctg | 3900 |
| tccccttctg gaagctttct gctcctgacg tgttgtgccc caaaccctgg ggctggctta | 3960 |
| ggaggcaaga aaactgcagg ggccgtgacc agccctctgc ctccagggag gccaactgac | 4020 |
| tctgagccag ggttcccca gggaactcag ttttcccata tgtaagatgg gaaagttagg | 4080 |
| cttgatgacc cagaatctag gattctctcc ctggctgaca ggtggggaga ccgaatccct | 4140 |
| ccctgggaag attcttggag ttactgaggt ggtaaattaa cttttttctg ttcagccagc | 4200 |
| taccctcaa ggaatcatag ctctctcctc gcactttat ccacccagga gctagggaag | 4260 |
| agaccctagc ctccctggct gctggctgag ctagggccta gccttgagca gtgttgcctc | 4320 |
| atccagaaga aagccagtct cctccctatg atgccagtcc ctgcgttccc tggcccgagc | 4380 |
| tggtctgggg ccattaggca gcctaattaa tgctggaggc tgagccaagt acaggacacc | 4440 |
| cccagcctgc agcccttgcc cagggcactt ggagcacacg cagccatagc aagtgcctgt | 4500 |
| gtccctgtcc ttcaggccca tcagtcctgg ggctttttct ttatcaccct cagtcttaat | 4560 |
| ccatccacca gagtctagaa ggccagacgg gccccgcatc tgtgatgaga atgtaaatgt | 4620 |
| gccagtgtgg agtggccacg tgtgtgtgcc agtatatggc cctggctctg cattggacct | 4680 |
| gctatgagc tttggaggaa tccctcaccc tctctgggcc tcagtttccc cttcaaaaaa | 4740 |
| tgaataagtc ggacttatta actctgagtg ccttgccagc actaacattc tagagtattc | 4800 |
| caggtggttg cacatttgtc cagatgaagc aaggccatat accctaaact tccatcctgg | 4860 |
| gggtcagctg ggctcctggg agattccaga tcacacatca cactctgggg actcaggaac | 4920 |
| catgccctt ccccaggccc ccagcaagtc tcaagaacac agctgcacag gccttgactt | 4980 |
| agagtgacag ccggtgtcct ggaaagcccc cagcagctgc cccagggaca tgggaagacc | 5040 |
| acgggacctc tttcactacc cacgatgacc tccgggggta tcctgggcaa aagggacaaa | 5100 |
| gagggcaaat gagatcacct cctgcagccc accactccag cacctgtgcc gaggtctgcg | 5160 |
| tcgaagacag aatggacagt gaggacagtt atgtcttgta aaagacaaga agcttcagat | 5220 |
| gggtacccca agaaggatgt gagaggtggg cgctttggag gtttgcccct cacccaccag | 5280 |
| ctgccccatc cctgaggcag cgctccatgg gggtatggtt ttgtcactgc ccagacctag | 5340 |
| cagtgacatc tcattgtccc cagcccagtg ggcattggag gtgccagggg agtcagggtt | 5400 |
| gtagccaaga cgccccgca cggggagggt tgggaagggg gtgcaggaag ctcaacccct | 5460 |
| ctgggcacca accctgcatt gcaggttggc accttacttc cctgggatcc ccagagttgg | 5520 |
| tccaaggagg gagagtgggt tctcaatacg gtaccaaaga tataatcacc taggtttaca | 5580 |
| aatatttta ggactcacgt taactcacat ttatacagca gaaatgctat tttgtatgct | 5640 |
| gttaagtttt tctatctgtg tacttttttt taagggaaag attttaatat taaacctggt | 5700 |
| gcttctcact cacaaaaa | 5718 |

<210> SEQ ID NO 15
<211> LENGTH: 1106
<212> TYPE: PRT
<213> ORGANISM: Homo sapiens

<400> SEQUENCE: 15

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
                20                  25                  30

Leu Val Val Thr Pro Gly Pro Glu Leu Val Leu Asn Val Ser Ser
            35              40                  45

Thr Phe Val Leu Thr Cys Ser Gly Ser Ala Pro Val Val Trp Glu Arg
50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415
```

```
Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Gln Glu Phe Glu Val Val Ser Thr Leu Arg
            485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
            645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
            725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
            770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
            805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
```

Arg Asp Ile Met Arg Asp Ser Asn Tyr Ile Ser Lys Gly Ser Thr Phe
             835                 840                 845
Leu Pro Leu Lys Trp Met Ala Pro Glu Ser Ile Phe Asn Ser Leu Tyr
850                 855                 860
Thr Thr Leu Ser Asp Val Trp Ser Phe Gly Ile Leu Leu Trp Glu Ile
865                 870                 875                 880
Phe Thr Leu Gly Gly Thr Pro Tyr Pro Glu Leu Pro Met Asn Glu Gln
             885                 890                 895
Phe Tyr Asn Ala Ile Lys Arg Gly Tyr Arg Met Ala Gln Pro Ala His
900                 905                 910
            915                 920                 925
Ala Ser Asp Glu Ile Tyr Glu Ile Met Gln Lys Cys Trp Glu Glu Lys
             930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Lys Tyr Gln Gln Val Asp Glu Glu
             965                 970                 975
Phe Leu Arg Ser Asp His Pro Ala Ile Leu Arg Ser Gln Ala Arg Leu
             980                 985                 990
Pro Gly Phe His Gly Leu Arg Ser Pro Leu Asp Thr Ser Ser Val Leu
             995                 1000                1005
Tyr Thr Ala Val Gln Pro Asn Glu Gly Asp Asn Asp Tyr Ile Ile
      1010                1015                1020
Pro Leu Pro Asp Pro Lys Pro Glu Val Ala Asp Glu Gly Pro Leu
      1025                1030                1035
Glu Gly Ser Pro Ser Leu Ala Ser Ser Thr Leu Asn Glu Val Asn
      1040                1045                1050
Thr Ser Ser Thr Ile Ser Cys Asp Ser Pro Leu Glu Pro Gln Asp
      1055                1060                1065
Glu Pro Glu Pro Glu Pro Gln Leu Glu Leu Gln Val Glu Pro Glu
      1070                1075                1080
Pro Glu Leu Glu Gln Leu Pro Asp Ser Gly Cys Pro Ala Pro Arg
      1085                1090                1095
Ala Glu Ala Glu Asp Ser Phe Leu
      1100                1105

<210> SEQ ID NO 16
<211> LENGTH: 3626
<212> TYPE: DNA
<213> ORGANISM: Homo sapiens

<400> SEQUENCE: 16

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta ttttgcttg ccattcccca | 240 |
| cttgaatcgg gccgacggct tggggagatt gctctacttc cccaaatcac tgtggatttt | 300 |
| ggaaaccagc agaagagga aagagtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgccccccag ccccagctac | 540 |

```
cacctcctcc ccggccggcg gcggacagtg gacgcggcgg cgagccgcgg gcagggccg      600 gagcccgcgc ccggaggcgg ggtggagggg gtcggggctc gcggcgtcgc actgaaactt      660
ttcgtccaac ttctgggctg ttctcgcttc ggaggagccg tggtccgcgc ggggaagcc      720 gagccgagcg gagccgcgag aagtgctagc tcggccgggg aggagccgca gccggaggag      780
ggggaggagg aagaagagaa ggaagaggag aggggccgc agtggcgact cggcgctcgg      840
aagccgggct catggacggg tgaggcgcg cgtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgcccctgat gcgatgcggg ggctgctgca atgacgaggg cctggagtgt     1320
gtgcccactg aggagtccaa catcaccatg cagattatgc ggatcaaacc tcaccaaggc     1380
cagcacatag gagagatgag cttcctacag cacaacaaat gtgaatgcag accaaagaaa     1440
gatagagcaa gacaagaaaa aaaatcagtt cgaggaaagg gaaaggggca aaaacgaaag     1500
cgcaagaaat cccggtataa gtcctggagc gttccctgtg ggccttgctc agagcggaga     1560
aagcatttgt ttgtacaaga tccgcagacg tgtaaatgtt cctgcaaaaa cacagactcg     1620
cgttgcaagg cgaggcagct tgagttaaac gaacgtactt gcagatgtga caagccgagg     1680
cggtgagccg ggcaggagga aggagcctcc ctcagggttt cgggaaccag atctctcacc     1740
aggaaagact gatacagaac gatcgataca gaaaccacgc tgccgccacc acaccatcac     1800
catcgacaga acagtcctta atccagaaac ctgaaatgaa ggaagaggag actctgcgca     1860
gagcactttg ggtccggagg gcgagactcc ggcggaagca ttcccgggcg ggtgacccag     1920
cacggtccct cttggaattg gattcgccat tttatttttc ttgctgctaa atcaccgagc     1980
ccggaagatt agagagtttt atttctggga ttcctgtaga cacacccacc cacatacata     2040
catttatata tatatatatt atatatatat aaaaataaat atctctattt tatatatata     2100
aaatatatat attctttttt taaattaaca gtgctaatgt tattggtgtc ttcactggat     2160
gtatttgact gctgtggact tgagttggga ggggaatgtt cccactcaga tcctgacagg     2220
gaagaggagg agatgagaga ctctggcatg atctttttt tgtcccactt ggtggggcca     2280
gggtcctctc ccctgcccag gaatgtgcaa ggccagggca tgggggcaaa tatgacccag     2340
ttttgggaac accgacaaac ccagccctgg cgctgagcct ctctacccca ggtcagacgg     2400
acagaaagac agatcacagg tacagggatg aggacaccgg ctctgaccag gagtttgggg     2460
agcttcagga cattgctgtg ctttggggat tccctccaca tgctgcacgc gcatctcgcc     2520 cccagggca ctgcctggaa gattcaggag cctgggcggc cttcgcttac tctcacctgc     2580
ttctgagttg cccaggagac cactggcaga tgtcccggcg aagagaagag acacattgtt     2640
ggaagaagca gccatgaca gctccccttc ctgggactcg ccctcatcct cttcctgctc     2700
cccttcctgg ggtgcagcct aaaaggacct atgtcctcac accattgaaa ccactagttc     2760
tgtcccccca ggagacctgg ttgtgtgtgt gtgagtggtt gaccttcctc catcccctgg     2820 tccttcccctt cccttcccga ggcacagaga gacagggcag gatccacgtg cccattgtgg     2880
aggcagagaa aagagaaagt gttttatata cggtacttat ttaatatccc ttttttaatta     2940
```

```
gaaattaaaa cagttaatttt aattaaagag tagggttttt tttcagtatt cttggttaat    3000
atttaatttc aactatttat gagatgtatc ttttgctctc tcttgctctc ttatttgtac    3060 cggttttttgt atataaaatt catgtttcca atctctctct ccctgatcgg tgacagtcac    3120
tagcttatct tgaacagata tttaattttg ctaacactca gctctgccct ccccgatccc    3180
ctggctcccc agcacacatt cctttgaaat aaggtttcaa tatacatcta catactatat    3240
atatatttgg caacttgtat ttgtgtgtat atatatatat atatgtttat gtatatatgt    3300
gattctgata aaatagacat tgctattctg tttttttatat gtaaaaacaa aacaagaaaa    3360
aatagagaat tctacatact aaatctctct cctttttaa ttttaatatt tgttatcatt    3420
tatttattgg tgctactgtt tatccgtaat aattgtgggg aaaagatatt aacatcacgt    3480
ctttgtctct agtgcagttt ttcgagatat tccgtagtac atatttattt ttaaacaacg    3540
acaaagaaat acagatatat cttaaaaaaa aaaaagcatt ttgtattaaa gaatttaatt    3600
ctgatctcaa aaaaaaaaaa aaaaaa                                          3626
```

<210> SEQ ID NO 17
<211> LENGTH: 395
<212> TYPE: PRT
<213> ORGANISM: Homo sapiens

<400> SEQUENCE: 17

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
```

```
                245                 250                 255
Cys Val Pro Leu Met Arg Cys Gly Gly Cys Cys Asn Asp Glu Gly Leu
            260                 265                 270
Glu Cys Val Pro Thr Glu Glu Ser Asn Ile Thr Met Gln Ile Met Arg
        275                 280                 285
Ile Lys Pro His Gln Gly Gln His Ile Gly Glu Met Ser Phe Leu Gln
    290                 295                 300
His Asn Lys Cys Glu Cys Arg Pro Lys Lys Asp Arg Ala Arg Gln Glu
305                 310                 315                 320
Lys Lys Ser Val Arg Gly Lys Gly Lys Gly Gln Lys Arg Lys Arg Lys
                325                 330                 335
Lys Ser Arg Tyr Lys Ser Trp Ser Val Pro Cys Gly Pro Cys Ser Glu
            340                 345                 350
Arg Arg Lys His Leu Phe Val Gln Asp Pro Gln Thr Cys Lys Cys Ser
        355                 360                 365
Cys Lys Asn Thr Asp Ser Arg Cys Lys Ala Arg Gln Leu Glu Leu Asn
    370                 375                 380
Glu Arg Thr Cys Arg Cys Asp Lys Pro Arg Arg
385                 390                 395

<210> SEQ ID NO 18
<211> LENGTH: 4017
<212> TYPE: DNA
<213> ORGANISM: Homo sapiens

<400> SEQUENCE: 18
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca ggggggaagc agcccataaa     180
tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ttttcgtaga gatgtacagt     420
gaaatccccg aaattataca catgactgaa ggaagggagc tcgtcattcc ctgccgggtt     480
acgtcaccta catcactgt  tacttttaaa agtttccac  ttgacacttt gatccctgat     540
ggaaaacgca taatctggga cagtagaaag ggcttcatca tatcaaatgc aacgtacaaa     600 gaaataggg  ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata gagagcttc  cgtaaggcga     840 cgaattgacc aaagcaattc ccatgccaac atattctaca gtgttcttac tattgacaaa     900
atgcagaaca agacaaagg  actttatact tgtcgtgtaa ggagtggacc atcattcaaa     960
tctgttaaca cctcagtgca tatatatgat aaagcattca tcactgtgaa acatcgaaaa    1020
cagcaggtgc ttgaaaccgt agctggcaag cggtcttacc ggctctctat gaaagtgaag    1080
gcatttccct cgccggaagt tgtatggtta aaagatgggt tacctgcgac tgagaaatct    1140
gctcgctatt tgactcgtgg ctactcgtta attatcaagg acgtaactga agaggatgca    1200
gggaattata caatcttgct gagcataaaa cagtcaaatg tgtttaaaaa cctcactgcc    1260
```

```
actctaattg tcaatgtgaa accccagatt tacgaaaagg ccgtgtcatc gtttccagac    1320
ccggctctct acccactggg cagcagacaa atcctgactt gtaccgcata tggtatccct    1380
caacctacaa tcaagtggtt ctggcacccc tgtaaccata atcattccga agcaaggtgt    1440
gacttttgtt ccaataatga agagtcctct atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga aactgtcttg cacagttaac    1740
aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagaga tcaggaagca    1980
ccatacctcc tgcgaaacct cagtgatcac acagtggcca tcagcagttc caccactta    2040 gactgtcatg ctaatggtgt ccccgagcct cagatcactt ggtttaaaaa caaccacaaa    2100
atacaacaag agcctggaat tatttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaaggtcttc ttctgaaata aagactgact acctatcaat tataatggac    2400
ccagatgaag ttcctttgga tgagcagtgt gagcggctcc cttatgatgc cagcaagtgg    2460
gagtttgccc gggagagact aaactgggca aaatcacttg gaagaggggc ttttggaaaa    2520
gtggttcaag catcagcatt tggcattaag aaaatcccta cgtgccggac tgtggctgtg    2580
aaaatgctga aagaggggca cacggccagc gagtacaaag ctctgatgac tgagctaaaa    2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca aacgtgactt atttttttctc aacaaggatg cagcactaca catggagcct    2820
aagaaagaaa aaatggagcc aggcctggaa caaggcaaga accaagact agatagcgtc    2880 accagcagcg aaagctttgc gagctccggc tttcaggaag ataaaagtct gagtgatgtt    2940
gaggaagagg aggattctga cggtttctac aaggagccca tcactatgga agatctgatt    3000
tcttacagtt ttcaagtggc cagaggcatg gagttcctgt cttccagaaa gtgcattcat    3060
cgggacctgg cagcgagaaa cattcttttta tctgagaaca cgtggtgaa gatttgtgat    3120 tttggccttg cccgggatat ttataagaac cccgattatg tgagaaaagg agatactcga    3180
cttcctctga atggatggc tcctgaatct atctttgaca aaatctacag caccaagagc    3240
gacgtgtggt cttacggagt attgctgtgg gaaatcttct ccttaggtgg gtctccatac    3300
ccaggagtac aaatggatga ggacttttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc ccaatcaatg ccatactgac aggaaatagt    3540
gggtttacat actcaactcc tgccttctct gaggacttct tcaaggaaag tatttcagct    3600 ccgaagtttta attcaggaag ctctgatgat gtcagatatg taaatgcttt caagttcatg    3660
```

```
agcctggaaa gaatcaaaac ctttgaagaa cttttaccga atgccacctc catgtttgat    3720
gactaccagg gcgacagcag cactctgttg gcctctccca tgctgaagcg cttcacctgg    3780
actgacagca aacccaaggc ctcgctcaag attgacttga gagtaaccag taaaagtaag    3840
gagtcggggc tgtctgatgt cagcaggccc agtttctgcc attccagctg tgggcacgtc    3900
agcgaaggca agcgcaggtt cacctacgac cacgctgagc tggaaaggaa aatcgcgtgc    3960
tgctccccgc ccccagacta caactcggtg gtcctgtact ccaccccacc catctag      4017
```

<210> SEQ ID NO 19
<211> LENGTH: 1338
<212> TYPE: PRT
<213> ORGANISM: Homo sapiens

<400> SEQUENCE: 19

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
```

```
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
                355                 360                 365
Trp Leu Lys Asp Gly Leu Pro Ala Thr Glu Lys Ser Ala Arg Tyr Leu
                370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
                435                 440                 445
Arg Gln Ile Leu Thr Cys Thr Ala Tyr Gly Ile Pro Gln Pro Thr Ile
                450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Ser Ile Leu Asp Ala Asp Ser
                485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
                515                 520                 525
Ile Ser Gly Ile Tyr Ile Cys Ile Ala Ser Asn Lys Val Gly Thr Val
                530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
                580                 585                 590
Arg Thr Val Asn Asn Arg Thr Met His Tyr Ser Ile Ser Lys Gln Lys
                595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
                660                 665                 670
Ala Ile Ser Ser Ser Thr Thr Leu Asp Cys His Ala Asn Gly Val Pro
                675                 680                 685
Glu Pro Gln Ile Thr Trp Phe Lys Asn Asn His Lys Ile Gln Gln Glu
                690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
```

-continued

Lys Gly Ser Val Glu Ser Ser Ala Tyr Leu Thr Val Gln Gly Thr Ser
              740                 745                 750

Asp Lys Ser Asn Leu Glu Leu Ile Thr Leu Thr Cys Thr Cys Val Ala
              755                 760                 765

Ala Thr Leu Phe Trp Leu Leu Leu Thr Leu Phe Ile Arg Lys Met Lys
              770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
              805                 810                 815

Ala Ser Lys Trp Glu Phe Ala Arg Glu Arg Leu Lys Leu Gly Lys Ser
              820                 825                 830

Leu Gly Arg Gly Ala Phe Gly Lys Val Val Gln Ala Ser Ala Phe Gly
              835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
              885                 890                 895

Ala Cys Thr Lys Gln Gly Gly Pro Leu Met Val Ile Val Glu Tyr Cys
              900                 905                 910

Lys Tyr Gly Asn Leu Ser Asn Tyr Leu Lys Ser Lys Arg Asp Leu Phe
              915                 920                 925

Phe Leu Asn Lys Asp Ala Ala Leu His Met Glu Pro Lys Lys Glu Lys
              930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
              965                 970                 975

Leu Ser Asp Val Glu Glu Glu Glu Asp Ser Asp Gly Phe Tyr Lys Glu
              980                 985                 990

Pro Ile Thr Met Glu Asp Leu Ile Ser Tyr Ser Phe Gln Val Ala Arg
              995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

| | | | | | | | | | | |
|---|---|---|---|---|---|---|---|---|---|---|
| Arg | Pro<br>1145 | Arg | Phe | Ala | Glu<br>1150 | Leu | Val | Glu | Lys | Leu<br>1155 | Gly | Asp | Leu | Leu |

Gln Ala Asn Val Gln Gln Asp Gly Lys Asp Tyr Ile Pro Ile Asn
 1160                1165                1170

Ala Ile Leu Thr Gly Asn Ser Gly Phe Thr Tyr Ser Thr Pro Ala
 1175                1180                1185

Phe Ser Glu Asp Phe Phe Lys Glu Ser Ile Ser Ala Pro Lys Phe
 1190                1195                1200

Asn Ser Gly Ser Ser Asp Asp Val Arg Tyr Val Asn Ala Phe Lys
 1205                1210                1215

Phe Met Ser Leu Glu Arg Ile Lys Thr Phe Glu Glu Leu Leu Pro
 1220                1225                1230

Asn Ala Thr Ser Met Phe Asp Asp Tyr Gln Gly Asp Ser Ser Thr
 1235                1240                1245

Leu Leu Ala Ser Pro Met Leu Lys Arg Phe Thr Trp Thr Asp Ser
 1250                1255                1260

Lys Pro Lys Ala Ser Leu Lys Ile Asp Leu Arg Val Thr Ser Lys
 1265                1270                1275

Ser Lys Glu Ser Gly Leu Ser Asp Val Ser Arg Pro Ser Phe Cys
 1280                1285                1290

His Ser Ser Cys Gly His Val Ser Glu Gly Lys Arg Arg Phe Thr
 1295                1300                1305

Tyr Asp His Ala Glu Leu Glu Arg Lys Ile Ala Cys Cys Ser Pro
 1310                1315                1320

Pro Pro Asp Tyr Asn Ser Val Val Leu Tyr Ser Thr Pro Pro Ile
 1325                1330                1335

<210> SEQ ID NO 20
<211> LENGTH: 5830
<212> TYPE: DNA
<213> ORGANISM: Homo sapiens

<400> SEQUENCE: 20

```
actgagtccc gggacccccgg gagagcggtc agtgtgtggt cgctgcgttt cctctgcctg      60
cgccgggcat cacttgcgcg ccgcagaaag tccgtctggc agcctggata tcctctccta     120
ccggcacccg cagacgcccc tgcagccgcc ggtcggcgcc cgggctcccct agccctgtgc    180
gctcaactgt cctgcgctgc ggggtgccgc gagttccacc tccgcgcctc cttctctaga    240
caggcgctgg gagaaagaac cggctcccga gttctgggca tttcgcccgg ctcgaggtgc    300
aggatgcaga gcaaggtgct gctggccgtc gccctgtggc tctgcgtgga gacccgggcc    360
gcctctgtgg gtttgcctag tgtttctctt gatctgccca ggctcagcat acaaaaagac    420
atacttacaa ttaaggctaa tacaactctt caaattactt gcaggggaca gagggacttg    480
gactggcttt ggcccaataa tcagagtggc agtgagcaaa gggtggaggt gactgagtgc    540
agcgatggcc tcttctgtaa gacactcaca attccaaaag tgatcggaaa tgacactgga    600
gcctacaagt gcttctaccg ggaaactgac ttggcctcgg tcatttatgt ctatgttcaa    660
gattacagat ctccatttat tgcttctgtt agtgaccaac atggagtcgt gtacattact    720
gagaacaaaa acaaaactgt ggtgattcca tgtctcgggt ccatttcaaa tctcaacgtg    780
tcactttgtg caagataccc agaaaagaga tttgttcctg atggtaacag aatttcctgg    840
gacagcaaga agggctttac tattcccagc tacatgatca gctatgctgg catggtcttc    900
tgtgaagcaa aaattaatga tgaaagttac cagtctatta tgtacatagt tgtcgttgta    960
```

```
gggtatagga tttatgatgt ggttctgagt ccgtctcatg gaattgaact atctgttgga      1020
gaaaagcttg tcttaaattg tacagcaaga actgaactaa atgtggggat tgacttcaac      1080
tgggaatacc cttcttcgaa gcatcagcat aagaaacttg taaaccgaga cctaaaaacc      1140
cagtctggga gtgagatgaa gaaattttg agcaccttaa ctatagatgg tgtaacccgg       1200
agtgaccaag gattgtacac ctgtgcagca tccagtgggc tgatgaccaa gaagaacagc      1260
acatttgtca gggtccatga aaaacctttt gttgcttttg gaagtggcat ggaatctctg      1320
gtggaagcca cggtggggga gcgtgtcaga atccctgcga agtaccttgg ttacccaccc      1380
ccagaaataa aatggtataa aaatggaata ccccttgagt ccaatcacac aattaaagcg      1440
gggcatgtac tgacgattat ggaagtgagt gaaagagaca caggaaatta cactgtcatc      1500
cttaccaatc ccattcaaa ggagaagcag agccatgtgg tctctctggt tgtgtatgtc        1560
ccaccccaga ttggtgagaa atctctaatc tctcctgtgg attcctacca gtacggcacc      1620
actcaaacgc tgacatgtac ggtctatgcc attcctcccc cgcatcacat ccactggtat      1680
tggcagttgg aggaagagtg cgccaacgag cccagccaag ctgtctcagt gacaaaccca      1740 taccccttgtg aagaatggag aagtgtggag gacttccagg gaggaaataa aattgaagtt     1800
aataaaaatc aatttgctct aattgaagga aaaaacaaaa ctgtaagtac ccttgttatc      1860
caagcggcaa atgtgtcagc tttgtacaaa tgtgaagcgg tcaacaaagt cgggagagga      1920 gagggtga tctccttcca cgtgaccagg ggtcctgaaa ttactttgca acctgacatg         1980
cagcccactg agcaggagag cgtgtctttg tggtgcactg cagacagatc tacgtttgag      2040
aacctcacat ggtacaagct ggcccacag cctctgccaa tccatgtggg agagttgccc        2100
acacctgttt gcaagaactt ggatactctt tggaaattga atgccaccat gttctctaat      2160
agcacaaatg acatttgat catggagctt aagaatgcat ccttgcagga ccaaggagac       2220
tatgtctgcc ttgctcaaga caggaagacc aagaaaagac attgcgtggt caggcagctc      2280
acagtcctag agcgtgtggc acccacgatc acaggaaacc tggagaatca gacgacaagt      2340
attggggaaa gcatcgaagt ctcatgcacg gcatctggga atcccctcc acagatcatg       2400 tggtttaaag ataatgagac ccttgtagaa gactcaggca ttgtattgaa ggatgggaac      2460
cggaacctca ctatccgcag agtgaggaag gaggacgaag gcctctacac ctgccaggca     2520
tgcagtgttc ttggctgtgc aaaagtggag gcatttttca taagaagg tgcccaggaa        2580 aagacgaact tggaaatcat tattctagta ggcacggcgg tgattgccat gttcttctgg      2640
ctacttcttg tcatcatcct acggaccgtt aagcgggcca atggagggga actgaagaca      2700
ggctacttgt ccatcgtcat ggatccagat gaactcccat tggatgaaca ttgtgaacga      2760
ctgccttatg atgccagcaa atgggaattc cccagagacc ggctgaagct aggtaagcct      2820
cttggccgtg gtgcctttgg ccaagtgatt gaagcagatg cctttggaat tgacaagaca      2880
gcaacttgca ggacagtagc agtcaaaatg ttgaaagaag gagcaacaca cagtgagcat      2940
cgagctctca tgtctgaact caagatcctc attcatattg gtcaccatct caatgtggtc      3000
aaccttctag gtgcctgtac caagccagga gggccactca tggtgattgt ggaattctgc      3060
aaatttggaa acctgtccac ttacctgagg agcaagagaa atgaatttgt ccctacaag      3120 accaaagggg cacgattccg tcaagggaaa gactacgttg gagcaatccc tgtggatctg      3180
aaacggcgct tggacagcat caccagtagc cagagctcag ccagctctgg atttgtggag     3240
gagaagtccc tcagtgatgt agaagaagag gaagctcctg aagatctgta taaggacttc      3300
ctgaccttgg agcatctcat ctgttacagc ttccaagtgg ctaagggcat ggagttcttg      3360
```

```
gcatcgcgaa agtgtatcca cagggacctg gcggcacgaa atatcctctt atcggagaag      3420
aacgtggtta aaatctgtga cttttggctt gcccgggata tttataaaga tccagattat      3480
gtcagaaaag gagatgctcg cctcccttttg aaatggatgg ccccagaaac aattttttgac    3540 agagtgtaca caatccagag tgacgtctgg tcttttggtg ttttgctgtg ggaaatattt      3600
tccttaggtg cttctccata tcctggggta aagattgatg aagaattttg taggcgattg      3660
aaagaaggaa ctagaatgag ggcccctgat tatactacac cagaaatgta ccagaccatg      3720
ctggactgct ggcacgggga gcccagtcag agacccacgt tttcagagtt ggtggaacat      3780
ttgggaaatc tcttgcaagc taatgctcag caggatggca aagactacat tgttcttccg      3840
atatcagaga ctttgagcat ggaagaggat tctggactct ctctgcctac ctcacctgtt      3900
tcctgtatgg aggaggagga agtatgtgac cccaaattcc attatgacaa cacagcagga      3960
atcagtcagt atctgcagaa cagtaagcga aagagccggc ctgtgagtgt aaaaacatttt     4020 gaagatatcc cgttagaaga accagaagta aaagtaatcc cagatgacaa ccagacggac      4080
agtggtatgg ttcttgcctc agaagagctg aaaactttgg aagacagaac caaattatct      4140
ccatcttttg gtggaatggt gcccagcaaa agcaggagt ctgtggcatc tgaaggctca       4200
aaccagacaa gcggctacca gtccggatat cactccgatg acacagacac caccgtgtac      4260
tccagtgagg aagcagaact tttaaagctg atagagattg gagtgcaaac cggtagcaca      4320
gcccagattc tccagcctga ctcggggacc acactgagct ctcctcctgt ttaaaaggaa      4380
gcatccacac cccaactccc ggacatcaca tgagaggtct gctcagattt tgaagtgttg      4440
ttctttccac cagcaggaag tagccgcatt tgattttcat ttcgacaaca gaaaaaggac      4500
ctcggactgc agggagccag tcttctaggc atatcctgga agaggcttgt gacccaagaa      4560
tgtgtctgtg tcttctccca gtgttgacct gatcctcttt tttcattcat ttaaaaagca     4620
ttatcatgcc cctgctgcgg gtctcaccat gggtttagaa caaagagctt caagcaatgg      4680
ccccatcctc aaagaagtag cagtacctgg ggagctgaca cttctgtaaa actagaagat      4740
aaaccaggca acgtaagtgt tcgaggtgtt gaagatggga aggatttgca gggctgagtc      4800
tatccaagag gctttgttta ggacgtgggt cccaagccaa gccttaagtg tggaattcgg      4860
attgatagaa aggaagacta acgttacctt gctttggaga gtactggagc ctgcaaatgc      4920
attgtgtttg ctctggtgga ggtgggcatg gggtctgttc tgaaatgtaa agggttcaga      4980
cggggtttct ggttttagaa ggttgcgtgt tcttcgagtt gggctaaagt agagttcgtt      5040
gtgctgtttc tgactcctaa tgagagttcc ttccagaccg ttagctgtct ccttgccaag      5100
ccccaggaag aaaatgatgc agctctggct ccttgtctcc caggctgatc ctttattcag      5160
aataccacaa agaaggaca ttcagctcaa ggctccctgc cgtgttgaag agttctgact        5220
gcacaaacca gcttctggtt tcttctggaa tgaatacct catatctgtc ctgatgtgat        5280
atgtctgaga ctgaatgcgg gaggttcaat gtgaagctgt gtgtggtgtc aaagtttcag      5340
gaaggatttt acccttttgt tcttcccct gtccccaacc cactctcacc ccgcaaccca       5400
tcagtatttt agttatttgg cctctactcc agtaaacctg attgggtttg ttcactctct      5460
gaatgattat tagccagact tcaaaattat tttatagccc aaattataac atctattgta      5520
ttatttagac ttttaacata tagagctatt tctactgatt tttgcccttg ttctgtcctt      5580
tttttcaaaa aagaaaatgt gttttttgtt tggtaccata gtgtgaaatg ctgggaacaa      5640
tgactataag acatgctatg gcacatatat ttatagtctg tttatgtaga aacaaatgta      5700
```

```
atatattaaa gccttatata taatgaactt tgtactattc acattttgta tcagtattat    5760
gtagcataac aaaggtcata atgctttcag caattgatgt cattttatta aagaacattg    5820
aaaaacttga                                                           5830
```

<210> SEQ ID NO 21
<211> LENGTH: 1356
<212> TYPE: PRT
<213> ORGANISM: Homo sapiens

<400> SEQUENCE: 21

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350
```

-continued

Lys Tyr Leu Gly Tyr Pro Pro Glu Ile Lys Trp Tyr Lys Asn Gly
            355             360             365

Ile Pro Leu Glu Ser Asn His Thr Ile Lys Ala Gly His Val Leu Thr
        370             375             380

Ile Met Glu Val Ser Glu Arg Asp Thr Gly Asn Tyr Thr Val Ile Leu
385             390             395             400

Thr Asn Pro Ile Ser Lys Glu Lys Gln Ser His Val Val Ser Leu Val
                405             410             415

Val Tyr Val Pro Pro Gln Ile Gly Glu Lys Ser Leu Ile Ser Pro Val
            420             425             430

Asp Ser Tyr Gln Tyr Gly Thr Thr Gln Thr Leu Thr Cys Thr Val Tyr
        435             440             445

Ala Ile Pro Pro His His Ile His Trp Tyr Trp Gln Leu Glu Glu
    450             455             460

Glu Cys Ala Asn Glu Pro Ser Gln Ala Val Ser Val Thr Asn Pro Tyr
465             470             475             480

Pro Cys Glu Glu Trp Arg Ser Val Glu Asp Phe Gln Gly Gly Asn Lys
            485             490             495

Ile Glu Val Asn Lys Asn Gln Phe Ala Leu Ile Glu Gly Lys Asn Lys
                500             505             510

Thr Val Ser Thr Leu Val Ile Gln Ala Ala Asn Val Ser Ala Leu Tyr
            515             520             525

Lys Cys Glu Ala Val Asn Lys Val Gly Arg Gly Glu Arg Val Ile Ser
    530             535             540

Phe His Val Thr Arg Gly Pro Glu Ile Thr Leu Gln Pro Asp Met Gln
545             550             555             560

Pro Thr Glu Gln Glu Ser Val Ser Leu Trp Cys Thr Ala Asp Arg Ser
            565             570             575

Thr Phe Glu Asn Leu Thr Trp Tyr Lys Leu Gly Pro Gln Pro Leu Pro
            580             585             590

Ile His Val Gly Glu Leu Pro Thr Pro Val Cys Lys Asn Leu Asp Thr
        595             600             605

Leu Trp Lys Leu Asn Ala Thr Met Phe Ser Asn Ser Thr Asn Asp Ile
    610             615             620

Leu Ile Met Glu Leu Lys Asn Ala Ser Leu Gln Asp Gln Gly Asp Tyr
625             630             635             640

Val Cys Leu Ala Gln Asp Arg Lys Thr Lys Lys Arg His Cys Val Val
            645             650             655

Arg Gln Leu Thr Val Leu Glu Arg Val Ala Pro Thr Ile Thr Gly Asn
        660             665             670

Leu Glu Asn Gln Thr Thr Ser Ile Gly Glu Ser Ile Glu Val Ser Cys
            675             680             685

Thr Ala Ser Gly Asn Pro Pro Pro Gln Ile Met Trp Phe Lys Asp Asn
690             695             700

Glu Thr Leu Val Glu Asp Ser Gly Ile Val Leu Lys Asp Gly Asn Arg
705             710             715             720

Asn Leu Thr Ile Arg Arg Val Arg Lys Glu Asp Glu Gly Leu Tyr Thr
            725             730             735

Cys Gln Ala Cys Ser Val Leu Gly Cys Ala Lys Val Glu Ala Phe Phe
        740             745             750

Ile Ile Glu Gly Ala Gln Glu Lys Thr Asn Leu Glu Ile Ile Leu
    755             760             765

```
Val Gly Thr Ala Val Ile Ala Met Phe Phe Trp Leu Leu Val Ile
770             775                 780

Ile Leu Arg Thr Val Lys Arg Ala Asn Gly Gly Glu Leu Lys Thr Gly
785             790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
                835                 840                 845

Ile Glu Ala Asp Ala Phe Gly Ile Asp Lys Thr Ala Thr Cys Arg Thr
850             855                 860

Val Ala Val Lys Met Leu Lys Glu Gly Ala Thr His Ser Glu His Arg
865             870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
```

```
                    1175                 1180                 1185
Asp Ser Gly Leu Ser Leu Pro Thr Ser Pro Val Ser Cys Met Glu
            1190                 1195                 1200
Glu Glu Glu Val Cys Asp Pro Lys Phe His Tyr Asp Asn Thr Ala
            1205                 1210                 1215
Gly Ile Ser Gln Tyr Leu Gln Asn Ser Lys Arg Lys Ser Arg Pro
            1220                 1225                 1230
Val Ser Val Lys Thr Phe Glu Asp Ile Pro Leu Glu Glu Pro Glu
            1235                 1240                 1245
Val Lys Val Ile Pro Asp Asp Asn Gln Thr Asp Ser Gly Met Val
            1250                 1255                 1260
Leu Ala Ser Glu Glu Leu Lys Thr Leu Glu Asp Arg Thr Lys Leu
            1265                 1270                 1275
Ser Pro Ser Phe Gly Gly Met Val Pro Ser Lys Ser Arg Glu Ser
            1280                 1285                 1290
Val Ala Ser Glu Gly Ser Asn Gln Thr Ser Gly Tyr Gln Ser Gly
            1295                 1300                 1305
Tyr His Ser Asp Asp Thr Asp Thr Thr Val Tyr Ser Ser Glu Glu
            1310                 1315                 1320
Ala Glu Leu Leu Lys Leu Ile Glu Ile Gly Val Gln Thr Gly Ser
            1325                 1330                 1335
Thr Ala Gln Ile Leu Gln Pro Asp Ser Gly Thr Thr Leu Ser Ser
            1340                 1345                 1350
Pro Pro Val
            1355

<210> SEQ ID NO 22
<211> LENGTH: 16
<212> TYPE: PRT
<213> ORGANISM: Homo sapiens

<400> SEQUENCE: 22

Cys Asn Asp Glu Gly Leu Glu Cys Val Pro Thr Glu Glu Ser Asn Ile
1               5                   10                  15

<210> SEQ ID NO 23
<211> LENGTH: 16
<212> TYPE: PRT
<213> ORGANISM: Homo sapiens

<400> SEQUENCE: 23

Cys Pro Asp Asp Gly Leu Glu Cys Val Pro Thr Gly Gln His Gln Val
1               5                   10                  15

<210> SEQ ID NO 24
<211> LENGTH: 1676
<212> TYPE: PRT
<213> ORGANISM: Homo sapiens

<400> SEQUENCE: 24

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
        50                  55                  60
```

```
Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
        435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480
```

-continued

```
His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
            530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
            595                 600                 605

Val Tyr Gly Val Gln Arg Gly Ala Lys Lys Pro Leu Glu Arg Val Phe
            610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
            675                 680                 685

Lys Tyr Lys His Ser Val Val Lys Lys Cys Cys Tyr Asp Gly Ala Cys
            690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
            770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
            850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Ser His Leu Val
                885                 890                 895

Thr Phe Thr Val Leu Pro Leu Glu Ile Gly Leu His Asn Ile Asn Phe
```

-continued

```
                900             905             910
Ser Leu Glu Thr Trp Phe Gly Lys Glu Ile Leu Val Lys Thr Leu Arg
            915             920             925

Val Val Pro Glu Gly Val Lys Arg Glu Ser Tyr Ser Gly Val Thr Leu
        930             935             940

Asp Pro Arg Gly Ile Tyr Gly Thr Ile Ser Arg Lys Glu Phe Pro
945             950             955             960

Tyr Arg Ile Pro Leu Asp Leu Val Pro Lys Thr Glu Ile Lys Arg Ile
            965             970             975

Leu Ser Val Lys Gly Leu Leu Val Gly Glu Ile Leu Ser Ala Val Leu
            980             985             990

Ser Gln Glu Gly Ile Asn Ile Leu Thr His Leu Pro Lys Gly Ser Ala
        995             1000            1005

Glu Ala Glu Leu Met Ser Val Val Pro Val Phe Tyr Val Phe His
    1010            1015            1020

Tyr Leu Glu Thr Gly Asn His Trp Asn Ile Phe His Ser Asp Pro
    1025            1030            1035

Leu Ile Glu Lys Gln Lys Leu Lys Lys Lys Leu Lys Glu Gly Met
    1040            1045            1050

Leu Ser Ile Met Ser Tyr Arg Asn Ala Asp Tyr Ser Tyr Ser Val
    1055            1060            1065

Trp Lys Gly Gly Ser Ala Ser Thr Trp Leu Thr Ala Phe Ala Leu
    1070            1075            1080

Arg Val Leu Gly Gln Val Asn Lys Tyr Val Glu Gln Asn Gln Asn
    1085            1090            1095

Ser Ile Cys Asn Ser Leu Leu Trp Leu Val Glu Asn Tyr Gln Leu
    1100            1105            1110

Asp Asn Gly Ser Phe Lys Glu Asn Ser Gln Tyr Gln Pro Ile Lys
    1115            1120            1125

Leu Gln Gly Thr Leu Pro Val Glu Ala Arg Glu Asn Ser Leu Tyr
    1130            1135            1140

Leu Thr Ala Phe Thr Val Ile Gly Ile Arg Lys Ala Phe Asp Ile
    1145            1150            1155

Cys Pro Leu Val Lys Ile Asp Thr Ala Leu Ile Lys Ala Asp Asn
    1160            1165            1170

Phe Leu Leu Glu Asn Thr Leu Pro Ala Gln Ser Thr Phe Thr Leu
    1175            1180            1185

Ala Ile Ser Ala Tyr Ala Leu Ser Leu Gly Asp Lys Thr His Pro
    1190            1195            1200

Gln Phe Arg Ser Ile Val Ser Ala Leu Lys Arg Glu Ala Leu Val
    1205            1210            1215

Lys Gly Asn Pro Pro Ile Tyr Arg Phe Trp Lys Asp Asn Leu Gln
    1220            1225            1230

His Lys Asp Ser Ser Val Pro Asn Thr Gly Thr Ala Arg Met Val
    1235            1240            1245

Glu Thr Thr Ala Tyr Ala Leu Leu Thr Ser Leu Asn Leu Lys Asp
    1250            1255            1260

Ile Asn Tyr Val Asn Pro Val Ile Lys Trp Leu Ser Glu Glu Gln
    1265            1270            1275

Arg Tyr Gly Gly Gly Phe Tyr Ser Thr Gln Asp Thr Ile Asn Ala
    1280            1285            1290

Ile Glu Gly Leu Thr Glu Tyr Ser Leu Leu Val Lys Gln Leu Arg
    1295            1300            1305
```

Leu Ser Met Asp Ile Asp Val Ser Tyr Lys His Lys Gly Ala Leu
    1310            1315            1320

His Asn Tyr Lys Met Thr Asp Lys Asn Phe Leu Gly Arg Pro Val
    1325            1330            1335

Glu Val Leu Leu Asn Asp Asp Leu Ile Val Ser Thr Gly Phe Gly
    1340            1345            1350

Ser Gly Leu Ala Thr Val His Val Thr Thr Val His Lys Thr
    1355            1360            1365

Ser Thr Ser Glu Glu Val Cys Ser Phe Tyr Leu Lys Ile Asp Thr
    1370            1375            1380

Gln Asp Ile Glu Ala Ser His Tyr Arg Gly Tyr Gly Asn Ser Asp
    1385            1390            1395

Tyr Lys Arg Ile Val Ala Cys Ala Ser Tyr Lys Pro Ser Arg Glu
    1400            1405            1410

Glu Ser Ser Ser Gly Ser Ser His Ala Val Met Asp Ile Ser Leu
    1415            1420            1425

Pro Thr Gly Ile Ser Ala Asn Glu Glu Asp Leu Lys Ala Leu Val
    1430            1435            1440

Glu Gly Val Asp Gln Leu Phe Thr Asp Tyr Gln Ile Lys Asp Gly
    1445            1450            1455

His Val Ile Leu Gln Leu Asn Ser Ile Pro Ser Ser Asp Phe Leu
    1460            1465            1470

Cys Val Arg Phe Arg Ile Phe Glu Leu Phe Glu Val Gly Phe Leu
    1475            1480            1485

Ser Pro Ala Thr Phe Thr Val Tyr Glu Tyr His Arg Pro Asp Lys
    1490            1495            1500

Gln Cys Thr Met Phe Tyr Ser Thr Ser Asn Ile Lys Ile Gln Lys
    1505            1510            1515

Val Cys Glu Gly Ala Ala Cys Lys Cys Val Glu Ala Asp Cys Gly
    1520            1525            1530

Gln Met Gln Glu Glu Leu Asp Leu Thr Ile Ser Ala Glu Thr Arg
    1535            1540            1545

Lys Gln Thr Ala Cys Lys Pro Glu Ile Ala Tyr Ala Tyr Lys Val
    1550            1555            1560

Ser Ile Thr Ser Ile Thr Val Glu Asn Val Phe Val Lys Tyr Lys
    1565            1570            1575

Ala Thr Leu Leu Asp Ile Tyr Lys Thr Gly Glu Ala Val Ala Glu
    1580            1585            1590

Lys Asp Ser Glu Ile Thr Phe Ile Lys Lys Val Thr Cys Thr Asn
    1595            1600            1605

Ala Glu Leu Val Lys Gly Arg Gln Tyr Leu Ile Met Gly Lys Glu
    1610            1615            1620

Ala Leu Gln Ile Lys Tyr Asn Phe Ser Phe Arg Tyr Ile Tyr Pro
    1625            1630            1635

Leu Asp Ser Leu Thr Trp Ile Glu Tyr Trp Pro Arg Asp Thr Thr
    1640            1645            1650

Cys Ser Ser Cys Gln Ala Phe Leu Ala Asn Leu Asp Glu Phe Ala
    1655            1660            1665

Glu Asp Ile Phe Leu Asn Gly Cys
    1670            1675

<210> SEQ ID NO 25
<211> LENGTH: 42

```
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'OH-guanosine
<220> FEATURE:
<221> NAME/KEY: misc_feature
<222> LOCATION: (2)..(2)
<223> OTHER INFORMATION: May be 2'OH-adenosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'OH-guanosine
<220> FEATURE:
<221> NAME/KEY: misc_feature
<222> LOCATION: (5)..(5)
<223> OTHER INFORMATION: May be 2'OH-adenosine
<220> FEATURE:
<221> NAME/KEY: misc_feature
<222> LOCATION: (6)..(6)
<223> OTHER INFORMATION: May be 2'-fluoro-2'-deoxyuridine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'OH-guanosine
<220> FEATURE:
<221> NAME/KEY: misc_feature
<222> LOCATION: (10)..(10)
<223> OTHER INFORMATION: May be 2'OH-guanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
<221> NAME/KEY: misc_feature
<222> LOCATION: (14)..(14)
<223> OTHER INFORMATION: May be 2'-fluoro-2'-deoxycytidine
<220> FEATURE:
<221> NAME/KEY: misc_feature
<222> LOCATION: (15)..(15)
<223> OTHER INFORMATION: May be 2'OH-adenosine
<220> FEATURE:
<221> NAME/KEY: misc_feature
<222> LOCATION: (16)..(16)
<223> OTHER INFORMATION: May be 2'-fluoro-2'-deoxyuridine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
```

```
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxyuridine
<220> FEATURE:
<221> NAME/KEY: misc_feature
<222> LOCATION: (21)..(21)
<223> OTHER INFORMATION: May be 2'-fluoro-2'-deoxycytidine
<220> FEATURE:
<221> NAME/KEY: misc_feature
<222> LOCATION: (22)..(22)
<223> OTHER INFORMATION: May be 2'OH-guanosine
<220> FEATURE:
<221> NAME/KEY: misc_feature
<222> LOCATION: (23)..(23)
<223> OTHER INFORMATION: May be 2'OH-adenosine
<220> FEATURE:
<221> NAME/KEY: misc_feature
<222> LOCATION: (24)..(24)
<223> OTHER INFORMATION: May be 2'OH-guanosine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'OH-guanosine
<220> FEATURE:
<221> NAME/KEY: misc_feature
<222> LOCATION: (27)..(27)
<223> OTHER INFORMATION: May be 2'-fluoro-2'-deoxyuridine
<220> FEATURE:
<221> NAME/KEY: misc_feature
<222> LOCATION: (28)..(28)
<223> OTHER INFORMATION: May be 2'OH-guanosine
<220> FEATURE:
<221> NAME/KEY: misc_feature
<222> LOCATION: (29)..(29)
<223> OTHER INFORMATION: May be 2'OH-adenosine
<220> FEATURE:
<221> NAME/KEY: misc_feature
<222> LOCATION: (30)..(30)
<223> OTHER INFORMATION: May be 2'OH-guanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'-fluoro-2'-deoxyuridine
<220> FEATURE:
<221> NAME/KEY: misc_feature
```

-continued

```
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'OH-guanosine
<220> FEATURE:
<221> NAME/KEY: misc_feature
<222> LOCATION: (41)..(41)
<223> OTHER INFORMATION: May be 2'-fluoro-2'-deoxyuridine
<220> FEATURE:
<221> NAME/KEY: misc_feature
<222> LOCATION: (42)..(42)
<223> OTHER INFORMATION: May be 2'-fluoro-2'-deoxycytidine

<400> SEQUENCE: 25
gacgaugcgg ucucaugcgu cgagugugag uuuaccuucg uc                        42

<210> SEQ ID NO 26
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
```

```
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'OH-adenosine
<220> FEATURE:
<221> NAME/KEY: misc_feature
<222> LOCATION: (32)..(32)
<223> OTHER INFORMATION: May be 2'-fluoro-2'-deoxycytidine
<220> FEATURE:
<221> NAME/KEY: misc_feature
<222> LOCATION: (33)..(33)
<223> OTHER INFORMATION: May be 2'-fluoro-2'-deoxycytidine
```

```
<220> FEATURE:
<221> NAME/KEY: misc_feature
<222> LOCATION: (34)..(34)
<223> OTHER INFORMATION: May be 2'-fluoro-2'-deoxyuridine
<220> FEATURE:
<221> NAME/KEY: misc_feature
<222> LOCATION: (35)..(35)
<223> OTHER INFORMATION: May be 2'-O-Methyl-2'-deoxyguanosine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-O-Methyl-2'-deoxyguanosine
<220> FEATURE:
<221> NAME/KEY: misc_feature
<222> LOCATION: (38)..(38)
<223> OTHER INFORMATION: May be an inverted orientation T (3'-3'-linked)

<400> SEQUENCE: 26
cgccgcgguc ucaggcgcug agucugaguu uaccugcgt                              39

<210> SEQ ID NO 27
<211> LENGTH: 44
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'OH-adenosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'OH-guanosine
<220> FEATURE:
<221> NAME/KEY: misc_feature
<222> LOCATION: (4)..(4)
<223> OTHER INFORMATION: May be 2'OH-adenosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'OH-guanosine
<220> FEATURE:
<221> NAME/KEY: misc_feature
<222> LOCATION: (7)..(7)
<223> OTHER INFORMATION: May be 2'OH-adenosine
<220> FEATURE:
<221> NAME/KEY: misc_feature
<222> LOCATION: (8)..(8)
<223> OTHER INFORMATION: May be 2'-fluoro-2'-deoxyuridine
<220> FEATURE:
<221> NAME/KEY: misc_feature
<222> LOCATION: (9)..(9)
<223> OTHER INFORMATION: May be 2'OH-guanosine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'OH-guanosine
<220> FEATURE:
<221> NAME/KEY: misc_feature
<222> LOCATION: (12)..(12)
```

```
<223> OTHER INFORMATION: May be 2'OH-guanosine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
<221> NAME/KEY: misc_feature
<222> LOCATION: (14)..(14)
<223> OTHER INFORMATION: May be 2'-fluoro-2'-deoxycytidine
<220> FEATURE:
<221> NAME/KEY: misc_feature
<222> LOCATION: (15)..(15)
<223> OTHER INFORMATION: May be 2'-fluoro-2'-deoxyuridine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-adenosine
<220> FEATURE:
<221> NAME/KEY: misc_feature
<222> LOCATION: (18)..(18)
<223> OTHER INFORMATION: May be 2'-fluoro-2'-deoxyuridine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'OH-guanosine
<220> FEATURE:
<221> NAME/KEY: misc_feature
<222> LOCATION: (22)..(22)
<223> OTHER INFORMATION: May be 2'-fluoro-2'-deoxyuridine
<220> FEATURE:
<221> NAME/KEY: misc_feature
<222> LOCATION: (23)..(23)
<223> OTHER INFORMATION: May be 2'-fluoro-2'-deoxycytidine
<220> FEATURE:
<221> NAME/KEY: misc_feature
<222> LOCATION: (24)..(24)
<223> OTHER INFORMATION: May be 2'OH-guanosine
<220> FEATURE:
<221> NAME/KEY: misc_feature
<222> LOCATION: (25)..(25)
<223> OTHER INFORMATION: May be 2'OH-adenosine
<220> FEATURE:
<221> NAME/KEY: misc_feature
<222> LOCATION: (26)..(26)
<223> OTHER INFORMATION: May be 2'OH-guanosine
<220> FEATURE:
<221> NAME/KEY: misc_feature
<222> LOCATION: (27)..(27)
<223> OTHER INFORMATION: May be 2'-fluoro-2'-deoxyuridine
<220> FEATURE:
<221> NAME/KEY: misc_feature
<222> LOCATION: (28)..(28)
<223> OTHER INFORMATION: May be 2'OH-guanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'OH-guanosine
<220> FEATURE:
<221> NAME/KEY: misc_feature
<222> LOCATION: (31)..(31)
<223> OTHER INFORMATION: May be 2'OH-adenosine
<220> FEATURE:
<221> NAME/KEY: misc_feature
```

-continued

```
<222> LOCATION: (32)..(32)
<223> OTHER INFORMATION: May be 2'OH-guanosine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'-fluoro-2'-deoxyuridine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'OH-adenosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-fluoro-2'-deoxycytidine
<220> FEATURE:
<221> NAME/KEY: misc_feature
<222> LOCATION: (39)..(39)
<223> OTHER INFORMATION: May be 2'-fluoro-2'-deoxyuridine
<220> FEATURE:
<221> NAME/KEY: misc_feature
<222> LOCATION: (40)..(40)
<223> OTHER INFORMATION: May be 2'-fluoro-2'-deoxyuridine
<220> FEATURE:
<221> NAME/KEY: misc_feature
<222> LOCATION: (41)..(41)
<223> OTHER INFORMATION: May be 2'-fluoro-2'-deoxycytidine
<220> FEATURE:
<221> NAME/KEY: misc_feature
<222> LOCATION: (42)..(42)
<223> OTHER INFORMATION: May be 2'OH-guanosine
<220> FEATURE:
<221> NAME/KEY: misc_feature
<222> LOCATION: (43)..(43)
<223> OTHER INFORMATION: May be 2'-fluoro-2'-deoxyuridine
<220> FEATURE:
<221> NAME/KEY: misc_feature
<222> LOCATION: (44)..(44)
<223> OTHER INFORMATION: May be 2'-fluoro-2'-deoxycytidine

<400> SEQUENCE: 27
aggacgaugc ggucucaugc gucgagugug aguuuaccuu cguc                    44

<210> SEQ ID NO 28
<211> LENGTH: 40
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'OH-adenosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
```

-continued

```
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
<221> NAME/KEY: misc_feature
<222> LOCATION: (14)..(14)
<223> OTHER INFORMATION: May be 2'-fluoro-2'-deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-fluoro-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
```

-continued

```
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-fluoro-2'-deoxycytidine
<220> FEATURE:
<221> NAME/KEY: misc_feature
<222> LOCATION: (27)..(27)
<223> OTHER INFORMATION: May be 2'-fluoro-2'-deoxyuridine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine

<400> SEQUENCE: 28
agcgccgcgg ucucaggcgc ugagucugag uuuaccugcg                            40

<210> SEQ ID NO 29
<211> LENGTH: 46
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
```

```
<223> OTHER INFORMATION: May be 2'OH-guanosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'OH-guanosine
<220> FEATURE:
<221> NAME/KEY: misc_feature
<222> LOCATION: (5)..(5)
<223> OTHER INFORMATION: May be 2'OH-adenosine
<220> FEATURE:
<221> NAME/KEY: misc_feature
<222> LOCATION: (6)..(6)
<223> OTHER INFORMATION: May be 2'-fluoro-2'-deoxyuridine
<220> FEATURE:
<221> NAME/KEY: misc_feature
<222> LOCATION: (7)..(7)
<223> OTHER INFORMATION: May be 2'-fluoro-2'-deoxyuridine
<220> FEATURE:
<221> NAME/KEY: misc_feature
<222> LOCATION: (8)..(8)
<223> OTHER INFORMATION: May be 2'OH-adenosine
<220> FEATURE:
<221> NAME/KEY: misc_feature
<222> LOCATION: (9)..(9)
<223> OTHER INFORMATION: May be 2'-fluoro-2'-deoxycytidine
<220> FEATURE:
<221> NAME/KEY: misc_feature
<222> LOCATION: (10)..(10)
<223> OTHER INFORMATION: May be 2'-fluoro-2'-deoxyuridine
<220> FEATURE:
<221> NAME/KEY: misc_feature
<222> LOCATION: (11)..(11)
<223> OTHER INFORMATION: May be 2'OH-guanosine
<220> FEATURE:
<221> NAME/KEY: misc_feature
<222> LOCATION: (12)..(12)
<223> OTHER INFORMATION: May be 2'OH-guanosine
<220> FEATURE:
<221> NAME/KEY: misc_feature
<222> LOCATION: (13)..(13)
<223> OTHER INFORMATION: May be 2'OH-guanosine
<220> FEATURE:
<221> NAME/KEY: misc_feature
<222> LOCATION: (14)..(14)
<223> OTHER INFORMATION: May be 2'OH-adenosine
<220> FEATURE:
<221> NAME/KEY: misc_feature
<222> LOCATION: (15)..(15)
<223> OTHER INFORMATION: May be 2'-fluoro-2'-deoxycytidine
<220> FEATURE:
<221> NAME/KEY: misc_feature
<222> LOCATION: (16)..(16)
<223> OTHER INFORMATION: May be 2'OH-guanosine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'OH-adenosine
<220> FEATURE:
<221> NAME/KEY: misc_feature
<222> LOCATION: (19)..(19)
<223> OTHER INFORMATION: May be 2'-fluoro-2'-deoxycytidine
<220> FEATURE:
<221> NAME/KEY: misc_feature
<222> LOCATION: (20)..(20)
<223> OTHER INFORMATION: May be 2'-fluoro-2'-deoxyuridine
<220> FEATURE:
<221> NAME/KEY: misc_feature
```

```
<222> LOCATION: (21)..(21)
<223> OTHER INFORMATION: May be 2'-fluoro-2'-deoxycytidine
<220> FEATURE:
<221> NAME/KEY: misc_feature
<222> LOCATION: (22)..(22)
<223> OTHER INFORMATION: May be 2'OH-guanosine
<220> FEATURE:
<221> NAME/KEY: misc_feature
<222> LOCATION: (23)..(23)
<223> OTHER INFORMATION: May be 2'-fluoro-2'-deoxycytidine
<220> FEATURE:
<221> NAME/KEY: misc_feature
<222> LOCATION: (24)..(24)
<223> OTHER INFORMATION: May be 2'OH-guanosine
<220> FEATURE:
<221> NAME/KEY: misc_feature
<222> LOCATION: (25)..(25)
<223> OTHER INFORMATION: May be 2'OH-adenosine
<220> FEATURE:
<221> NAME/KEY: misc_feature
<222> LOCATION: (26)..(26)
<223> OTHER INFORMATION: May be 2'-fluoro-2'-deoxyuridine
<220> FEATURE:
<221> NAME/KEY: misc_feature
<222> LOCATION: (27)..(27)
<223> OTHER INFORMATION: May be 2'OH-guanosine
<220> FEATURE:
<221> NAME/KEY: misc_feature
<222> LOCATION: (28)..(28)
<223> OTHER INFORMATION: May be 2'-fluoro-2'-deoxyuridine
<220> FEATURE:
<221> NAME/KEY: misc_feature
<222> LOCATION: (29)..(29)
<223> OTHER INFORMATION: May be 2'OH-guanosine
<220> FEATURE:
<221> NAME/KEY: misc_feature
<222> LOCATION: (30)..(30)
<223> OTHER INFORMATION: May be 2'OH-adenosine
<220> FEATURE:
<221> NAME/KEY: misc_feature
<222> LOCATION: (31)..(31)
<223> OTHER INFORMATION: May be 2'OH-guanosine
<220> FEATURE:
<221> NAME/KEY: misc_feature
<222> LOCATION: (32)..(32)
<223> OTHER INFORMATION: May be 2'-fluoro-2'-deoxycytidine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'OH-adenosine
<220> FEATURE:
<221> NAME/KEY: misc_feature
<222> LOCATION: (36)..(36)
<223> OTHER INFORMATION: May be 2'OH-guanosine
<220> FEATURE:
<221> NAME/KEY: misc_feature
<222> LOCATION: (37)..(37)
<223> OTHER INFORMATION: May be 2'OH-adenosine
<220> FEATURE:
<221> NAME/KEY: misc_feature
<222> LOCATION: (38)..(38)
<223> OTHER INFORMATION: May be 2'-fluoro-2'-deoxycytidine
<220> FEATURE:
<221> NAME/KEY: misc_feature
<222> LOCATION: (39)..(39)
<223> OTHER INFORMATION: May be 2'OH-guanosine
<220> FEATURE:
<221> NAME/KEY: misc_feature
<222> LOCATION: (40)..(40)
<223> OTHER INFORMATION: May be 2'OH-adenosine
<220> FEATURE:
```

<221> NAME/KEY: misc_feature
<222> LOCATION: (41)..(41)
<223> OTHER INFORMATION: May be 2'-fluoro-2'-deoxycytidine
<220> FEATURE:
<221> NAME/KEY: misc_feature
<222> LOCATION: (42)..(42)
<223> OTHER INFORMATION: May be 2'-fluoro-2'-deoxyuridine
<220> FEATURE:
<221> NAME/KEY: misc_feature
<222> LOCATION: (43)..(43)
<223> OTHER INFORMATION: May be 2'-fluoro-2'-deoxycytidine
<220> FEATURE:
<221> NAME/KEY: misc_feature
<222> LOCATION: (44)..(44)
<223> OTHER INFORMATION: May be 2'OH-guanosine
<220> FEATURE:
<221> NAME/KEY: misc_feature
<222> LOCATION: (45)..(45)
<223> OTHER INFORMATION: May be 2'-fluoro-2'-deoxycytidine
<220> FEATURE:
<221> NAME/KEY: misc_feature
<222> LOCATION: (46)..(46)
<223> OTHER INFORMATION: May be 2'-fluoro-2'-deoxycytidine

<400> SEQUENCE: 29
ggcgauuacu gggacggacu cgcgauguga gcccagacga cucgcc          46

<210> SEQ ID NO 30
<211> LENGTH: 40
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'OH-guanosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxyuridine
<220> FEATURE:
<221> NAME/KEY: misc_feature
<222> LOCATION: (5)..(5)
<223> OTHER INFORMATION: May be 2'-fluoro-2'-deoxyuridine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-fluoro-2'-deoxyuridine
<220> FEATURE:
<221> NAME/KEY: misc_feature
<222> LOCATION: (8)..(8)
<223> OTHER INFORMATION: May be 2'OH-guanosine
<220> FEATURE:
<221> NAME/KEY: misc_feature
<222> LOCATION: (9)..(9)
<223> OTHER INFORMATION: May be 2'OH-adenosine
<220> FEATURE:
<221> NAME/KEY: misc_feature
<222> LOCATION: (10)..(10)
<223> OTHER INFORMATION: May be 2'OH-adenosine
<220> FEATURE:
<221> NAME/KEY: misc_feature
<222> LOCATION: (11)..(11)
<223> OTHER INFORMATION: May be 2'OH-guanosine -continued

```
<220> FEATURE:
<221> NAME/KEY: misc_feature
<222> LOCATION: (12)..(12)
<223> OTHER INFORMATION: May be 2'OH-adenosine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
<221> NAME/KEY: misc_feature
<222> LOCATION: (14)..(14)
<223> OTHER INFORMATION: May be 2'-fluoro-2'-deoxyuridine
<220> FEATURE:
<221> NAME/KEY: misc_feature
<222> LOCATION: (15)..(15)
<223> OTHER INFORMATION: May be 2'OH-adenosine
<220> FEATURE:
<221> NAME/KEY: misc_feature
<222> LOCATION: (16)..(16)
<223> OTHER INFORMATION: May be 2'-fluoro-2'-deoxyuridine
<220> FEATURE:
<221> NAME/KEY: misc_feature
<222> LOCATION: (17)..(17)
<223> OTHER INFORMATION: May be 2'-fluoro-2'-deoxyuridine
<220> FEATURE:
<221> NAME/KEY: misc_feature
<222> LOCATION: (18)..(18)
<223> OTHER INFORMATION: May be 2'-fluoro-2'-deoxyuridine
<220> FEATURE:
<221> NAME/KEY: misc_feature
<222> LOCATION: (19)..(19)
<223> OTHER INFORMATION: May be 2'-fluoro-2'-deoxycytidine
<220> FEATURE:
<221> NAME/KEY: misc_feature
<222> LOCATION: (20)..(20)
<223> OTHER INFORMATION: May be 2'OH-guanosine
<220> FEATURE:
<221> NAME/KEY: misc_feature
<222> LOCATION: (21)..(21)
<223> OTHER INFORMATION: May be 2'-fluoro-2'-deoxycytidine
<220> FEATURE:
<221> NAME/KEY: misc_feature
<222> LOCATION: (22)..(22)
<223> OTHER INFORMATION: May be 2'OH-guanosine
<220> FEATURE:
<221> NAME/KEY: misc_feature
<222> LOCATION: (23)..(23)
<223> OTHER INFORMATION: May be 2'OH-adenosine
<220> FEATURE:
<221> NAME/KEY: misc_feature
<222> LOCATION: (24)..(24)
<223> OTHER INFORMATION: May be 2'-fluoro-2'-deoxyuridine
<220> FEATURE:
<221> NAME/KEY: misc_feature
<222> LOCATION: (25)..(25)
<223> OTHER INFORMATION: May be 2'OH-guanosine
<220> FEATURE:
<221> NAME/KEY: misc_feature
<222> LOCATION: (26)..(26)
<223> OTHER INFORMATION: May be 2'-fluoro-2'-deoxyuridine
<220> FEATURE:
<221> NAME/KEY: misc_feature
<222> LOCATION: (27)..(27)
<223> OTHER INFORMATION: May be 2'OH-guanosine
<220> FEATURE:
<221> NAME/KEY: misc_feature
<222> LOCATION: (28)..(28)
<223> OTHER INFORMATION: May be 2'OH-adenosine
<220> FEATURE:
<221> NAME/KEY: misc_feature
<222> LOCATION: (29)..(29)
<223> OTHER INFORMATION: May be 2'OH-adenosine
<220> FEATURE:
<221> NAME/KEY: misc_feature
<222> LOCATION: (30)..(30)
<223> OTHER INFORMATION: May be 2'-fluoro-2'-deoxycytidine
<220> FEATURE:
<221> NAME/KEY: misc_feature
<222> LOCATION: (31)..(31)
```

```
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxycytidine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'OH-guanosine
<220> FEATURE:
<221> NAME/KEY: misc_feature
<222> LOCATION: (36)..(36)
<223> OTHER INFORMATION: May be 2'OH-adenosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-fluoro-2'-deoxycytidine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-fluoro-2'-deoxycytidine

<400> SEQUENCE: 30
ggcuucugaa gauuauuucg cgaugugaac uccagacccc                    40

<210> SEQ ID NO 31
<211> LENGTH: 40
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'OH-guanosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'OH-guanosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
```

```
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'OH-guanosine
<220> FEATURE:
<221> NAME/KEY: misc_feature
<222> LOCATION: (10)..(10)
<223> OTHER INFORMATION: May be 2'OH-guanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
<221> NAME/KEY: misc_feature
<222> LOCATION: (14)..(14)
<223> OTHER INFORMATION: May be 2'-fluoro-2'-deoxycytidine
<220> FEATURE:
<221> NAME/KEY: misc_feature
<222> LOCATION: (15)..(15)
<223> OTHER INFORMATION: May be 2'OH-adenosine
<220> FEATURE:
<221> NAME/KEY: misc_feature
<222> LOCATION: (16)..(16)
<223> OTHER INFORMATION: May be 2'OH-guanosine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-fluoro-2'-deoxyuridine
<220> FEATURE:
<221> NAME/KEY: misc_feature
<222> LOCATION: (22)..(22)
<223> OTHER INFORMATION: May be 2'OH-guanosine
<220> FEATURE:
<221> NAME/KEY: misc_feature
<222> LOCATION: (23)..(23)
<223> OTHER INFORMATION: May be 2'OH-adenosine
<220> FEATURE:
<221> NAME/KEY: misc_feature
<222> LOCATION: (24)..(24)
<223> OTHER INFORMATION: May be 2'OH-guanosine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-fluoro-2'-deoxycytidine
<220> FEATURE:
<221> NAME/KEY: misc_feature
<222> LOCATION: (27)..(27)
<223> OTHER INFORMATION: May be 2'-fluoro-2'-deoxyuridine
<220> FEATURE:
```

```
<221> NAME/KEY: misc_feature
<222> LOCATION: (28)..(28)
<223> OTHER INFORMATION: May be 2'OH-guanosine
<220> FEATURE:
<221> NAME/KEY: misc_feature
<222> LOCATION: (29)..(29)
<223> OTHER INFORMATION: May be 2'OH-adenosine
<220> FEATURE:
<221> NAME/KEY: misc_feature
<222> LOCATION: (30)..(30)
<223> OTHER INFORMATION: May be 2'OH-guanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'OH-guanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'OH-guanosine

<400> SEQUENCE: 31
ggcgccgcgg ucucaggcgc ugagucugag uuuaccugcg                           40

<210> SEQ ID NO 32
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
```

-continued

```
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
```

```
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be deoxycytidine
<220> FEATURE:
<221> NAME/KEY: misc_feature
<222> LOCATION: (34)..(34)
<223> OTHER INFORMATION: May be deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 32
cgccgcgguc tcaggcgcug agtctgaguu uaccugcgt                              39

<210> SEQ ID NO 33
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxycytidine
<220> FEATURE:
<221> NAME/KEY: misc_feature
```

```
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
```

```
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be deoxycytidine
<220> FEATURE:
<221> NAME/KEY: misc_feature
<222> LOCATION: (34)..(34)
<223> OTHER INFORMATION: May be deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-O-Methyl-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 33
cgccgcgguc tcaggcgcug agtctgaguu uaccugcgt                          39

<210> SEQ ID NO 34
<211> LENGTH: 38
```

```
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
```

```
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'OH-cytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 34
```
cgccgcgguc tcaggcgcug agtctgaguu uaccugcg          38

<210> SEQ ID NO 35
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:

```
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be deoxycytidine
```

```
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 35
cgccgcgguc tcaggcgcug agtctgaguu uaccugcg                               38

<210> SEQ ID NO 36
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
```

```
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
```

<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 36
cgccgcgguc tcaggcgcug agtctgaguu uaccugcg                38

<210> SEQ ID NO 37
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:

```
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
```

-continued

```
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 37
cgccgcgguc tcaggcgcug agtctgaguu uaccugcg                              38

<210> SEQ ID NO 38
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
```

```
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
```

<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 38
cgccgcgguc tcaggcgcug agtctgaguu uaccugcg                                38

<210> SEQ ID NO 39
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:

```
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
```

-continued

```
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 39
cgccgcgguc tcaggcgcug agtctgaguu uaccugcg                               38

<210> SEQ ID NO 40
<211> LENGTH: 37
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
```

```
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
```

-continued

```
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxyuridine
<220> FEATURE:
<221> NAME/KEY: misc_feature
<222> LOCATION: (35)..(35)
<223> OTHER INFORMATION: May be 2'-O-Methyl-2'-deoxyguanosine
<220> FEATURE:
<221> NAME/KEY: misc_feature
<222> LOCATION: (36)..(36)
<223> OTHER INFORMATION: May be 2'-O-Methyl-2'-deoxycytidine
<220> FEATURE:
<221> NAME/KEY: misc_feature
<222> LOCATION: (37)..(37)
<223> OTHER INFORMATION: May be 2'-O-Methyl-2'-deoxyguanosine

<400> SEQUENCE: 40
cgccgcgguc tcaggcgcug agtctgaguu uacugcg                                    37

<210> SEQ ID NO 41
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
```

```
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
```

-continued

```
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 41
cgccgcgguc tcaggcgcug agtctgaguu uaccugcg                             38

<210> SEQ ID NO 42
<211> LENGTH: 37
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
```

```
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
```

```
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxyuridine
<220> FEATURE:
<221> NAME/KEY: misc_feature
<222> LOCATION: (35)..(35)
<223> OTHER INFORMATION: May be 2'-O-Methyl-2'-deoxyguanosine
<220> FEATURE:
<221> NAME/KEY: misc_feature
<222> LOCATION: (36)..(36)
<223> OTHER INFORMATION: May be 2'-O-Methyl-2'-deoxycytidine
<220> FEATURE:
<221> NAME/KEY: misc_feature
<222> LOCATION: (37)..(37)
<223> OTHER INFORMATION: May be 2'-O-Methyl-2'-deoxyguanosine

<400> SEQUENCE: 42
cgccgcgguc tcaggcgcug agtctgaguu uacugcg                              37

<210> SEQ ID NO 43
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
```

```
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
```

-continued

```
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'OH-cytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 43
cgccgcgguc tcaggcgcug agtctgaguu uaccugcg                              38

<210> SEQ ID NO 44
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
```

```
<223> OTHER INFORMATION: May be deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
```

<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 44
cgccgcgguc tcaggcgcug agtctgaguu uaccugcg                              38

<210> SEQ ID NO 45
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be deoxycytidine
<220> FEATURE:

```
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
```

<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 45
cgccgcgguc tcaggcgcug agtctgaguu uaccugcg                                38

<210> SEQ ID NO 46
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)

```
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
```

```
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 46
cgccgcgguc tcaggcgcug agtctgaguu uaccugcg                                  38

<210> SEQ ID NO 47
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
```

-continued

```
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-thymidine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
```

<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 47
cgccgcgguc tcaggcgctg agtctgaguu uaccugcg                                   38

<210> SEQ ID NO 48
<211> LENGTH: 38
<212> TYPE: DNA
<213> ORGANISM: Artificial Sequence
<220> FEATURE:

-continued

```
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-thymidine
<220> FEATURE:
<221> NAME/KEY: misc_feature
```

```
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 48
cgccgcgguc tcaggcgctg agtctgaguu uaccugcg                              38
```

```
<210> SEQ ID NO 49
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
```

```
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'OH-thymidine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
```

-continued

<223> OTHER INFORMATION: May be 2'-O-Methyl-2'-deoxyguanosine

<400> SEQUENCE: 49
cgccgcgguc tcaggcgcug agtctgagtu uaccugcg                    38

<210> SEQ ID NO 50
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature

```
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'OH-thymidine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
```

```
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 50
cgccgcgguc tcaggcgcug agtctgagut uaccugcg                                 38

<210> SEQ ID NO 51
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
```

-continued

```
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
```

```
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 51
cgccgcgguc tcaggcgcug agtctgaguu taccugcg                              38

<210> SEQ ID NO 52
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
```

```
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'OH-thymidine
<220> FEATURE:
<221> NAME/KEY: misc_feature
<222> LOCATION: (30)..(30)
<223> OTHER INFORMATION: May be 2'OH-thymidine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
```

```
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 52
cgccgcgguc tcaggcgcug agtctgagtt taccugcg                              38

<210> SEQ ID NO 53
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
```

-continued

```
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
```

```
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'OH-thymidine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 53
cgccgcgguc tcaggcgcug agtctgaguu uacctgcg                               38

<210> SEQ ID NO 54
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-O-Methyl-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
```

```
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
```

```
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be deoxycytidine
<220> FEATURE:
<221> NAME/KEY: misc_feature
<222> LOCATION: (34)..(34)
<223> OTHER INFORMATION: May be deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 54
cgccgcgguc tcaggcgcug agtctgaguu uaccugcg                                38

<210> SEQ ID NO 55
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
```

```
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
```

```
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 55
cgccgcgguc tcaggcgcug agtctgaguu uaccugcg                                 38

<210> SEQ ID NO 56
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-O-Methyl-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
```

```
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
```

```
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 56
cgccgcgguc tcaggcgcug agtctgaguu uaccugcg                                38

<210> SEQ ID NO 57
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-O-Methyl-2'-deoxycytidine
```

-continued

```
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
```

```
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 57
cgccgcgguc tcaggcgcug agtctgaguu uaccugcg                              38

<210> SEQ ID NO 58
<211> LENGTH: 37
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'OH-guanosine
<220> FEATURE:
<221> NAME/KEY: misc_feature
```

```
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-O-Methyl-2'-deoxyguanosine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-fluoro-2'-deoxyuridine
<220> FEATURE:
<221> NAME/KEY: misc_feature
<222> LOCATION: (9)..(9)
<223> OTHER INFORMATION: May be deoxycytidine
<220> FEATURE:
<221> NAME/KEY: misc_feature
<222> LOCATION: (10)..(10)
<223> OTHER INFORMATION: May be 2'-fluoro-2'-deoxyuridine
<220> FEATURE:
<221> NAME/KEY: misc_feature
<222> LOCATION: (11)..(11)
<223> OTHER INFORMATION: May be deoxycytidine
<220> FEATURE:
<221> NAME/KEY: misc_feature
<222> LOCATION: (12)..(12)
<223> OTHER INFORMATION: May be 2'-O-Methyl-2'-deoxyadenosine
<220> FEATURE:
<221> NAME/KEY: misc_feature
<222> LOCATION: (13)..(13)
<223> OTHER INFORMATION: May be 2'-O-Methyl-2'-deoxyguanosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be deoxycytidine
<220> FEATURE:
<221> NAME/KEY: misc_feature
<222> LOCATION: (16)..(16)
<223> OTHER INFORMATION: May be 2'OH-guanosine
<220> FEATURE:
<221> NAME/KEY: misc_feature
<222> LOCATION: (17)..(17)
<223> OTHER INFORMATION: May be 2'-O-Methyl-2'-deoxycytidine
<220> FEATURE:
<221> NAME/KEY: misc_feature
<222> LOCATION: (18)..(18)
<223> OTHER INFORMATION: May be 2'-fluoro-2'-deoxyuridine
<220> FEATURE:
<221> NAME/KEY: misc_feature
<222> LOCATION: (19)..(19)
<223> OTHER INFORMATION: May be 2'-O-Methyl-2'-deoxyguanosine
<220> FEATURE:
<221> NAME/KEY: misc_feature
<222> LOCATION: (20)..(20)
<223> OTHER INFORMATION: May be 2'-O-Methyl-2'-deoxyadenosine
<220> FEATURE:
<221> NAME/KEY: misc_feature
<222> LOCATION: (21)..(21)
<223> OTHER INFORMATION: May be 2'-O-Methyl-2'-deoxyguanosine
<220> FEATURE:
<221> NAME/KEY: misc_feature
<222> LOCATION: (22)..(22)
<223> OTHER INFORMATION: May be 2'-fluoro-2'-deoxyuridine
<220> FEATURE:
<221> NAME/KEY: misc_feature
<222> LOCATION: (23)..(23)
<223> OTHER INFORMATION: May be deoxycytidine
<220> FEATURE:
<221> NAME/KEY: misc_feature
<222> LOCATION: (24)..(24)
<223> OTHER INFORMATION: May be 2'-fluoro-2'-deoxyuridine
<220> FEATURE:
```

```
<221> NAME/KEY: misc_feature
<222> LOCATION: (25)..(25)
<223> OTHER INFORMATION: May be 2'-O-Methyl-2'-deoxyguanosine
<220> FEATURE:
<221> NAME/KEY: misc_feature
<222> LOCATION: (26)..(26)
<223> OTHER INFORMATION: May be 2'-O-Methyl-2'-deoxyadenosine
<220> FEATURE:
<221> NAME/KEY: misc_feature
<222> LOCATION: (27)..(27)
<223> OTHER INFORMATION: May be 2'-O-Methyl-2'-deoxyguanosine
<220> FEATURE:
<221> NAME/KEY: misc_feature
<222> LOCATION: (28)..(28)
<223> OTHER INFORMATION: May be 2'-fluoro-2'-deoxyuridine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'OH-adenosine
<220> FEATURE:
<221> NAME/KEY: misc_feature
<222> LOCATION: (32)..(32)
<223> OTHER INFORMATION: May be 2'-fluoro-2'-deoxycytidine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxyuridine
<220> FEATURE:
<221> NAME/KEY: misc_feature
<222> LOCATION: (35)..(35)
<223> OTHER INFORMATION: May be 2'-O-Methyl-2'-deoxyguanosine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-O-Methyl-2'-deoxyguanosine

<400> SEQUENCE: 58
cgcgcggucu caggcgcuga gucugaguuu accugcg                           37

<210> SEQ ID NO 59
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
```

```
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-O-Methyl-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
```

```
<223> OTHER INFORMATION: May be deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 59
cgccgcgguc ucaggcgcug agucugaguu uaccugcg                                 38

<210> SEQ ID NO 60
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
```

```
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-O-Methyl-2'-deoxycytidine
<220> FEATURE:
<221> NAME/KEY: misc_feature
<222> LOCATION: (19)..(19)
<223> OTHER INFORMATION: May be 2'-O-Methyl-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
```

```
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 60
cgccgcgguc ucaggcgcug agucugaguu uaccugcg                            38

<210> SEQ ID NO 61
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
```

```
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
```

<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 61
cgccgcgguc tcaggcgcug agtctgaguu uaccugcg                               38

<210> SEQ ID NO 62
<211> LENGTH: 38
<212> TYPE: DNA
<213> ORGANISM: Artificial Sequence -continued

```
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
```

```
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-O-Methyl-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 62
cgccgcgguc tcaggcgcug agtctgaguu uaccugcg                               38
```

```
<210> SEQ ID NO 63
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
```

```
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-O-Methyl-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
```

<222> LOCATION: (38)..(38)
<223> OTHER INFORMATION: May be 2'-O-Methyl-2'-deoxyguanosine

<400> SEQUENCE: 63
cgccgcgguc tcaggcgcug agtctgaguu uaccugcg          38

<210> SEQ ID NO 64
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:

```
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyuridine
<220> FEATURE:
<221> NAME/KEY: misc_feature
<222> LOCATION: (30)..(30)
<223> OTHER INFORMATION: May be 2'-O-Methyl-2'-deoxyuridine
<220> FEATURE:
<221> NAME/KEY: misc_feature
<222> LOCATION: (31)..(31)
<223> OTHER INFORMATION: May be 2'-O-Methyl-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
```

<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 64
cgccgcgguc tcaggcgcug agtctgaguu uaccugcg        38

<210> SEQ ID NO 65
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)

```
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
```

-continued

```
<222> LOCATION: (35)..(35)
<223> OTHER INFORMATION: May be 2'-O-Methyl-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 65
cgccgcgguc tcaggcgcug agtctgaguu uaccugcg                    38

<210> SEQ ID NO 66
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be deoxyguanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
```

```
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
```

```
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 66
cgccgcgguc tcaggcgcug agtctgaguu uaccugcg                              38

<210> SEQ ID NO 67
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
```

```
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be deoxyguanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
```

```
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'OH-cytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 67
cgccgcgguc tcaggcgcug agtctgaguu uaccugcg                               38

<210> SEQ ID NO 68
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
```

```
-continued

<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
```

```
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be deoxyadenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine

<400> SEQUENCE: 68
cgccgcgguc tcaggcgcug agtctgaguu uaccugcg                                38

<210> SEQ ID NO 69
<211> LENGTH: 40
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-fluoro-2'-deoxycytidine
<220> FEATURE:
<221> NAME/KEY: misc_feature
<222> LOCATION: (3)..(3)
<223> OTHER INFORMATION: May be 2'-O-Methyl-2'-deoxyguanosine
<220> FEATURE:
<221> NAME/KEY: misc_feature
<222> LOCATION: (4)..(4)
<223> OTHER INFORMATION: May be 2'-fluoro-2'-deoxyuridine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'OH-guanosine
<220> FEATURE:
<221> NAME/KEY: misc_feature
<222> LOCATION: (7)..(7)
<223> OTHER INFORMATION: May be 2'-fluoro-2'-deoxycytidine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
```

```
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-fluoro-2'-deoxyuridine
<220> FEATURE:
<221> NAME/KEY: misc_feature
<222> LOCATION: (11)..(11)
<223> OTHER INFORMATION: May be deoxycytidine
<220> FEATURE:
<221> NAME/KEY: misc_feature
<222> LOCATION: (12)..(12)
<223> OTHER INFORMATION: May be 2'OH-thymidine
<220> FEATURE:
<221> NAME/KEY: misc_feature
<222> LOCATION: (13)..(13)
<223> OTHER INFORMATION: May be deoxycytidine
<220> FEATURE:
<221> NAME/KEY: misc_feature
<222> LOCATION: (14)..(14)
<223> OTHER INFORMATION: May be 2'-O-Methyl-2'-deoxyadenosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be deoxycytidine
<220> FEATURE:
<221> NAME/KEY: misc_feature
<222> LOCATION: (18)..(18)
<223> OTHER INFORMATION: May be 2'OH-guanosine
<220> FEATURE:
<221> NAME/KEY: misc_feature
<222> LOCATION: (19)..(19)
<223> OTHER INFORMATION: May be 2'-fluoro-2'-deoxycytidine
<220> FEATURE:
<221> NAME/KEY: misc_feature
<222> LOCATION: (20)..(20)
<223> OTHER INFORMATION: May be 2'-fluoro-2'-deoxyuridine
<220> FEATURE:
<221> NAME/KEY: misc_feature
<222> LOCATION: (21)..(21)
<223> OTHER INFORMATION: May be 2'-O-Methyl-2'-deoxyguanosine
<220> FEATURE:
<221> NAME/KEY: misc_feature
<222> LOCATION: (22)..(22)
<223> OTHER INFORMATION: May be 2'-O-Methyl-2'-deoxyadenosine
<220> FEATURE:
<221> NAME/KEY: misc_feature
<222> LOCATION: (23)..(23)
<223> OTHER INFORMATION: May be 2'-O-Methyl-2'-deoxyguanosine
<220> FEATURE:
<221> NAME/KEY: misc_feature
<222> LOCATION: (24)..(24)
<223> OTHER INFORMATION: May be 2'OH-thymidine
<220> FEATURE:
<221> NAME/KEY: misc_feature
<222> LOCATION: (25)..(25)
<223> OTHER INFORMATION: May be deoxycytidine
<220> FEATURE:
<221> NAME/KEY: misc_feature
<222> LOCATION: (26)..(26)
<223> OTHER INFORMATION: May be 2'OH-thymidine
<220> FEATURE:
<221> NAME/KEY: misc_feature
<222> LOCATION: (27)..(27)
<223> OTHER INFORMATION: May be 2'-O-Methyl-2'-deoxyguanosine
<220> FEATURE:
<221> NAME/KEY: misc_feature
<222> LOCATION: (28)..(28)
<223> OTHER INFORMATION: May be 2'-O-Methyl-2'-deoxyadenosine
<220> FEATURE:
<221> NAME/KEY: misc_feature
```

<222> LOCATION: (29)..(29)
<223> OTHER INFORMATION: May be 2'-O-Methyl-2'-deoxyguanosine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'OH-adenosine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxyuridine
<220> FEATURE:
<221> NAME/KEY: misc_feature
<222> LOCATION: (37)..(37)
<223> OTHER INFORMATION: May be 2'-O-Methyl-2'-deoxyadenosine
<220> FEATURE:
<221> NAME/KEY: misc_feature
<222> LOCATION: (38)..(38)
<223> OTHER INFORMATION: May be 2'-fluoro-2'-deoxycytidine
<220> FEATURE:
<221> NAME/KEY: misc_feature
<222> LOCATION: (39)..(39)
<223> OTHER INFORMATION: May be 2'-O-Methyl-2'-deoxyguanosine
<220> FEATURE:
<221> NAME/KEY: misc_feature
<222> LOCATION: (40)..(40)
<223> OTHER INFORMATION: May be 2'-O-Methyl-2'-deoxycytidine

<400> SEQUENCE: 69
gcgucgcggu ctcaggcgcu gagtctgagu uuaccuacgc                    40

<210> SEQ ID NO 70
<211> LENGTH: 38
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxyguanosine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:

```
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be deoxycytidine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'OH-thymidine
<220> FEATURE:
<221> NAME/KEY: misc_feature
<222> LOCATION: (24)..(24)
<223> OTHER INFORMATION: May be deoxycytidine
<220> FEATURE:
<221> NAME/KEY: misc_feature
<222> LOCATION: (25)..(25)
<223> OTHER INFORMATION: May be 2'OH-thymidine
```

<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxycytidine
<220> FEATURE:
<221> NAME/KEY: misc_feature
<222> LOCATION: (37)..(37)
<223> OTHER INFORMATION: May be 2'-O-Methyl-2'-deoxycytidine
<220> FEATURE:
<221> NAME/KEY: misc_feature
<222> LOCATION: (38)..(38)
<223> OTHER INFORMATION: May be 2'-O-Methyl-2'-deoxycytidine

<400> SEQUENCE: 70
gggcgcgguc tcaggcgcug agtctgaguu uaccuccc                    38

<210> SEQ ID NO 71
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-fluoro-2'-deoxycytidine
<220> FEATURE:
<221> NAME/KEY: misc_feature
<222> LOCATION: (3)..(3)
<223> OTHER INFORMATION: May be 2'-O-Methyl-2'-deoxyguanosine
<220> FEATURE:
<221> NAME/KEY: misc_feature
<222> LOCATION: (4)..(4)

```
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'OH-guanosine
<220> FEATURE:
<221> NAME/KEY: misc_feature
<222> LOCATION: (7)..(7)
<223> OTHER INFORMATION: May be 2'-fluoro-2'-deoxycytidine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-fluoro-2'-deoxyuridine
<220> FEATURE:
<221> NAME/KEY: misc_feature
<222> LOCATION: (11)..(11)
<223> OTHER INFORMATION: May be deoxycytidine
<220> FEATURE:
<221> NAME/KEY: misc_feature
<222> LOCATION: (12)..(12)
<223> OTHER INFORMATION: May be 2'OH-thymidine
<220> FEATURE:
<221> NAME/KEY: misc_feature
<222> LOCATION: (13)..(13)
<223> OTHER INFORMATION: May be deoxycytidine
<220> FEATURE:
<221> NAME/KEY: misc_feature
<222> LOCATION: (14)..(14)
<223> OTHER INFORMATION: May be 2'-O-Methyl-2'-deoxyadenosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be deoxycytidine
<220> FEATURE:
<221> NAME/KEY: misc_feature
<222> LOCATION: (18)..(18)
<223> OTHER INFORMATION: May be 2'OH-guanosine
<220> FEATURE:
<221> NAME/KEY: misc_feature
<222> LOCATION: (19)..(19)
<223> OTHER INFORMATION: May be 2'-fluoro-2'-deoxycytidine
<220> FEATURE:
<221> NAME/KEY: misc_feature
<222> LOCATION: (20)..(20)
<223> OTHER INFORMATION: May be 2'-fluoro-2'-deoxyuridine
<220> FEATURE:
<221> NAME/KEY: misc_feature
<222> LOCATION: (21)..(21)
<223> OTHER INFORMATION: May be 2'-O-Methyl-2'-deoxyguanosine
<220> FEATURE:
<221> NAME/KEY: misc_feature
<222> LOCATION: (22)..(22)
<223> OTHER INFORMATION: May be 2'-O-Methyl-2'-deoxyadenosine
<220> FEATURE:
<221> NAME/KEY: misc_feature
<222> LOCATION: (23)..(23)
<223> OTHER INFORMATION: May be 2'-O-Methyl-2'-deoxyguanosine
<220> FEATURE:
<221> NAME/KEY: misc_feature
```

<222> LOCATION: (24)..(24)
<223> OTHER INFORMATION: May be 2'OH-thymidine
<220> FEATURE:
<221> NAME/KEY: misc_feature
<222> LOCATION: (25)..(25)
<223> OTHER INFORMATION: May be deoxycytidine
<220> FEATURE:
<221> NAME/KEY: misc_feature
<222> LOCATION: (26)..(26)
<223> OTHER INFORMATION: May be 2'OH-thymidine
<220> FEATURE:
<221> NAME/KEY: misc_feature
<222> LOCATION: (27)..(27)
<223> OTHER INFORMATION: May be 2'-O-Methyl-2'-deoxyguanosine
<220> FEATURE:
<221> NAME/KEY: misc_feature
<222> LOCATION: (28)..(28)
<223> OTHER INFORMATION: May be 2'-O-Methyl-2'-deoxyadenosine
<220> FEATURE:
<221> NAME/KEY: misc_feature
<222> LOCATION: (29)..(29)
<223> OTHER INFORMATION: May be 2'-O-Methyl-2'-deoxyguanosine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'OH-adenosine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-O-Methyl-2'-deoxycytidine

<400> SEQUENCE: 71
gcgccgcggu ctcaggcgcu gagtctgagu uuacugcgc                                39

<210> SEQ ID NO 72
<211> LENGTH: 43
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:

```
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxyadenosine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'-O-Methyl-2'-deoxyguanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-fluoro-2'-deoxycytidine
<220> FEATURE:
<221> NAME/KEY: misc_feature
<222> LOCATION: (8)..(8)
<223> OTHER INFORMATION: May be 2'OH-guanosine
<220> FEATURE:
<221> NAME/KEY: misc_feature
<222> LOCATION: (9)..(9)
<223> OTHER INFORMATION: May be 2'-fluoro-2'-deoxycytidine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-O-Methyl-2'-deoxyguanosine
<220> FEATURE:
<221> NAME/KEY: misc_feature
<222> LOCATION: (12)..(12)
<223> OTHER INFORMATION: May be 2'-fluoro-2'-deoxyuridine
<220> FEATURE:
<221> NAME/KEY: misc_feature
<222> LOCATION: (13)..(13)
<223> OTHER INFORMATION: May be 2'-fluoro-2'-deoxycytidine
<220> FEATURE:
<221> NAME/KEY: misc_feature
<222> LOCATION: (14)..(14)
<223> OTHER INFORMATION: May be 2'-fluoro-2'-deoxyuridine
<220> FEATURE:
<221> NAME/KEY: misc_feature
<222> LOCATION: (15)..(15)
<223> OTHER INFORMATION: May be 2'-fluoro-2'-deoxycytidine
<220> FEATURE:
<221> NAME/KEY: misc_feature
<222> LOCATION: (16)..(16)
<223> OTHER INFORMATION: May be 2'-O-Methyl-2'-deoxyadenosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be 2'-O-Methyl-2'-deoxyguanosine
<220> FEATURE:
<221> NAME/KEY: misc_feature
<222> LOCATION: (19)..(19)
<223> OTHER INFORMATION: May be 2'-fluoro-2'-deoxycytidine
<220> FEATURE:
<221> NAME/KEY: misc_feature
<222> LOCATION: (20)..(20)
<223> OTHER INFORMATION: May be 2'OH-guanosine
<220> FEATURE:
<221> NAME/KEY: misc_feature
<222> LOCATION: (21)..(21)
<223> OTHER INFORMATION: May be 2'-fluoro-2'-deoxycytidine
```

-continued

```
<220> FEATURE:
<221> NAME/KEY: misc_feature
<222> LOCATION: (22)..(22)
<223> OTHER INFORMATION: May be 2'-fluoro-2'-deoxyuridine
<220> FEATURE:
<221> NAME/KEY: misc_feature
<222> LOCATION: (23)..(23)
<223> OTHER INFORMATION: May be 2'-O-Methyl-2'-deoxyguanosine
<220> FEATURE:
<221> NAME/KEY: misc_feature
<222> LOCATION: (24)..(24)
<223> OTHER INFORMATION: May be 2'-O-Methyl-2'-deoxyadenosine
<220> FEATURE:
<221> NAME/KEY: misc_feature
<222> LOCATION: (25)..(25)
<223> OTHER INFORMATION: May be 2'-O-Methyl-2'-deoxyguanosine
<220> FEATURE:
<221> NAME/KEY: misc_feature
<222> LOCATION: (26)..(26)
<223> OTHER INFORMATION: May be 2'-fluoro-2'-deoxyuridine
<220> FEATURE:
<221> NAME/KEY: misc_feature
<222> LOCATION: (27)..(27)
<223> OTHER INFORMATION: May be 2'-fluoro-2'-deoxycytidine
<220> FEATURE:
<221> NAME/KEY: misc_feature
<222> LOCATION: (28)..(28)
<223> OTHER INFORMATION: May be 2'-fluoro-2'-deoxyuridine
<220> FEATURE:
<221> NAME/KEY: misc_feature
<222> LOCATION: (29)..(29)
<223> OTHER INFORMATION: May be 2'-O-Methyl-2'-deoxyguanosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxyuridine
<220> FEATURE:
<221> NAME/KEY: misc_feature
<222> LOCATION: (37)..(37)
<223> OTHER INFORMATION: May be 2'-O-Methyl-2'-deoxyguanosine
<220> FEATURE:
<221> NAME/KEY: misc_feature
<222> LOCATION: (38)..(38)
<223> OTHER INFORMATION: May be 2'-fluoro-2'-deoxycytidine
<220> FEATURE:
<221> NAME/KEY: misc_feature
<222> LOCATION: (39)..(39)
<223> OTHER INFORMATION: May be 2'-O-Methyl-2'-deoxyguanosine
<220> FEATURE:
<221> NAME/KEY: misc_feature
<222> LOCATION: (40)..(40)
<223> OTHER INFORMATION: May be 2'-fluoro-2'-deoxyuridine
<220> FEATURE:
<221> NAME/KEY: misc_feature
<222> LOCATION: (41)..(41)
```

<223> OTHER INFORMATION: May be 2'-fluoro-2'-deoxycytidine
<220> FEATURE:
<221> NAME/KEY: misc_feature
<222> LOCATION: (42)..(42)
<223> OTHER INFORMATION: May be 2'-fluoro-2'-deoxyuridine
<220> FEATURE:
<221> NAME/KEY: misc_feature
<222> LOCATION: (43)..(43)
<223> OTHER INFORMATION: May be an inverted orientation T (3'-3'-linked)

<400> SEQUENCE: 72
ggacgccgcg gucucaggcg cugagucugg uuuacugcgu cut        43

<210> SEQ ID NO 73
<211> LENGTH: 42
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'OH-thymidine
<220> FEATURE:
<221> NAME/KEY: misc_feature
<222> LOCATION: (14)..(14)
<223> OTHER INFORMATION: May be deoxycytidine
<220> FEATURE:
<221> NAME/KEY: misc_feature

```
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-O-Methyl-2'-deoxycytidine
<220> FEATURE:
<221> NAME/KEY: misc_feature
<222> LOCATION: (21)..(21)
<223> OTHER INFORMATION: May be 2'-O-Methyl-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be deoxycytidine
<220> FEATURE:
<221> NAME/KEY: misc_feature
<222> LOCATION: (27)..(27)
<223> OTHER INFORMATION: May be 2'OH-thymidine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
```

```
<221> NAME/KEY: misc_feature
<222> LOCATION: (35)..(35)
<223> OTHER INFORMATION: May be deoxycytidine
<220> FEATURE:
<221> NAME/KEY: misc_feature
<222> LOCATION: (36)..(36)
<223> OTHER INFORMATION: May be deoxycytidine
<220> FEATURE:
<221> NAME/KEY: misc_feature
<222> LOCATION: (37)..(37)
<223> OTHER INFORMATION: May be 2'OH-thymidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine
<220> FEATURE:
<221> NAME/KEY: misc_feature
<222> LOCATION: (41)..(41)
<223> OTHER INFORMATION: May be 2'-O-Methyl-2'-deoxycytidine
<220> FEATURE:
<221> NAME/KEY: misc_feature
<222> LOCATION: (42)..(42)
<223> OTHER INFORMATION: May be 2'-O-Methyl-2'-deoxycytidine

<400> SEQUENCE: 73
ggcgccgcgg uctcaggcgc ugagtctgag tuuacctgcg cc                           42

<210> SEQ ID NO 74
<211> LENGTH: 40
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
```

-continued

```
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'OH-thymidine
<220> FEATURE:
<221> NAME/KEY: misc_feature
<222> LOCATION: (14)..(14)
<223> OTHER INFORMATION: May be deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-O-Methyl-2'-deoxycytidine
<220> FEATURE:
<221> NAME/KEY: misc_feature
<222> LOCATION: (21)..(21)
<223> OTHER INFORMATION: May be 2'-O-Methyl-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be deoxycytidine
<220> FEATURE:
<221> NAME/KEY: misc_feature
<222> LOCATION: (27)..(27)
<223> OTHER INFORMATION: May be 2'OH-thymidine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
```

```
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxythymidine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be deoxycytidine
<220> FEATURE:
<221> NAME/KEY: misc_feature
<222> LOCATION: (34)..(34)
<223> OTHER INFORMATION: May be deoxycytidine
<220> FEATURE:
<221> NAME/KEY: misc_feature
<222> LOCATION: (35)..(35)
<223> OTHER INFORMATION: May be 2'OH-thymidine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-O-Methyl-2'-deoxycytidine
<220> FEATURE:
<221> NAME/KEY: misc_feature
<222> LOCATION: (40)..(40)
<223> OTHER INFORMATION: May be 2'-O-Methyl-2'-deoxycytidine

<400> SEQUENCE: 74
ggcgccgcgg uctcaggcgc ugagtctgat tacctgcgcc                          40

<210> SEQ ID NO 75
<211> LENGTH: 42
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be deoxycytidine
<220> FEATURE:
<221> NAME/KEY: misc_feature
```

```
<222> LOCATION: (6)..(6)
<223> OTHER INFORMATION: May be deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'OH-thymidine
<220> FEATURE:
<221> NAME/KEY: misc_feature
<222> LOCATION: (14)..(14)
<223> OTHER INFORMATION: May be deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-O-Methyl-2'-deoxycytidine
<220> FEATURE:
<221> NAME/KEY: misc_feature
<222> LOCATION: (21)..(21)
<223> OTHER INFORMATION: May be 2'-O-Methyl-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'OH-thymidine
<220> FEATURE:
```

<221> NAME/KEY: misc_feature
<222> LOCATION: (26)..(26)
<223> OTHER INFORMATION: May be deoxycytidine
<220> FEATURE:
<221> NAME/KEY: misc_feature
<222> LOCATION: (27)..(27)
<223> OTHER INFORMATION: May be 2'OH-thymidine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'OH-thymidine
<220> FEATURE:
<221> NAME/KEY: misc_feature
<222> LOCATION: (33)..(33)
<223> OTHER INFORMATION: May be 2'OH-thymidine
<220> FEATURE:
<221> NAME/KEY: misc_feature
<222> LOCATION: (34)..(34)
<223> OTHER INFORMATION: May be 2'-O-Methyl-2'-deoxyadenosine
<220> FEATURE:
<221> NAME/KEY: misc_feature
<222> LOCATION: (35)..(35)
<223> OTHER INFORMATION: May be deoxycytidine
<220> FEATURE:
<221> NAME/KEY: misc_feature
<222> LOCATION: (36)..(36)
<223> OTHER INFORMATION: May be deoxycytidine
<220> FEATURE:
<221> NAME/KEY: misc_feature
<222> LOCATION: (37)..(37)
<223> OTHER INFORMATION: May be 2'OH-thymidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine
<220> FEATURE:
<221> NAME/KEY: misc_feature
<222> LOCATION: (41)..(41)
<223> OTHER INFORMATION: May be 2'-O-Methyl-2'-deoxycytidine
<220> FEATURE:
<221> NAME/KEY: misc_feature
<222> LOCATION: (42)..(42)
<223> OTHER INFORMATION: May be 2'-O-Methyl-2'-deoxycytidine

<400> SEQUENCE: 75
ggcgccgcgg tctcaggcgc ugagtctgag tttacctgcg cc        42

<210> SEQ ID NO 76
<211> LENGTH: 42
<212> TYPE: DNA
<213> ORGANISM: Artificial Sequence
<220> FEATURE:
<223> OTHER INFORMATION: Synthetic C5 specific aptamer -continued

```
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-O-Methyl-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be deoxycytidine
<220> FEATURE:
<221> NAME/KEY: misc_feature
<222> LOCATION: (6)..(6)
<223> OTHER INFORMATION: May be deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'OH-thymidine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'-O-Methyl-2'-deoxyuridine
<220> FEATURE:
<221> NAME/KEY: misc_feature
<222> LOCATION: (14)..(14)
<223> OTHER INFORMATION: May be 2'-O-Methyl-2'-deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
```

```
<223> OTHER INFORMATION: May be 2'-O-Methyl-2'-deoxycytidine
<220> FEATURE:
<221> NAME/KEY: misc_feature
<222> LOCATION: (21)..(21)
<223> OTHER INFORMATION: May be 2'-O-Methyl-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'-O-Methyl-2'-deoxyuridine
<220> FEATURE:
<221> NAME/KEY: misc_feature
<222> LOCATION: (26)..(26)
<223> OTHER INFORMATION: May be 2'-O-Methyl-2'-deoxycytidine
<220> FEATURE:
<221> NAME/KEY: misc_feature
<222> LOCATION: (27)..(27)
<223> OTHER INFORMATION: May be 2'-O-Methyl-2'-deoxyuridine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'OH-thymidine
<220> FEATURE:
<221> NAME/KEY: misc_feature
<222> LOCATION: (32)..(32)
<223> OTHER INFORMATION: May be 2'OH-thymidine
<220> FEATURE:
<221> NAME/KEY: misc_feature
<222> LOCATION: (33)..(33)
<223> OTHER INFORMATION: May be 2'OH-thymidine
<220> FEATURE:
<221> NAME/KEY: misc_feature
<222> LOCATION: (34)..(34)
<223> OTHER INFORMATION: May be 2'-O-Methyl-2'-deoxyadenosine
<220> FEATURE:
<221> NAME/KEY: misc_feature
<222> LOCATION: (35)..(35)
<223> OTHER INFORMATION: May be deoxycytidine
<220> FEATURE:
<221> NAME/KEY: misc_feature
<222> LOCATION: (36)..(36)
<223> OTHER INFORMATION: May be deoxycytidine
<220> FEATURE:
<221> NAME/KEY: misc_feature
<222> LOCATION: (37)..(37)
<223> OTHER INFORMATION: May be 2'OH-thymidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be deoxycytidine
<220> FEATURE:
<221> NAME/KEY: misc_feature
```

```
<222> LOCATION: (40)..(40)
<223> OTHER INFORMATION: May be 2'-O-Methyl-2'-deoxyguanosine
<220> FEATURE:
<221> NAME/KEY: misc_feature
<222> LOCATION: (41)..(41)
<223> OTHER INFORMATION: May be 2'-O-Methyl-2'-deoxycytidine
<220> FEATURE:
<221> NAME/KEY: misc_feature
<222> LOCATION: (42)..(42)
<223> OTHER INFORMATION: May be 2'-O-Methyl-2'-deoxycytidine

<400> SEQUENCE: 76
ggcgccgcgg tcucaggcgc ugagucugag tttacctgcg cc                        42

<210> SEQ ID NO 77
<211> LENGTH: 40
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have biotin conjugated to the 5' end
<220> FEATURE:
<221> NAME/KEY: misc_feature
<222> LOCATION: (1)..(1)
<223> OTHER INFORMATION: May be 2'OH-adenosine
<220> FEATURE:
<221> NAME/KEY: misc_feature
<222> LOCATION: (2)..(2)
<223> OTHER INFORMATION: May be 2'OH-guanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-fluoro-2'-deoxyuridine
<220> FEATURE:
```

```
<221> NAME/KEY: misc_feature
<222> LOCATION: (14)..(14)
<223> OTHER INFORMATION: May be 2'-fluoro-2'-deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-fluoro-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-fluoro-2'-deoxycytidine
<220> FEATURE:
<221> NAME/KEY: misc_feature
<222> LOCATION: (27)..(27)
<223> OTHER INFORMATION: May be 2'-fluoro-2'-deoxyuridine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
```

```
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine

<400> SEQUENCE: 77
agcgccgcgg ucucaggcgc ugagucugag uuuaccugcg                    40

<210> SEQ ID NO 78
<211> LENGTH: 42
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
```

```
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be deoxycytidine
<220> FEATURE:
<221> NAME/KEY: misc_feature
<222> LOCATION: (13)..(13)
<223> OTHER INFORMATION: May be 2'OH-thymidine
<220> FEATURE:
<221> NAME/KEY: misc_feature
<222> LOCATION: (14)..(14)
<223> OTHER INFORMATION: May be deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-fluoro-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
<220> FEATURE:
<221> NAME/KEY: misc_feature
<222> LOCATION: (25)..(25)
<223> OTHER INFORMATION: May be 2'OH-thymidine
<220> FEATURE:
<221> NAME/KEY: misc_feature
<222> LOCATION: (26)..(26)
<223> OTHER INFORMATION: May be deoxycytidine
<220> FEATURE:
<221> NAME/KEY: misc_feature
<222> LOCATION: (27)..(27)
<223> OTHER INFORMATION: May be 2'OH-thymidine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
```

```
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine
<220> FEATURE:
<221> NAME/KEY: misc_feature
<222> LOCATION: (41)..(41)
<223> OTHER INFORMATION: May be 2'-O-Methyl-2'-deoxycytidine
<220> FEATURE:
<221> NAME/KEY: misc_feature
<222> LOCATION: (42)..(42)
<223> OTHER INFORMATION: May be 2'-O-Methyl-2'-deoxycytidine

<400> SEQUENCE: 78
ggcgccgcgg uctcaggcgc ugagtctgag uuuaccugcg cc                42

<210> SEQ ID NO 79
<211> LENGTH: 42
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-O-Methyl-2'-deoxyguanosine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-O-Methyl-2'-deoxyguanosine
<220> FEATURE:
```

```
<221> NAME/KEY: misc_feature
<222> LOCATION: (5)..(5)
<223> OTHER INFORMATION: May be 2'-fluoro-2'-deoxycytidine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'OH-guanosine
<220> FEATURE:
<221> NAME/KEY: misc_feature
<222> LOCATION: (8)..(8)
<223> OTHER INFORMATION: May be 2'-fluoro-2'-deoxycytidine
<220> FEATURE:
<221> NAME/KEY: misc_feature
<222> LOCATION: (9)..(9)
<223> OTHER INFORMATION: May be 2'-O-Methyl-2'-deoxyguanosine
<220> FEATURE:
<221> NAME/KEY: misc_feature
<222> LOCATION: (10)..(10)
<223> OTHER INFORMATION: May be 2'-O-Methyl-2'-deoxyguanosine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-O-Methyl-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyuridine
<220> FEATURE:
<221> NAME/KEY: misc_feature
<222> LOCATION: (14)..(14)
<223> OTHER INFORMATION: May be 2'-O-Methyl-2'-deoxycytidine
<220> FEATURE:
<221> NAME/KEY: misc_feature
<222> LOCATION: (15)..(15)
<223> OTHER INFORMATION: May be 2'-O-Methyl-2'-deoxyadenosine
<220> FEATURE:
<221> NAME/KEY: misc_feature
<222> LOCATION: (16)..(16)
<223> OTHER INFORMATION: May be 2'-O-Methyl-2'-deoxyguanosine
<220> FEATURE:
<221> NAME/KEY: misc_feature
<222> LOCATION: (17)..(17)
<223> OTHER INFORMATION: May be 2'-O-Methyl-2'-deoxyguanosine
<220> FEATURE:
<221> NAME/KEY: misc_feature
<222> LOCATION: (18)..(18)
<223> OTHER INFORMATION: May be 2'-O-Methyl-2'-deoxycytidine
<220> FEATURE:
<221> NAME/KEY: misc_feature
<222> LOCATION: (19)..(19)
<223> OTHER INFORMATION: May be 2'OH-guanosine
<220> FEATURE:
<221> NAME/KEY: misc_feature
<222> LOCATION: (20)..(20)
<223> OTHER INFORMATION: May be 2'-fluoro-2'-deoxycytidine
<220> FEATURE:
<221> NAME/KEY: misc_feature
<222> LOCATION: (21)..(21)
<223> OTHER INFORMATION: May be 2'-fluoro-2'-deoxyuridine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-O-Methyl-2'-deoxyadenosine
<220> FEATURE:
<221> NAME/KEY: misc_feature
<222> LOCATION: (24)..(24)
<223> OTHER INFORMATION: May be 2'-O-Methyl-2'-deoxyguanosine
```

```
<220> FEATURE:
<221> NAME/KEY: misc_feature
<222> LOCATION: (25)..(25)
<223> OTHER INFORMATION: May be 2'-O-Methyl-2'-deoxyuridine
<220> FEATURE:
<221> NAME/KEY: misc_feature
<222> LOCATION: (26)..(26)
<223> OTHER INFORMATION: May be 2'-O-Methyl-2'-deoxycytidine
<220> FEATURE:
<221> NAME/KEY: misc_feature
<222> LOCATION: (27)..(27)
<223> OTHER INFORMATION: May be 2'-O-Methyl-2'-deoxyuridine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-O-Methyl-2'-deoxyadenosine
<220> FEATURE:
<221> NAME/KEY: misc_feature
<222> LOCATION: (30)..(30)
<223> OTHER INFORMATION: May be 2'-O-Methyl-2'-deoxyguanosine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-fluoro-2'-deoxyuridine
<220> FEATURE:
<221> NAME/KEY: misc_feature
<222> LOCATION: (33)..(33)
<223> OTHER INFORMATION: May be 2'-fluoro-2'-deoxyuridine
<220> FEATURE:
<221> NAME/KEY: misc_feature
<222> LOCATION: (34)..(34)
<223> OTHER INFORMATION: May be 2'OH-adenosine
<220> FEATURE:
<221> NAME/KEY: misc_feature
<222> LOCATION: (35)..(35)
<223> OTHER INFORMATION: May be 2'-fluoro-2'-deoxycytidine
<220> FEATURE:
<221> NAME/KEY: misc_feature
<222> LOCATION: (36)..(36)
<223> OTHER INFORMATION: May be 2'-fluoro-2'-deoxycytidine
<220> FEATURE:
<221> NAME/KEY: misc_feature
<222> LOCATION: (37)..(37)
<223> OTHER INFORMATION: May be 2'-fluoro-2'-deoxyuridine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be 2'-fluoro-2'-deoxycytidine
<220> FEATURE:
<221> NAME/KEY: misc_feature
<222> LOCATION: (40)..(40)
<223> OTHER INFORMATION: May be 2'-O-Methyl-2'-deoxyguanosine
<220> FEATURE:
<221> NAME/KEY: misc_feature
<222> LOCATION: (41)..(41)
<223> OTHER INFORMATION: May be 2'-O-Methyl-2'-deoxycytidine
<220> FEATURE:
<221> NAME/KEY: misc_feature
<222> LOCATION: (42)..(42)
<223> OTHER INFORMATION: May be 2'-O-Methyl-2'-deoxycytidine

<400> SEQUENCE: 79
ggcgccgcgg ucucaggcgc ugagucugag uuuaccugcg cc                    42

<210> SEQ ID NO 80
```

-continued

```
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
```

```
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-O-Methyl-2'-deoxyadenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
```

```
<221> NAME/KEY: misc_feature
<222> LOCATION: (39)..(39)
<223> OTHER INFORMATION: May be an inverted orientation T (3'-3'-linked)

<400> SEQUENCE: 80
cgccgcgguc ucaggcgcug agucugaguu uaccugcgt                              39

<210> SEQ ID NO 81
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
```

```
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-O-Methyl-2'-deoxycytidine
<220> FEATURE:
<221> NAME/KEY: misc_feature
<222> LOCATION: (19)..(19)
<223> OTHER INFORMATION: May be 2'-O-Methyl-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
```

-continued

```
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 81
cgccgcgguc ucaggcgcug agucugaguu uaccugcgt                              39

<210> SEQ ID NO 82
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
```

```
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'OH-thymidine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
```

```
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 82
cgccgcgguc ucaggcgcug agucugagtu uaccugcgt                              39

<210> SEQ ID NO 83
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
```

```
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-O-Methyl-2'-deoxycytidine
<220> FEATURE:
<221> NAME/KEY: misc_feature
<222> LOCATION: (19)..(19)
<223> OTHER INFORMATION: May be 2'-O-Methyl-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
```

<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-O-Methyl-2'-deoxyadenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 83
cgccgcgguc ucaggcgcug agucugaguu uaccugcgt                                39

<210> SEQ ID NO 84
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature

```
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-O-Methyl-2'-deoxycytidine
<220> FEATURE:
<221> NAME/KEY: misc_feature
<222> LOCATION: (19)..(19)
<223> OTHER INFORMATION: May be 2'-O-Methyl-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
```

<221> NAME/KEY: misc_feature
<222> LOCATION: (29)..(29)
<223> OTHER INFORMATION: May be 2'OH-thymidine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'-O-Methyl-2'-deoxyadenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 84
cgccgcgguc ucaggcgcug agucugagtu uaccugcgt                              39

<210> SEQ ID NO 85
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a 20 kDa polyethylene glycol group
    attached via a hexylamine linker
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)

```
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
```

```
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 85
cgccgcgguc ucaggcgcug agucugaguu uaccugcgt                             39

<210> SEQ ID NO 86
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a 30 kDa polyethylene glycol group
      attached via a hexylamine linker
<220> FEATURE:
<221> NAME/KEY: misc_feature
<222> LOCATION: (1)..(1)
<223> OTHER INFORMATION: May be 2'-fluoro-2'-deoxycytidine
```

```
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
```

```
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 86
cgccgcgguc ucaggcgcug agucugaguu uaccugcgt                    39
```

```
<210> SEQ ID NO 87
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a hexylamine terminal group
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
```

```
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
```

```
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 87
cgccgcgguc ucaggcgcug agucugaguu uaccugcgt                                39

<210> SEQ ID NO 88
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a 10 kDa polyethylene glycol group
      attached via a hexylamine linker
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
```

```
-continued

<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
```

```
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 88
cgccgcgguc ucaggcgcug agucugaguu uaccugcgt                    39

<210> SEQ ID NO 89
<211> LENGTH: 75
<212> TYPE: RNA
<213> ORGANISM: Artificial Sequence
<220> FEATURE:
<223> OTHER INFORMATION: Synthetic C5 specific aptamer

<400> SEQUENCE: 89
gggagaggag agaacguucu accuugguuu ggcacaggca uacauacgca ggggucgauc    60
gaucgaucau cgaug                                              75

<210> SEQ ID NO 90
<211> LENGTH: 32
<212> TYPE: RNA
<213> ORGANISM: Artificial Sequence
<220> FEATURE:
<223> OTHER INFORMATION: Synthetic C5 specific aptamer

<400> SEQUENCE: 90
ccuugguuug gcacaggcau acauacgcag gg                           32

<210> SEQ ID NO 91
<211> LENGTH: 47
<212> TYPE: RNA
<213> ORGANISM: Artificial Sequence
<220> FEATURE:
<223> OTHER INFORMATION: Synthetic C5 specific aptamer

<400> SEQUENCE: 91
cguucuaccu ugguuuggca caggcauaca uacgcagggg ucgaucg           47

<210> SEQ ID NO 92
<211> LENGTH: 39
<212> TYPE: DNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a 40 kDa polyethylene glycol group
      attached via a hexylamine linker
<220> FEATURE:
```

```
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
```

```
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (39)..(39)
<223> OTHER INFORMATION: May be an inverted orientation T (3'-3'-linked)

<400> SEQUENCE: 92
```
cgccgcgguc ucaggcgcug agucugaguu uaccugcgt    39

<210> SEQ ID NO 93
<211> LENGTH: 38
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (1)..(1)
<223> OTHER INFORMATION: May have a 20 kDa polyethylene glycol group
      attached via a hexylamine linker
<220> FEATURE:
<221> NAME/KEY: misc_feature
<222> LOCATION: (1)..(1)
<223> OTHER INFORMATION: May be 2'-fluoro-2'-deoxycytidine
<220> FEATURE:
<221> NAME/KEY: misc_feature
<222> LOCATION: (2)..(2)
<223> OTHER INFORMATION: May be 2'-O-Methyl-2'-deoxyguanosine
<220> FEATURE:
<221> NAME/KEY: misc_feature
<222> LOCATION: (3)..(3)
<223> OTHER INFORMATION: May be 2'-fluoro-2'-deoxycytidine
<220> FEATURE:
<221> NAME/KEY: misc_feature
<222> LOCATION: (4)..(4)
<223> OTHER INFORMATION: May be 2'-fluoro-2'-deoxycytidine
<220> FEATURE:
<221> NAME/KEY: misc_feature
<222> LOCATION: (5)..(5)
<223> OTHER INFORMATION: May be 2'OH-guanosine
<220> FEATURE:
<221> NAME/KEY: misc_feature
<222> LOCATION: (6)..(6)
<223> OTHER INFORMATION: May be 2'-fluoro-2'-deoxycytidine
<220> FEATURE:
<221> NAME/KEY: misc_feature
<222> LOCATION: (7)..(7)
<223> OTHER INFORMATION: May be 2'-O-Methyl-2'-deoxyguanosine
<220> FEATURE:
<221> NAME/KEY: misc_feature
<222> LOCATION: (8)..(8)
<223> OTHER INFORMATION: May be 2'-O-Methyl-2'-deoxyguanosine
<220> FEATURE:
<221> NAME/KEY: misc_feature
<222> LOCATION: (9)..(9)
<223> OTHER INFORMATION: May be 2'-fluoro-2'-deoxyuridine
<220> FEATURE:
<221> NAME/KEY: misc_feature
<222> LOCATION: (10)..(10)
<223> OTHER INFORMATION: May be 2'-fluoro-2'-deoxycytidine
<220> FEATURE:
<221> NAME/KEY: misc_feature
<222> LOCATION: (11)..(11)
<223> OTHER INFORMATION: May be 2'-fluoro-2'-deoxyuridine
<220> FEATURE:
<221> NAME/KEY: misc_feature
<222> LOCATION: (12)..(12)
<223> OTHER INFORMATION: May be 2'-fluoro-2'-deoxycytidine
<220> FEATURE:
<221> NAME/KEY: misc_feature
<222> LOCATION: (13)..(13)
<223> OTHER INFORMATION: May be 2'-O-Methyl-2'-deoxyadenosine
<220> FEATURE:
<221> NAME/KEY: misc_feature
<222> LOCATION: (14)..(14)
<223> OTHER INFORMATION: May be 2'-O-Methyl-2'-deoxyguanosine
<220> FEATURE:
<221> NAME/KEY: misc_feature
<222> LOCATION: (15)..(15)
<223> OTHER INFORMATION: May be 2'-O-Methyl-2'-deoxyguanosine
<220> FEATURE:
<221> NAME/KEY: misc_feature
<222> LOCATION: (16)..(16)
<223> OTHER INFORMATION: May be 2'-fluoro-2'-deoxycytidine
<220> FEATURE:

```
<221> NAME/KEY: misc_feature
<222> LOCATION: (17)..(17)
<223> OTHER INFORMATION: May be 2'OH-guanosine
<220> FEATURE:
<221> NAME/KEY: misc_feature
<222> LOCATION: (18)..(18)
<223> OTHER INFORMATION: May be 2'-fluoro-2'-deoxycytidine
<220> FEATURE:
<221> NAME/KEY: misc_feature
<222> LOCATION: (19)..(19)
<223> OTHER INFORMATION: May be 2'-fluoro-2'-deoxyuridine
<220> FEATURE:
<221> NAME/KEY: misc_feature
<222> LOCATION: (20)..(20)
<223> OTHER INFORMATION: May be 2'-O-Methyl-2'-deoxyguanosine
<220> FEATURE:
<221> NAME/KEY: misc_feature
<222> LOCATION: (21)..(21)
<223> OTHER INFORMATION: May be 2'-O-Methyl-2'-deoxyadenosine
<220> FEATURE:
<221> NAME/KEY: misc_feature
<222> LOCATION: (22)..(22)
<223> OTHER INFORMATION: May be 2'-O-Methyl-2'-deoxyguanosine
<220> FEATURE:
<221> NAME/KEY: misc_feature
<222> LOCATION: (23)..(23)
<223> OTHER INFORMATION: May be 2'-fluoro-2'-deoxyuridine
<220> FEATURE:
<221> NAME/KEY: misc_feature
<222> LOCATION: (24)..(24)
<223> OTHER INFORMATION: May be 2'-fluoro-2'-deoxycytidine
<220> FEATURE:
<221> NAME/KEY: misc_feature
<222> LOCATION: (25)..(25)
<223> OTHER INFORMATION: May be 2'-fluoro-2'-deoxyuridine
<220> FEATURE:
<221> NAME/KEY: misc_feature
<222> LOCATION: (26)..(26)
<223> OTHER INFORMATION: May be 2'-O-Methyl-2'-deoxyguanosine
<220> FEATURE:
<221> NAME/KEY: misc_feature
<222> LOCATION: (27)..(27)
<223> OTHER INFORMATION: May be 2'-O-Methyl-2'-deoxyadenosine
<220> FEATURE:
<221> NAME/KEY: misc_feature
<222> LOCATION: (28)..(28)
<223> OTHER INFORMATION: May be 2'-O-Methyl-2'-deoxyguanosine
<220> FEATURE:
<221> NAME/KEY: misc_feature
<222> LOCATION: (29)..(29)
<223> OTHER INFORMATION: May be 2'-fluoro-2'-deoxyuridine
<220> FEATURE:
<221> NAME/KEY: misc_feature
<222> LOCATION: (30)..(30)
<223> OTHER INFORMATION: May be 2'-fluoro-2'-deoxyuridine
<220> FEATURE:
<221> NAME/KEY: misc_feature
<222> LOCATION: (31)..(31)
<223> OTHER INFORMATION: May be 2'-fluoro-2'-deoxyuridine
<220> FEATURE:
<221> NAME/KEY: misc_feature
<222> LOCATION: (32)..(32)
<223> OTHER INFORMATION: May be 2'OH-adenosine
<220> FEATURE:
<221> NAME/KEY: misc_feature
<222> LOCATION: (33)..(33)
<223> OTHER INFORMATION: May be 2'-fluoro-2'-deoxycytidine
<220> FEATURE:
<221> NAME/KEY: misc_feature
<222> LOCATION: (34)..(34)
<223> OTHER INFORMATION: May be 2'-fluoro-2'-deoxycytidine
<220> FEATURE:
<221> NAME/KEY: misc_feature
<222> LOCATION: (35)..(35)
<223> OTHER INFORMATION: May be 2'-fluoro-2'-deoxyuridine
<220> FEATURE:
<221> NAME/KEY: misc_feature
<222> LOCATION: (36)..(36)
<223> OTHER INFORMATION: May be 2'-O-Methyl-2'-deoxyguanosine
```

```
<220> FEATURE:
<221> NAME/KEY: misc_feature
<222> LOCATION: (37)..(37)
<223> OTHER INFORMATION: May be 2'-fluoro-2'-deoxycytidine
<220> FEATURE:
<221> NAME/KEY: misc_feature
<222> LOCATION: (38)..(38)
<223> OTHER INFORMATION: May be 2'-O-Methyl-2'-deoxyguanosine
<220> FEATURE:
<221> NAME/KEY: misc_feature
<222> LOCATION: (38)..(38)
<223> OTHER INFORMATION: May have a 20 kDa polyethylene glycol group
      attached via a hexylamine linker

<400> SEQUENCE: 93
cgccgcgguc ucaggcgcug agucugaguu uaccugcg                              38

<210> SEQ ID NO 94
<211> LENGTH: 80
<212> TYPE: RNA
<213> ORGANISM: Artificial Sequence
<220> FEATURE:
<223> OTHER INFORMATION: Synthetic C5 specific aptamer

<400> SEQUENCE: 94
gggagaggag agaacguucu accuugguuu ggcccaggca uauauacgca gggauugauc      60
cguuacgacu agcaucgaug                                                  80

<210> SEQ ID NO 95
<211> LENGTH: 79
<212> TYPE: RNA
<213> ORGANISM: Artificial Sequence
<220> FEATURE:
<223> OTHER INFORMATION: Synthetic C5 specific aptamer

<400> SEQUENCE: 95
gggagaggag agaacguucu accuuagguu cgcacuguca uacauacaca cgggcaaucg      60
guuacgacua gcaucgaug                                                   79

<210> SEQ ID NO 96
<211> LENGTH: 75
<212> TYPE: RNA
<213> ORGANISM: Artificial Sequence
<220> FEATURE:
<223> OTHER INFORMATION: Synthetic C5 specific aptamer
<220> FEATURE:
<221> NAME/KEY: misc_feature
<222> LOCATION: (34)..(34)
<223> OTHER INFORMATION: n is a, c, g, or u
<220> FEATURE:
<221> NAME/KEY: misc_feature
<222> LOCATION: (43)..(43)
<223> OTHER INFORMATION: n is a, c, g, or u

<400> SEQUENCE: 96
gggagaggag agaacguucu accuugguuu ggcncaggca uanauacgca cgggucgauc      60
gguuacgacu agcau                                                       75

<210> SEQ ID NO 97
<211> LENGTH: 126
<212> TYPE: PRT
<213> ORGANISM: Unknown
<220> FEATURE:
<223> OTHER INFORMATION: ankyrin binding domain

<400> SEQUENCE: 97

Gly Ser Asp Leu Gly Lys Lys Leu Leu Glu Ala Ala Arg Ala Gly Gln
```

```
1               5                   10                  15
Asp Asp Glu Val Arg Ile Leu Met Ala Asn Gly Ala Asp Val Asn Thr
                20                  25                  30

Ala Asp Ser Thr Gly Trp Thr Pro Leu His Leu Ala Val Pro Trp Gly
                35                  40                  45

His Leu Glu Ile Val Glu Val Leu Leu Lys Tyr Gly Ala Asp Val Asn
            50                  55                  60

Ala Lys Asp Phe Gln Gly Trp Thr Pro Leu His Leu Ala Ala Ala Ile
65              70                  75                  80

Gly His Gln Glu Ile Val Glu Val Leu Leu Lys Asn Gly Ala Asp Val
                    85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala
                115                 120                 125
```

<210> SEQ ID NO 98
<211> LENGTH: 552
<212> TYPE: PRT
<213> ORGANISM: Artificial Sequence
<220> FEATURE:
<223> OTHER INFORMATION: recombinant human soluble VEGF receptor fusion
      protein

<400> SEQUENCE: 98

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
                20                  25                  30

Met Tyr Ser Glu Ile Pro Glu Ile Ile His Met Thr Glu Gly Arg Glu
                35                  40                  45

Leu Val Ile Pro Cys Arg Val Thr Ser Pro Asn Ile Thr Val Thr Leu
            50                  55                  60

Lys Lys Phe Pro Leu Asp Thr Leu Ile Pro Asp Gly Lys Arg Ile Ile
65              70                  75                  80

Trp Asp Ser Arg Lys Gly Phe Ile Ile Ser Asn Ala Thr Tyr Lys Glu
                    85                  90                  95

Ile Gly Leu Leu Thr Cys Glu Ala Thr Val Asn Gly His Leu Tyr Lys
                100                 105                 110

Thr Asn Tyr Leu Thr His Arg Gln Thr Asn Thr Ile Ile Asp Val Val
            115                 120                 125

Leu Ser Pro Ser His Gly Ile Glu Leu Ser Val Gly Glu Lys Leu Val
130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
                180                 185                 190

Leu Thr Ile Asp Gly Val Thr Arg Ser Asp Gln Gly Leu Tyr Thr Cys
            195                 200                 205

Ala Ala Ser Ser Gly Leu Met Thr Lys Lys Asn Ser Thr Phe Val Arg
            210                 215                 220

Val His Glu Lys Pro Phe Val Ala Phe Gly Ser Gly Met Glu Ser Leu
225                 230                 235                 240
```

-continued

```
Val Glu Ala Thr Val Gly Glu Arg Val Arg Leu Pro Ala Lys Tyr Leu
                245                 250                 255
Gly Tyr Pro Pro Pro Glu Ile Lys Trp Tyr Lys Asn Gly Ile Pro Leu
            260                 265                 270
Glu Ser Asn His Thr Ile Lys Ala Gly His Val Leu Thr Ile Met Glu
        275                 280                 285
Val Ser Glu Arg Asp Thr Gly Asn Tyr Thr Val Ile Leu Thr Asn Pro
    290                 295                 300
Ile Ser Lys Glu Lys Gln Ser His Val Val Ser Leu Val Val Tyr Val
305                 310                 315                 320
Pro Pro Gly Pro Gly Asp Lys Thr His Thr Cys Pro Leu Cys Pro Ala
                325                 330                 335
Pro Glu Leu Leu Gly Gly Pro Ser Val Phe Leu Phe Pro Pro Lys Pro
            340                 345                 350
Lys Asp Thr Leu Met Ile Ser Arg Thr Pro Glu Val Thr Cys Val Val
        355                 360                 365
Val Asp Val Ser His Glu Asp Pro Glu Val Lys Phe Asn Trp Tyr Val
    370                 375                 380
Asp Gly Val Glu Val His Asn Ala Lys Thr Lys Pro Arg Glu Glu Gln
385                 390                 395                 400
Tyr Asn Ser Thr Tyr Arg Val Val Ser Val Leu Thr Val Leu His Gln
                405                 410                 415
Asp Trp Leu Asn Gly Lys Glu Tyr Lys Cys Lys Val Ser Asn Lys Ala
            420                 425                 430
Leu Pro Ala Pro Ile Glu Lys Thr Ile Ser Lys Ala Lys Gly Gln Pro
        435                 440                 445
Arg Glu Pro Gln Val Tyr Thr Leu Pro Pro Ser Arg Asp Glu Leu Thr
    450                 455                 460
Lys Asn Gln Val Ser Leu Thr Cys Leu Val Lys Gly Phe Tyr Pro Ser
465                 470                 475                 480
Asp Ile Ala Val Glu Trp Glu Ser Asn Gly Gln Pro Glu Asn Asn Tyr
                485                 490                 495
Lys Ala Thr Pro Pro Val Leu Asp Ser Asp Gly Ser Phe Phe Leu Tyr
            500                 505                 510
Ser Lys Leu Thr Val Asp Lys Ser Arg Trp Gln Gln Gly Asn Val Phe
        515                 520                 525
Ser Cys Ser Val Met His Glu Ala Leu His Asn His Tyr Thr Gln Lys
    530                 535                 540
Ser Leu Ser Leu Ser Pro Gly Lys
545                 550
```